(12) United States Patent
Masukawa

(10) Patent No.: US 9,605,207 B2
(45) Date of Patent: *Mar. 28, 2017

(54) ORTHOESTER DERIVATIVE, LIQUID CRYSTAL COMPOSITION AND LIQUID CRYSTAL DISPLAY DEVICE

(75) Inventor: Tokifumi Masukawa, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 10 days.

This patent is subject to a terminal disclaimer.

(21) Appl. No.: 14/007,330

(22) PCT Filed: Mar. 7, 2012

(86) PCT No.: PCT/JP2012/055753
§ 371 (c)(1),
(2), (4) Date: Sep. 25, 2013

(87) PCT Pub. No.: WO2012/132796
PCT Pub. Date: Oct. 4, 2012

(65) Prior Publication Data
US 2014/0021407 A1    Jan. 23, 2014

(30) Foreign Application Priority Data
Mar. 25, 2011   (JP) ................ 2011-068002

(51) Int. Cl.
C09K 19/34    (2006.01)
C07D 493/08   (2006.01)
G02F 1/137    (2006.01)

(52) U.S. Cl.
CPC ........ *C09K 19/3402* (2013.01); *C07D 493/08* (2013.01); *C09K 2019/3425* (2013.01); *C09K 2019/3427* (2013.01); *G02F 1/137* (2013.01); *G02F 2001/13706* (2013.01); *G02F 2001/13712* (2013.01)

(58) Field of Classification Search
CPC .................................................. C09K 19/3402
See application file for complete search history.

(56) References Cited

U.S. PATENT DOCUMENTS

| | | | |
|---|---|---|---|
| 4,772,624 A | | 9/1988 | Palmer et al. |
| 4,876,274 A | * | 10/1989 | Palmer et al. ............... 514/452 |
| 8,609,208 B2 | * | 12/2013 | Yamamoto et al. .......... 428/1.1 |
| 8,795,795 B2 | * | 8/2014 | Yanai et al. ................. 428/1.1 |
| 2009/0237610 A1 | | 9/2009 | Saito et al. |
| 2011/0051023 A1 | * | 3/2011 | Fujita et al. ................... 349/19 |
| 2013/0155338 A1 | * | 6/2013 | Junge ............................. 349/20 |

FOREIGN PATENT DOCUMENTS

| CN | 101143808 | 3/2008 |
|---|---|---|
| DE | 248122 | 7/1987 |

(Continued)

OTHER PUBLICATIONS

Palmer et al. "1,4-disubstituted 2,6,7-trioxabicyclo[2.2.2]octanes: A New Class of Insecticides", Jun. 24, 1985, Journal of Agricultural Food Chemistry, 33, 976-980.*
R. Paschke et al, "Synthesis and liquid-crystalline properties of compounds incorporating the 2,6,7-trioxa-bicyclo (2.2.2)octane", Liquid Crystals, Accepted May 18, 1989, pp. 397-407, vol. 6, Issue 4, Taylor & Francis Ltd.
Loretta M. Cole et al., "Structure-Biodegradability Relationships of Insecticidal 1,4-Disubstituted-2,6,7-trioxabicyclo [2.2.2]octanes", J. Agric. Food Chem., Mar.1991, pp. 560-565, 39, American Chemical Society.
"Office Action of Taiwan Counterpart Application", issued on May 6, 2015, p. 1-p. 17, with English translation thereof.
"Office Action of Taiwan Counterpart Application", issued on Sep. 17, 2015, p. 1-p. 12, with English translation thereof.
(Continued)

*Primary Examiner* — Cynthia H. Kelly
*Assistant Examiner* — Anna Malloy
(74) *Attorney, Agent, or Firm* — Jinaq Chyun IP Office

(57) ABSTRACT

A liquid crystal compound is described, having a large dielectric anisotropy, a high voltage holding ratio and stability to heat, light and so forth, maintaining a nematic phase in a wide temperature range, and having a suitable optical anisotropy and an excellent compatibility with other liquid crystal compounds. Particularly, a liquid crystal compound having a large dielectric anisotropy is described. The compound is represented by formula (1):

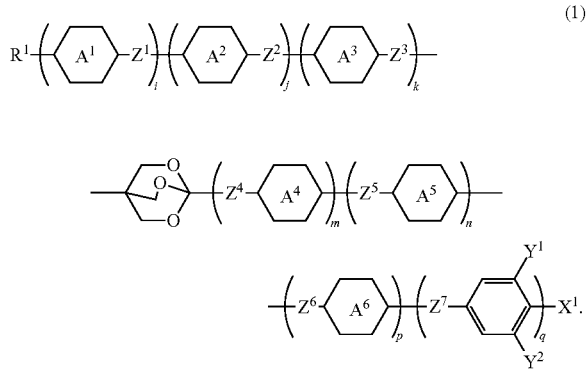

In the formula, for example, $R^1$ is alkyl having 1 to 20 carbons; ring $A^1$, ring $A^2$, ring $A^3$, ring $A^4$, ring $A^5$ and ring $A^6$ are independently 1,4-cyclohexylene or 1,4-phenylene; $Z^1$, $Z^2$, $Z^3$, $Z^4$, $Z^5$, $Z^6$ and $Z^7$ are independently a single bond, $-(CH_2)_2-$, $-COO-$, $-OCO-$, $-CF_2O-$, $-OCF_2-$ or $-CH=CH-$; $X^1$ is fluorine, $-CF_3$ or $-OCF_3$; and $Y^1$ and $Y^2$ are independently hydrogen or fluorine.

18 Claims, No Drawings

(56) References Cited

FOREIGN PATENT DOCUMENTS

| | | |
|---|---|---|
| DE | 248136 | 7/1987 |
| EP | 279698 | 8/1988 |
| EP | 1046694 | 10/2000 |
| EP | 1801186 | 6/2007 |
| JP | 2001-003053 | 1/2001 |
| JP | 2007-091796 | 4/2007 |
| JP | 2007-169460 | 7/2007 |
| JP | 2008-069153 | 3/2008 |
| JP | 2009-256614 | 11/2009 |
| WO | 8503203 | 8/1985 |
| WO | 2004089885 | 10/2004 |
| WO | 2006037982 | 4/2006 |

OTHER PUBLICATIONS

"Third Office Action of China Counterpart Application", issued on Jan. 4, 2016, pp. 1-6, with English translation thereof.

* cited by examiner

ORTHOESTER DERIVATIVE, LIQUID CRYSTAL COMPOSITION AND LIQUID CRYSTAL DISPLAY DEVICE

CROSS-REFERENCE TO RELATED APPLICATION

This application is a 371 application of an international PCT application serial no. PCT/JP2012/055753, filed on Mar. 7, 2012, which claims the priority benefit of Japan application no. 2011-068002, filed on Mar. 25, 2011. The entirety of each of the abovementioned patent applications is hereby incorporated by reference herein and made a part of this specification.

TECHNICAL FIELD

The present invention relates to a new liquid crystal compound and liquid crystal composition. More specifically, the invention relates to a liquid crystal compound that has a 2,6,7-trioxabicyclo[2.2.2]octane ring, and has a large dielectric anisotropy and a high voltage holding ratio, a liquid crystal composition containing the compound, and a liquid crystal display device including the liquid crystal composition.

BACKGROUND ART

A display device using a liquid crystal compound (in the present application, a term "liquid crystal compound" is used as a generic term for a compound having a liquid crystal phase, and a compound having no liquid crystal phase but being useful as a component of a liquid crystal composition) has widely been used for a display for a watch, a calculator, a word processor or the like. The display devices utilize optical anisotropy, dielectric anisotropy and so forth of the liquid crystal compound.

The liquid crystal display device typified by a liquid crystal display panel, a liquid crystal display module and so forth utilizes optical anisotropy, dielectric anisotropy and so forth of the liquid crystal compound. As an operating mode of the liquid crystal display device, a variety of modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode and a polymer sustained alignment (PSA) mode.

The liquid crystal display devices include a liquid crystal composition having suitable physical properties. In order to improve characteristics of the liquid crystal display device, the liquid crystal composition preferable has suitable physical properties. As general physical properties necessary for the liquid crystal compound being a component of the liquid crystal composition, the liquid crystal composition is required to have characteristics shown in (1) to (6), more specifically.

(1) chemical stability and physical stability, (2) a high clearing point (clearing point: transition temperature between a liquid crystal phase and an isotropic phase);

(3) a low minimum temperature of the liquid crystal phase (a nematic phase, a smectic phase or the like), in particular, a low minimum temperature of the nematic phase;

(4) a suitable optical anisotropy;

(5) a suitable dielectric anisotropy, and (6) an excellent compatibility with other liquid crystal compounds.

When a composition containing a compound having a chemical and physical stability as described in (1) is used for a liquid crystal display device, a voltage holding ratio can be increased. In particular, a high voltage holding ratio is required for a TFT active matrix liquid crystal display device that currently constitutes a mainstream.

In a composition containing a liquid crystal compound having a high clearing point or a low minimum temperature of the liquid crystal phase as described in (2) and (3), a temperature range of the nematic phase is wide, and therefore the device can be used in a wide temperature range.

Furthermore, in the case of a display device using a composition containing a compound having a suitable optical anisotropy as described in (4), contrast of the device can be improved. A device requires compositions having a small to large optical anisotropy depending on a design of the device. A technique has been recently studied for improving response speed by decreasing cell thickness, and accordingly a liquid crystal composition having a large optical anisotropy is also required.

As is well known, threshold voltage ($V_{th}$) is represented according to the following equation (H. J. Deuling et al., Mol. Cryst. Liq. Cryst., 27 (1975) 81):

$$V_{th} = \pi(K/\varepsilon_0 \Delta\varepsilon)^{1/2}$$

wherein, in the equation, K represents an elastic constant and $\varepsilon_0$ represents a dielectric constant of vacuum. As is known from the equation, two ways are conceivable in order to decrease $V_{th}$: either increasing a value of dielectric anisotropy ($\Delta\varepsilon$) or decreasing K. However, according to the present technology, actual control of K is still difficult. Therefore, under the present situation, a liquid crystal material having a large $\Delta\varepsilon$ is ordinarily used to respond to the requirement. Under such circumstances, a development has been actively made for a liquid crystal compound having a suitable dielectric anisotropy, as described in (5), particularly, a liquid crystal compound having a large dielectric anisotropy.

In a passive matrix liquid crystal display device, the STN mode is most frequently applied. In the STN mode, a compound having a cyano group is mainly used as a liquid crystal compound having a large dielectric anisotropy. However, the compound having the cyano group has a low voltage holding ratio, and thus the compound having the cyano group is not currently used in the TFT active matrix liquid crystal display device in the mainstream, and a fluorine liquid crystal compound is used.

The liquid crystal compound is generally used in the form of a composition prepared by mixing the compound with many other liquid crystal compounds in order to develop characteristics that are difficult to be attained by a single compound. Accordingly, a liquid crystal compound used for the display device has an excellent compatibility with other liquid crystal compounds and so forth as described in (6). Moreover, the display device may be occasionally used in a wide temperature range including a freezing point, and therefore a compound exhibiting an excellent compatibility from a low temperature range may be occasionally preferred.

Specific examples of a liquid crystal compound having a 2,6,7-trioxabicyclo[2.2.2]octane ring are disclosed in Patent literature No. 1, Patent literature No. 2 and Non-patent literature No. 1. The literatures show compound (a), (b) or the like. However, compound (a) has a small dielectric anisotropy and is quite difficult to be used for the purpose of decreasing driving voltage of the liquid crystal display device, or the like. Moreover, compound (b) has a cyano group, and therefore has a low voltage holding ratio. Further, dipoles of the cyano group and the 2,6,7-trioxabicyclo[2.2.2] octane ring are reversely directed, and therefore the dielectric anisotropy does not increase.

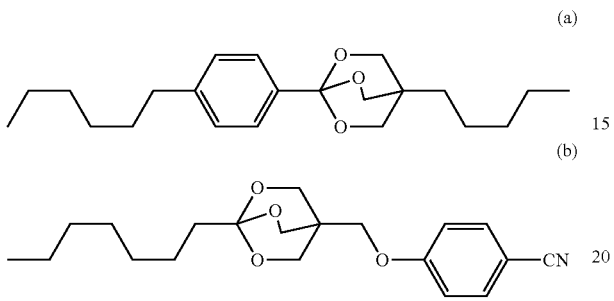

Patent literatures No. 3 to No. 7 describe a compound having a 2,6,7-trioxabicyclo[2.2.2]octane ring. However, all the literatures relate to an insecticide or innovative drug development, and describe nothing on an application as a liquid crystal material.

REFERENCE LIST

Patent Literature

Patent literature No. 1: DD 248122 Z/A2.
Patent literature No. 2: DD 248136 Z/A2.
Patent literature No. 3: WO85/03203 A.
Patent literature No. 4: EP 279698A.
Patent literature No. 5: U.S. Pat. No. 4,772,624B.
Patent literature No. 6: WO2004/089885 A.
Patent literature No. 7: WO2006/037982 A.
Non-patent literature No. 1: Liquid Crystals, 6(4), 397 (1989).

SUMMARY OF INVENTION

Technical Problem

A first object of the invention is to provide a liquid crystal compound having a large dielectric anisotropy, a high voltage holding ratio, a high stability to heat, light and so forth, maintaining a nematic phase in a wide temperature range, and having a suitable optical anisotropy and an excellent compatibility with other liquid crystal compounds, in particular, to provide a liquid crystal compound having a large dielectric anisotropy.

A second object of the invention is to provide a compound having stability to heat, light and so forth, a small viscosity, a suitable optical anisotropy, a large dielectric anisotropy and a low threshold voltage, and also to provide a liquid crystal composition that contains the compound and satisfies at least one of characteristics such as a high maximum temperature of a nematic phase (maximum temperature: phase transition temperature between the nematic phase and an isotropic phase), and a low minimum temperature of the nematic phase. A further object is to provide a liquid crystal composition having a suitable balance regarding at least two of the characteristics.

A third object of the invention is to provide a liquid crystal display device that contains a liquid crystal composition, and has a short response time, a small electric power consumption and a small driving voltage, a large contrast ratio and being usable in a wide temperature range.

Solution to Problem

In view of the objects, the present inventors have diligently continued to conduct research, as a result, have found that a specific structure compound having a 2,6,7-trioxabicyclo[2.2.2]octane ring and fluorine particularly develops an excellent effect of having increased dielectric anisotropy ($\Delta\in$), and a high voltage holding ratio and stability to heat, light and so forth. The present inventors have found that the objects can be achieved by utilizing the effect, and thus have completed the invention.

More specifically, the invention has a constitution as described in items 1 to 20, or the like.

Item 1. A compound represented by formula (1):

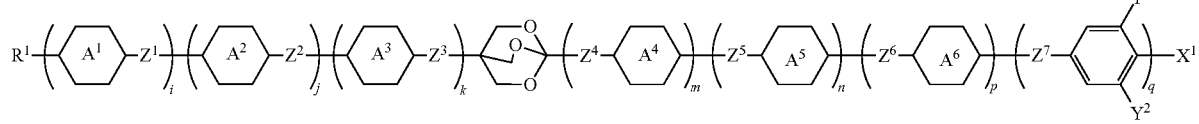

(1)

wherein, in the formula, $R^1$ is alkyl having 1 to 10 carbons, and in the alkyl, at least one of —$CH_2$— may be replaced by —O—, at least one of —$(CH_2)_2$— may be replaced by —CH=CH—, and at least one of hydrogen may be replaced by halogen; ring $A^1$, ring $A^2$, ring $A^3$, ring $A^4$, ring $A^5$ and ring $A^6$ are independently 1,4-cyclohexylene or 1,4-phenylene, at least one of —$CH_2$— in the 1,4-cyclohexylene may be replaced by —O—, at least one of —$(CH_2)_2$— in the 1,4-cyclohexylene may be replaced by —CH=CH—, at least one of —CH= in the 1,4-phenylene may be replaced by —N=, and at least one of hydrogen in the 1,4-phenylene may be replaced by halogen; $Z^1$, $Z^2$, $Z^3$, $Z^4$, $Z^5$, $Z^6$ and $Z^7$ are independently a single bond, —$(CH_2)_2$—, —COO—, —OCO—, —$CF_2O$—, —$OCF_2$— or —CH=CH—; $X^1$ is fluorine, —$CF_3$ or —$OCF_3$; $Y^1$ and $Y^2$ are independently hydrogen or fluorine; i, j, k, m, n, p and q are independently 0 or 1; and a sum of i, j, k, m, n, p and q is 1, 2, 3 or 4.

Item 2. The compound according to item 1, wherein, in formula (1) according to item 1, a sum of i, j, k, m, n, p and q is 2, 3 or 4.

Item 3. The compound according to item 1 or 2, wherein, in formula (1) according to item 1, q is 1.

Item 4. The compound according to any one of items 1 to 3, wherein, in formula (1) according to item 1, $R^1$ is alkyl having 1 to 10 carbons, alkenyl having 2 to 10 carbons or alkoxy having 1 to 9 carbons; ring $A^1$, ring $A^2$, ring $A^3$, ring $A^4$, ring $A^5$ and ring $A^6$ are independently 1,4-cyclohexylene, 1,4-cyclohexenylene, tetrahydropyran-2,5-diyl, 1,3-dioxane-2,5-diyl, 1,4-phenylene in which at least one of hydrogen may be replaced by fluorine or chlorine, or pyrimidine-2,5-diyl; and $Z^1$, $Z^2$, $Z^3$, $Z^4$, $Z^5$, $Z^6$ and $Z^7$ are independently a single bond, —$(CH_2)_2$—, —COO—, —$CF_2O$— or —CH=CH—.

Item 5. The compound according to any one of items 1 to 4, wherein, in formula (1) according to item 1, $R^1$ is alkyl having 1 to 10 carbons; ring $A^1$, ring $A^2$, ring $A^3$, ring $A^4$, ring $A^5$ and ring $A^1$ are independently 1,4-cyclohexylene, 1,4-phenylene, 3-fluoro-1,4-phenylene or 3,5-difluoro-1,4-phenylene; and $Z^1$, $Z^2$, $Z^3$, $Z^4$, $Z^5$, $Z^6$ and $Z^7$ are independently a single bond, —$(CH_2)_2$—, —COO—, —$CF_2O$— or —CH=CH—.

Item 6. The compound according to item 1, represented by formula (1-1-1):

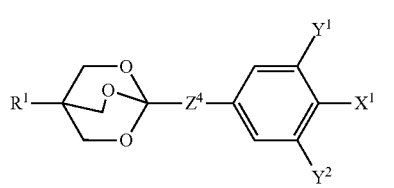

(1-1-1)

wherein, in the formula, $R^1$ is alkyl having 1 to 10 carbons; $Z^4$ is independently a single bond, —$(CH_2)_2$—, —COO—, —$CF_2O$— or —CH=CH—; $X^1$ is fluorine, —$CF_3$ or —$OCF_3$; and $Y^1$ and $Y^2$ are independently hydrogen or fluorine.

Item 7. The compound according to item 1, represented by formula (1-2-1) or (1-2-2):

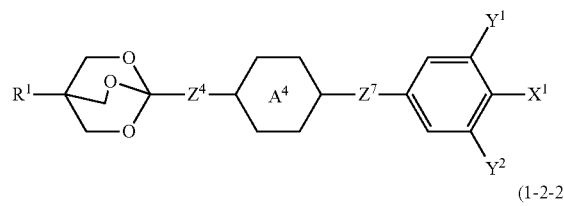

(1-2-1)

(1-2-2)

wherein, in the formulas, $R^1$ is alkyl having 1 to 10 carbons; ring $A^1$ and ring $A^1$ are independently 1,4-cyclohexylene, 1,4-phenylene, 3-fluoro-1,4-phenylene or 3,5-difluoro-1,4-phenylene; $Z^1$, $Z^4$ and $Z^7$ are independently a single bond, —$(CH_2)_2$—, —COO—, —$CF_2O$— or —CH=CH—; $X^1$ is fluorine, —$CF_3$ or —$OCF_3$; $Y^1$ and $Y^2$ are independently hydrogen or fluorine; in formula (1-2-1), at least one of $Z^4$ and $Z^7$ is a single bond; and in formula (1-2-2), at least one of $Z^1$ and $Z^7$ is a single bond.

Item 8. The compound according to item 7, wherein, in formula (1-2-1) according to item 7, any one of $Z^4$ and $Z^7$ is —$CF_2O$—, or in formula (1-2-2), any one of $Z^1$ and $Z^7$ is —$CF_2O$—.

Item 9. The compound according to item 1, represented by formula (1-3-1), (1-3-2) or (1-3-3):

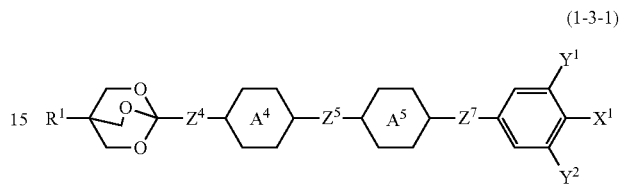

(1-3-1)

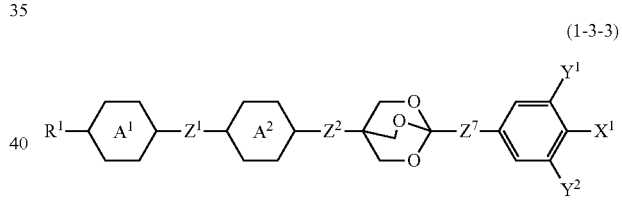

(1-3-2)

(1-3-3)

wherein, in the formulas, $R^1$ is alkyl having 1 to 10 carbons; ring $A^1$, ring $A^2$, ring $A^4$ and ring $A^5$ are independently 1,4-cyclohexylene, 1,4-phenylene, 3-fluoro-1,4-phenylene or 3,5-difluoro-1,4-phenylene; $Z^1$, $Z^2$, $Z^4$, $Z^5$ and $Z^7$ are independently a single bond, —$(CH_2)_2$—, —COO—, —$CF_2O$— or —CH=CH—; $X^1$ is fluorine, —$CF_3$ or —$OCF_3$; and $Y^1$ and $Y^2$ are independently hydrogen or fluorine;

in formula (1-3-1), at least two of $Z^4$, $Z^5$ and $Z^7$ are a single bond;

in formula (1-3-2), at least two of $Z^1$, $Z^4$ and $Z^7$ are a single bond; and in formula (1-3-3), at least two of $Z^1$, $Z^2$ and $Z^7$ are a single bond.

Item 10. The compound according to item 9, wherein, in formula (1-3-1) according to item 9, any one of $Z^4$, $Z^5$ and $Z^7$ is —$CF_2O$—; in formula (1-3-2), any one of $Z^1$, $Z^4$ and $Z^7$ is —$CF_2O$—; or in formula (1-3-3), any one of $Z^1$, $Z^2$ and $Z^7$ is —$CF_2O$—.

Item 11. The compound according to item 1, represented by formula (1-4-1), (1-4-2), (1-4-3) or (1-4-4):

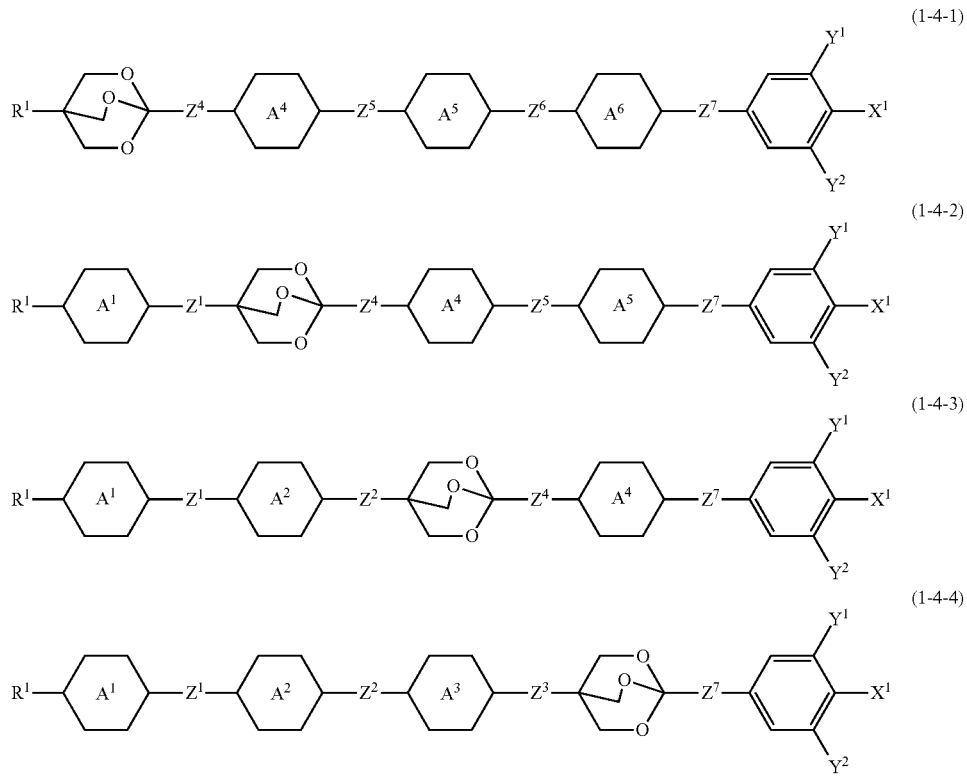

wherein, in the formulas, $R^1$ is alkyl having 1 to 10 carbons; ring $A^1$, ring $A^2$, ring $A^3$, ring $A^4$, ring $A^1$ and ring $A^6$ are independently 1,4-cyclohexylene, 1,4-phenylene, 3-fluoro-1,4-phenylene or 3,5-difluoro-1,4-phenylene; $Z^1$, $Z^2$, $Z^3$, $Z^4$, $Z^5$, $Z^6$ and $Z^7$ are independently a single bond, —(CH$_2$)$_2$—, —COO—, —CF$_2$O— or —CH=CH—; $X^1$ is fluorine, —CF$_3$ or —OCF$_3$; $Y^1$ and $Y^2$ are independently hydrogen or fluorine;

in formula (1-4-1), at least three of $Z^4$, $Z^5$, $Z^6$ and $Z^7$ are a single bond;

in formula (1-4-2), at least three of $Z^1$, $Z^4$, $Z^5$ and $Z^7$ are a single bond;

in formula (1-4-3), at least three of $Z^1$, $Z^2$, $Z^4$ and $Z^7$ are a single bond; and in formula (1-4-4), at least three of $Z^1$, $Z^2$, $Z^3$ and $Z^7$ are a single bond.

Item 12. The compound according to item 11, wherein, in formula (1-4-1) according to item 11, any one of $Z^4$, $Z^5$, $Z^6$ and $Z^7$ is —CF$_2$O—; in formula (1-4-2), any one of $Z^1$, $Z^4$, $Z^5$ and $Z^7$ is —CF$_2$O—; in formula (1-4-3), any one of $Z^1$, $Z^2$, $Z^4$ and $Z^7$ is —CF$_2$O—; or in formula (1-4-4), any one of $Z^1$, $Z^2$, $Z^3$ and $Z^7$ is —CF$_2$O—.

Item 13. A liquid crystal composition containing a first component and a second component, wherein the first component is at least one compound selected from the compounds according to any one of items 1 to 11.

Item 14. The liquid crystal composition according to item 13, wherein the second component is at least one compound selected from the group of compounds represented by formulas (2), (3) and (4):

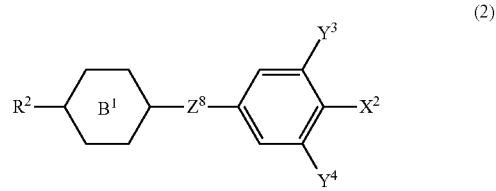

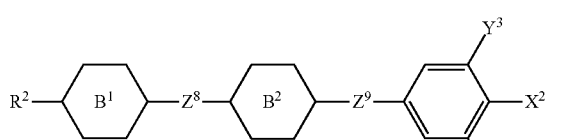

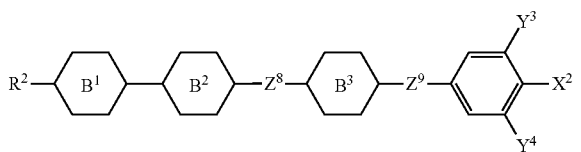

wherein, in formulas (2) to (4), $R^2$ is independently alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;

$X^2$ is independently fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring $B^1$, ring $B^2$ and ring $B^3$ are independently 1,4-cyclohexylene, 1,3-dioxane-2,5-diyl, pyrimidine-2,5-diyl, tetrahydropyran-2,5-diyl, or 1,4-phenylene in which at least one of hydrogen may be replaced by fluorine;

$Z^8$ and $Z^9$ are independently —$(CH_2)_2$—, —$(CH_2)_4$—, —COO—, —$CF_2O$—, —$OCF_2$—, —CH=CH—, —C≡C—, —$CH_2O$— or a single bond; and $Y^3$ and $Y^4$ are independently hydrogen or fluorine.

Item 15. The liquid crystal composition according to item 13, wherein the second component is at least one compound selected from the group of compounds represented by formulas (5), (6), (7), (8), (9) and (10):

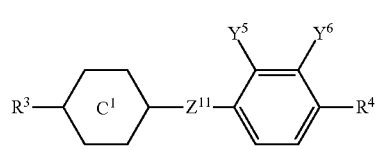
(5)

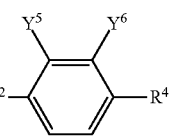
(6)

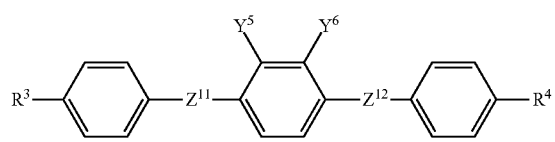
(7)

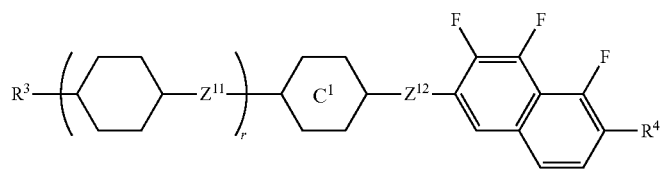
(8)

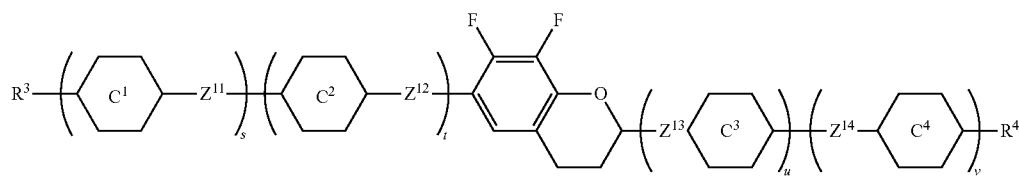
(9)

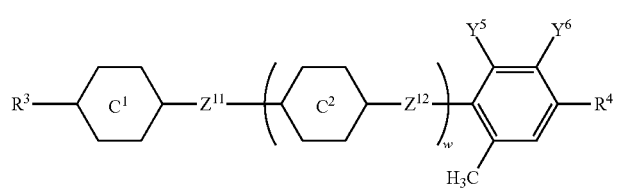
(10)

wherein, in formulas (5) to (10), $R^3$ and $R^4$ are independently alkyl having 1 to 10 carbons or alkenyl having 2 to 10 carbons, at least one of —$CH_2$— in the alkyl or the alkenyl may be replaced by —O—, and at least one of hydrogen in the alkenyl may be replaced by fluorine; ring $C^1$, ring $C^2$, ring $C^3$ and ring $C^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl; $Z^{11}$, $Z^{12}$, $Z^{13}$ and $Z^{14}$ are independently —$(CH_2)_2$—, —COO—, —$CH_2O$—, —$OCF_2$—, —$OCF_2(CH_2)_2$— or a single bond;

$Y^5$ and $Y^6$ are independently fluorine or chlorine; and r, s, t, u, v and w are independently 0 or 1, and a sum of s, t, u and v is 1 or 2.

Item 16. The liquid crystal composition according to item 13, wherein the second component is at least one compound selected from the group of compounds represented by formulas (11), (12) and (13):

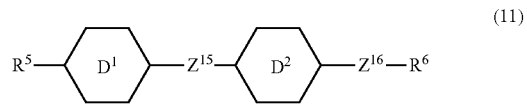
(11)

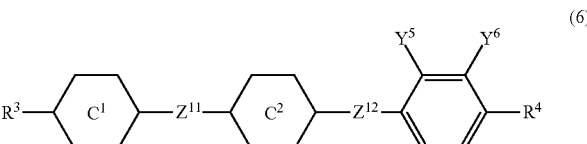
(12)

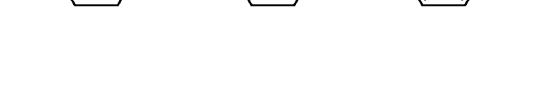

-continued

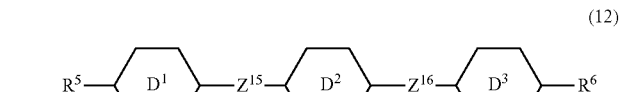
(12)

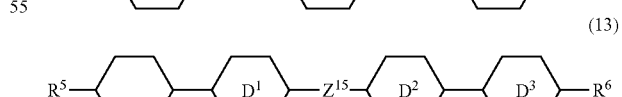
(13)

wherein, in formulas (11) to (13), $R^5$ and $R^6$ are independently alkyl having 1 to 10 carbons or alkenyl having 2 to 10 carbons, at least one of —$CH_2$— in the alkyl or the alkenyl may be replaced by —O—, and at least one of hydrogen in the alkenyl may be replaced by fluorine; ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{15}$ and $Z^{16}$ are independently —C≡C—, —COO—, —(CH$_2$)$_2$—, —CH=CH— or a single bond.

Item 17. The liquid crystal composition according to item 14, further containing at least one compound selected from the group of compounds represented by formulas (11), (12) and (13) according to item 16.

Item 18. The liquid crystal composition according to item 15, further containing at least one compound selected from the group of compounds represented by formulas (11), (12) and (13) according to item 16.

Item 19. The liquid crystal composition according to any one of items 13 to 18, further containing at least one optically active compound and/or at least one polymerizable compound.

Item 20. The liquid crystal composition according to any one of items 13 to 19, further containing at least one antioxidant and/or at least one ultraviolet light absorber.

Item 21. A liquid crystal display device including the liquid crystal composition according to any one of items 13 to 20.

Advantageous Effects of Invention

A compound of the invention has general physical properties necessary for the compound, namely, stability to heat, light and so forth, a wide temperature range of a liquid crystal phase, a good compatibility with other compounds, a large dielectric anisotropy and a suitable optical anisotropy. A liquid crystal composition of the invention contains at least one of the compounds, and has a high maximum temperature of a nematic phase, a low minimum temperature of the nematic phase, a small viscosity and a low threshold voltage. A liquid crystal display device of the invention includes the composition, and has a large temperature range in which the device can be used, a short response time, a small electric power consumption, a large contrast ratio and a low driving voltage.

DESCRIPTION OF EMBODIMENTS

Usage of terms herein is as described below. A liquid crystal compound is a generic term for a compound having a liquid crystal phase such as a nematic phase or a smectic phase, and a compound having no liquid crystal phase but being useful as a component of a liquid crystal composition. The liquid crystal compound, the liquid crystal composition and a liquid crystal display device may be occasionally abbreviated as "compound," "composition" and "device," respectively. "Liquid crystal display device" is a generic term for a liquid crystal display panel and a liquid crystal display module. A maximum temperature of the nematic phase is a phase transition temperature between the nematic phase and an isotropic phase, and may be occasionally abbreviated simply as a clearing point or the maximum temperature. "Minimum temperature of the nematic phase" may be abbreviated simply as "minimum temperature." "Compound represented by formula (1)" may be occasionally abbreviated as "compound (1)." The abbreviation may occasionally apply to a compound represented by formula (2) or the like. In formula (1) to formula (13), a symbol B, D, E or the like surrounded by a hexagonal shape corresponds to ring B, ring D, ring E or the like, respectively. An amount of the compound expressed in terms of "percentage" is expressed in terms of "weight percent (% by weight)" based on the total weight of the composition. A plurality of symbols such as $A^1$, $Y^1$ and ring B are described in an identical formula or different formulas, but groups selected by the symbols may be identical or different.

An expression "at least one" in the context of "may be replaced" shows that not only a position but also the number can be freely selected. An expression "at least one of A may be replaced by B, C or D" includes a case where arbitrary A is replaced by B, a case where one of A is replaced by C, and a case where one of A is replaced by D, and also a case where two or more of A are replaced by at least two of B to D. For example, alkyl in which arbitrary —CH$_2$— may be replaced by —O— or —CH=CH— includes alkyl, alkenyl, alkoxy, alkoxyalkyl, alkoxyalkenyl and alkenyloxyalkyl. In addition, according to the invention, replacement of two successive —CH$_2$— by —O— to form —O—O— or the like is not preferred. Then, replacement of —CH$_2$— in a terminal of alkyl by —O— is not preferred, either.

The invention will be further explained below.

1-1 Compound of the Invention

A first embodiment of the invention relates to a compound represented by formula (1):

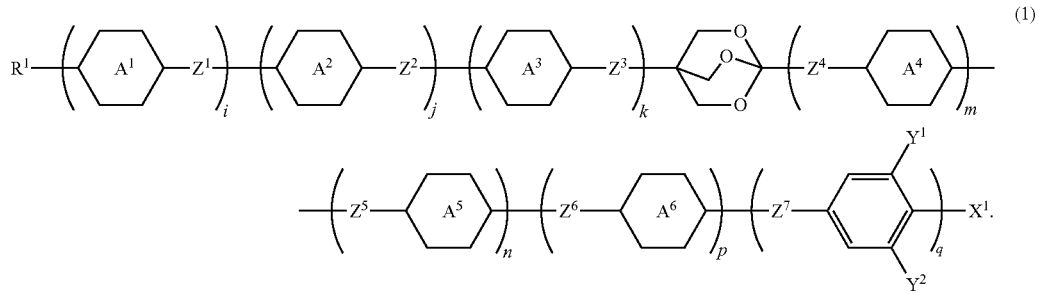

(1)

In formula (1), $R^1$ is alkyl having 1 to 10 carbons, and in the alkyl, at least one of —CH$_2$— may be replaced by O—, at least one of —(CH$_2$)$_2$— may be replaced by —CH=CH—, and at least one of hydrogen may be replaced by halogen.

$R^1$ is alkyl, alkoxy, alkoxyalkyl, alkoxyalkoxy, alkenyl, alkenyloxy, alkenyloxyalkyl, alkoxyalkenyl or the like. In general, when the groups are branched in a liquid crystal compound, a maximum temperature of the nematic phase decreases and viscosity increases as compared with compounds in which the groups are linear. In the groups, therefore, a straight chain is preferred to a branched chain. However, in a driving mode such as a blue phase mode in which a response speed does not depend on viscosity, a compound in which $R^1$ is a branched chain group may be used in order to improve compatibility. A preferred configuration of —CH=CH— in alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. Alkenyl having a preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327. In a compound in which hydrogen of R$^1$ is replaced by halogen, a maximum temperature of the nematic phase decreases and viscosity increases as compared with a compound in which hydrogen is not replaced by halogen. In the groups, therefore, R$^1$ is preferably an alkyl group or the like in which hydrogen is not replaced by halogen. However, in the driving mode such as the blue phase mode in which the response speed does not depend on the viscosity, a compound in which hydrogen of R$^1$ is replaced by halogen may be used in order to improve compatibility.

Specific examples of alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$ and —C$_{10}$H$_{21}$.

Specific examples of alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$ and —OC$_9$H$_{19}$.

Specific examples of alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—C$_3$H$_7$, —(CH$_2$)$_3$—OCH$_3$, —(CH$_2$)$_4$—OCH$_3$ and —(CH$_2$)$_5$—OCH$_3$.

Specific examples of alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Specific examples of alkenyloxy include —OCH$_2$CH=CH$_2$, —OCH$_2$CH=CHCH$_3$ and —OCH$_2$CH=CHC$_2$H$_5$.

R$^1$ is preferably alkyl having 1 to 10 carbons. Preferred examples of R$^1$ include —CH$_3$, —C$_2$H$_5$, —C$_3$H$_7$, —CH$_9$, —C$_5$H$_{11}$, —C$_6$H$_{13}$, —C$_7$H$_{15}$, —C$_5$H$_{17}$, —C$_9$H$_{19}$ and —C$_{10}$H$_{21}$.

In formula (1), ring A$^1$, ring A$^2$, ring A$^3$, ring A$^4$, ring A$^5$ or ring A$^6$ is 1,4-cyclohexylene (14-1), 1,4-cyclohexenylene (14-2) or (14-3), 1,3-dioxane-2,5-diyl (14-4), tetrahydropyran-2,5-diyl (14-5), pyrimidine-2,5-diyl (14-6), pyridine-2,5-diyl (14-7), 1,4-phenylene (14-8), or 1,4-phenylene in which at least one of hydrogen is replaced by halogen. Then, 1,4-phenylene in which at least one of hydrogen is replaced by halogen includes groups (14-9) to (14-26). Preferred examples include groups (14-9) to (14-20).

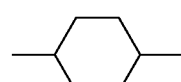

(14-1)

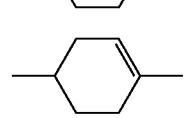

(14-2)

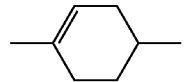

(14-3)

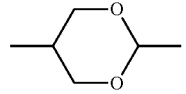

(14-4)

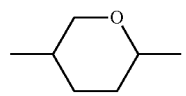

(14-5)

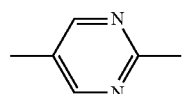

(14-6)

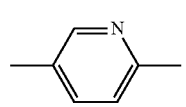

(14-7)

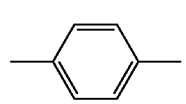

(14-8)

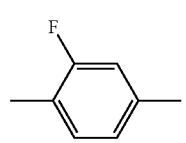

(14-9)

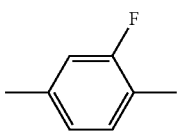

(14-10)

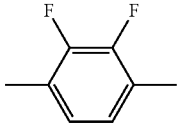

(14-11)

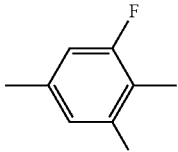

(14-12)

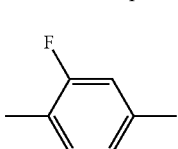

(14-13)

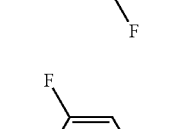

(14-14)

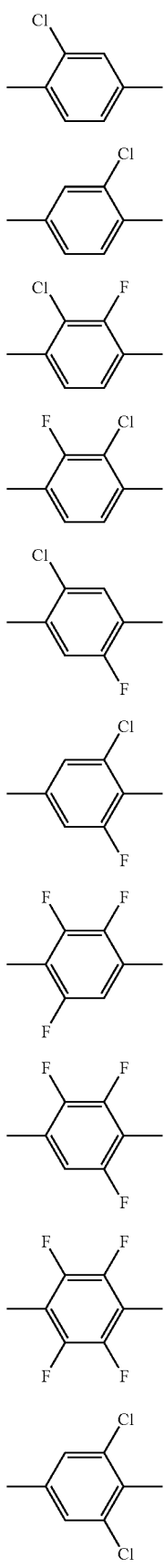

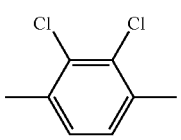

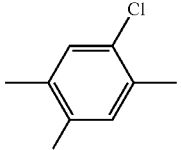

Preferred examples of ring $A^1$, ring $A^2$, ring $A^3$, ring $A^4$, ring $A^5$, or ring $A^6$ include 1,4-cyclohexylene (14-1), 1,4-cyclohexenylene (14-2) or (14-3), 1,4-phenylene (14-8), 2-fluoro-1,4-phenylene (14-10), 3,5-difluoro-1,4-phenylene (14-12), 2,5-difluoro-1,4-phenylene (14-13) and 3-chloro-5-fluoro-1,4-phenylene (14-20).

Most preferred examples of ring $A^1$, ring $A^2$, ring $A^3$, ring $A^4$, ring $A^5$, ring $A^6$, ring $A^7$ or ring $A^8$ include 1,4-cyclohexylene (14-1), 1,4-phenylene (14-8), 2-fluoro-1,4-phenylene (14-10), 3,5-difluoro-1,4-phenylene (14-12) and 2,5-difluoro-1,4-phenylene (14-13).

In formula (1), $Z^1$, $Z^2$, $Z^3$, $Z^4$, $Z^5$, $Z^6$ and $Z^7$ are independently a single bond, —(CH$_2$)$_2$—, —COO—, —OCO—, —CF$_2$O—, —OCF$_2$— or —CH═CH—.

Preferable examples of $Z^1$, $Z^2$, $Z^3$, $Z^4$, $Z^5$, $Z^6$ or $Z^7$ include a single bond, —(CH$_2$)$_2$—, —COO—, —CF$_2$O—, or —CH═CH—. In the bonding, with regard to a configuration of a double bond of a bonding group such as —CH═CH—, trans is preferred to cis. Most preferred $Z^1$, $Z^2$, $Z^3$, $Z^4$, $Z^5$, $Z^6$ or $Z^7$ is a single bond, —(CH$_2$)$_2$—, —COO— or —CF$_2$O—.

In formula (1), $X^1$ is fluorine, —CF$_3$ or —OCF$_3$.

In formula (1), $Y^1$ and $Y^2$ are independently hydrogen or fluorine.

In formula (1), i, j, k, m, n, p and q are independently 0 or 1, and a sum of i, j, k, m, n, p and q is 1, 2, 3 or 4.

A further preferred sum of i, j, k, m, n, p and q is 2, 3 or 4. Furthermore, q is particularly preferably 1.

1-2 Properties of a Compound of the Invention and a Method for Adjusting the Same Compound (1) of the invention will be explained in more detail. The compound is physically and chemically very stable both under conditions in which a device is ordinarily used, and has a good compatibility with other liquid crystal compounds. A composition containing the compound is stable under conditions in which the device is ordinarily used. Even if the composition is stored at a low temperature, the compound does not precipitate in the form of crystals (or a smectic phase). The compound has general physical properties required for a compound, namely, a suitable optical anisotropy and a suitable dielectric anisotropy. Moreover, compound (1) has a large positive dielectric anisotropy. A compound having a large dielectric anisotropy is useful as a component for decreasing threshold voltage of a composition.

In compound (1), physical properties such as a clearing point, optical anisotropy and dielectric anisotropy can be adjusted for any purpose by appropriately selecting a combination of $R^1$, ring $A^1$, ring $A^2$, ring $A^3$, ring $A^1$, ring $A^5$, ring $A^6$, $Z^1$, $Z^2$, $Z^3$, $Z^4$, $Z^5$, $Z^6$, $Z^7$, $X^1$, $Y^1$, $Y^2$, i, j, k, m, n, p and q. Effects of the combinations on the physical properties of compound (1) are explained below.

In a case of combination where a sum of i, j, k, m, n, p and q is 1, compatibility with other compounds is particularly high, and a maximum temperature of the nematic phase is low. In a case of combination where the sum is 2, compatibility with other compounds is high, and a temperature range of the liquid phase is wide. In a case of combination where the sum is 3 or 4, a clearing point is high, and a compound having a very large dielectric anisotropy is formed by suitably selecting rings and bonding groups.

When all of ring $A^1$, ring $A^2$, ring $A^3$, ring $A^4$, ring $A^5$ and ring $A^6$ are 1,4-cyclohexylene, a clearing point is high and viscosity is small. When at least one of ring $A^1$, ring $A^2$, ring $A^3$, ring $A^4$, ring $A^5$ and ring $A^1$ is 1,4-phenylene, optical anisotropy is relatively large and an orientational order parameter is relatively large. Moreover, when all of ring $A^1$, ring $A^2$, ring $A^3$, ring $A^4$, ring $A^1$, ring $A^6$, ring $A^7$ and ring $A^8$ are 1,4-phenylene, optical anisotropy is particularly large. Furthermore, when ring $A^1$, ring $A^2$, ring $A^3$, ring $A^4$, ring $A^5$, ring $A^6$, ring $A^7$ and ring $A^1$ are 1,4-phenylene replaced by halogen as represented by a group (14-10), (14-12) or (14-20), dielectric anisotropy is large.

When $Z^1$, $Z^2$, $Z^3$, $Z^4$, $Z^5$, $Z^6$ or $Z^7$ is a single bond, —CH$_2$CH$_2$—, —CH=CH—, —CF$_2$O— or —OCF$_2$—, viscosity is small. When $Z^1$, $Z^2$, $Z^3$, $Z^4$, $Z^5$, $Z^6$ or $Z^7$ is —CH=CH—, a temperature range of the liquid crystal phase is wide, and an elastic constant ratio $K_{33}/K_{11}$ ($K_{33}$: bend elastic constant, $K_{11}$: splay elastic constant) is large. When $Z^1$, $Z^2$, $Z^3$, $Z^4$, $Z^5$, $Z^6$ or $Z^7$ is a single bond, —(CH$_2$)$_2$—, —COO—, —OCO—, —CF$_2$O— or —OCF$_2$—, the compound is relatively chemically stable, and relatively hard to cause deterioration. When $Z^1$, $Z^2$, $Z^3$, $Z^4$, $Z^5$, $Z^6$ or $Z^7$ is —COO— or —OCO—, a maximum temperature of the nematic phase is high.

When $X^1$ is fluorine, dielectric anisotropy is large, and viscosity is small. When $X^1$ is —CF$_3$, dielectric anisotropy is particularly large. When $X^1$ is —OCF$_3$, dielectric anisotropy is large, and compatibility with other compounds is high.

As described above, a compound having objective physical properties can be obtained by suitably selecting kinds of ring A, bonding group Z or the like. Therefore, compound (1) is useful as a component of a composition used for a device such as a TN, OCB, IPS or VA device.

1-3 Specific Examples of Compound (1)

Preferred examples of compound (1) include compounds represented by formula (1-1-1) shown in item 6, formulas (1-2-1) to (1-2-2) shown in item 7, formulas (1-3-1) to (1-3-3) shown in item 9 and formulas (1-4-1) to (1-4-4) shown in item 11.

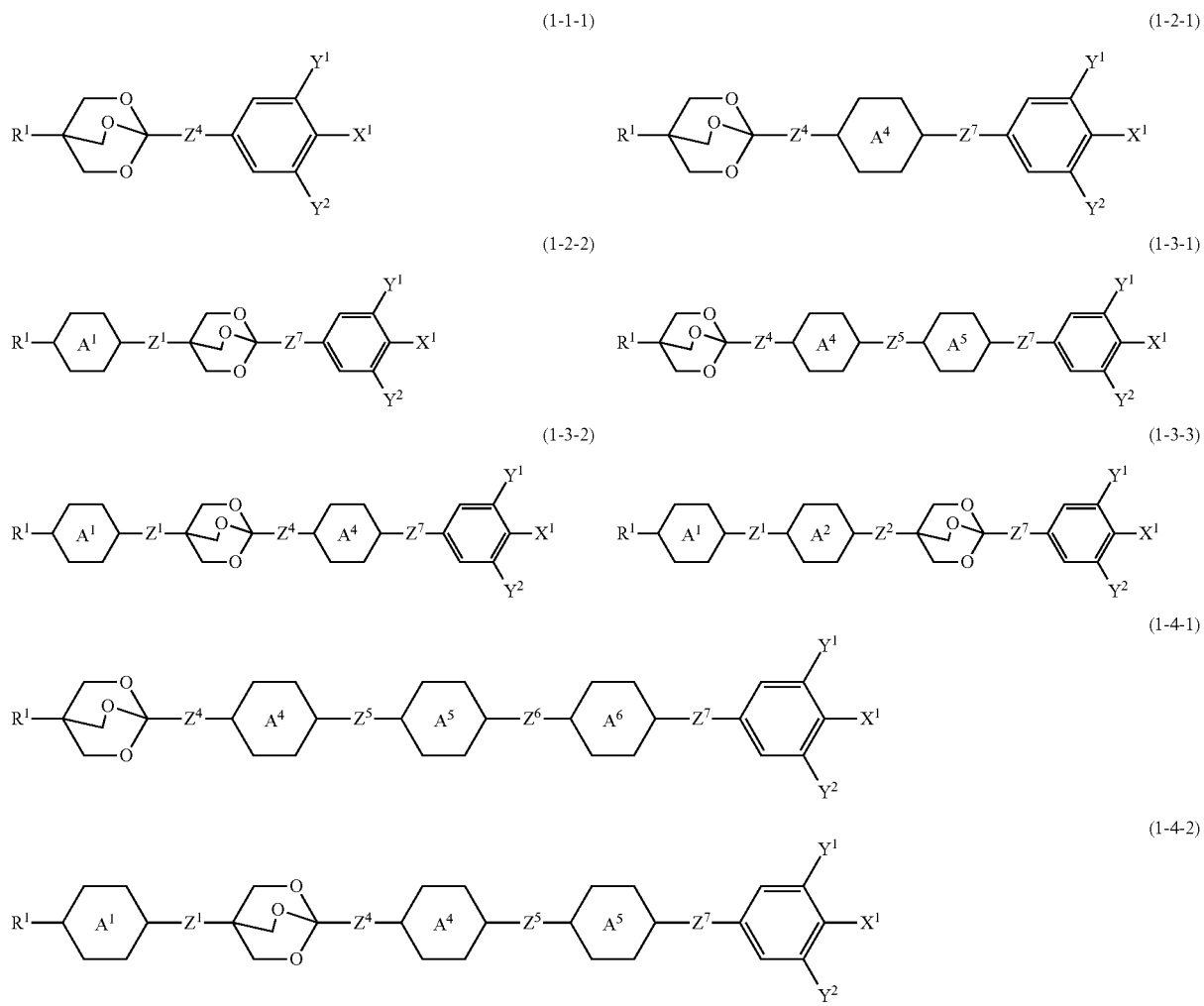

-continued

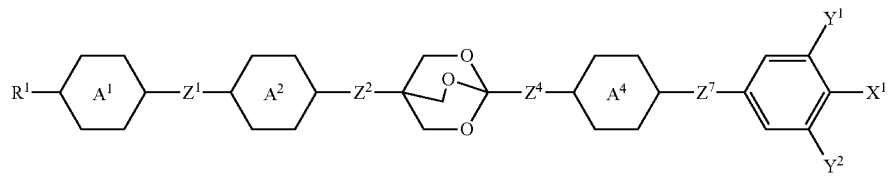
(1-4-3)

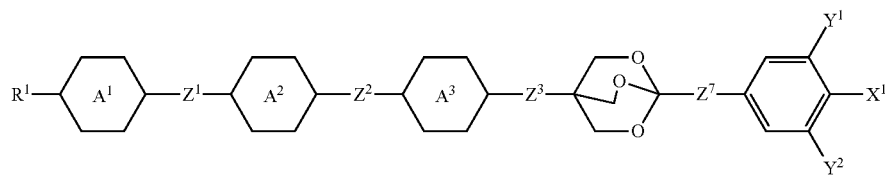
(1-4-4)

In the formulas, $R^1$ is alkyl having 1 to 10 carbons; ring $A^1$, ring $A^2$, ring $A^3$, ring $A^4$, ring $A^5$ and ring $A^6$ are independently 1,4-cyclohexylene, 1,4-phenylene, 3-fluoro-1,4-phenylene or 3,5-difluoro-1,4-phenylene; $Z^1$, $Z^2$, $Z^3$, $Z^4$, $Z^5$, $Z^6$ and $Z^7$ are independently a single bond, —(CH$_2$)$_2$—, —COO—, —CF$_2$O— or —CH=CH—; $X^1$ is fluorine, —CF$_3$ or —OCF$_3$; and $Y^1$ and $Y^2$ are independently hydrogen or fluorine.

Here, in formula (1-2-1), at least one of $Z^4$ and $Z^7$ is a single bond; in formula (1-2-2), at least one of $Z^1$ and $Z^7$ is a single bond; in formula (1-3-1), at least two of $Z^4$, $Z^5$ and $Z^7$ are a single bond; in formula (1-3-2), at least two of $Z^1$, $Z^4$ and $Z^7$ are a single bond; in formula (1-3-3), at least two of $Z^1$, $Z^2$ and $Z^7$ are a single bond; in formula (1-4-1), at least three of $Z^4$, $Z^5$, $Z^6$ and $Z^7$ are a single bond; in formula (1-4-2), at least three of $Z^1$, $Z^4$, $Z^5$ and $Z^7$ are a single bond; in formula (1-4-3), at least three of $Z^1$, $Z^2$, $Z^4$ and $Z^7$ are a single bond; and in formula (1-4-4), at least three of and $Z^1$, $Z^2$, $Z^3$ and $Z^7$ are a single bond.

1-4 Synthesis of Compound (1)

Next, synthesis of compound (1) will be explained. Compound (1) can be prepared by suitably combining techniques in synthetic organic chemistry. Methods for introducing objective terminal groups, rings and bonding groups into a starting material are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

1-4-1 Method for Forming Bonding Group Z

One example of a method for forming bonding group Z in compound (1) is as shown in a scheme below. In the scheme, MSG$^1$ or MSG$^2$ is a monovalent organic group having at least one ring. A plurality of MSG$^1$ (or MSG$^2$) used in the scheme may be identical or different. Compounds (1A) to (1J) correspond to compound (1).

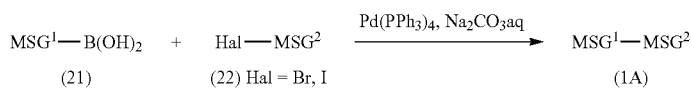

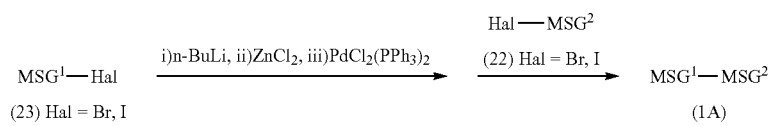

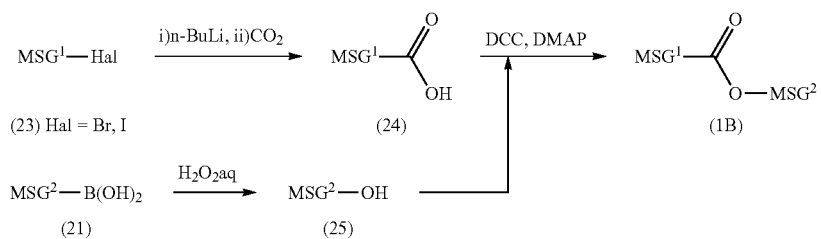

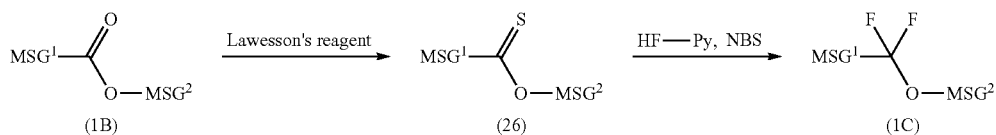

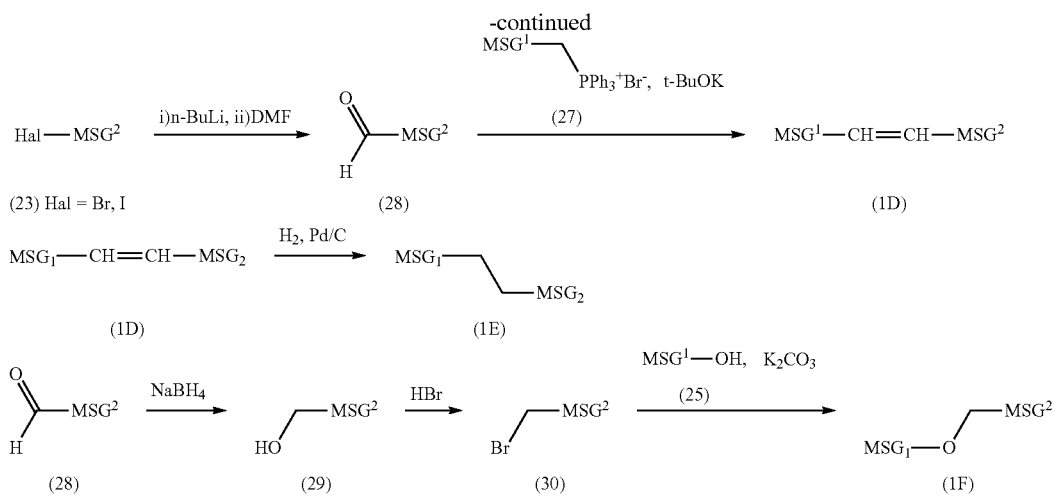

Next, methods for forming various types of bonds with regard to bonding group Z in compound (1) will be explained in sections (I) to (IV) below.

(I) Formation of a Single Bond

Compound (1A) is prepared by allowing aryl boronic acid (21) to react, in the presence of an aqueous solution of carbonate and a catalyst such as tetrakis(triphenylphosphine)palladium, with compound (22) prepared according to a known method. Compound (1A) is also prepared by allowing compound (23) prepared according to a known method to react with n-butyllithium and subsequently with zinc chloride, and further with compound (22) in the presence of a catalyst such as dichlorobis(triphenylphosphine) palladium.

(II) Formation of —COO— or —OCO—

Carboxylic acid (24) is obtained by allowing compound (23) to react with n-butyllithium and subsequently with carbon dioxide. Compound (1B) having —COO— is prepared by dehydrating, in the presence of 1,3-dicyclohexylcarbodiimide (DCC) and 4-dimethylaminopyridine (DMAP), carboxylic acid (24) and phenol (25) prepared according to a known method. A compound having OCO— is also prepared according to the method.

(III) Formation of —CF$_2$O or OCF$_2$

Compound (26) is obtained by treating compound (1B) with a thiation reagent such as Lawesson's reagent. Compound (1C) having —CF$_2$O— is prepared by fluorinating compound (26) with a hydrogen fluoride-pyridine complex and N-bromosuccinimide (NBS). See M. Kuroboshi et al., Chem. Lett., 1992, 827. Compound (1C) is also prepared by fluorinating compound (26) with (diethylamino)sulfurtrifluoride (DAST). See W. H. Bunnelle et al., J. Org. Chem. 1990, 55, 768. A compound having —OCF$_2$— is also prepared according to the method. The bonding groups can also be formed according to the method described in Peer. Kirsch et al., Angew. Chem. Int. Ed. 2001, 40, 1480.

(IV) Formation of —CH═CH—

Aldehyde (28) is obtained by treating compound (23) with n-butyllithium and then allowing a treated product to react with formamide such as N,N-dimethylformamide (DMF). Compound (1D) is prepared by allowing aldehyde (28) to react with phosphorus ylide generated by treating with a base such as potassium tert-butoxide phosphonium salt (27) prepared according to a known method. A cis form may be generated depending on reaction conditions, and therefore the cis form is isomerized into a trans form according to a known method, when necessary.

(V) Formation of —(CH$_2$)$_2$—

Compound (1E) is prepared by hydrogenating compound (1D) in the presence of a catalyst such as palladium on carbon.

(VI) Formation of —CH$_2$O— or —OCH$_2$—

Compound (29) is obtained by reducing compound (28) with a reducing agent such as sodium boron hydride. Compound (30) is obtained by halogenating compound (29) with hydrobromic acid or the like. Compound (1F) is prepared by allowing compound (30) to react with compound (25) in the presence of potassium carbonate or the like.

1-4-2 Method for Synthesizing Ring A

With regard to a ring such as 1,4-cyclohexylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene or 2,3,5,6-tetrafluoro-1,4-phenylene, a starting material is commercially available or a synthetic process is well known.

1-4-3 Method for Synthesizing 2,6,7-trioxabicyclo[2.2.2] octane Ring

One example of a method for preparing a 2,6,7-trioxabicyclo[2.2.2]octane ring is shown below. When aldehyde derivative (31) is allowed to react with two equivalent of formaldehyde in the presence of a base such as sodium hydroxide, an Aldol reaction and subsequently a Cannizzaro reaction take place and thus triol (32) is formed. If the triol (32) is heated with diethyl carbonate and a catalyst amount of potassium carbonate, oxetane derivative (33) is formed by a dehydration reaction. Next, carboxylic acid (24) and oxetane derivative (33) obtained by the methods as described in the methods for forming bonding group Z are esterified using a dehydration condensation agent such as dicyclohexylcarbodiimide. The step may also apply a method for converting carboxylic acid (24) with thionyl chloride into acid chloride, and successively allowing the acid chloride to react with oxetane derivative (33). Then, compound (35) having a 2,6,7-trioxabicyclo[2.2.2]octane ring is obtained by allowing reaction of the thus obtained ester derivative (34) in the presence of a catalyst amount of Lewis acid such as a boron trifluoride-diethyl ether complex.

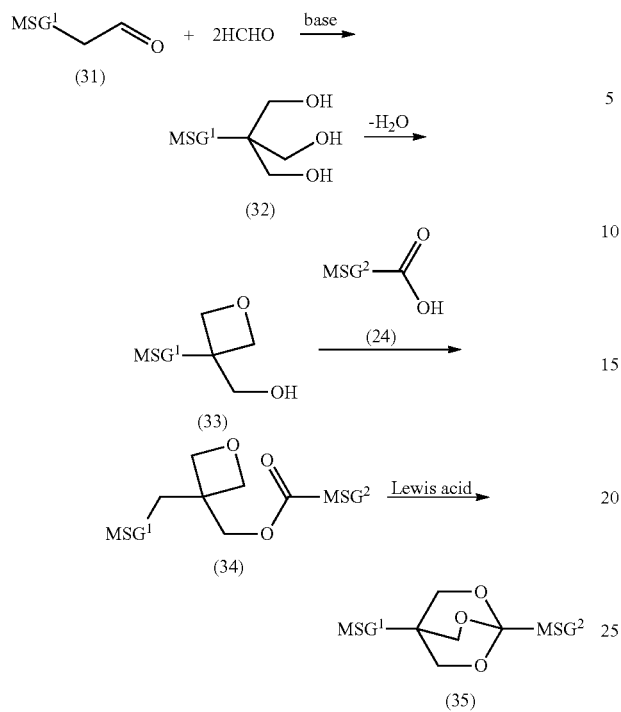

2 Composition of the Invention

A second embodiment of the invention refers to a composition containing a compound represented by formula (1), preferably, a liquid crystal composition that can be used for a liquid crystal material. The liquid crystal composition of the invention is required to contain, as component A, the compound represented by formula (1) according to the invention. The liquid crystal composition of the invention may be a composition consisting of the component A, or a composition containing any other component whose name is not described herein, but when a component selected from the group of components B, C, D and E described below is added to the component A, a liquid crystal composition having a variety of characteristics according to the invention can be provided.

As a component to be added to component A, component B containing at least one compound selected from the group of compounds represented by formulas (2), (3) and (4), or component C containing at least one compound selected from the group of products represented by formulas (5), (6), (7), (8), (9) and (10) is preferably mixed.

Furthermore, when component D containing at least one compound selected from the group of products represented by formulas (11), (12) and (13) is mixed, threshold voltage, a liquid crystal phase temperature range, an optical anisotropy value, a dielectric constant anisotropy value, viscosity or the like can be adjusted.

Moreover, each component of the liquid crystal composition used for the invention has no significant difference in physical characteristics, even when each component is an analog including an isotopic element of each element.

Among types of component B above, suitable examples of compound (2) include compounds (2-1) to (2-16), suitable examples of compound (3) include compounds (3-1) to (3-112), and suitable examples of compound (4) include compounds (4-1) to (4-55).

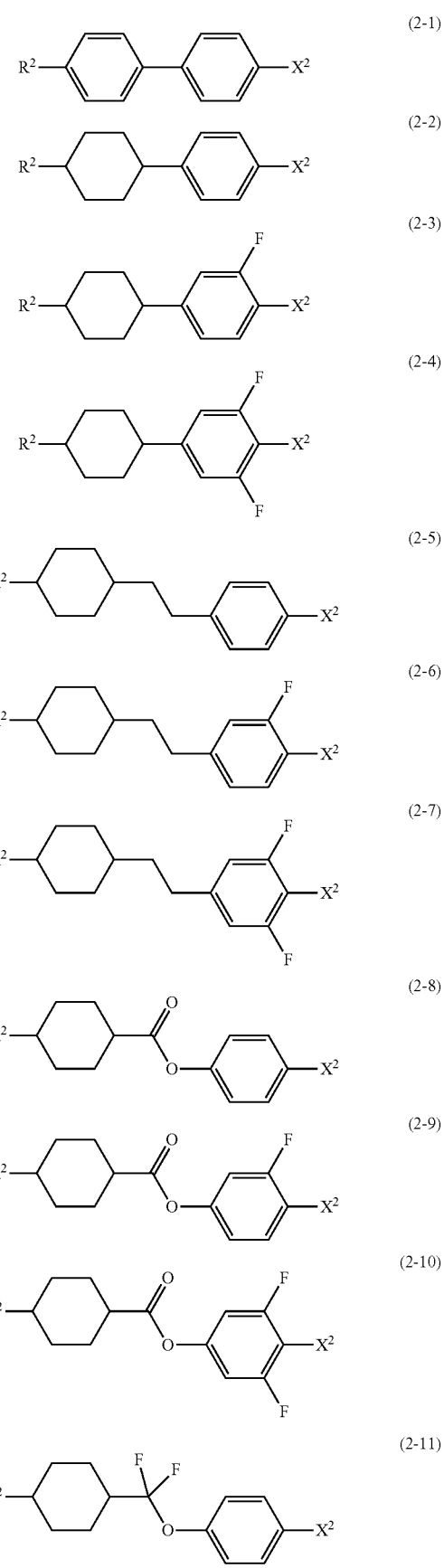

(2-12)
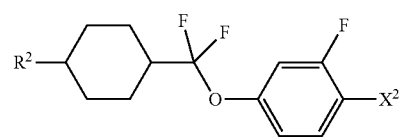
(2-13)
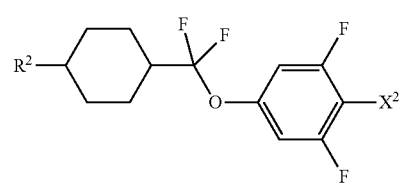
(2-14)
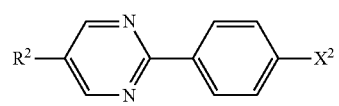
(2-15)
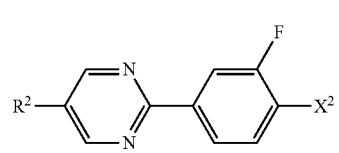
(2-16)
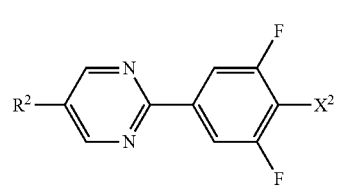
(3-1)
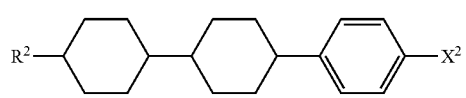
(3-2)
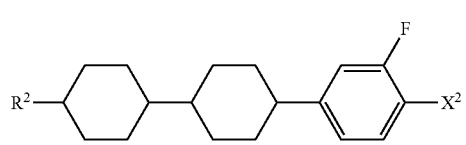
(3-3)
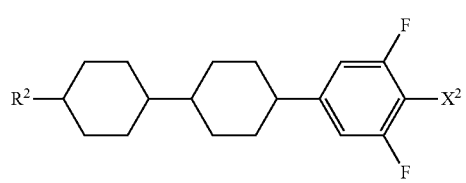
(3-4)
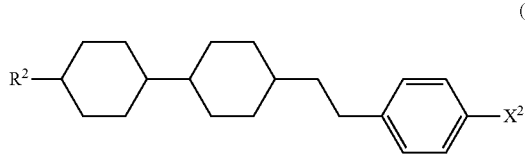
(3-5)
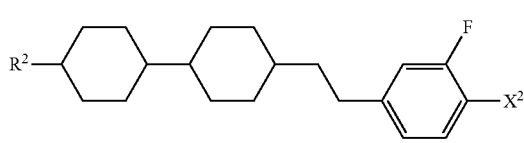
(3-6)
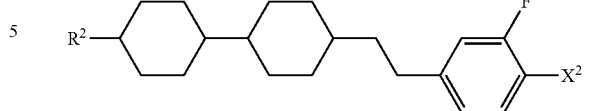
(3-7)
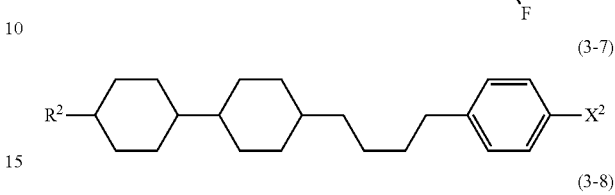
(3-8)
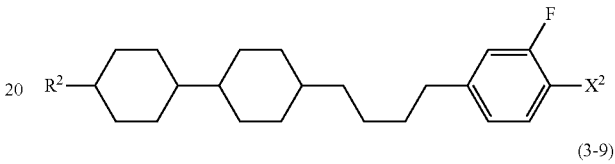
(3-9)
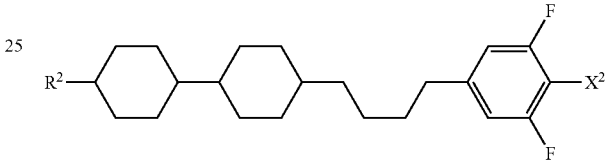
(3-10)
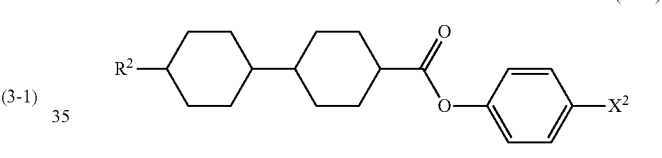
(3-11)
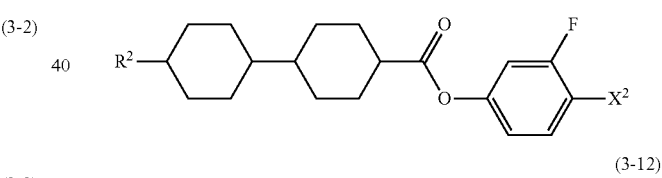
(3-12)
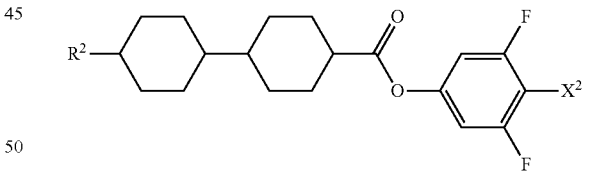
(3-13)
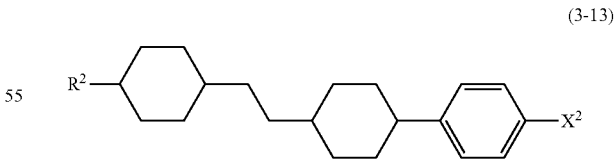
(3-14)
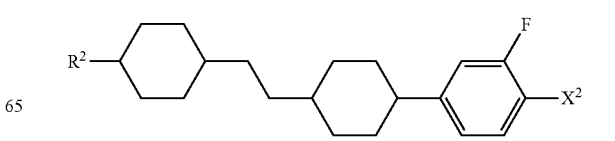

(3-15) 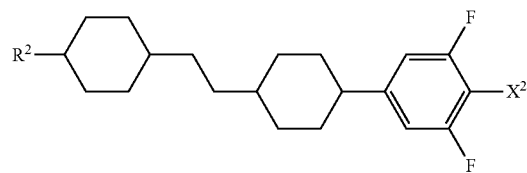
(3-16) 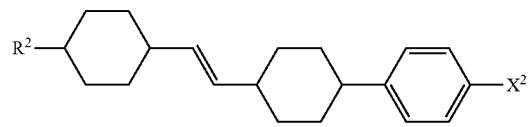
(3-17) 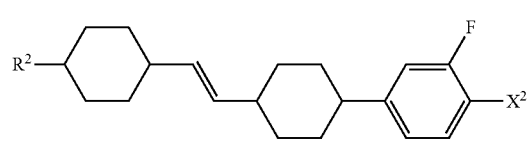
(3-18) 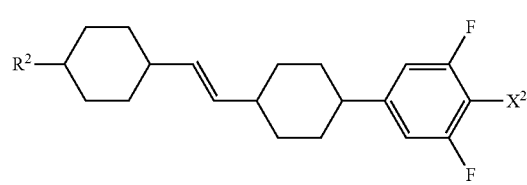
(3-19) 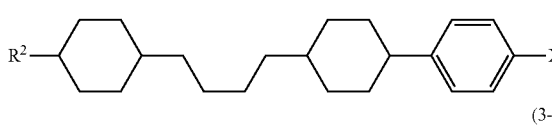
(3-20) 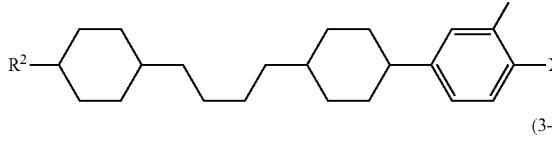
(3-21) 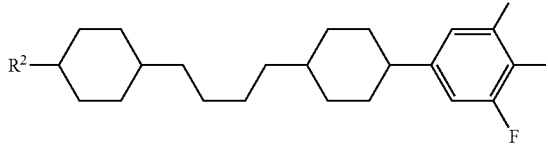
(3-22) 
(3-23) 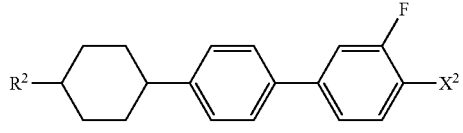
(3-24) 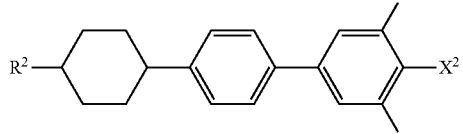
(3-25) 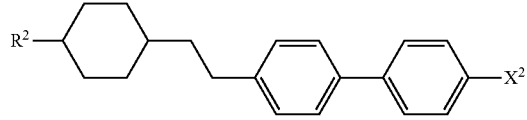
(3-26) 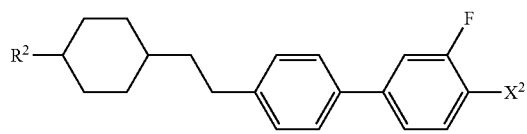
(3-27) 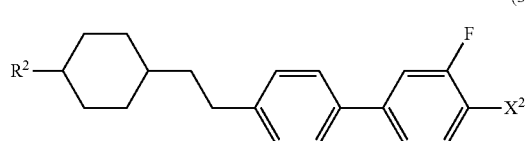
(3-28) 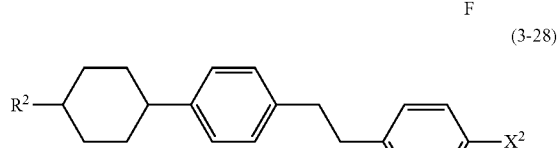
(3-29) 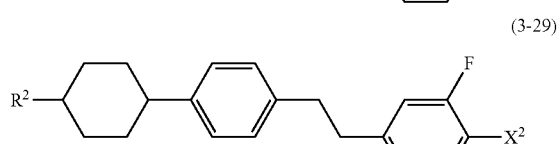
(3-30) 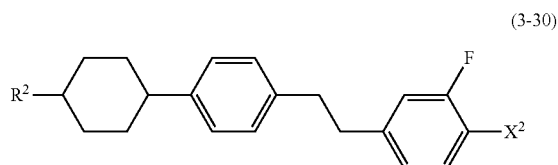
(3-31) 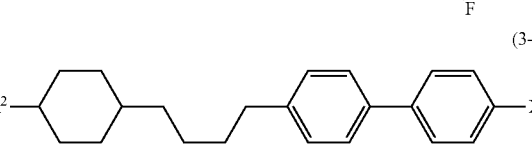
(3-32) 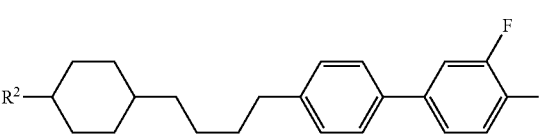
(3-33) 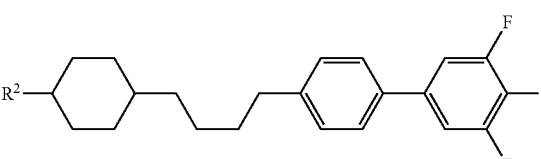
(3-34) 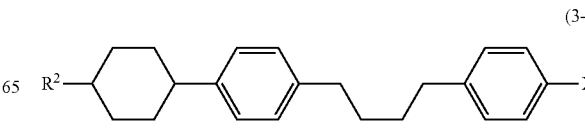

(3-35) 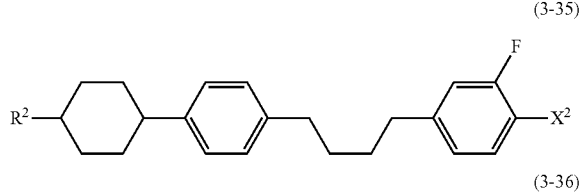
(3-36) 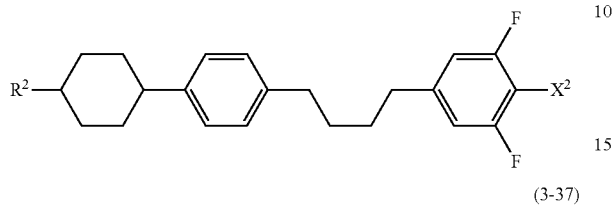
(3-37) 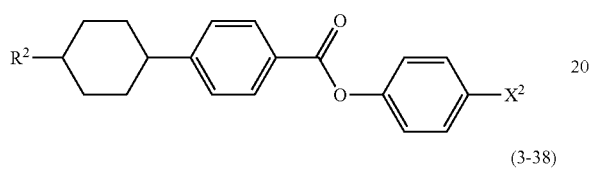
(3-38) 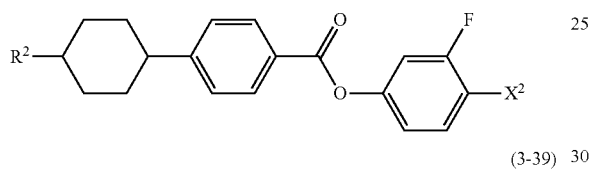
(3-39) 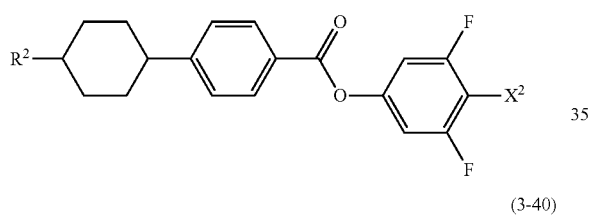
(3-40) 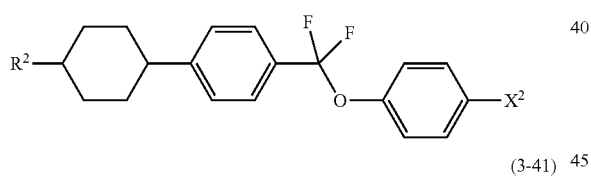
(3-41) 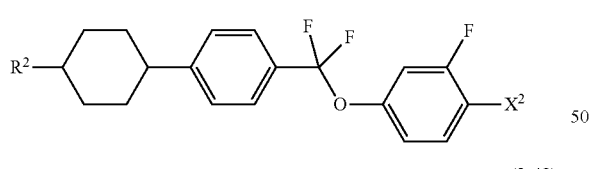
(3-42) 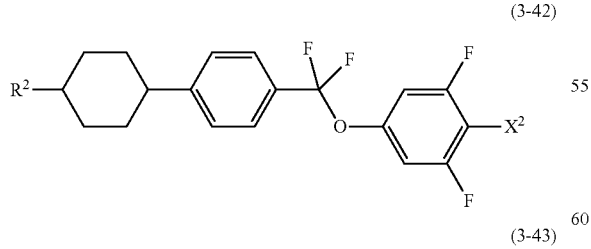
(3-43) 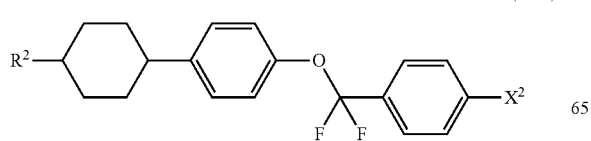
(3-44) 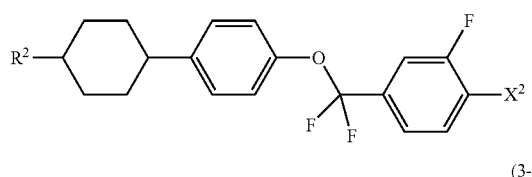
(3-45) 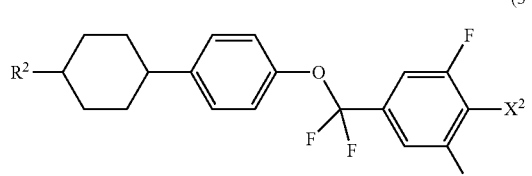
(3-46) 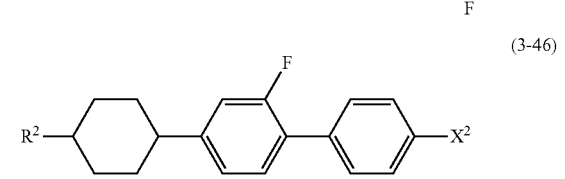
(3-47) 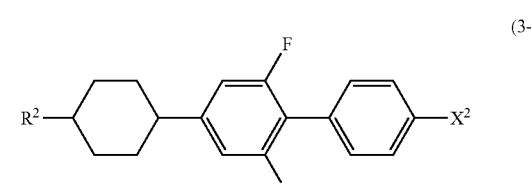
(3-48) 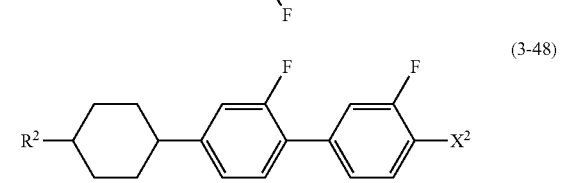
(3-49) 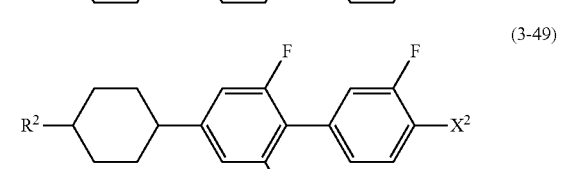
(3-50) 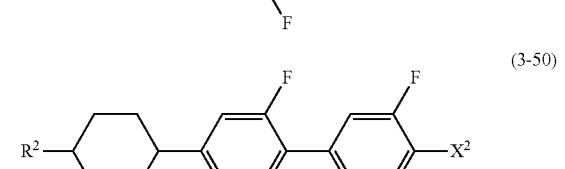
(3-51) 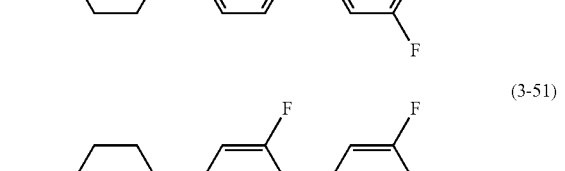
(3-52) 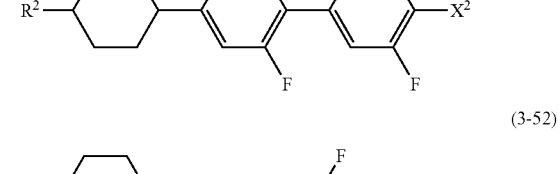

(3-53) 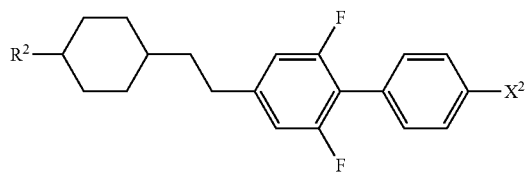
(3-54) 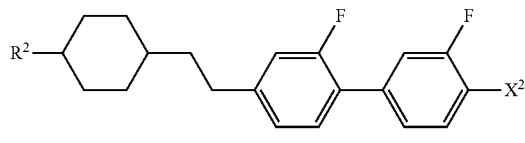
(3-55) 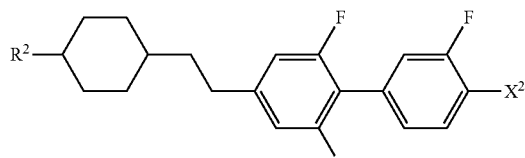
(3-56) 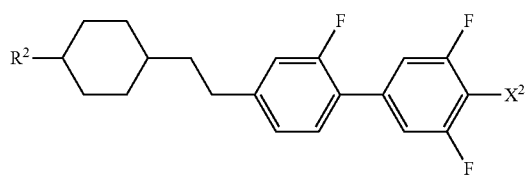
(3-57) 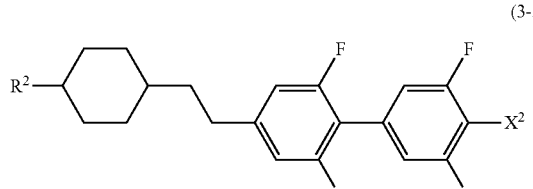
(3-58) 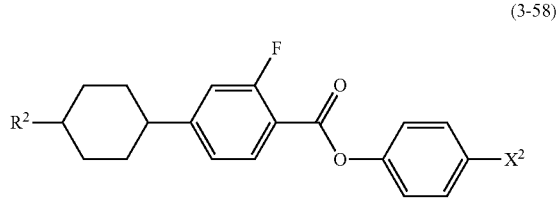
(3-59) 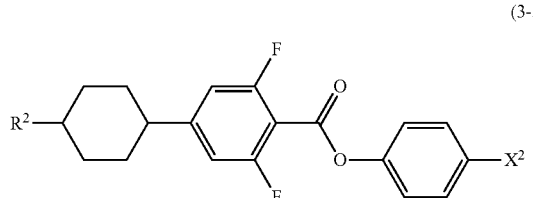
(3-60) 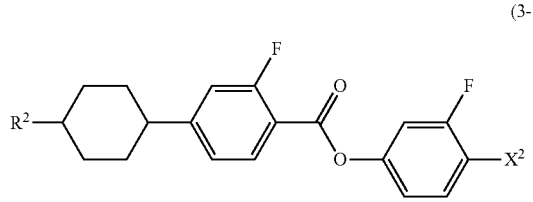
(3-61) 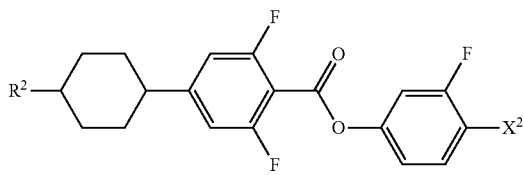
(3-62) 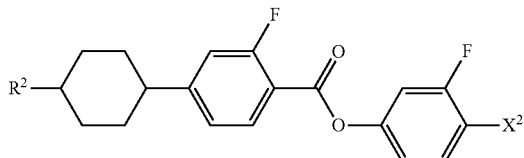
(3-63) 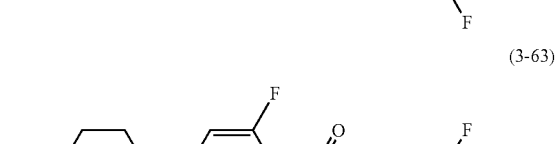
(3-64) 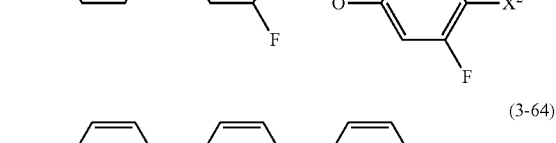
(3-65) 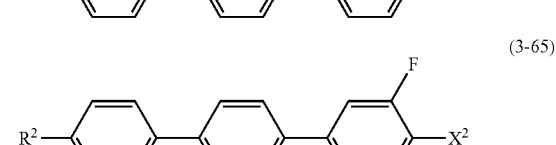
(3-66) 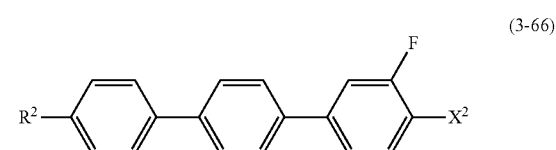
(3-67) 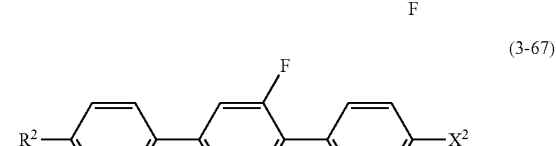
(3-68) 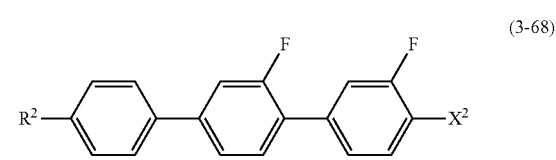
(3-69) 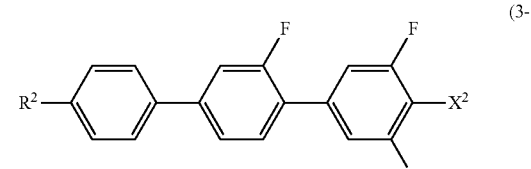

(3-70) 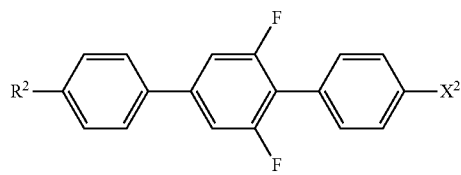
(3-71) 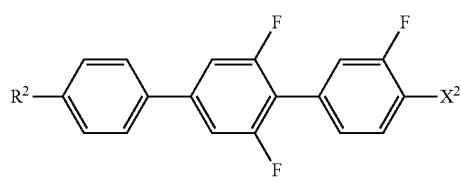
(3-72) 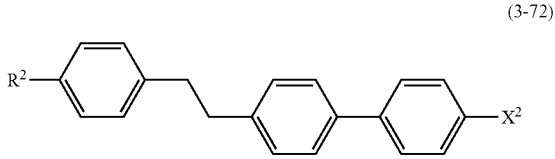
(3-73) 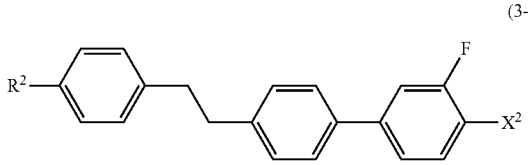
(3-74) 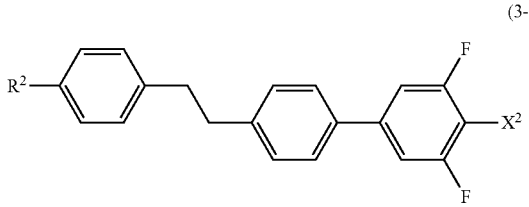
(3-75) 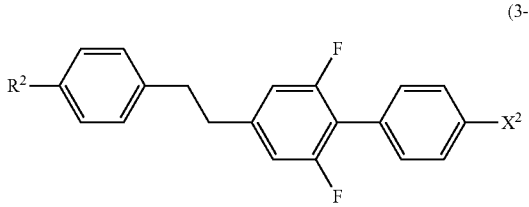
(3-76) 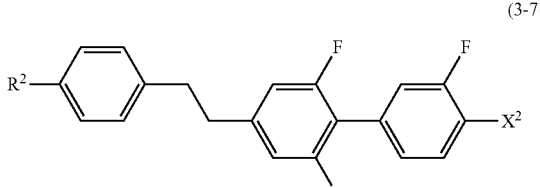
(3-77) 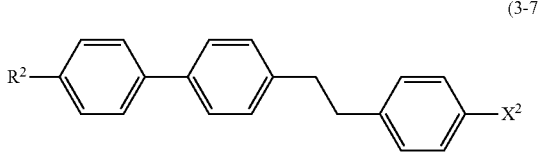
(3-78) 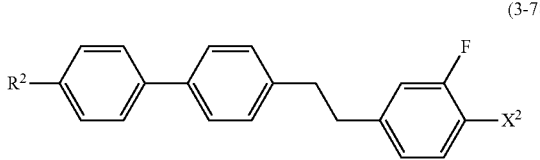
(3-79) 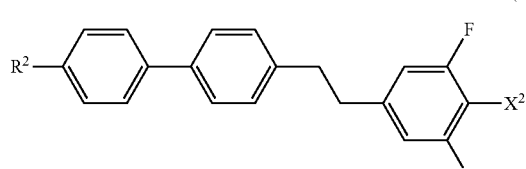
(3-80) 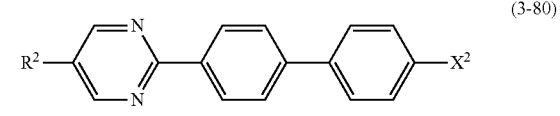
(3-81) 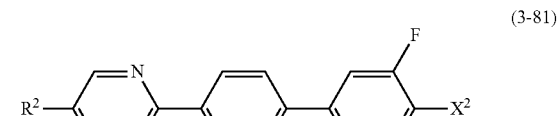
(3-82) 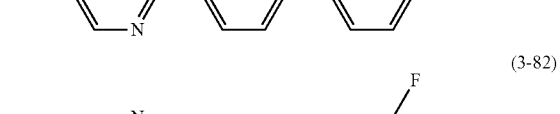
(3-83) 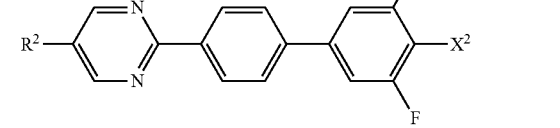
(3-84) 
(3-85) 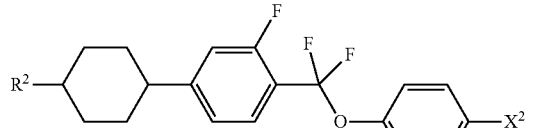
(3-86) 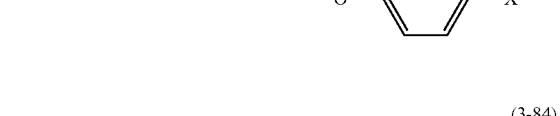
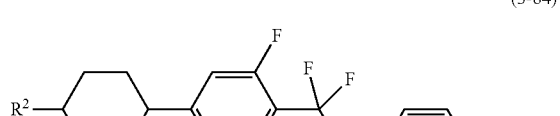
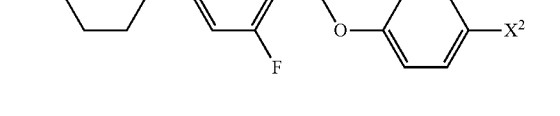
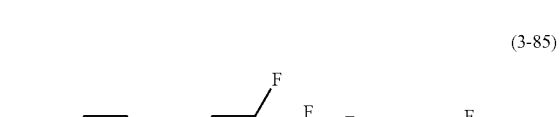
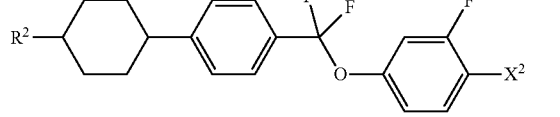
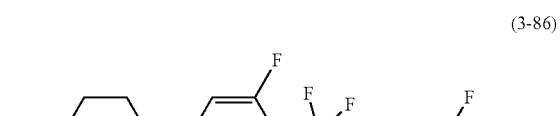

(3-87)
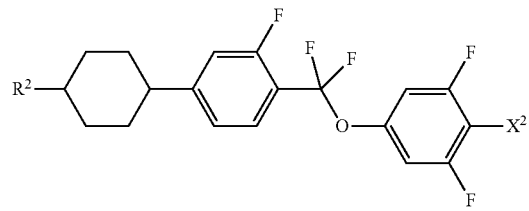
(3-88)
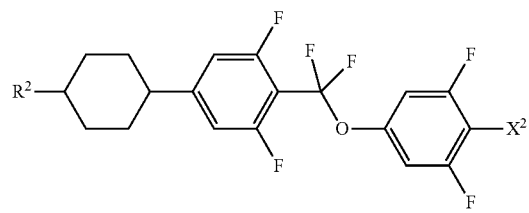
(3-89)
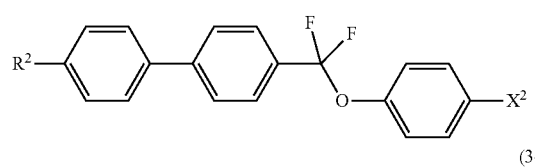
(3-90)
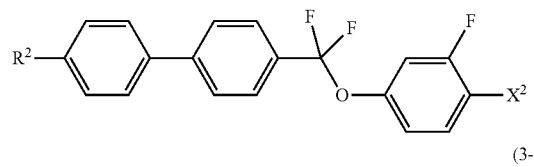
(3-91)
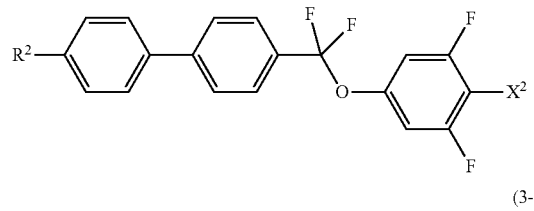
(3-92)
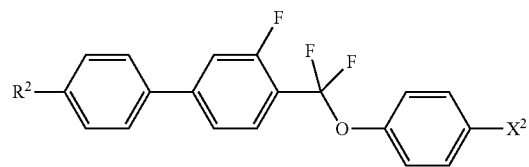
(3-93)
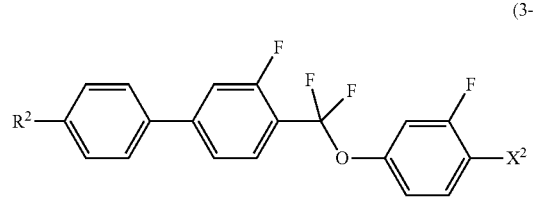
(3-94)
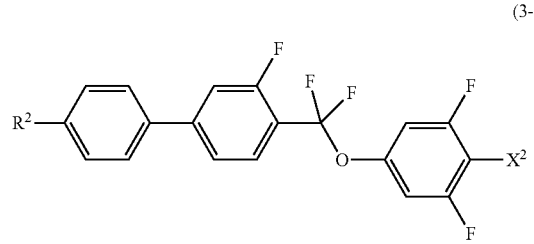
(3-95)
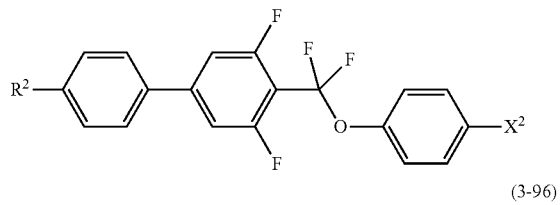
(3-96)
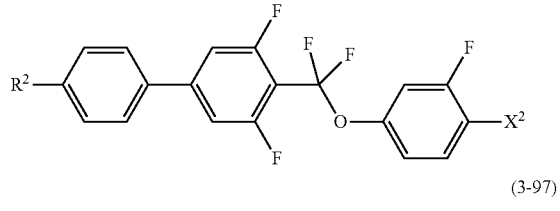
(3-97)
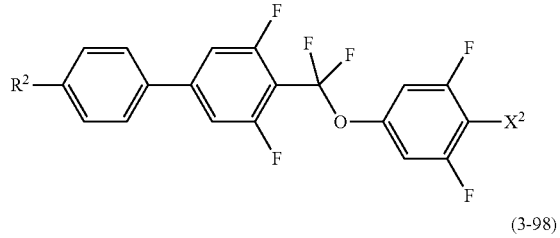
(3-98)
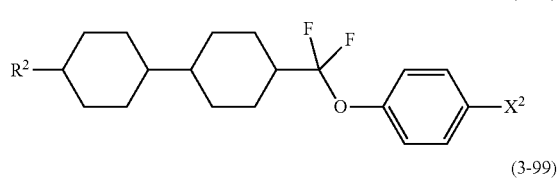
(3-99)
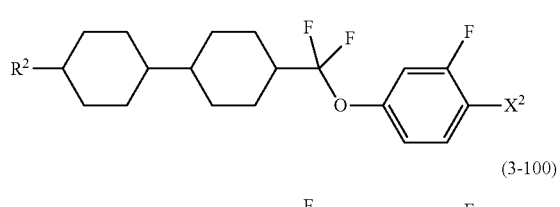
(3-100)
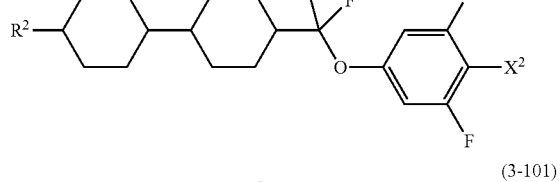
(3-101)
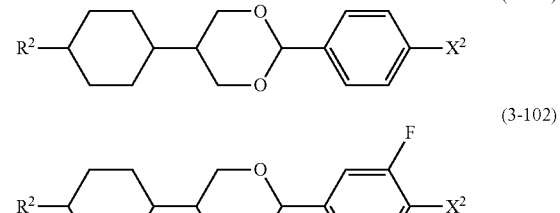
(3-102)
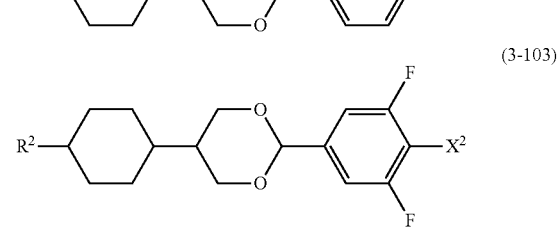
(3-103)

(3-104)
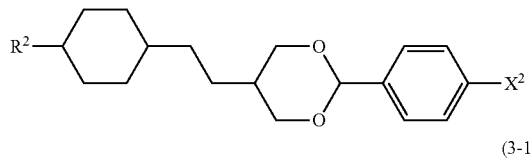
(3-105)
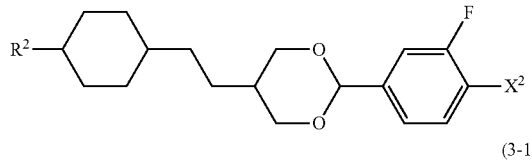
(3-106)
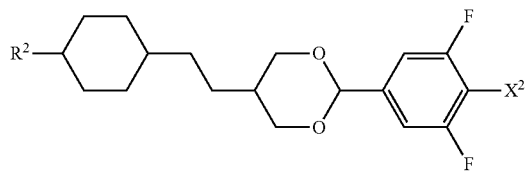
(3-107)
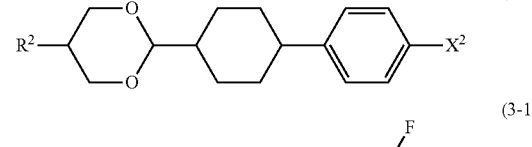
(3-108)
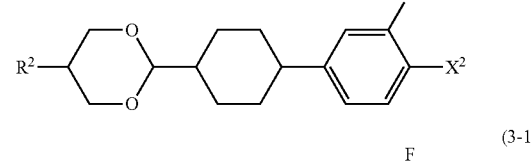
(3-109)
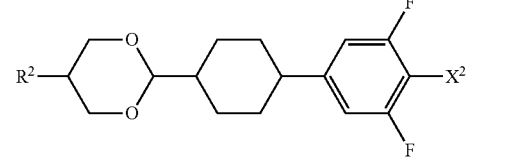
(3-110)
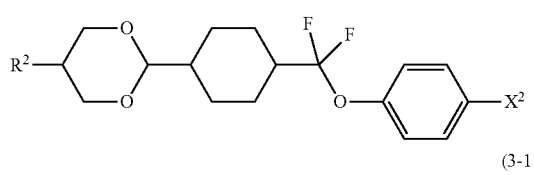
(3-111)
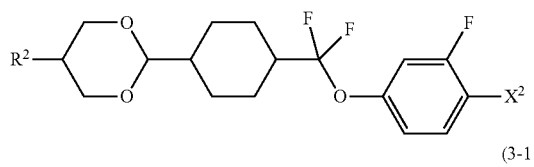
(3-112)
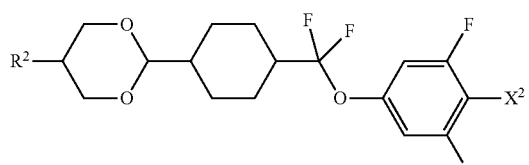
(4-1)
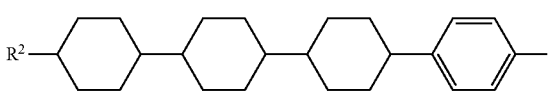
(4-2)
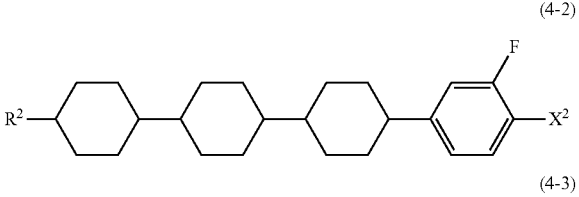
(4-3)
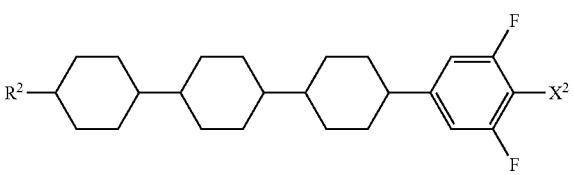
(4-4)
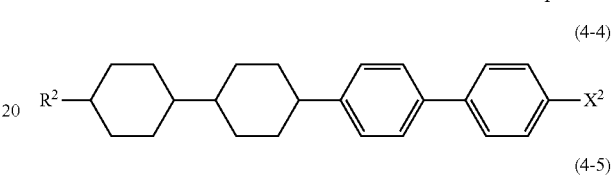
(4-5)
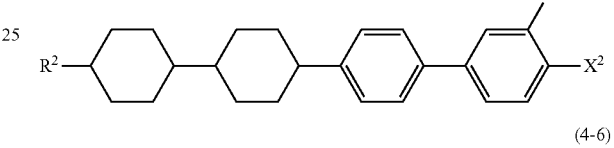
(4-6)
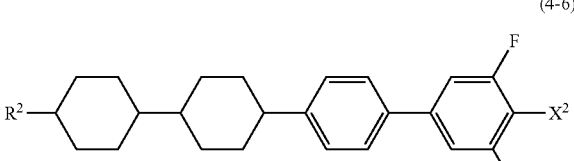
(4-7)
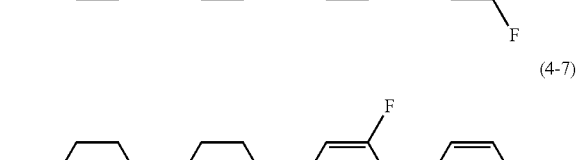
(4-8)
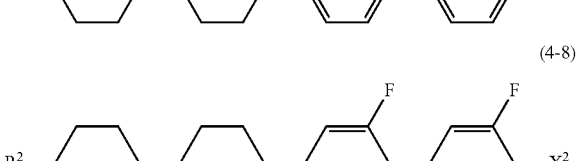
(4-9)
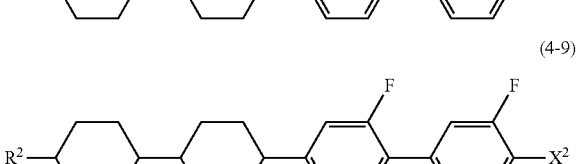
(4-10)
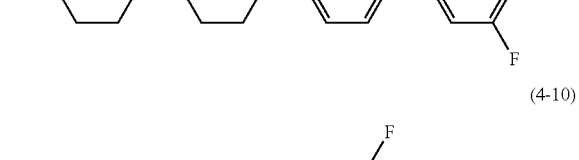

(4-11) 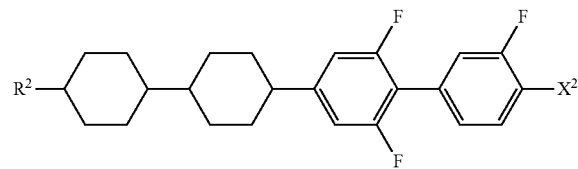
(4-20) 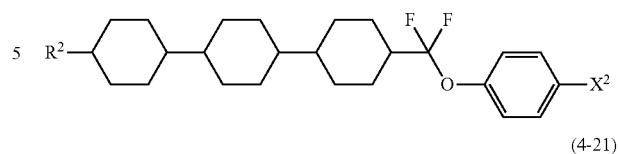
(4-12) (4-21)
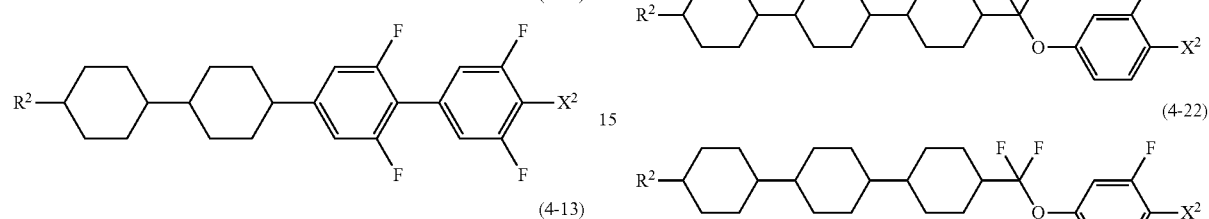
(4-13) (4-22)
(4-14) (4-23)
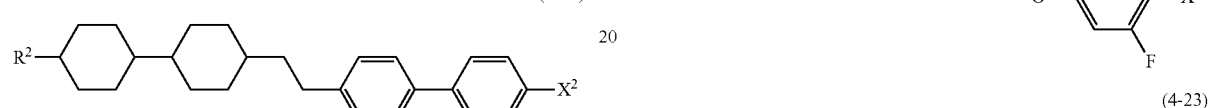
(4-15) (4-24)
(4-16) (4-25)
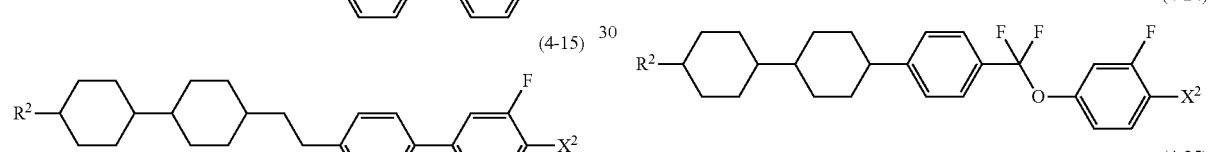
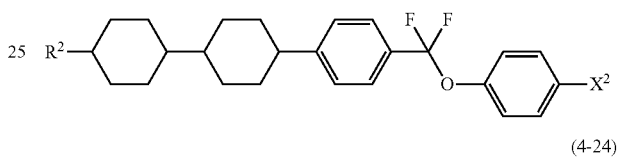
(4-17) (4-26)
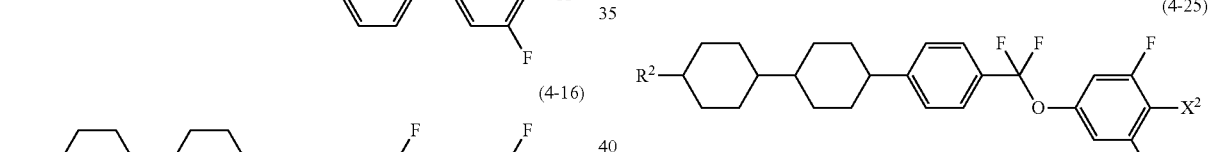
(4-18) (4-27)
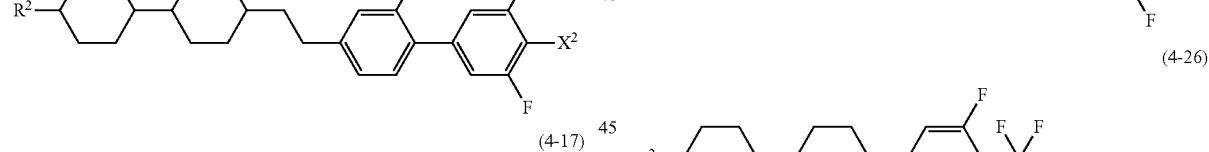
(4-19) (4-28)
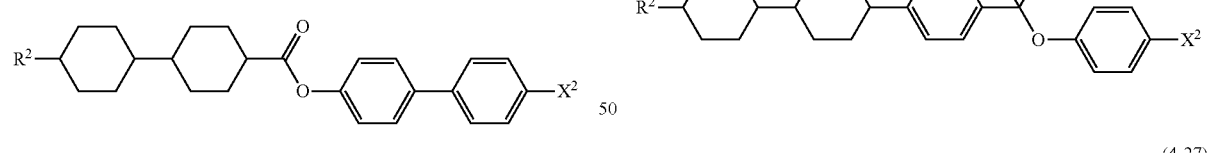
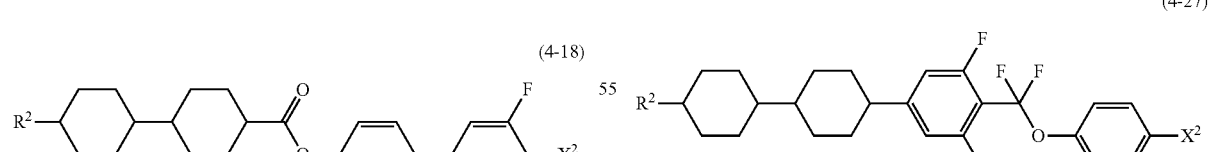
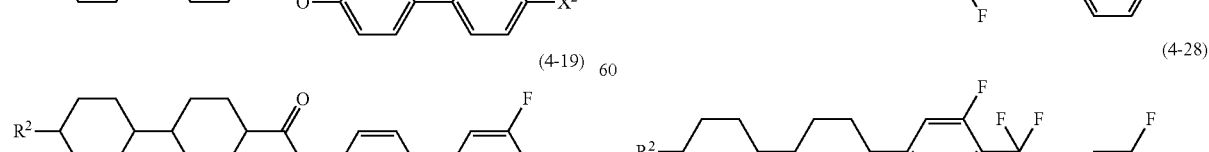

(4-29)
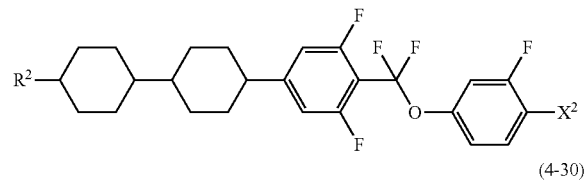
(4-30)
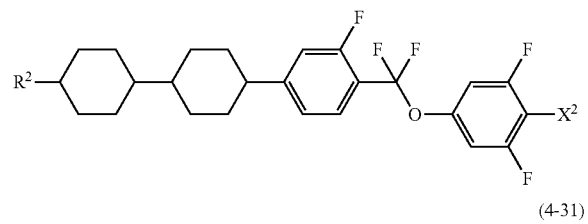
(4-31)
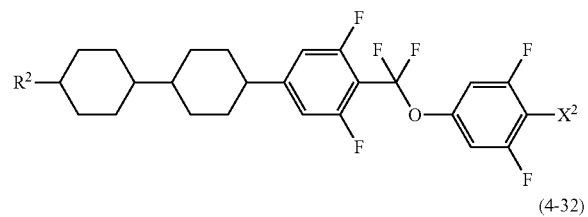
(4-32)
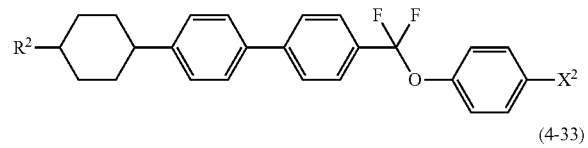
(4-33)
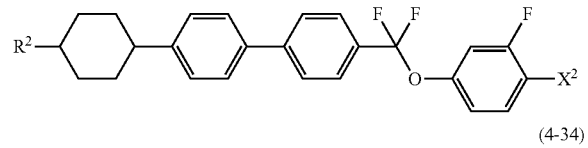
(4-34)
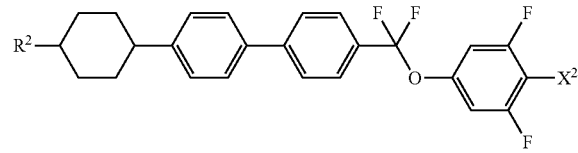
(4-35)
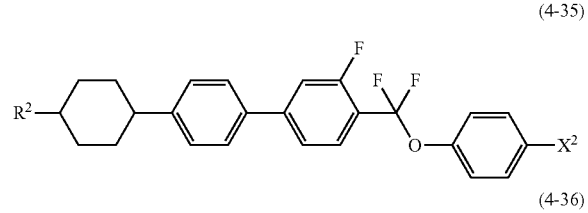
(4-36)
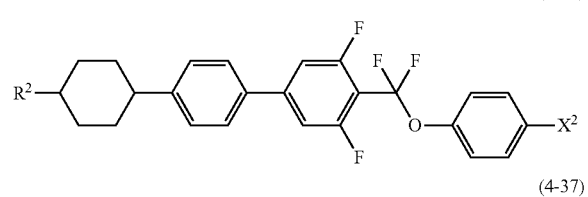
(4-37)
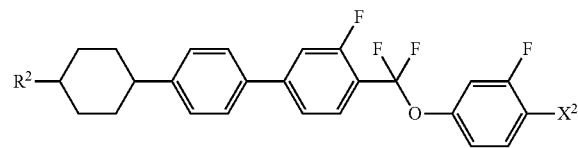
(4-38)
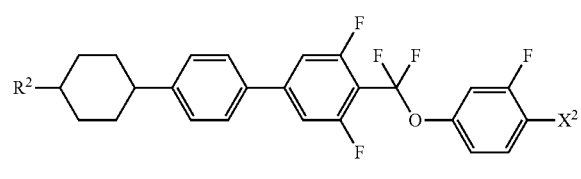
(4-39)
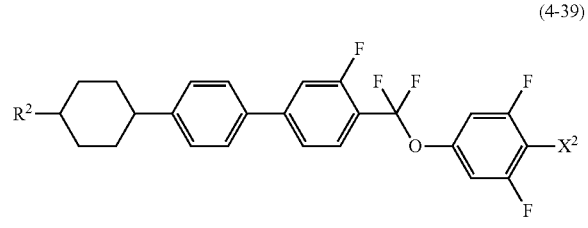
(4-40)
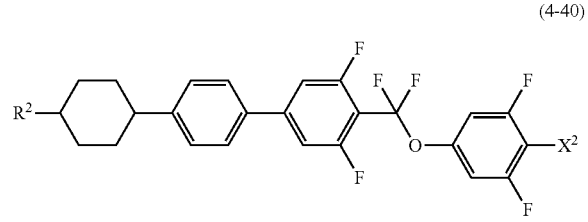
(4-41)
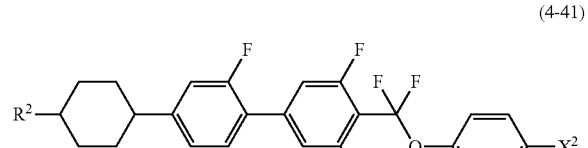
(4-42)
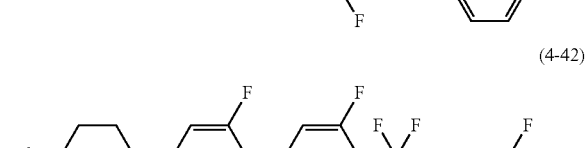
(4-43)
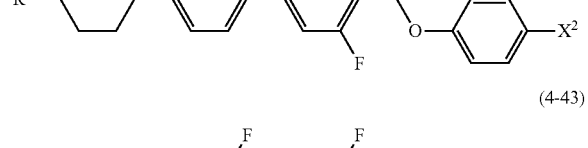
(4-44)
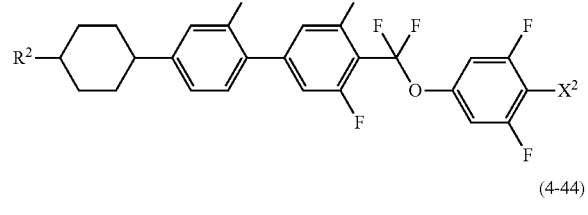
(4-45)
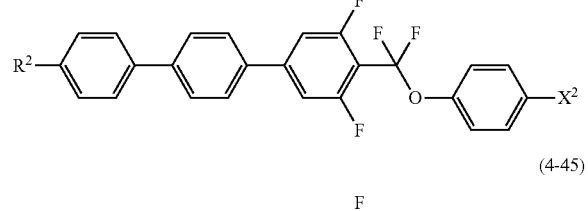
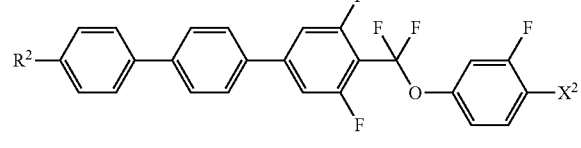

(4-46)
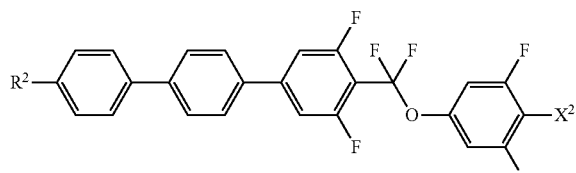

(4-47)
(4-48)
(4-49)
(4-50)
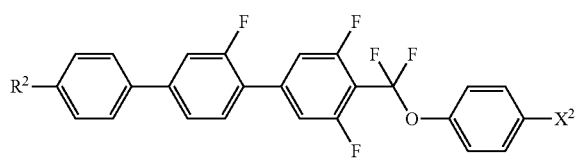
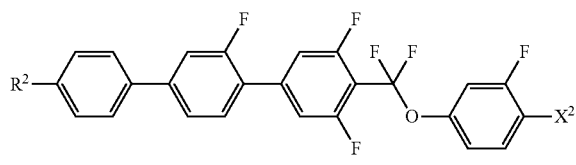
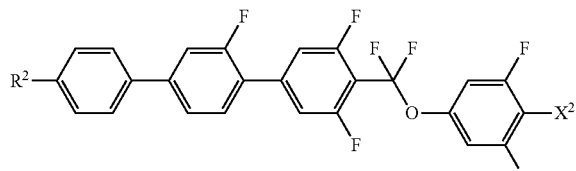
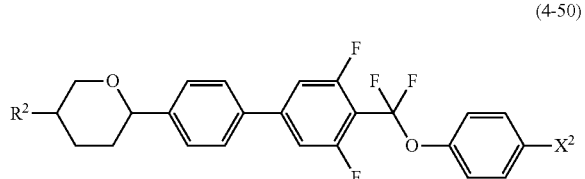

(4-51)
(4-52)
(4-53)
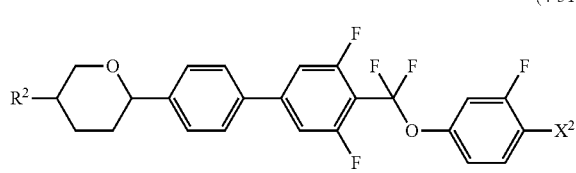
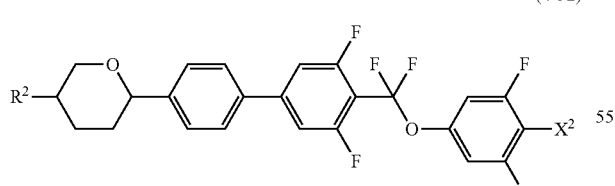
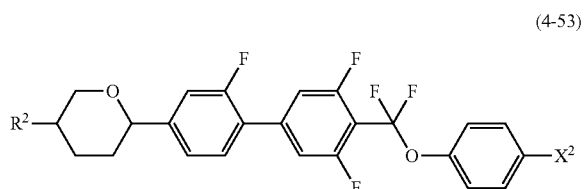

(4-54)
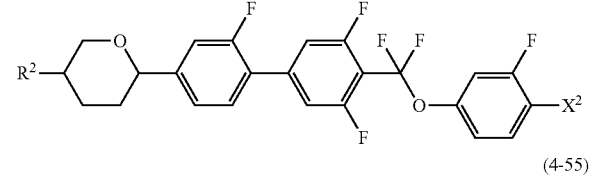

(4-55)
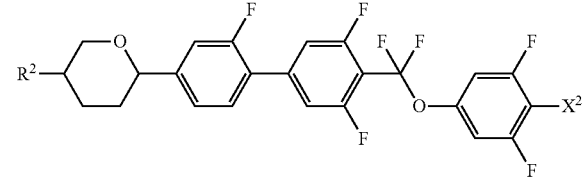

In the formulas, $R^2$ and $X^2$ are defined in a manner identical with the definitions in item 13.

Compounds (2) to (4), namely, component B, have a positive dielectric anisotropy and a superb thermal stability and chemical stability, and therefore are used for preparing a liquid crystal composition for the TFT mode. Content of component B in the liquid crystal composition of the invention is suitably in the range of about 1% by weight to about 99% by weight, preferably, about 10% by weight to about 97% by weight, further preferably, about 40% by weight to about 95% by weight, based on the total weight of the liquid crystal composition. Moreover, the viscosity can be adjusted by further incorporating compounds (11) to (13) (component D) into the composition.

Component C including compounds (5) to (10) is preferred in preparing a liquid crystal composition having a negative dielectric anisotropy for use in a device having the vertical alignment mode (VA mode), the polymer sustained alignment mode (PSA mode) or the like according to the invention.

Suitable examples of compounds (5) to (10) include compounds (5-1) to (5-6), (6-1) to (6-15), (7-1), (8-1) to (8-3), (9-1) to (9-11) and (10-1) to (10-10).

(5-1)
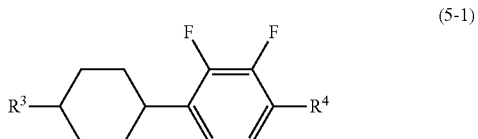

(5-2)
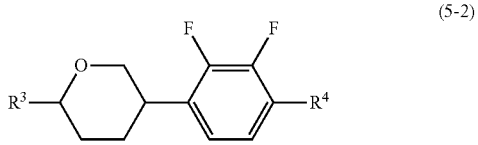

(5-3)
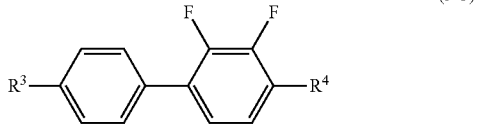

(5-4)
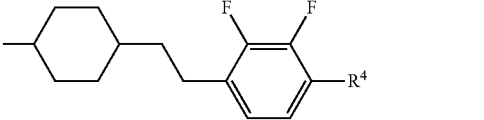

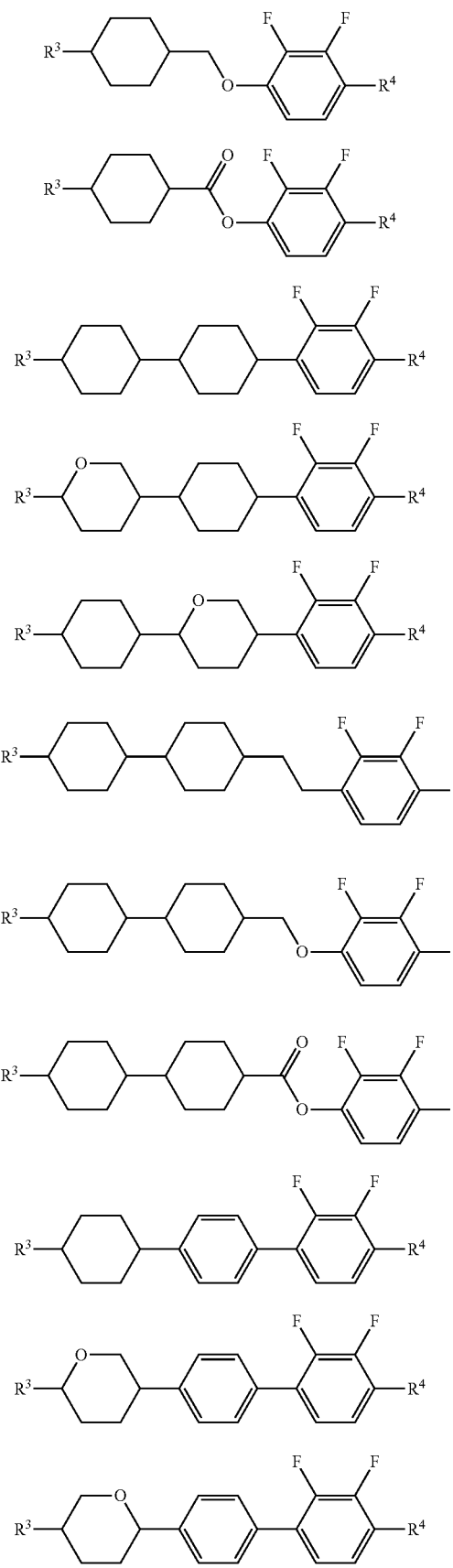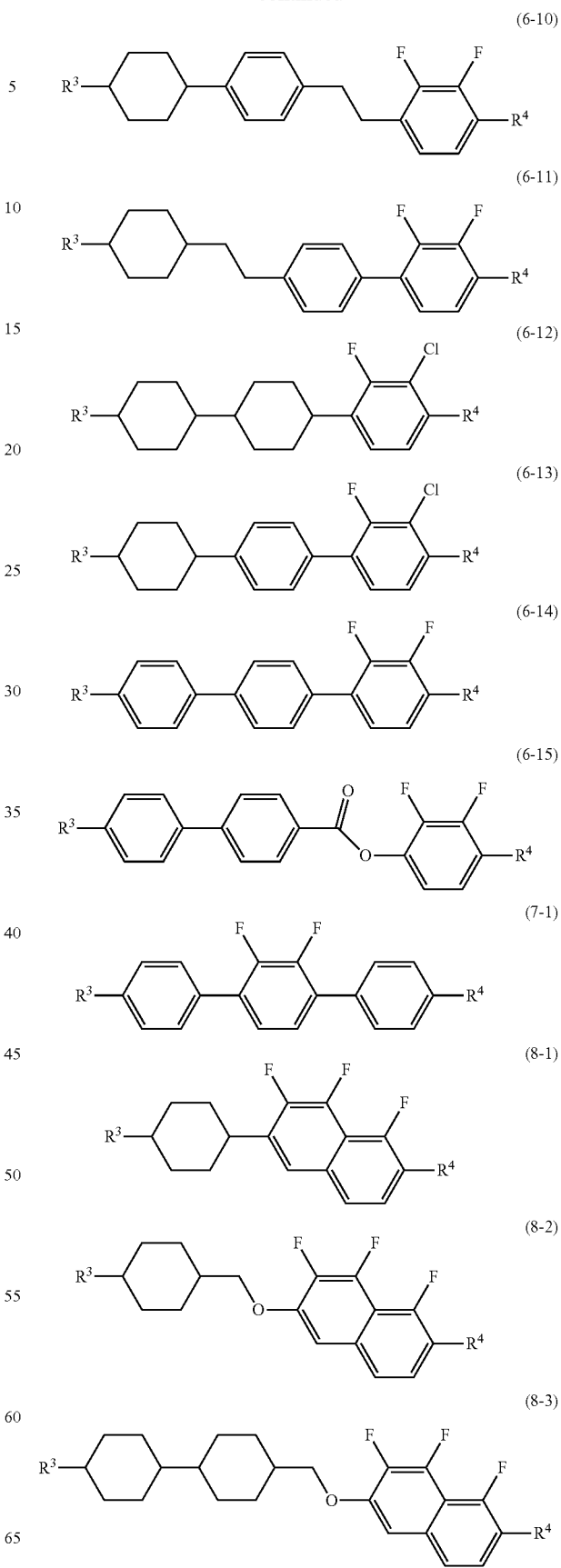

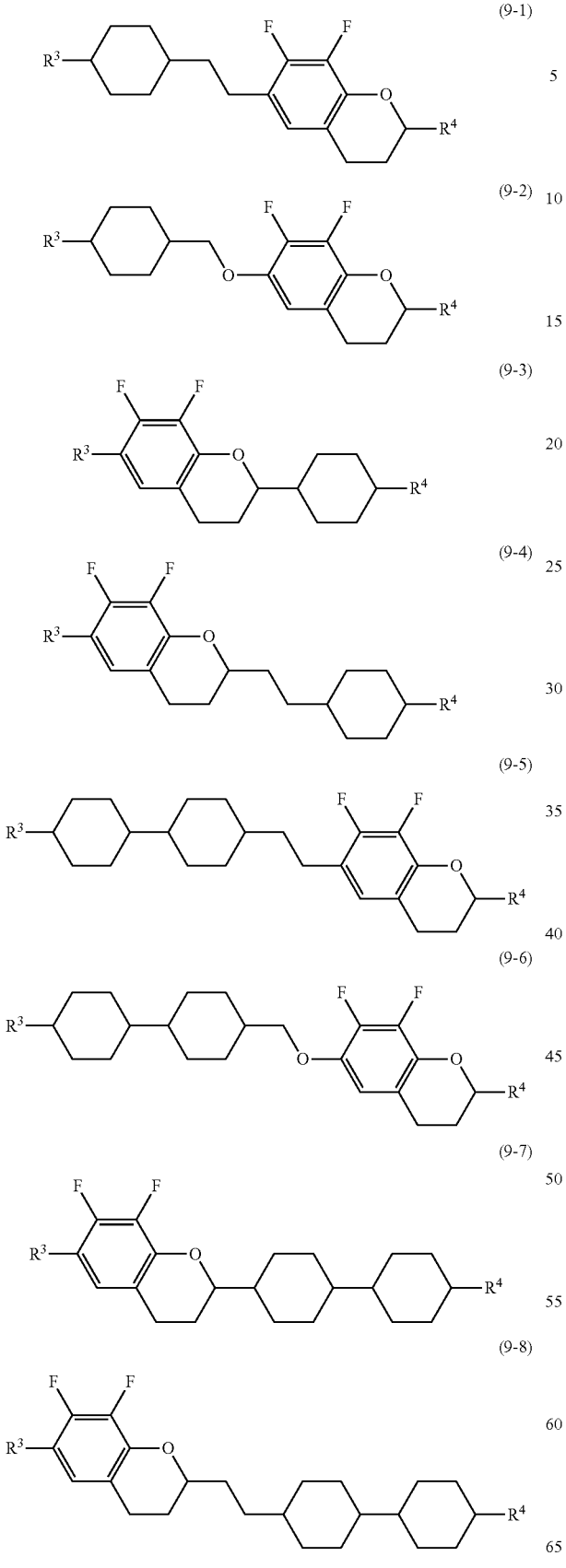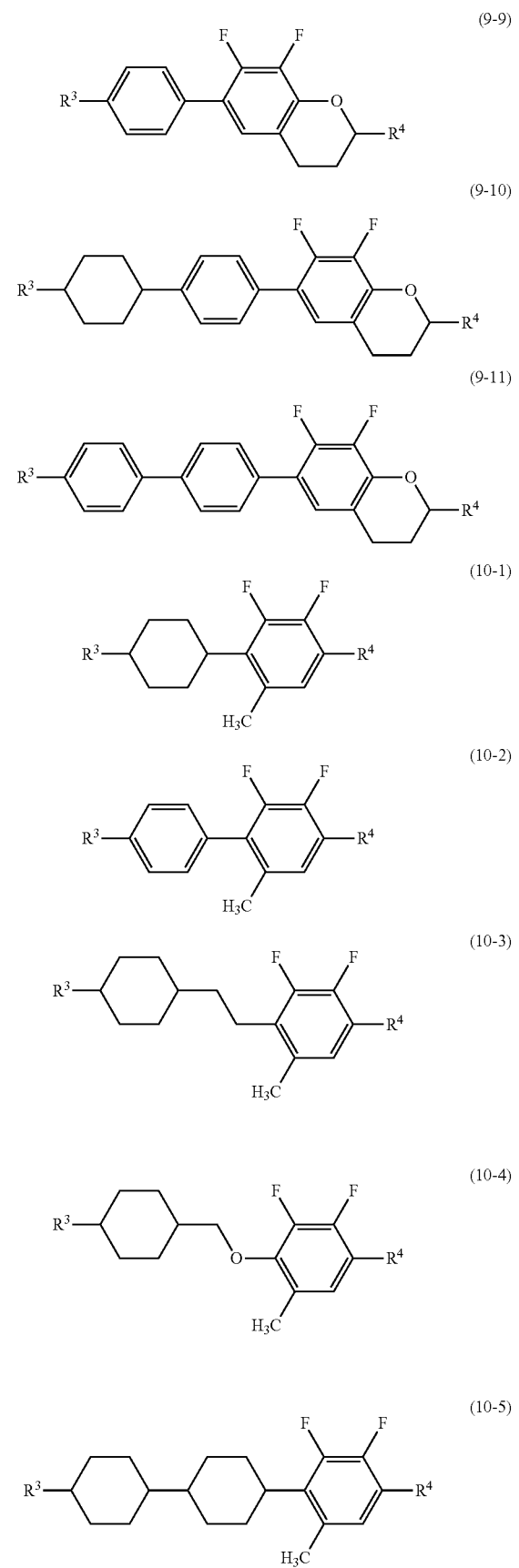

-continued

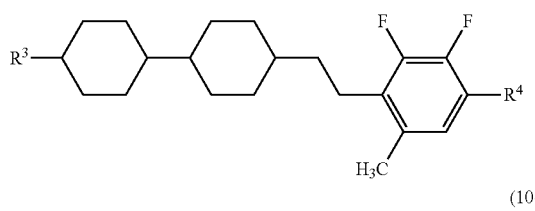
(10-6)

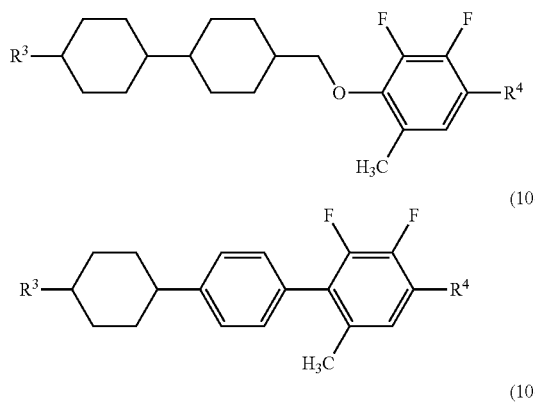
(10-7)
(10-8)

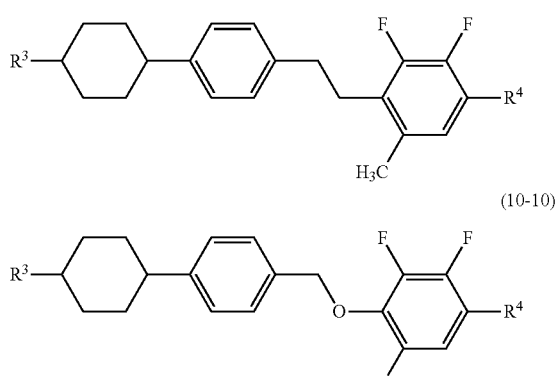
(10-9)
(10-10)

In the formulas, $R^3$ and $R^4$ are defined in a manner identical with the definitions in item 14.

The compounds of component C are mainly used for a liquid crystal composition having a negative value of dielectric anisotropy for use in the VA mode. When the content thereof is increased, the threshold voltage of the composition decreases but the viscosity increases. Accordingly, the content is preferably minimized as long as a desired value of the threshold voltage is satisfied. However, an absolute value of dielectric anisotropy is about 5, and therefore if the content less than about 40% by weight occasionally does not allow voltage driving.

Among types of component C, compound (5) is a bicyclic compound and therefore effective mainly in adjusting the threshold voltage, adjusting the viscosity and adjusting the optical anisotropy. Moreover, compounds (6) and (7) are a tricyclic compound, and therefore effective in increasing the clearing point, increasing a nematic phase range, decreasing the threshold voltage, increasing the optical anisotropy or the like.

The content of component C is, when a composition for the VA mode is prepared, preferably about 40% by weight or more, further preferably, in the range of about 50% by weight to about 95% by weight, based on the total weight of the composition. Moreover, when component C is mixed, an elastic constant can be controlled and a voltage-transmittance curve of the composition can be controlled. When component C is added to a composition having a positive dielectric anisotropy, the content of component C is preferably about 30% by weight or less based on the total weight of the composition.

Suitable examples of compounds (11), (12) and (13) (component D) include compounds (11-1) to (11-11), (12-1) to (12-18) and (13-1) to (13-6).

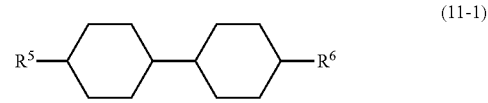
(11-1)

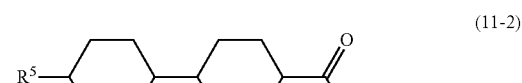
(11-2)

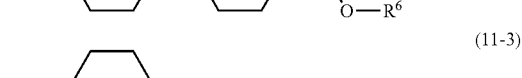
(11-3)

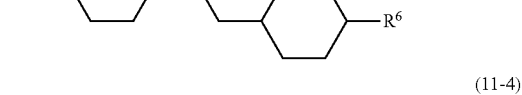
(11-4)

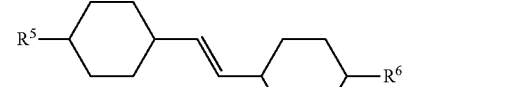
(11-5)

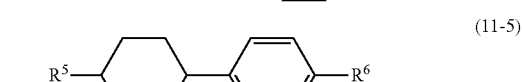
(11-6)

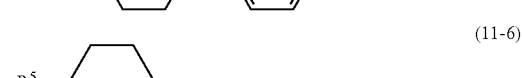
(11-7)

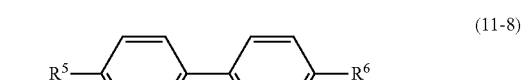
(11-8)

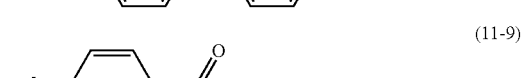
(11-9)

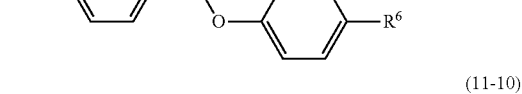
(11-10)

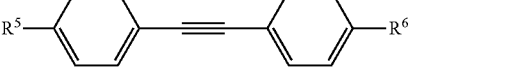
(11-11)

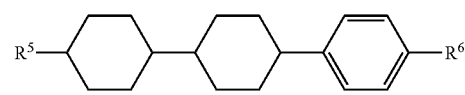 (12-1)
 (12-2)
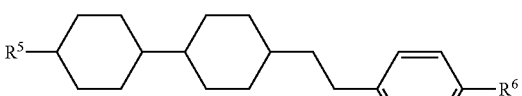 (12-3)
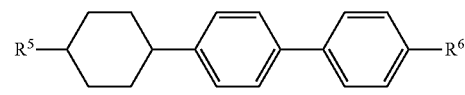 (12-4)
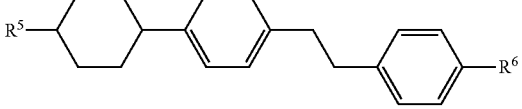 (12-5)
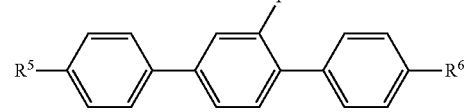 (12-6)
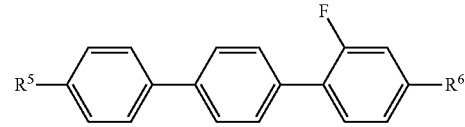 (12-7)
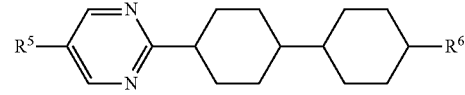 (12-8)
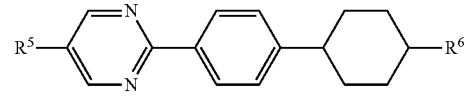 (12-9)
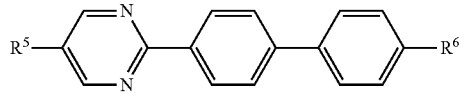 (12-10)
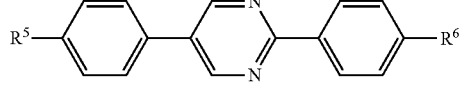 (12-11)
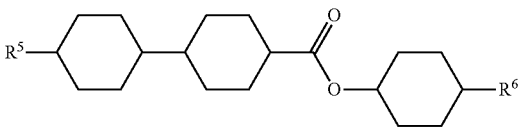 (12-12)
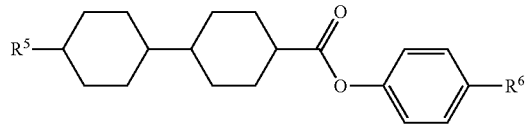 (12-13)
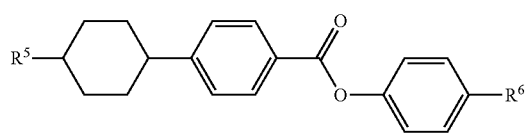 (12-14)
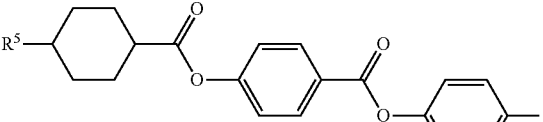 (12-15)
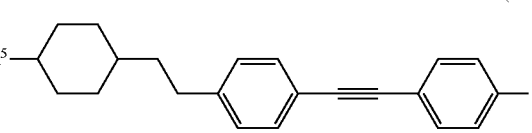 (12-16)
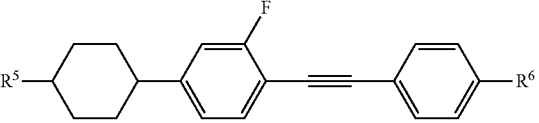 (12-17)
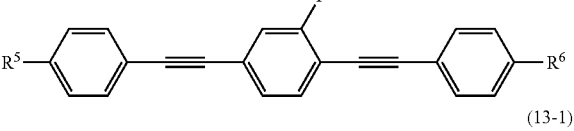 (12-18)
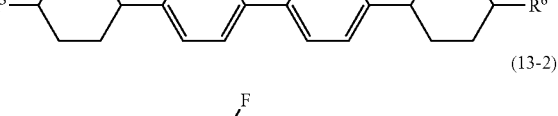 (13-1)
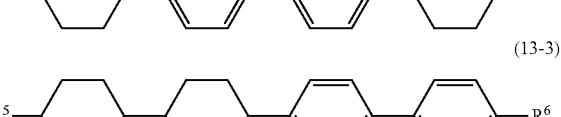 (13-2)
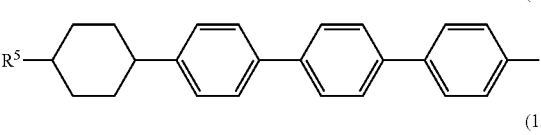 (13-3)
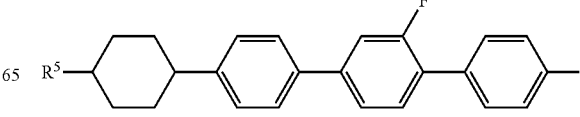 (13-4)
(13-5)

-continued (13-6)

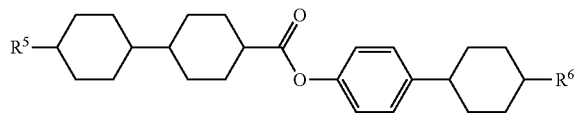

In the formulas, $R^5$ and $R^6$ are defined in a manner identical with the definitions in item 15.

Compounds (11) to (13) (component D) each have a small absolute value of dielectric anisotropy and are close to neutrality. Compound (11) is effective mainly in adjusting the viscosity or a value of optical anisotropy. Compounds (12) and (13) are effective in extending the nematic phase range, such as increasing the clearing point, or adjusting a value of refractive index anisotropy.

When the content of the compound represented by component D is increased, the threshold voltage of the liquid crystal composition increases and the viscosity decreases. Accordingly, the content is desirably high as long as a desired value of the threshold voltage of the liquid crystal composition is satisfied. When a liquid crystal composition for the TFT mode is prepared, the content of component D is preferably about 30% by weight or more, further preferably, about 50% by weight or more, based on the total weight of the composition.

The liquid crystal composition of the invention preferably contains at least one kind of compound represented by formula (1) according to the invention in a ratio of about 0.1% to about 99% by weight for developing excellent characteristics.

The liquid crystal composition of the invention is generally prepared according to a publicly known method such as dissolving necessary components with each other at a high temperature. Moreover, an additive well-known to those skilled in the art is added according to an application, and thus, for example, a liquid crystal composition containing the optically active compound, or a liquid crystal composition for a guest host (GH) mode in which a dye is added according to the invention as described below can be prepared. The additive is ordinarily well known to those skilled in the art, and is described in literatures or the like in detail.

The liquid crystal composition of the invention may further contain at least one optically active compound in the liquid crystal composition of the invention as described above.

As the optically active compound, a publicly known chiral dopant can be added. The chiral dopant is effective in inducing a helical structure in liquid crystals to adjust a necessary twist angle and to prevent an inverted twist. Specific examples of the chiral dopants include the optically active compounds (Op-1) to (Op-13) below.

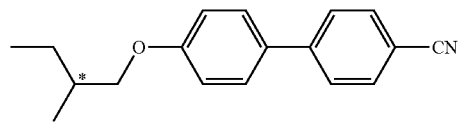

(Op-1)

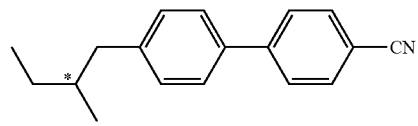

(Op-2)

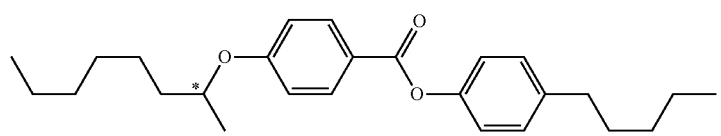

(Op-3)

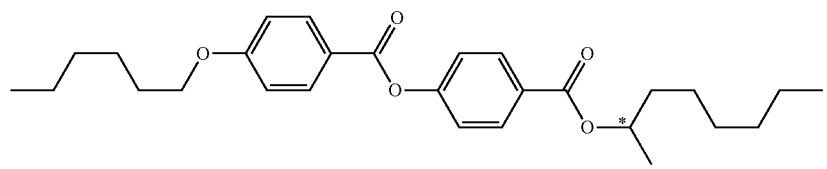

(Op-4)

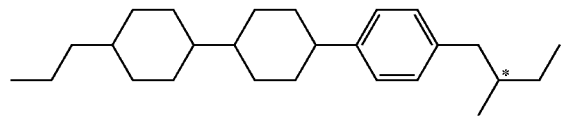

(Op-5)

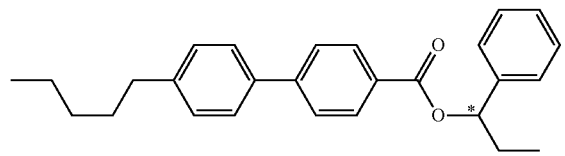

(Op-6)

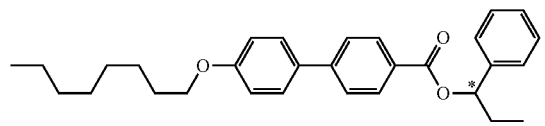

(Op-7)

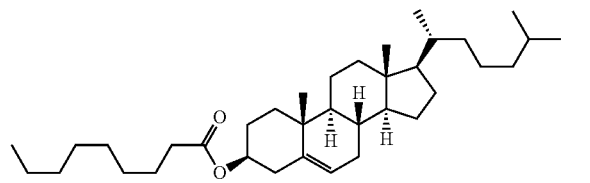

(Op-8)

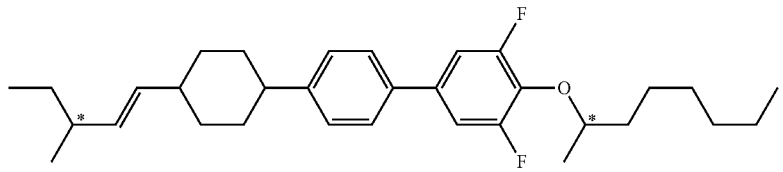

(Op-9)

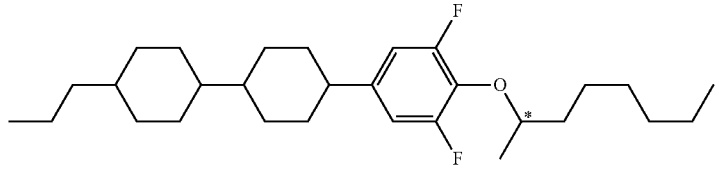

(Op-10)

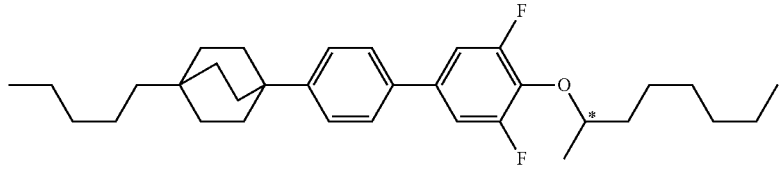

(Op-11)

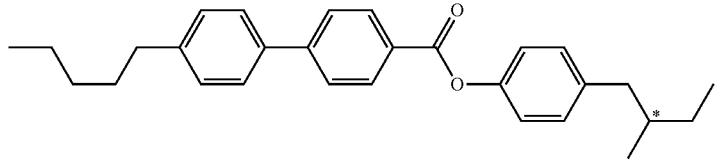

(Op-12)

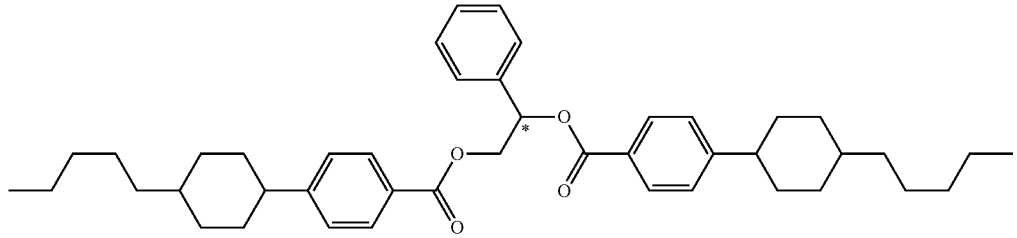

(Op-13)

The helical pitch of the liquid crystal composition of the invention is ordinarily adjusted by adding the optically active compounds. The helical pitch is preferably adjusted in the range of about 40 micrometers to about 200 micrometers for a liquid crystal composition for use in the TFT mode and the TN mode. The helical pitch is preferably adjusted in the range of about 1.5 micrometers to about 4 micrometers for a liquid crystal composition for use in a bistable TN mode. Two or more of optically active compounds may be added for the purpose of adjusting temperature dependence of the helical pitch.

The liquid crystal composition of the invention can also be used as a liquid crystal composition for use in a GH mode by adding a dichroic dye such as a merocyanine, stylyl, azo, azomethine, azoxy, quinophthalone, anthraquinone or tetrazine dye.

Moreover, the liquid crystal composition of the invention can also be used for NCAP prepared by microencapsulating nematic liquid crystals, a polymer dispersed liquid crystal display device (PDLCD) prepared by forming a three-dimensional network polymer in liquid crystals, such as a polymer network liquid crystal display device (PNLCD), and also a liquid crystal composition for use in an electrically controlled birefringence (ECB) mode or a DS mode.

EXAMPLES

Hereinafter, the invention will be explained in more detail by way of Examples, but the invention is not limited by the Examples. Unless otherwise noted, "%" is expressed in terms of "% by weight."

Compounds obtained were identified by nuclear magnetic resonance spectra obtained by means of $^1$H-NMR analysis, gas chromatograms obtained by means of gas chromatography (GC) analysis and so forth, and therefore analytical methods will be first explained.

$^1$H-NMR Analysis:

As a measuring apparatus, DRX-500 (made by Bruker BioSpin Corporation) was used. A sample prepared in Example or the like was dissolved into a deuterated solvent such as $CDCl_3$ in which the sample was soluble, and measurement was carried out under the conditions of room temperature, 500 MHz and 16 times of accumulation. In the explanation of the nuclear magnetic resonance spectra obtained, s, d, t, q and m stand for a singlet, a doublet, a triplet, a quartet, and a multiplet, respectively. Tetramethylsilane (TMS) was used as a standard reference material for a zero point of chemical shifts (δ values).

GC Analysis:

As a measuring apparatus, GC-14B Gas Chromatograph made by Shimadzu Corporation was used. A capillary column CBP1-M25-025 (length 25 m, bore 0.22 mm, film thickness 0.25 μm; dimethylpolysiloxane as a stationary liquid phase; non-polar) made by Shimadzu Corporation was used. Helium was used as a carrier gas, and a flow rate was adjusted at 1 milliliter per minute. Temperature in a sample injector was set at 300° C. and temperature of a detector (FID) part was set at 300° C.

A sample was dissolved into toluene and prepared to be a 1% solution, and then 1 microliter of the solution obtained was injected into the sample injector.

As a recorder, C-R6A Chromatopac made by Shimadzu Corporation or an equivalent thereof was used. The resulting gas chromatogram showed a retention time of a peak and a value of a peak area corresponding to a component compound.

As a solvent for diluting a sample, chloroform or hexane, for example, may also be used. Moreover, as the column, capillary column DB-1 (length 30 m, bore 0.32 mm, film thickness 0.25 pin) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd., or the like may also be used.

A ratio of peak areas in the gas chromatogram corresponds to a ratio of component compounds. In general, the percentage by weight of each component compound in an analytical sample is not completely identical with the percentage of each peak area in the analytical sample. In However, when the column described above is used in the invention, a correction coefficient is essentially 1 (one), and therefore the percentage by weight of the component compound in the analytical sample corresponds substantially to the percentage of the peak area in the analytical sample. The reason is that no significant difference exists among the correction coefficients of the components in the liquid crystal compounds. In order to more accurately determine a composition ratio of the liquid crystal compounds in the liquid crystal composition by means of the gas chromatograms, an internal standard method using gas chromatograms is applied. Each liquid crystal compound component (test-component) accurately weighed in a fixed amount and a standard liquid crystal compound (standard reference material) are simultaneously measured according to gas chromatography, and relative intensity of ratios of the peak areas obtained between the test-component and the standard reference material is calculated in advance. When the composition ratio is corrected using the relative intensity of the peak area of each component to the peak area of standard reference material, the composition ratio of the liquid crystal compounds in the liquid crystal composition can be more accurately determined by means of the gas-chromatographic analysis.

Samples for Determining Values of Physical Properties of a Compound or the Like

A sample for determining values of physical properties of a liquid crystal compound includes two types of cases: a case where the compound per se is used as the sample, and a case where the compound is mixed with a base liquid crystal to be used as the sample.

In the latter case where the sample prepared by mixing the compound with the base liquid crystal is used, measurement is carried out according to the method described below. First, a sample is prepared by mixing 15% of liquid crystal compound obtained and 85% of base liquid crystal. Then, extrapolated values are calculated according to an extrapolation method based on an equation as presented below from measured values of the sample obtained. The extrapolated values are described as the values of physical properties of the compound.

{Extrapolated value}={100×(measured value of a sample)−(% of base liquid crystal)×(measured value of the base liquid crystal)}/(% of the compound).

When a smectic phase or crystals precipitated even at the ratio of the compound to the base liquid crystal at 25° C., a ratio of the liquid crystal compound to the base liquid crystal was changed in the order of (10% by weight: 90% by weight), (5% by weight: 95% by weight) and (1% by weight: 99% by weight). Physical properties of the sample were measured at a ratio in which the smectic phase or the crystals did not precipitate at 25° C. Extrapolated values were determined according to the equation above, and described as values of physical properties of the liquid crystal compound.

As the base liquid crystal used for measurement, a variety of types exist. For example, components of base liquid crystal A (% by weight) and each ratio of the components is as described below.

Base Liquid Crystal A:

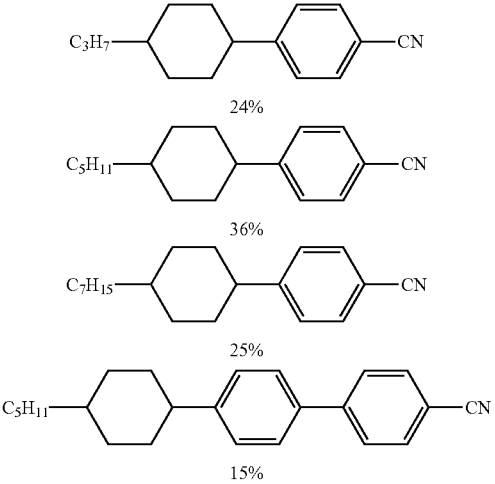

Methods for Determining Values of Physical Properties of a Compound or the Like

Values of physical properties were determined according to the methods described below. Most of the measuring methods are described in EIAJ ED-2521 A of the Standard of Electronic Industries Association of Japan, or modified thereon. Moreover, no TFT was attached to a TN device used for measurement.

Among measured values, in the case where the liquid crystal compound per se was used as the sample, values obtained were described as experimental data. In the case where a mixture of the liquid crystal compound with the base liquid crystal was used as the sample, values obtained according to the extrapolation method were described as experimental data.

Phase Structure and Phase Transition Temperature (° C.):

Measurement was carried out according to methods (1) and (2) described below.

(1) A compound was placed on a hot plate of a melting point apparatus (FP-52 Hot Stage made by Mettler-Toledo International Inc.) equipped with a polarizing microscope, and a state of phase and a change thereof were observed with the polarizing microscope while the compound was heated at a rate of 3° C. per minute, and a kind of the liquid crystal phase was specified.

(2) A sample was heated and then cooled at a rate of 3° C. per minute using a differential scanning calorimeter, Diamond DSC System, made by PerkinElmer, Inc. A starting point (on set) of an endothermic peak or an exothermic peak caused by a change of phases of the sample was obtained by means of extrapolation, and thus a phase transition temperature was determined.

Hereinafter, the crystals were expressed as C, and when the crystals were further distinguishable, each of the crystals was expressed as $C_1$ or $C_2$. A smectic phase or a nematic phase was expressed as S or N. A liquid (isotropic) was expressed as I. When smectic A phase, smectic B phase, smectic C phase or the like was distinguishable among the smectic phases, the phases were expressed as $S_A$, $S_B$ or $S_C$, respectively. As an expression of phase transition temperature, for example, "C 50.0 N 100.0 I" presents that, upon increasing temperature, a phase transition temperature (CN) from a crystal to a nematic phase is 50.0° C., and a phase transition temperature (NI) from the nematic phase to a liquid is 100.0° C. A same rule applied to any other expression.

Maximum Temperature of a Nematic Phase ($T_{NI}$; ° C.):

A sample (a mixture of a liquid crystal compound and a base liquid crystal) was placed on a hot plate of a melting point apparatus (FP52 Hot Stage made by Mettler-Toledo International Inc.) equipped with a polarizing microscope, and was observed with the polarizing microscope while the sample was heated at a rate of 1° C. per minute. Temperature at which part of the sample changed from a nematic phase to an isotropic liquid was described as a maximum temperature of the nematic phase. Hereinafter, the maximum temperature of the nematic phase may be occasionally abbreviated simply as "maximum temperature."

Compatibility at a Low Temperature:

Samples were prepared by mixing a liquid crystal compound with a base liquid crystal for a mixing ratio of the liquid crystal compound to be 20% by weight, 15% by weight, 10% by weight, 5% by weight, 3% by weight and 1% by weight, and put in glass vials. The glass vials were kept in a freezer at −10° C. or −20° C. for a fixed period of time, and then whether or not crystals or a smectic phase precipitated was observed.

Viscosity (Bulk Viscosity; η; Measured at 20° C.; mPa·s):

A mixture of a liquid crystal compound and a base liquid crystal was measured cone-plate (E type) rotational viscometer.

Optical Anisotropy (Refractive Index Anisotropy; Δn):

Measurement was carried out by means of an Abbe refractometer with a polarizing plate mounted on an ocular by using light at a wavelength of 589 nanometers at a temperature of 25° C. A surface of a main prism was rubbed in one direction, and then a sample (a mixture of a liquid crystal compound and a base liquid crystal) was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy was calculated from an equation: Δn=n∥−n⊥.

Dielectric Anisotropy (Δ∈; Measured at 25° C.):

A sample (a mixture of a liquid crystal compound and a base liquid crystal) was put liquid crystal cell in which a distance (gap) between two glass substrates was about 9 micrometers and a twist angle was 80 degrees. A voltage of 20 V was applied to the cell, and a dielectric constant (∈∥) in the major axis direction of liquid crystal molecules was measured. A voltage of 0.5 V was applied to the cell, and a dielectric constant (∈⊥) in the minor axis direction of the liquid crystal molecules was measured. A value of dielectric anisotropy was calculated from an equation: Δ∈=∈∥−∈⊥.

Example 1

Synthesis of 4-propyl-1-(4-(3,4,5-trifluorophenyl) cyclohexyl)-2,6,7-trioxabicyclo[2.2.2]octane (No. 21)

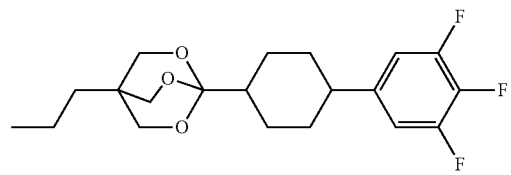 [SMILES: CCCC12COC(C3CCC(c4cc(F)c(F)c(F)c4)CC3)(OC1)OC2]

First Step

Into a reaction vessel under a nitrogen atmosphere, 4.8 g (120 mmol) of well-dried and powdery sodium hydroxide, 100 mL of acetonitrile and 9.9 g (330 mmol) of paraformaldehyde were put, and while stirring the resultant mixture at room temperature, 8.4 g (97 mmol) of valeraldehyde was added dropwise over 20 minutes. After completion of the dropwise addition, temperature was 60° C. Subsequently, temperature was increased to 80° C. and the mixture was stirred for 30 minutes. The mixture was cooled to room temperature, an insoluble matter was separated by filtration, and a solvent was distilled off under reduced pressure. A residue was purified according to fractionation by column chromatography using ethyl acetate as an eluent and silica gel as a filler, and dried, and thus 6.6 g of 2-(hydroxymethyl)-2-propylpropane-1,3-diol was obtained as a white solid.

Second Step

Into a reaction vessel under a nitrogen atmosphere, 6.6 g (45 mmol) of 2-(hydroxymethyl)-2-propylpropane-1,3-diol obtained in the first step, 5.3 g (45 mmol) of diethyl carbonate and 0.053 g (0.37 mmol) of potassium carbonate were put, and the resultant mixture was stirred at 125° C. for 6 hours. The mixture was purified by vacuum distillation (1 mmHg, 100° C.), and thus 3.7 g of 3-propyl-3-hydroxymethyloxetane was obtained as a colorless liquid.

Third Step

Into a reaction vessel under a nitrogen atmosphere, 4.4 g (17 mmol) of 4-(3,4,5-trifluorophenyl)cyclohexanecarboxylic acid, 50 mL of toluene, and 2.4 mL (34 mmol) of thionyl chloride were put, and the resultant mixture was stirred at 85° C. for 1.5 hours. Excessive thionyl chloride was distilled off under a nitrogen flow, a solvent was distilled off by means of a rotary evaporator, and thus acid chloride was obtained. In a separately-provided reaction vessel under a nitrogen atmosphere, 2.4 g (19 mmol) of 3-propyl-3-hydroxymethyloxetane obtained in the second step, 35 mL of THF and 1.7 mL (21 mmol) of pyridine were put, the THF solution of acid chloride was added dropwise thereto at room temperature, and the resultant mixture was stirred for 20 hours. Then, 50 mL of diethyl ether and 30 mL of water were added to separate the mixture into an organic layer and an aqueous layer, and an extraction operation was applied. The organic layer obtained was separated, washed with saturated brine, and dried over anhydrous magnesium sulfate, and then an insoluble matter was separated by filtration and then a filtrate was concentrated under reduced pressure. A residue was purified according to fractionation by column chromatography using a mixed solvent of heptane and ethyl acetate (ethyl acetate:heptane=1:3 in a volume ratio) as an eluent and silica gel as a filler, and thus 5.4 g of 4-(3,4,5-trifluorophenyl)cyclohexanecarboxylate(3-propyloxetane-3-yl)methyl was obtained as a light-orange oily matter.

Fourth Step

Into a reaction vessel under a nitrogen atmosphere, 5.4 g (15 mmol) of 4-(3,4,5-trifluorophenyl)cyclohexanecarboxylate(3-propyloxetane-3-yl)methyl obtained in the third step and 60 mL of dichloromethane were put, the resultant mixture was cooled to −70° C., and 0.44 g (3.5 mmol) of boron trifluoride-diethyl ether complex was added dropwise thereto. The resultant mixture was warmed to room temperature and stirred for 15 hours. Then, 0.67 mL (4.8 mmol) of triethylamine was added thereto, and the resultant mixture was concentrated by means of a rotary evaporator. Then, 30 mL of diethyl ether was added thereto, the resultant mixture was washed with saturated brine, and dried over anhydrous magnesium sulfate, and an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (volume ratio heptane/ethyl acetate=80/20), and thus 1.4 g of 4-propyl-1-(4-(3,4,5-trifluorophenyl)cyclohexyl)-2,6,7-trioxabicyclo[2.2.2]octane was obtained as a white solid.

Chemical shifts (δ (ppm)) according to $^1$H-NMR analysis was as described below, and the compound obtained was identified to be 4-propyl-1-(4-(3,4,5-trifluorophenyl)cyclohexyl)-2,6,7-trioxabicyclo[2.2.2]octane. A solvent for measurement was CDCl$_3$.

Chemical shifts (δ (ppm)); 6.78 (m, 2H), 3.91 (s, 6H), 2.39 (m, 1H), 1.97 (m, 2H), 1.90 (m, 2H), 1.62 (m, 1H), 1.4-1.1 (m, 8H), 0.90 (t, 3H).

A transition temperature of compound (No. 21) obtained is as described below.

Transition temperature: C 141.0 I.

Physical Properties of Compound (No. 21)

Liquid crystal composition B including 95% by weight of base liquid crystal A and 5% by weight of 4-propyl-1-(4-(3,4,5-trifluorophenyl)cyclohexyl)-2,6,7-trioxabicyclo[2.2.2]octane (No. 21) obtained in Example 1 was prepared. Physical properties of liquid crystal composition B obtained were measured, and extrapolated values of physical properties of compound (No. 21) were calculated by extrapolating measured values. Values thereof are as described below.

Maximum temperature (T$_{NI}$)=55.7° C.; dielectric anisotropy (Δ∈)=42.1; optical anisotropy (Δn)=0.077; viscosity (η)=129.2.

Example 2

Synthesis of 4-ethyl-1-(4-(3,4,5-trifluorophenyl)cyclohexyl)-2,6,7-trioxabicyclo[2.2.2]octane (No. 20)

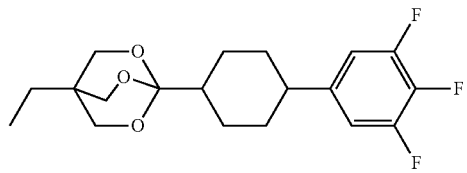

Then, 4-ethyl-1-(4-(3,4,5-trifluorophenyl)cyclohexyl)-2,6,7-trioxabicyclo[2.2.2]octane was prepared by performing synthesis in a manner similar to the operations in the third step and the fourth step in Example 1 using 3-ethyl-3-hydroxymethyloxetane in place of 3-propyl-3-hydroxymethyloxetane.

Chemical shifts (δ (ppm)) according to $^1$H-NMR analysis are as described below, and the compound obtained was identified to be 4-ethyl-1-(4-(3,4,5-trifluorophenyl)cyclohexy)-2,6,7-trioxabiyclo[2.2.2]octane. A solvent for measurement was CDCl$_3$.

Chemical shifts (δ (ppm)); 6.79 (m, 2H), 3.91 (s, 6H), 2.39 (m, 1H), 1.98 (m, 2H), 1.90 (m, 2H), 1.60 (m, 1H), 1.3-1.1 (m, 6H), 0.83 (t, 3H).

A transition temperature of compound (No. 20) obtained is as described below.

Transition temperature: C 168.5 I.

Physical Properties of Compound (No. 20)

Liquid crystal composition C including 95% by weight of base liquid crystal A and 5% by weight of 4-ethyl-(4-(3,4,5-trifluorophenyl)cyclohexyl)-2,6,7-trioxabicyclo[2.2.2]octane (No. 20) obtained in Example 2 was prepared. Physical properties of liquid crystal composition C obtained were measured, and extrapolated values of physical properties of compound (No. 20) were calculated by extrapolating measured values. Values thereof are as described below.

Maximum temperature (T$_{NI}$)=25.7° C.; dielectric anisotropy (Δ∈)=47.9; optical anisotropy (Δn)=0.037; viscosity (η)=104.9.

Example 3

Synthesis of 4-butyl-1-(4-(3,4,5-trifluorophenyl)cyclohexyl)-2,6,7-trioxabicyclo[2.2.2]octane (No. 22)

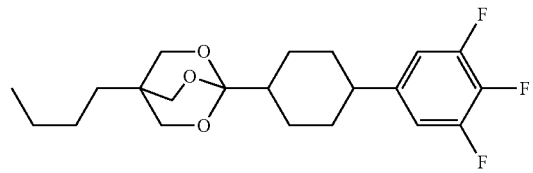 [SMILES: CCCCC12COC(C3CCC(c4cc(F)c(F)c(F)c4)CC3)(OC1)OC2]

Then, 4-butyl-1-(4-(3,4,5-trifluorophenyl)cyclohexyl)-2,6,7-trioxabicyclo[2.2.2]octane was prepared by performing synthesis in a manner similar to the operations in Example 1 using
1-hexanal in place of valeraldehyde.

Chemical shifts (δ (ppm)) according to ¹H-NMR analysis are as described below, and the compound obtained was identified to be 4-buthyl-1-(4-(3,4,5-trifluorophenyl)cyclohexyl)-2,6,7-trioxabicyclo[2.2.2]octane. A solvent for measurement was CDCl₃.

Chemical shifts (δ (ppm)) according to ¹H-NMR analysis are as described below, and the compound obtained was identified to be 4-buthyl-1-(4-(3,4,5-trifluorophenyl)cyclohexyl)-2,6,7-trioxabicyclo[2.2.2]octane. A solvent for measurement was CDCl₃.

Chemical shifts (δ(ppm)); 6.77 (m, 2H), 3.90 (s, 6H), 2.39 (m, 1H), 1.98 (m, 2H), 1.90 (m, 2H), 1.60 (m, 1H), 1.3-1.1 (m, 10H), 0.89 (t, 3H).

A transition temperature of compound (No. 22) obtained is as described below.

Transition temperature: C 133.5 S$_B$ 135.6 I.

Physical Properties of Compound (No. 22)

Liquid crystal composition D including 90% by weight of base liquid crystal A and 10% by weight of 4-butyl-1-(4-(3,4,5-trifluorophenyl)cyclohexyl)-2,6,7-trioxabicyclo[2.2.2]octane (No. 22) obtained in Example 3 was prepared. Physical properties of liquid crystal composition D obtained were measured, and extrapolated values of physical properties of compound (No. 22) were calculated by extrapolating measured values. Values thereof are as described below.

Maximum temperature (T$_{NI}$)=56.7° C.; dielectric anisotropy (Δ∈)=40.1; optical anisotropy (Δn)=0.067; viscosity (η)=112.6.

Example 4

Synthesis of 4-pentyl-1-(4-(3,4,5-trifluorophenyl)cyclohexyl)-2,6,7-trioxabicyclo[2.2.2]octane (No. 23)

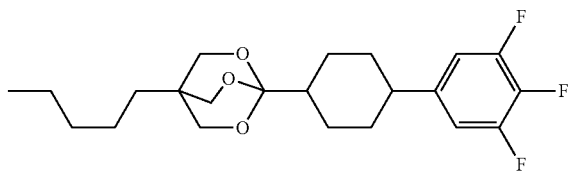 [SMILES: CCCCCC12COC(C3CCC(c4cc(F)c(F)c(F)c4)CC3)(OC1)OC2]

Then, 4-pentyl-1-(4-(3,4,5-trifluorophenyl)cyclohexyl)-2,6,7-trioxabicyclo[2.2.2]octane was prepared by performing synthesis in a manner similar to the operations in Example 1 using 1-heptanal in place of valeraldehyde.

Chemical shifts (δ (ppm)) according to ¹H-NMR analysis are as described below, and the compound obtained was identified to be 4-pentyl-(4-(3,4,5-trifluorophenyl)cyclohexyl)-2,6,7-trioxabicyclo[2.2.2]octane. A solvent for measurement was CDC₃.

Chemical shifts (δ (ppm)); 6.76 (m, 2H), 3.91 (s, 6H), 2.39 (m, 1H), 1.98 (m, 2H), 1.90 (m, 2H), 1.61 (m, 1H), 1.4-1.1 (m, 12H), 0.88 (t, 3H).

A transition temperature of compound (No. 23) obtained is as described below. Transition temperature: C 126.2 S$_B$ 135.0 I.

Physical Properties of Compound (No. 23)

Liquid crystal composition E including 90% by weight of base liquid crystal A and 10% by weight of 4-pentyl-1-(4-(3,4,5-trifluorophenyl)cyclohexyl)-2,6,7-trioxabicyclo[2.2.2]octane (No. 23) obtained in Example 4 was prepared. Physical properties of liquid crystal composition E obtained were measured, and extrapolated values of physical properties of compound (No. 23) were calculated by extrapolating measured values. Values thereof are as described below.

Maximum temperature (T$_{NI}$)=67.7° C.; dielectric anisotropy (Δ∈)=37.9; optical anisotropy (Δn)=0.067; viscosity (η)=1162.

Example 5

Synthesis of 4-heptyl-1-(4-(3,4,5-trifluorophenyl)cyclohexyl)-2,6,7-trioxabicyclo[2.2.2]octane (No. 24)

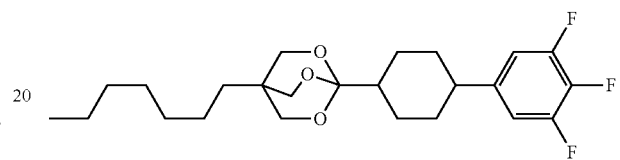

Then, 4-heptyl-1-4-(3,4,5-trifluorophenyl)cyclohexyl)-2,6,7-trioxabicyclo[2.2.2]octane was prepared by performing synthesis in a manner similar to the operations in Example 1 using 1-nonanal in place of valeraldehyde.

Chemical shifts (δ (ppm)) according to ¹H-NMR analysis are as described below, and the compound obtained was identified to be 4-heptyl-1-(4-(3,4,5-trifluorophenyl)cyclohexyl)-2,6,7-trioxabicyclo[2.2.2]octane. A solvent for measurement was CDCl₃.

Chemical shifts (δ (ppm)); 6.77 (m, 2H), 3.90 (s, 6H), 2.39 (m, 1H), 1.98 (m, 2H), 1.90 (m, 2H), 1.62 (m, 1H), 1.4-1.1 (m, 16H), 0.88 (t, 3H).

A transition temperature of compound (No. 24) obtained is as described below.

Transition temperature: C 86.2 S$_B$ 130.6 I.

Physical Properties of Compound (No. 24)

Liquid crystal composition F including 85% by weight of base liquid crystal A and 15% by weight of 4-heptyl-1-(4-(3,4,5-trifluorophenyl)cyclohexyl)-2,6,7-trioxabicyclo[2.2.2]octane (No. 24) obtained in Example 5 was prepared. Physical properties of liquid crystal composition F obtained were measured, and extrapolated values of physical properties of compound (No. 24) were calculated by extrapolating measured values. Values thereof are as described below.

Maximum temperature (T$_{NI}$)=69.0° C.; dielectric anisotropy (Δ∈)=34.1; optical anisotropy (Δn)=0.064; viscosity (η)=119.9.

Example 6

Synthesis of 4-pentyl-1-(2-(4-(3,4,5-trifluorophenyl)cyclohexyl)ethyl)-2,6,7-trioxabicyclo[2.2.2]octane (No. 41)

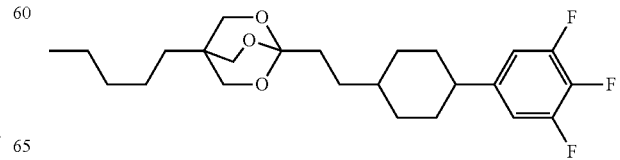

First Step

Into a reaction vessel under a nitrogen atmosphere, 7.2 g (165 mmol) of sodium hydride (55% in oil) and 150 mL of THF were put, the resultant mixture was cooled to −20° C., a THF (70 mL) solution of 33.6 g (150 mmol) of diethylphosphonoethyl acetate was added dropwise thereto, and the resultant mixture was stirred at −20° C. for 1 hour. Next, a THF (100 mL) solution of 36.3 g (150 mmol) of 4-(3,4,5-trifluorophenyl)cyclohexane carboaldehyde was added dropwise thereto at −20° C. The resultant mixture was warmed to room temperature, and poured into 200 mL of water. The resultant mixture was extracted with ethyl acetate, and organic layers were combined, washed with water, and dried over anhydrous magnesium sulfate, and then an insoluble matter was separated by filtration and then a filtrate was concentrated under reduced pressure. A residue was purified according to fractionation by column chromatography using a mixed solvent of heptane and ethyl acetate (ethyl acetate:heptane=1:9 in a volume ratio) as an eluent and silica gel as a filler, and thus 40.0 g of (E)-ethyl-3-(4-(3,4,5-trifluorophenyl)cyclohexyl)acrylate was obtained as a white solid.

Second Step

Into a reaction vessel, 20.0 g (64.0 mmol) of (E)-ethyl-3-(4-(3,4,5-trifluorophenyl)cyclohexyl)acrylate obtained in the first step, 50 mL of toluene, 150 mL of Solmix A-11 and 1.0 g of Pd/C (E type) were put, and an atmosphere inside of the system was replaced by hydrogen. Under a nitrogen atmosphere, the resultant mixture was stirred at room temperature until no hydrogen absorption caused. After reaction completion, Pd/C was removed by filtration and a solvent was distilled off. A residue was purified according to fractionation by column chromatography using a mixed solvent of heptane and ethyl acetate (ethyl acetate:heptane=1:9 in a volume ratio) as an eluent and silica gel as a filler. The resultant mixture was further purified by recrystallization (heptane/ethyl acetate=80/20 in a volume ratio), and thus 13.5 g of ethyl-3-(4-(3,4,5-trifluorophenyl)cyclohexyl)propanoate was obtained as a white solid.

Third Step

Into a reaction vessel under a nitrogen atmosphere, 13.5 g (42.9 mmol) of ethyl 3-(4-(3,4,5-trifluorophenyl)cyclohexyl)propanoate obtained in the second step, 200 mL of ethanol and 3.6 g (64 mmol) of potassium hydroxide were put, and the resultant mixture was refluxed for 1 hour. The resultant mixture was cooled to room temperature, concentrated by means of a rotary evaporator, and poured into 200 mL of hydrochloric acid (2 N). The resultant mixture was extracted with ethyl acetate, and organic layers were combined, washed with saturated brine, and dried over anhydrous magnesium sulfate. An insoluble matter was separated by filtration, a filtrate was concentrated under reduced pressure, and thus 12.1 g of 3-(4-(3,4,5-trifluorophenyl)cyclohexyl)propionic acid was obtained as a white solid.

Fourth Step

Into a reaction vessel under a nitrogen atmosphere, 6.0 g (21.1 mmol) of 3-(4-(3,4,5-trifluorophenyl)cyclohexyl) propionic acid obtained in the third step, 3.3 g (21.1 mmol) of 3-pentyl-3-hydroxymethyloxetane, 0.26 g (2.1 mmol) of 4-dimethylamino pyridine and 50 mL of dichloromethane were put, and a dichloromethane (15 mL) solution of 4.57 g (22.1 mmol) of dicyclohexylcarbodiimide was added dropwise thereto at room temperature. The resultant mixture was stirred for 15 hours at room temperature, and then an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 7.8 g of (3-pentyloxetane-3-yl)methyl-3-(4-(3,4,5-trifluorophenyl)cyclohexyl)propanoate was obtained as a colorless liquid.

Fifth Step

Into a reaction vessel under a nitrogen atmosphere, 7.8 g (18.4 mmol) of (3-pentyloxetane-3-yl)methyl-3-(4-(3,4,5-trifluorophenyl)cyclohexyl)propanoate obtained in the fourth step and 100 mL of dichloromethane were put, the resultant mixture was cooled to −70° C., and 0.58 mL (4.6 mmol) of boron trifluoride-diethyl ether complex was added dropwise thereto. The resultant mixture was warmed to room temperature, and stirred for 25 hours. Then, 1.3 mL (9.2 mmol) of triethylamine was added thereto, and the resultant mixture was concentrated by means of a rotary evaporator. Then, 100 mL of diethyl ether was added thereto, the resultant mixture was washed with saturated brine, and dried over anhydrous magnesium sulfate. An insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 3.7 g of 4-pentyl-1-(2-(4-(3,4,5-trifluorophenyl)cyclohexyl)ethyl)-2,6,7-trioxabicyclo[2.2.2]octane was obtained as a white solid.

Chemical shifts (δ (ppm)) according to $^1$H-NMR analysis are as described below, and the compound obtained was identified to be 4-pentyl-1-(2-(4-(3,4,5-trifluorophenyl)cyclohexyl)ethyl)-2,6,7-trioxabicyclo[2.2.2]octane. A solvent for measurement was $CDCl_3$.

Chemical shifts (δ (ppm)); 6.77 (m, 2H), 3.92 (s, 6H), 2.38 (m, 1H), 1.84 (m, 4H), 1.70 (m, 2H), 1.4-1.1 (m, 13H), 1.03 (m, 2H), 0.88 (t, 3H).

A transition temperature of compound (No. 41) obtained is as described below.

Transition temperature: C 128.1 ($S_B$ 117.0) I.

Physical Properties of Compound (No. 41)

Liquid crystal composition G including 85% by weight of base liquid crystal A and 15% by weight of 4-pentyl-1-(2-(4-(3,4,5-trifluorophenyl)cyclohexyl)ethyl)-2,6,7-trioxabicyclo[2.2.2]octane (No. 41) obtained in Example 6 was prepared. Physical properties of liquid crystal composition G obtained were measured, and extrapolated values of physical properties of compound (No. 41) were calculated by extrapolating measured values. Values thereof are as described below.

Maximum temperature ($T_{NI}$)=65.0° C.; dielectric anisotropy (Δ∈)=30.6; optical anisotropy (Δn)=0.070; viscosity (η)=129.6.

Example 7

Synthesis of (E)-4-pentyl-1-(2-(4-(3,4,5-trifluorophenyl)cyclohexyl)vinyl)-2,6,7-trioxabicyclo[2.2.2]octane (No. 42)

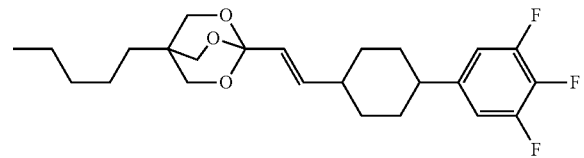 [SMILES: CCCCCC12COC(/C=C/C3CCC(c4cc(F)c(F)c(F)c4)CC3)(OC1)OC2]

First Step

Into a reaction vessel under a nitrogen atmosphere, 20.0 g (62.5 mmol) of (E)-ethyl-3-(4-(3,4,5-trifluorophenyl)cyclohexyl)acrylate obtained in the first step in Example 6, 200 mL of ethanol and 5.4 g (94 mmol) of potassium hydroxide were put, and the resultant mixture was refluxed for 4 hours. The resultant mixture was cooled to room temperature, concentrated by means of a rotary evaporator, and poured into 200 mL of hydrochloric acid (2 N). The resultant mixture was extracted with ethyl acetate, and organic layers were combined, washed with saturated brine, and dried over anhydrous magnesium sulfate. An insoluble matter was separated by filtration, a filtrate was concentrated under reduced pressure, and thus 7.6 g of (E)-3-(4-(3,4,5-trifluorophenyl)cyclohexyl)acrylic acid was obtained as a white solid.

Second Step

Into a reaction vessel under a nitrogen atmosphere, 6.0 g (21.1 mmol) of (E)-3-(4-(3,4,5-trifluorophenyl)cyclohexyl) acrylic acid obtained in the first step, 3.3 g (21.1 mmol) of 3-pentyl-3-hydroxymethyloxetane, 0.26 g (2.1 mmol) of 4-dimethylaminopyridine and 50 mL of dichloromethane were put, and a dichloromethane (15 mL) solution of 4.57 g (22.1 mmol) of dicyclohexylcarbodiimide was added dropwise thereto at room temperature. The resultant mixture was stirred at room temperature for 15 hours, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 6.8 g of (E)-(3-pentyloxetane-3-yl)methyl-3-(4-(3,4,5-trifluorophenyl)cyclohexyl)acrylate was obtained as a colorless liquid.

Third Step

Into a reaction vessel under a nitrogen atmosphere, 6.8 g (16.1 mmol) of (E)-(3-pentyloxetane-3-yl)meth-3-3-(4-(3,4,5-trifluorophenyl)cyclohexyl acrylate obtained in the second step and 50 mL of dichloromethane were put, the resultant mixture was cooled to −70° C., and 0.50 mL (4.0 mmol) of boron trifluoride-diethyl ether complex was added dropwise thereto. The resultant mixture was warmed to room temperature, and stirred for 45 hours. Then, 3.0 mL (21 mmol) of triethylamine was added thereto, and the resultant mixture was concentrated by means of a rotary evaporator. Then, 100 mL of diethyl ether was added thereto, the resultant mixture was washed with saturated brine, and dried over anhydrous magnesium sulfate. An insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 (volume ratio)), and thus 0.6 g of (E)-4-pentyl-1-(2-(4-(3,4,5-trifluorophenyl)cyclohexyl)vinyl)-2,6,7-trioxabicyclo[2.2.2]octane was obtained as a white solid.

Chemical shifts (δ (ppm)) according to ¹H-NMR analysis are as described below, and the compound obtained was identified to be (E)-4-pentyl-1-(2-(4-(3,4,5-trifluorophenyl)cyclohexyl)vinyl)-2,6,7-trioxabicyclo[2.2.2]octane. A solvent for measurement was CDCl$_3$.

Chemical shifts (s (δ (ppm)); 6.78 (m, 2H), 6.10 (m, 1H), 5.47 (d, 1H), 3.99 (s, 6H), 239 (m, 1H), 2.03 (m, 1H), 1.90 (m, 4H), 1.4-1.2 (m, 12H), 0.88 (t, 3H).

Example 8

Synthesis of 1-(4'-(difluoro(3,4,5-trifluorophenoxy)methyl)-2,3',5'-trifluoro-[1,1'-biphenyl]-4-yl)-4-pentyl-2,6,7-trioxabicyclo[2.2.2]octane (No. 106)

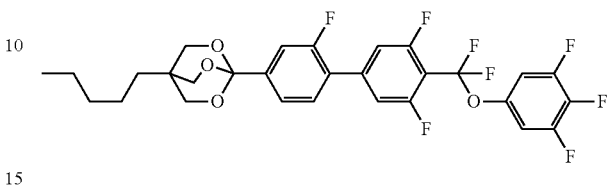

First Step

Into a reaction vessel under a nitrogen atmosphere, 100 mL (130 mmol) of isopropyl magnesium chloride/lithium chloride complex (1.3 M, THF solution) was put, and while stirring at room temperature, 28.7 g (100 mmol) of 4-bromo-2,3',5'-trifluoro-1,1-biphenyl was added little by little, and subsequently the resultant mixture was stirred at room temperature for 2 hours. Next, while the resultant mixture was cooled to 5 to 15° C. in an ice bath, a dry carbon dioxide gas was blown thereinto until heat generation stopped. A reaction liquid was poured into 200 mL of 2 N hydrochloric acid, and extracted with diethyl ether. Organic layers were combined, washed with saturated brine, and dried over anhydrous magnesium sulfate. Then, an insoluble matter was separated by filtration and then a filtrate was concentrated under reduced pressure. A residue was purified according to fractionation by column chromatography using ethyl acetate as an eluent and silica gel as a filler. The resultant mixture was further purified by recrystallization (volume ratio heptane/ethanol=30/70), and thus 10.3 g of 2,3',5'-trifluoro-1,1'-biphenyl-4-carboxylic acid was obtained as a white solid.

Second Step

Into a reaction vessel under a nitrogen atmosphere, 10.3 g (40.7 mmol) of 2,3',5'-trifluoro-1,1'-biphenyl-4-carboxylic acid obtained in the first step, 6.40 g (40.7 mmol) of 3-pentyl-3-hydroxymethyloxetane, 0.5 g (4 mmol) of 4-dimethylaminopyridine, and 100 mL of dichloromethane were put, a dichloromethane (30 mL) solution of 8.8 g (42.8 mmol) of dicyclohexylcarbodiimide was added dropwise thereto at room temperature, and the resultant mixture was stirred at room temperature for 15 hours. Then, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 13.7 g of 2,3',5'-trifluoro-[1,1'-biphenyl]-4-methylcarboxylate(3-pentyloxetane-3-yl) was obtained as a colorless liquid.

Third Step

Into a reaction vessel under a nitrogen atmosphere, 13.7 g (34.9 mmol) of 2,3',5'-trifluoro-[1,1'-biphenyl]-4-methylcarboxylate(3-pentyloxetane-3-yl) obtained in the second step and 100 mL of dichloromethane were put, the resultant mixture was cooled to −70° C., and 1.1 mL (8.8 mmol) of boron trifluoride-diethyl ether complex was added dropwise thereto. The resultant mixture was warmed to room temperature and stirred for 20 hours. Then, 1.5 mL (11 mmol) of triethylamine was added thereto, and the resultant mixture was concentrated by means of a rotary evaporator. Then, 100 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 10.9 g of 4-pentyl-1-(2,3',5'-trifluoro-[1,1'-biphenyl]-4-yl)-2,6,7-trioxabicyclo[2.2.2]octane was obtained as a white solid.

Fourth Step

Into a reaction vessel under a nitrogen atmosphere, 2.0 g (5.1 mmol) of 4-pentyl-1-(2,3',5'-trifluoro-[1,1'-biphenyl]-4-yl)-2,6,7-trioxabicyclo[2.2.2]octane obtained in the third step and 70 mL of THF were put, the resultant mixture was cooled to −70° C., 4.1 mL (6.6 mmol) of n-butyl lithium (1.62 M, hexane solution) was added dropwise thereto, and the resultant mixture was stirred at −70° C. for 1 hour. Next, a THF (10 mL) solution of 1.6 g (7.7 mmol) of dibromodifluoromethane was added dropwise thereto at −70° C., and the resultant mixture was stirred at −70° C. for 1 hour. The resultant mixture was poured into 100 mL of ice water, extracted with toluene, and organic layers were combined, washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 2.4 g of 1-(4'-(bromodifluoromethyl)-2,3',5'-trifluoro-[1,1'-biphenyl]-4-yl)-4-pentyl-2,6,7-trioxabicyclo[2.2.2]octane was obtained as a white solid.

Fifth Step

Into a reaction vessel under a nitrogen atmosphere, 2.4 g (4.6 mmol) of 1-(4'-(bromodifluoromethyl)-2,3',5'-trifluoro-[1,1'-biphenyl]-4-yl)-4-pentyl-2,6,7-trioxabicyclo[2.2.2]octane obtained in the fourth step, 0.68 g (4.6 mmol) of 3,4,5-trifluorophenol, 1.9 g (14 mmol) of potassium carbonate and 40 mL of DMF were put, and the resultant mixture was stirred at 85° C. for 2 hours. The mixture was cooled to room temperature, 100 mL of toluene and 100 mL of water were added thereto, an organic layer was separated and an aqueous layer was extracted with toluene. Organic layers were combined, washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 0.7 g of 1-(4'-(difluoro(3,4,5-trifluorophenoxy) methyl)-2,3',5'-trifluoro-[1,1'-biphenyl]-4-yl)-4-pentyl-2,6,7-trioxabicyclo[2.2.2]octane was obtained as a white solid.

Chemical shifts (δ (ppm)) according to ¹H-NMR analysis are as describe below, and the compound obtained was identified to be 1-(4'-(difluoro(3,4,5-trifluorophenoxy) methyl)-2,3',5'-trifluoro-[, 1'-biphenyl]-4-yl)-4-pentyl-2,6,7-trioxabicyclo[2.2.2]octane. A solvent for measurement was CDCl₃.

Chemical shifts (s (δ (ppm)); 7.51 (m, 1H), 7.47 (m, 1H), 7.41 (m, 1H), 7.19 (m, 2H), 6.99 (m, 2H), 4.13 (s, 6H), 1.4-1.2 (m, 8H), 0.90 (t, 3H).

A transition temperature of compound (No. 106) obtained is as described below.

Transition temperature: C 108.3 (S$_A$ 91.8) N 151.5 I.

Here, an expression of C 108.3 (S$_A$ 91.8) N means that no S$_A$ phase was observed during a temperature increase, transition from a crystal to a nematic phase took place at 108° C., and transition from the nematic phase to a S$_A$ phase was observed at 91.8° C. during a temperature decrease.

Physical Properties of Compound (No. 106)

Liquid crystal composition H including 85% by weight of base liquid crystal A and 15% by weight of 1-(4'-(difluoro (3,4,5-trifluorophenoxy)methyl)-2,3',5'-trifluoro-[biphenyl]-4-yl)-4-pentyl-2,6,7-trioxabicyclo[2.2.2]octane (No. 106) obtained in Example 8 was prepared. Physical properties of liquid crystal composition H obtained were measured, and extrapolated values of physical properties of compound (No. 106) were calculated by extrapolating measured values. Values thereof are as described below.

Maximum temperature (T$_{NI}$)=110.4° C.; dielectric anisotropy (Δ∈)=52.1; optical anisotropy (Δn)=0.144; viscosity (η)=141.1.

Example 9

Synthesis of 1-(4'-(difluoro(3,4-difluorophenoxy) methyl)-2,3,5'-trifluoro-[1,1'-phenyl]-4-yl)-4-pentyl-2,6,7-trioxabicyclo[2.2.2]octane (No. 105)

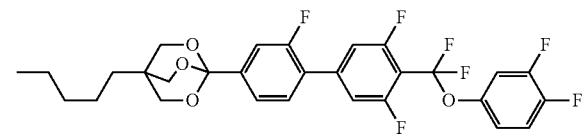 [SMILES: CCCCCC12COC(c3ccc(-c4cc(F)c(C(F)(F)Oc5ccc(F)c(F)c5)c(F)c4)c(F)c3)(OC1)OC2]

Then, 1-(4'-(difluoro(3,4-difluorophenoxy)methyl)-2,3', 5'-trifluoro-[1,1'-biphenyl]-4-yl)-4-pentyl-2,6,7-trioxabicyclo[2.2.2]octane was prepared by performing synthesis in a manner similar to the operations in Example 8 using 3,4-difluorophenol in place of 3,4,5-trifluorophenol in the fifth step in Example 8.

Chemical shifts (δ (ppm)) according to ¹H-NMR analysis are as describe below, and the compound obtained was identified to be 1-(4'-(difluoro(3,4-difluorophenoxy) methyl)-2,3',5'-trifluoro-[1,1'-biphenyl]-4-yl)-4-pentyl-2,6, 7-trioxabicyclo[2.2.2]octane. A solvent for measurement was CDCl₃.

Chemical shifts (δ (ppm)); 7.51 (m, 1H), 7.48 (m, 1H), 7.42 (m, 1H), 7.21 (m, 2H), 7.18 (m, 2H), 7.05 (m, 1H), 4.13 (s, 6H), 1.4-1.2 (m, 8H), 0.90 (t, 3H).

A transition temperature of compound (No. 105) obtained is as described below.

Transition temperature: C 99.1 S$_B$ 164.2 I.

Physical Properties of Compound (No. 105)

Liquid crystal composition I including 85% by weight of base liquid crystal A and 15% by weight of 1-(4'-(di fluoro (3,4-difluorophenoxy)methyl)-2,3',5'-trifluoro-[1,1'-biphenyl]-4-yl)-4-pentyl-2,6,7-trioxabicyclo[2.2.2]octane (No. 105) obtained in Example 9 was prepared. Physical properties of liquid crystal composition I obtained were measured, and extrapolated values of physical properties of compound (No. 105) were calculated by extrapolating measured values. Values thereof are as described below.

Maximum temperature (T$_{NI}$)=121.0° C.; dielectric anisotropy (Δ∈)=38.8; optical anisotropy (Δn)=0.148; viscosity (η)=129.8.

Example 10

Synthesis of 1-(4-(difluoro(3,4,5-trifluorophenoxy)methyl)-3,5-difluorophenyl)-4-propyl-2,6,7-trioxabicyclo[2.2.2]octane (No. 64)

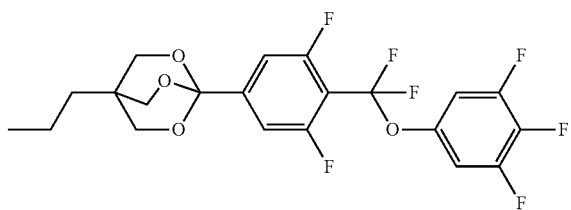 [SMILES: CCCC12COC(c3cc(F)c(C(F)(F)Oc4cc(F)c(F)c(F)c4)c(F)c3)(OC1)OC2]

First Step

Into a reaction vessel under a nitrogen atmosphere, 22.7 g (933 mmol) of magnesium pieces was put, and the resultant mixture was stirred at room temperature for 3 days. Then, 80 mL of THF and one piece of iodine were added thereto. Further, a THF (100 mL) solution of 150 g (777 mmol) of 1-bromo-3,5-difluorobenzene was added little by little at room temperature, and subsequently the resultant mixture was refluxed for 1 hour. Next, the mixture was cooled to −10° C., 75 g (1.710 mmol) of dry ice was added little by little, and the resultant mixture was stirred at room temperature for 1 hour. The reaction liquid was poured into 500 mL of 1 N hydrochloric acid, and extracted with ethyl acetate. Organic layers were combined, washed with water, and dried over anhydrous magnesium sulfate. Then, an insoluble matter was separated by filtration and then a filtrate was concentrated under reduced pressure. A residue was washed with n-heptane, and thus 66.3 g of 3,5-difluorobenzoic acid was obtained as a white solid.

Second Step

Into a reaction vessel under a nitrogen atmosphere, 35.0 g (221 mmol) of 3,5-difluorobenzoic acid obtained in the first step, 28.8 g (221 mmol) of 3-propyl-3-hydroxymethyloxetane, 2.7 g (22 mmol) of 4-dimethylaminopyridine, and 325 mL of dichloromethane were put, a dichloromethane (175 mL) solution of 48.0 g (232 mmol) of dicyclohexylcarbodiimide was added dropwise thereto at room temperature, and the resultant mixture was stirred at room temperature for 3 hours. An insoluble matter was separated by filtration, and a solution was sequentially washed with 1 N hydrochloric acid, an aqueous solution of sodium hydrogencarbonate and water, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 52.2 g of 3,5-difluoro-benzoate(3-propyloxetane-3-yl)methyl was obtained as a light yellow liquid.

Third Step

Into a reaction vessel under a nitrogen atmosphere, 52.2 g (193 mmol) of 3,5-difluoro-benzoate(3-propyloxetane 3-yl)methyl obtained in the second step and 350 mL of dichloromethane were put, the resultant mixture was cooled to −70° C., and 6.1 mL (48 mmol) of boron trifluoride-diethyl ether complex was added dropwise thereto. The resultant mixture was warmed to room temperature, and stirred for 24 hours. Then, 10 mL (72 mmol) of triethylamine was added thereto, and the resultant mixture was concentrated by means of a rotary evaporator. Subsequently, 300 mL of diethyl ether was added thereto, and the resultant mixture was washed with water and dried over anhydrous magnesium sulfate. An insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 37.5 g of 4-propyl-1-(3,5-difluorophenyl)-2,6,7-trioxabicyclo[2.2]octane was obtained as a white solid.

Fourth Step

Into a reaction vessel under a nitrogen atmosphere, 37.5 g (139 mmol) of 4-propyl-1-(3,5-difluorophenyl)-2,6,7-trioxabicyclo[2.2.2]octane obtained in the third step and 830 mL of THF were put, the resultant mixture was cooled to −70° C., 83 mL (139 mmol) of n-butyl lithium (1.67 M, hexane solution) was added dropwise thereto, and the resultant mixture was stirred at −70° C. for 1 hour. Next, a THF (100 mL) solution of 34.9 g (166 mmol) of dibromodifluoromethane was added dropwise thereto at −70° C., and the resultant mixture was stirred at −70° C. for 1 hour. The resultant mixture was poured into 1,000 mL of ice water, extracted with toluene, and organic layers were combined, washed sequentially with saturated brine and water, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 50.9 g of 1-(4-(bromodifluoromethyl)-3,5-difluorophenyl)-4-propyl-2,6,7-trioxabicyclo[2.2.2]octane was obtained as a white solid.

Fifth Step

Into a reaction vessel under a nitrogen atmosphere, 10.0 g (25.1 mmol) of 1-(4-(bromodifluoromethyl)-3,5-difluorophenyl)-4-propyl-2,6,7-trioxabicyclo[2.2.2]octane obtained in the fourth step, 4.5 g (30 mmol) of 3,4,5-trifluorophenol, 3.5 g (25 mmol) of potassium carbonate, and 2.6 g (7.5 mmol) of tetrabutyl phosphonium bromide, 50 mL of $H_2O$ and 5 mL of n-heptane were put, and the resultant mixture was refluxed at 82 to 85° C. for 10 hours. The mixture was cooled to room temperature, 100 mL of toluene and 100 mL of water were added thereto, an organic layer was separated, and an aqueous layer was extracted with toluene. Organic layers were combined, washed sequentially with an aqueous solution of sodium hydrogencarbonate and water, and dried over anhydrous magnesium sulfate, and then an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (isopropanol/ethyl acetate=80/20 in a volume ratio), and thus 5.9 g of 1-(4-(difluoro(3,4,5-trifluorophenoxy)methyl)-3,5-difluorophenyl)-4-propyl-2,6,7-trioxabicyclo[2.2.2]octane was obtained as a white solid.

Chemical shifts (δ (ppm)) according to $^1$H-NMR analysis are as describe below, and the compound obtained was identified to be 1-(4-(difluoro(3,4,5-trifluorophenoxy)methyl)-3,5-difluorophenyl)-4-propyl-2,6,7-trioxabicyclo[2.2.2]octane. A solvent for measurement was $CDCl_3$.

Chemical shifts (δ (ppm)); 7.25 (m, 2H), 6.94 (m, 2H), 4.10 (s, 6H), 1.3-1.2 (m, 4H), 0.94 (t, 3H).

A transition temperature of compound (No. 64) obtained is as described below.

Transition temperature: C 94.5 I.

Physical Properties of Compound (No. 64)

Liquid crystal composition J including 90% by weight of base liquid crystal A and 10% Y, by weight of 1-(4'-(difluoro (3,4,5-trifluorophenoxy)methyl)-2,3',5'-trifluoro-[1,1'-biphenyl]-4-yl)-4-pentyl-2,6,7-trioxabicyclo[2.2.2]octane (No. 51) obtained in Example 10 was prepared. Physical properties of liquid crystal composition J obtained were measured, and extrapolated values of physical properties of compound (No. 64) were calculated by extrapolating measured values. Values thereof are as described below.

Maximum temperature ($T_{NI}$)=15.7° C.; dielectric anisotropy ($\Delta\varepsilon$)=46.1; optical anisotropy ($\Delta n$)=0.087; viscosity ($\eta$)=76.7.

Example 11

Synthesis of 1-(4-(difluoro(3,4-difluorophenoxy) methyl)-3,5-difluorophenyl)-4-propyl-2,6,7-trioxabicyclo[2.2.2]octane (No. 63)

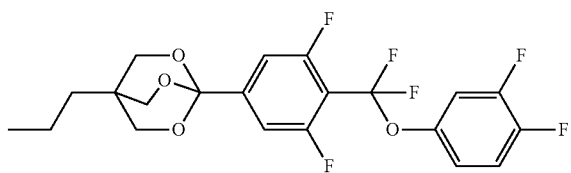 [SMILES: CCCC12COC(c3cc(F)c(C(F)(F)Oc4ccc(F)c(F)c4)c(F)c3)(OC1)OC2]

Then, 1-(4-(difluoro(3,4-difluorophenoxy)methyl)-3,5-difluorophenyl)-4-propyl-2,6,7-trioxabicyclo[2.2.2]octane was prepared by performing synthesis in a manner similar to the operations in Example 10 using 3,4-difluorophenol in place of 3,4,5-trifluorophenol in the fifth step in Example 10.

Chemical shifts ($\delta$ (ppm)) according to $^1$H-NMR analysis are as described below, and the compound obtained was identified to be 1-(4-(difluoro(3,4-difluorophenoxy) methyl)-3,5-difluorophenyl)-4-propyl-2,6,7-trioxabicyclo[2.2.2]octane. A solvent for measurement was CDC$_3$.

Chemical shifts ($\delta$ (ppm)); 7.25 (m, 2H), 7.13 (m, 2H), 7.00 (m, 1H), 4.10 (s, 6H), 1.3-1.2 (m, 4H), 0.94 (t, 3H).

A transition temperature of compound (No. 63) obtained is as described below.

Transition temperature: C 102.0 I.

Physical Properties of Compound (No. 63)

Liquid crystal composition K including 90% by weight of base liquid crystal A and 10% by weight of 1-(4-(difluoro (3,4-difluorophenoxy)methyl)-3,5-difluorophenyl)-4-propyl-2,6,7-trioxabicyclo[2.2.2]octane (No. 63) obtained in Example 11 was prepared. Physical properties of liquid crystal composition K obtained were measured, and extrapolated values of physical properties of the liquid crystal compound (No. 63) were calculated by extrapolating measured values. Values thereof are as described below.

Maximum temperature ($T_{NI}$)=23.7° C.; dielectric anisotropy ($\Delta\varepsilon$)=35.2; optical anisotropy ($\Delta n$)=0.087; viscosity ($\eta$)=75.4.

Comparative Example 1

Synthesis of 4-propyl-1-(4-((3,4,5-trifluorophenoxy) methyl)cyclohexyl)-2,6,7-trioxabicyclo[2.2.2]octane (Comparative Compound 1)

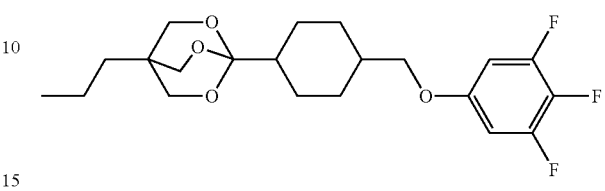

First Step

Into a reaction vessel under a nitrogen atmosphere, 10.5 g (73 mmol) of cyclohexane-1,4-diylmethanol, 10.7 g (73 mmol) of 3,4,5-trifluorophenol, 24.7 g (94 mmol) of triphenyl phosphine, and 200 mL of THF were put, and 43 mL (94 mmol) of diethyl azodicarboxylate (2.2 M, toluene solution) was added dropwise at 3 to 14° C. in an ice bath. The resultant mixture was stirred at room temperature for 20 hours, and then 50 mL of a saturated aqueous solution of sodium thiosulfate was added thereto. The resultant mixture was extracted with diethyl ether, and the resultant extract was washed with saturated brine, and dried over anhydrous magnesium sulfate, and then an insoluble matter was separated by filtration and then a filtrate was concentrated under reduced pressure. A residue was purified according to fractionation by column chromatography using a mixed solvent of heptane and ethyl acetate (ethyl acetate:heptane=1:2 in a volume ratio) as an eluent and silica gel as a filler, and thus 4.41 g of (4-((3,4,5-trifluorophenol)methyl)cyclohexyl) methanol was obtained as a yellow liquid.

Second Step

Into a reaction vessel under a nitrogen atmosphere, 4.41 g (7.2 mmol) of (4-((3,4,5-trifluorophenol)methyl)cyclohexyl)methanol obtained in the first step and 40 mL of acetone were put. A Jones reagent was added dropwise thereto in an ice bath until an orange color did not fade away, and then 2-propanol was added thereto. An insoluble matter was separated by filtration, a filtrate was concentrated by means of a rotary evaporator, diethyl ether was added thereto, and then washed with water. The resultant mixture was dried over anhydrous magnesium sulfate, and then an insoluble matter was separated by filtration and then a filtrate was concentrated under reduced pressure. A residue was purified according to fractionation by column chromatography using ethyl acetate as an eluent and silica gel as a filler. The resultant mixture was further purified by recrystallization (n-heptane/ethanol=50/50 in a volume ratio), and thus 2.1 g of 4-((3,4,5-trifluorophenol)methyl)cyclohexanecarboxylic acid was obtained as a light yellow solid.

Third Step

Into a reaction vessel under a nitrogen atmosphere, 2.1 g (7.4 mmol) of 4-((3,4,5-trifluorophenol)methyl)cyclohexanecarboxylic acid obtained in the second step, 1.7 g (8.8 mmol) of 1-ethyl-3-(3-dimethylaminopropyl)carbodiimide hydrochloride, 0.09 g (0.7 mmol) of 4-dimethylaminopyridine and 60 mL of dichloromethane were put, and a dichloromethane (20 mL) solution of 1.15 g (8.8 mmol) of 3-propyl-3-hydroxymethyloxetane was added dropwise thereto at room temperature. The resultant mixture was stirred at room temperature for 20 hours, and then concentrated by means of a rotary evaporator, ethyl acetate was added thereto, and washed with water. The resultant mixture was dried over anhydrous magnesium sulfate, and then an insoluble matter was separated by filtration and a solvent is distilled off. A residue was purified according to fractionation by column chromatography using a mixed solvent of heptane and ethyl acetate (ethyl acetate:heptane=1:4 in a volume ratio) as an eluent and silica gel as a filler, and thus 2.35 g of (3-propyloxetane-3-yl)methyl-4-((3,4,5-trifluorophenoxy)methyl)cyclohexanecarboxylate was obtained as a yellow liquid.

Fourth Step

Into a reaction vessel under a nitrogen atmosphere, 2.35 g (5.87 mmol) of (3-propyloxetane-3-yl)methyl-4-((3,4,5-trifluorophenoxy)methyl)cyclohexanecarboxylate obtained in the third step and 50 mL of dichloromethane were put, the resultant mixture was cooled to −70° C., and 0.18 mL (1.5 mmol) of boron trifluoride-diethyl ether complex was added dropwise thereto. The mixture was warmed to room temperature, and stirred for 15 hours. Then, 0.7 mL (5 mmol) of triethylamine was added thereto, and the resultant mixture was concentrated by means of a rotary evaporator. Then, 30 mL of diethyl ether was added thereto, and the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethanol=80/20 in a volume ratio), and thus 0.9 g of 4-propyl-1-(4-((3,4,5-trifluorophenoxy)methyl)cyclohexyl)-2,6,7-trioxabicyclo[2.2.2]octane was obtained as a white solid.

Chemical shifts (δ (ppm)) according to $^1$H-NMR analysis are as described below, and the compound obtained was identified to be 4-propyl-1-(4-((3,4,5-trifluorophenoxy)methyl)cyclohexyl)-2,6,7-trioxabicyclo[2.2.2]octane. A solvent for measurement was CDCl$_3$.

Chemical shifts (δ (ppm)); 6.47 (m, 2H), 3.90 (s, 6H), 3.64 (d, 2H), 1.91 (m, 4H), 1.71 (m, 1H), 1.56 (m, 1H), 1.3-1.1 (m, 6H), 0.98 (m, 2H), 0.90 (t, 3H).

A transition temperature of compound obtained (No. 51) is as described below.

Transition temperature: C 123.9 (S$_B$ 112.7) I.

Physical Properties of Compound (Comparative Compound 1)

Liquid crystal composition L including 95% by weight of base liquid crystal A and 5% by weight of 4-propyl-1-(4-((3,4,5-trifluorophenoxy)methyl)cyclohexyl)-2,6,7-trioxabicyclo[2.2.2]octane (comparative compound 1) obtained in Reference Example 1 was prepared. Physical properties of liquid crystal composition L obtained were measured, and extrapolated values of physical properties of compound (comparative compound 1) were calculated by extrapolating measured values. Values thereof are as described below.

Maximum temperature (T$_{NI}$)=49.7° C.; dielectric anisotropy (Δ∈)=29.8; optical anisotropy (Δn)=0.077; viscosity (η)=129.0.

Example 12

Synthesis of 4-propyl-1-(3,4,5-trifluorophenyl)-2,6,7-trioxabicyclo[2.2.2]octane (No. 5)

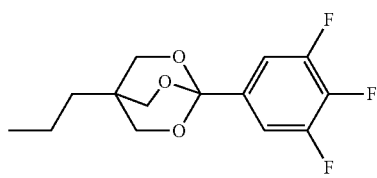 [SMILES: CCCC12COC(c3cc(F)c(F)c(F)c3)(OC1)OC2]

Then, 4-propyl-1-(3,4,5-trifluorophenyl)-2,6,7-trioxabicyclo[2.2.2]octane was prepared by performing synthesis in a manner similar to the operations in the third step and the fourth step in Example 1 using 3,4,5-trifluorobenzoic acid in place of 4-(3,4,5-trifluorophenyl)cyclohexanecarboxylic acid.

Chemical shifts (δ(ppm)) according to $^1$H-NMR analysis are as described below, and the compound obtained was identified to be 4-propyl-1-(3,4,5-trifluorophenyl)-2,6,7-trioxabicyclo[2.2.2]octane. A solvent for measurement was CDCl$_3$.

Chemical shifts (δ (ppm)); 7.25 (t, 2H), 4.08 (s, 6H), 1.3-12 (m, 4H), 0.91 (t, 3H).

A transition temperature of compound obtained (No. 5) is as described below.

Transition temperature: C 127.5 I.

Physical Properties of Compound (No. 5)

Liquid crystal composition M including 95% by weight of base liquid crystal A and 5% by weight of 4-propyl-1-(3,4,5-trifluorophenyl)-2,6,7-trioxabicyclo[2.2.2]octane (No. 5) obtained in Example 12 was prepared. Physical properties of liquid crystal composition M obtained were measured, and extrapolated values of physical properties of compound (No. 5) were calculated by extrapolating measured values. Values thereof are as described below.

Maximum temperature (T$_{NI}$)=−74.3° C.; dielectric anisotropy (Δ∈)=32.1; optical anisotropy (Δn)=0.017; viscosity (η)=69.2.

Example 13

Synthesis of 1-difluoro(3,4,5-trifluorophenoxy)methyl)-4-pentyl-2,6,7-trioxabicyclo[2.2.2]octane (No. 17)

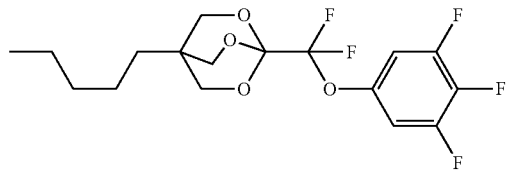 [SMILES: CCCCCC12COC(C(F)(F)Oc3cc(F)c(F)c(F)c3)(OC1)OC2]

First Step

Into a reaction vessel under a nitrogen atmosphere, 25.0 g (123 mmol) of 2-bromo-2,2-difluoroacetic acid ethyl ester, 18.2 g (123 mmol) of 3,4,5-trifluorophenol, 17.02 g (123 mmol) of potassium carbonate, 3.97 g (12.3 mmol) of tetrabutylammonium bromide and 150 mL of DMF were put, and the resultant mixture was stirred at 90° C. for 3 hours. Then, 100 mL of saturated brine was added thereto, the resultant mixture was extracted with diethyl ether, the resultant extract was washed with a saturated aqueous solution of sodium hydrogencarbonate, and subsequently with water, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:10 in a volume ratio) as an eluent and silica gel as a filler, and thus 25.0 g of ethyl 2,2-difluoro-2-(3,4,5-trifluorophenoxy)acetate was obtained.

Second Step

Into a reaction vessel under a nitrogen atmosphere, 12.0 g of ethyl 2,2-difluoro-2-2-(3,4,5-trifluorophenoxy)acetate obtained in the first step, 140 mL of methanol and 23 mL of aqueous solution of sodium hydroxide (2 N) were put, and the resultant mixture was stirred at room temperature for 2 hours. Hydrochloric acid (1 N) was added thereto until the mixture acidified. The resultant mixture was extracted with ethyl acetate, and the resultant extract was washed with water, and dried over anhydrous magnesium sulfate. Then, an insoluble matter was separated by filtration and then a filtrate was concentrated under reduced pressure. A residue was washed with heptane and dried, and thus 7.25 g of 2,2-difluoro-2-(3,4,5-trifluorophenoxy)acetic acid was obtained.

Third Step

Into a reaction vessel under a nitrogen atmosphere, 7.25 g (29.9 mmol) of 2,2-difluoro-2-(3,4,5-trifluorophenoxy)acetic acid obtained in the second step, 4.74 g (29.9 mmol) of 3-pentyl-3-hydroxymethyloctane, 0.37 g (2.99 mmol) of 4-dimethylaminopyridine and 150 mL of dichloromethane were put, and the resultant mixture was cooled to 0° C. Then, 50 mL of dichloromethane (50 mL) solution of 6.49 g (31.4 mmol) of dicyclohexylcarbodiimide was added dropwise thereto at 0° C., and the resultant mixture was stirred at room temperature for 15 hours. Then, an insoluble matter was separated by Celite filtration, a filtrate was washed sequentially with hydrochloric acid (1 N), a saturated aqueous solution of sodium hydrogencarbonate and water, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 5.64 g of (3-pentyloxetane-3-yl)methyl 2,2-difluoro-2-(3,4,5-trifluorophenoxy)acetate was obtained.

Fourth Step

Into a reaction vessel under a nitrogen atmosphere, 5.64 g (14.8 mmol) of (3-pentyloxetane-3-yl)methyl 2,2-difluoro-2-3,4,5-trifluorophenoxy)acetate obtained in the third step and 60 mL of dichloromethane were put, the resultant mixture was cooled to −70° C., and 0.47 mL (3.7 mmol) of boron trifluoride-diethyl ether complex was added dropwise thereto. The resultant mixture was warmed to room temperature, and stirred for 24 hours. Then, 0.8 mL (6 mmol) of triethylamine was added thereto, and the resultant mixture was concentrated by means of a rotary evaporator. Then, 40 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:5 in a volume ratio) as an eluent and silica gel as a filler. The resultant mixture was further purified by recrystallization (heptane/ethanol=80/20 in a volume ratio), and thus 2.5 g of 1-(difluoro(3,4,5-trifluorophenoxy)methyl)-4-pentyl-2,6,7-trioxabicyclo[2.2.2]octane was obtained as a white solid.

Chemical shifts (δ (ppm)) according to $^1$H-NMR analysis are as described below, and the compound obtained was identified to be 1-(difluoro(3,4,5-trifluorophenoxy)methyl)-4-pentyl-2,6,7-trioxabicyclo[2.2.2]octane. A solvent for measurement was $CDCl_3$.

Chemical shifts (δ (ppm)); 6.92 (t, 2H), 4.11 (s, 6H), 1.4-1.2 (m, 8H), 0.89 (t, 3H).

A transition temperature of compound (No. 17) obtained is as described below.

Transition temperature: C 70.5 (SB 64.7 I).

Physical Properties of Compound (No. 17)

Liquid crystal composition N including 85% by weight of base liquid crystal A and 15% by weight of 1-(difluoro(3,4,5-trifluorophenoxy)methyl)-4-pentyl-2,6,7-trioxabicyclo[2.2.2]octane (No. 17) obtained in Example 13 was prepared. Physical properties of liquid crystal composition N obtained were measured, and extrapolated values of physical properties of compound (No. 17) were calculated by extrapolating measured values. Values thereof are as described below.

Maximum temperature (T)=−83.0° C.; dielectric anisotropy (Δ∈)=20.6; optical anisotropy (Δn)=−0.010; viscosity (η)=118.9.

Example 14

Synthesis of 4-(4-pentylcyclohexyl)-1-(3,4,5-trifluorophenyl)-2,6,7-trioxabicyclo[2.2.2]octane (No. 26)

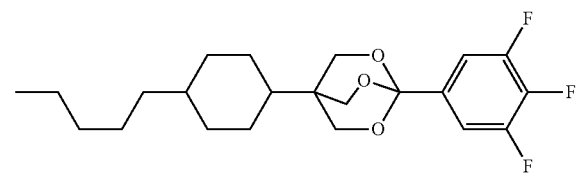 [SMILES: CCCCCC1CCC(C23COC(c4cc(F)c(F)c(F)c4)(OC2)OC3)CC1]

First Step

Into a reaction vessel under a nitrogen atmosphere, 10.5 g (59.5 mmol) of 3,4,5-trifluorobenzoic acid, 13.7 g (71.4 mmol) of 1-ethyl-3-(3-dimethylaminopropyl)carbodiimide hydrochloride, 0.72 g (6.0 mmol) of 4-dimethylaminopyridine and 100 mL of dichloromethane were put, a dichloromethane (10 mL) solution of 4.8 g (65.5 mmol) of diethylamine was added dropwise thereto at room temperature, and the resultant mixture was stirred at room temperature for 15 hours. Then, 50 mL of water was added and the resultant mixture was extracted with diethyl ether, and the resultant extract was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate: heptane=1:4 in a volume ratio) as an eluent and silica gel as a filler, and thus 11.4 g of N,N-diethyl-3,4,5-trifluorobenzamide was obtained.

Second Step

Into a reaction vessel under a nitrogen atmosphere, 9.36 g of N,N-diethyl-3,4,5-trifluorobenzamide obtained in the first step and 45 mL of dichloromethane were put, 3.7 mL (43 mmol) of oxalyl chloride was added dropwise thereto at room temperature, and the resultant mixture was stirred at room temperature for 30 minutes, and then at 40° C. for 3 hours. The mixture was cooled to 0° C., 4.7 mL (29 mmol) of triethylamine trihydrofluoride was added dropwise thereto, and subsequently 8.2 mL (58 mmol) of triethylamine was added dropwise thereto, and the resultant mixture was stirred at room temperature for 30 minutes. A reaction mixture was filtered, and a solid separated by filtration was washed with hexane, and then a filtrate was concentrated under reduced pressure. A small amount of hexane was added to the residue, the resultant mixture was filtered, a filtrate was concentrated under reduced pressure, and a residue was distilled under reduced pressure of 1 mmHg at 40° C., and thus 9.7 g of N-(difluoro(3,4,5-trifluorophenyl)methyl-N-ethylethanamine was obtained.

Third Step

Into a reaction vessel under a nitrogen atmosphere, 7.30 g (183 mmol) of well dried and powdery sodium hydroxide, 100 mL of acetonitrile and 13.8 g (459 mmol) of paraformaldehyde were put, and while stirring the resultant mixture at room temperature, an acetonitrile (30 mL) solution of 30.0 g (153 mmol) of 2-(4-pentylcyclohexyl)acetaldehyde was added dropwise thereto over 40 minutes. After completion of dropwise addition, temperature was 34° C. The resultant mixture was stirred at room temperature for 30 minutes, and then heated to 70° C. and stirred for 20 minutes. The resultant mixture was cooled to room temperature, an insoluble matter was separated by filtration, and a solvent was distilled off under reduced pressure. A residue obtained was purified according to fractionation by column chromatography using ethyl acetate as an eluent and silica gel as a filler and dried, and thus 11.0 g of 2-(hydroxymethyl)-2-(4-pentylcyclohexyl)propane-1,3-diol was obtained as a white solid.

Fourth Step

Into a reaction vessel under a nitrogen atmosphere, 2.48 g (9.29 mmol) of 2-(hydroxymethyl)-2-(4-pentylcyclohexyl)propane-1,3-diol obtained in the third step, 30 mL of DMF, and 1.8 g of molecular sieve 4A were put, and the resultant mixture was stirred at room temperature for 1 hour. The mixture was cooled to 0° C. and 2.35 g (9.29 mmol) of N-difluoro(3,4,5-trifluorophenyl)methyl-N-ethylethanamine obtained in the second step was added dropwise thereto, and the resultant mixture was stirred at room temperature for 2 hours. Then, 1.5 mL of triethylamine was added, and then the resultant mixture was poured into 100 mL of aqueous solution of sodium hydroxide (2 N), and the resultant mixture was extracted with dichloromethane. The resultant extract was dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (acetonitrile), and thus 1.1 g of 4-(4-pentylcyclohexyl)-1-(3,4,5-trifluorophenyl)-2,6,7-trioxabicyclo[2.2.2]octane was obtained as a white solid.

Chemical shifts (δ(ppm)) according to $^1$H-NMR analysis are as described below, and the compound obtained was identified to be 4-(4-pentylcyclohexyl)-1-(3,4,5-trifluorophenyl)-2,6,7-trioxabicyclo[2.2.2]octane. A solvent for measurement was CDCl$_3$.

Chemical shifts (δ (ppm)); 7.24 (t, 2H), 4.11 (s, 6H), 1.81 (m, 2H), 1.64 (m, 2H), 1.4-1.1 (m, 10H), 1.01 (m, 2H), 0.9-0.8 (m, 5H).

A transition temperature of compound (No. 26) obtained is as described below.

Transition temperature: C 155.3 I.

Physical Properties of Compound (No. 26)

Liquid crystal composition O including 95% by weight of base liquid crystal A and 5% by weight of 4-(4-pentylcyclohexyl)-1-(3,4,5-trifluorophenyl)-2,6,7-trioxabicyclo[2.2.2]octane (No. 26) obtained in Example 14 was prepared. Physical properties of liquid crystal composition O obtained were measured, and extrapolated values of physical properties of compound (No. 26) were calculated by extrapolating measured values.

Values thereof are as described below.

Maximum temperature ($T_N$1)=89.7° C.; dielectric anisotropy (Δε)=20.2; optical anisotropy (Δn)=0.097; viscosity (η)=87.2.

Example 15

Synthesis of 4-pentyl-1-(2,3',4',5'-tetrafluoro[1,1'-biphenyl]-4-yl)-2,6,7-trioxabicyclo[2.2.2]octane (No. 34)

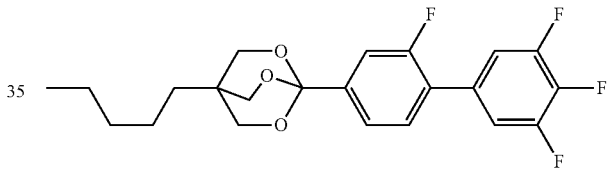

First Step

Into a reaction vessel under a nitrogen atmosphere, 50.0 g (166 mmol) of 4-bromo-2-fluoro-1-iodobenzene, 29.3 g (166 mmol) of (3,4,5-trifluorophenyl)boronic acid, 45.9 g (332 mmol) of potassium carbonate, 10.7 g (33.2 mmol) of tetrabutylammonium bromide (TBAB), 2.7 g (2.3 mmol) of tetrakis(triphenyl phosphine)palladium, 300 mL of toluene and 200 mL of 1-butanol were put, and the resultant mixture was subjected to heating reflux for 6 hours. A reaction liquid was poured into 300 mL of water, and then the resultant mixture was extracted with toluene, and the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using heptane as an eluent and silica gel as a filler, and thus 36.8 g of 4-bromo-2,3',4',5'-tetrafluoro-1,1'-biphenyl was obtained.

Second Step

Into a reaction vessel under a nitrogen atmosphere, 30.0 g (98.3 mmol) of 4-bromo-2,3',4',5'-tetrafluoro-1,1'-biphenyl obtained in the first step and 30 mL of THF were put, 98.3 mL (128 mmol) of isopropylmagnesium chloride-lithium chloride complex solution (1.3 M) was added dropwise thereto at room temperature, and the resultant mixture was stirred at room temperature for 2 hours. Thereto, 25 g (570 mmol) of dry ice was added at 0° C., and the resultant mixture was warmed to room temperature and then stirred for 15 hours. The mixture was cooled to 0° C. and 70 mL of hydrochloric acid (3 M) was added dropwise thereto, extracted with ethyl acetate, and the resultant extract was washed with water and dried over anhydrous magnesium sulfate. Then, an insoluble matter was separated by filtration and then a filtrate was concentrated under reduced pressure. A residue was recrystallized in toluene, and thus 22.0 g of 2,3',4',5'-tetrafluoro[1,1'-biphenyl]-4-carboxylic acid was obtained.

Third Step

Into a reaction vessel under a nitrogen atmosphere, 10.0 g (37.0 mmol) of 2,3',4',5'-tetrafluoro[1,1'-biphenyl]-4-carboxylic acid obtained in the second step, 5.9 g (37 mmol) of 3-pentyl-3-hydroxymethyloxetane, 4.5 g (37 mmol) of 4-dimethylaminopyridine and 100 mL of dichloromethane were put, and the resultant mixture was cooled to 0° C. Then, a dichloromethane (50 mL) solution of 8.0 g (39 mmol) of dicyclohexylcarbodiimide was added dropwise thereto at 0° C., and the resultant mixture was stirred at room temperature for 15 hours. Then, an insoluble matter was separated by Celite filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 13.9 g of (3-pentyloxetane-3-yl)methyl 2,3',4',5'-tetrafluoro-[1,1'-biphenyl]-4-carboxylate was obtained.

Fourth Step

Into a reaction vessel under a nitrogen atmosphere, 13.9 g (33.9 mmol) of (3-pentyloxetane-3-yl)methyl 2,3',4',5'-tetrafluoro-[1,1'-biphenyl]-4-carboxylate obtained in the third step and 70 mL of dichloromethane were put and cooled to −70° C., and 1.2 g (8.5 mmol) of boron trifluoride-diethyl ether complex was added dropwise thereto. The resultant mixture was warmed to room temperature, and stirred for 15 hours. Then, 5.0 mL (37 mmol) of triethylamine was added thereto, and the resultant mixture was concentrated by means of a rotary evaporator. Then, 100 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using dichloromethane as an eluent and silica gel as a filler. The resultant mixture was further purified by recrystallization (heptane), and thus 9.1 g of 4-pentyl-1-(2,3',4',5'-tetrafluoro[1,1'-biphenyl]-4-yl)-2,6,7-trioxabicyclo[2.2.2]octane was obtained as a white solid.

Chemical shifts (δ (ppm)) according to ¹H-NMR analysis are as describe below, and the obtained compound was identified to be 4-pentyl-1-(2,3',4',5'-tetrafluoro[1,1'-biphenyl]-4-yl)-2,6,7-trioxabicyclo[2.2.2]octane. A solvent for measurement was CDC$_3$.

Chemical shifts (δ (ppm)); 7.5-7.4 (m, 2H), 7.34 (t, 1H), 7.15 (m, 2H), 4.11 (s, 6H), 1.4-1.2 (m, 8H), 0.89 (t, 3H).

A transition temperature of compound (No. 34) obtained is as described below.

Transition temperature: C 110.2 (N 73.1 I).

Physical Properties of Compound (No. 34)

Liquid crystal composition N including 90% by weight of base liquid crystal A and 10% by weight of 4-pentyl-1-(2, 3',4',5'-tetrafluoro[1,1'-biphenyl]-4-yl)-2,6,7-trioxabicyclo [2.2.2]octane (No. 34) obtained in Example 15 was prepared. Physical properties of liquid crystal composition N obtained were measured, and extrapolated values of physical properties of compound (No. 34) were calculated by extrapolating measured values. Values thereof are as described below.

Maximum temperature (T$_{NI}$)=65.7° C.; dielectric anisotropy (Δ∈)=36.1; optical anisotropy (Δn)=0.117; viscosity (η)=122.9.

Example 16

Synthesis of 4-pentyl-1-(4'-(trifluoromethyl)-[1,1'-bi (cyclohexane)]-3'-en-4-yl)-2,6,7-trioxabicyclo[2.2.2] octane (No. 40)

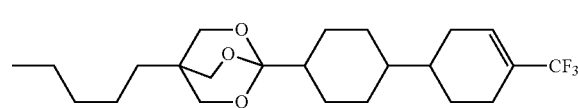 [SMILES: CCCCCC12COC(C3CCC(C4CC=C(C(F)(F)F)CC4)CC3)(OC1)OC2]

First Step

Into a reaction vessel under a nitrogen atmosphere, 17.2 g (64.0 mmol) of 4-(1,4-dioxaspiro[4,5]decane-8-yl)cyclohexanone, 10.0 g (70.0 mmol) of trimethyl(trifluoromethyl) silane and 100 mL of THF were put, and 70 mL (70 mmol) of tetrabutylammonium fluoride (1.0 M, THF solution) was added dropwise thereto at 0° C. The resultant mixture was returned to room temperature and 150 mL of hydrochloric acid (2 N) was added thereto, and extracted with diethyl ether, the resultant extract was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:2 in a volume ratio) as an eluent and silica gel as a filler, and thus 8.0 g of 4-(1,4-dioxaspiro[4,5]decane-8-yl)-1-(trifluoromethyl)cyclohexanol was obtained.

Second Step

Into a reaction vessel under a nitrogen atmosphere, 6.4 g (20.8 mmol) of 4-(1,4-dioxaspiro[4,5]decane-8-yl)-1-(trifluoromethyl)cyclohexanol obtained in the first step and 60 mL of THF were put, 4.7 mL (35.6 mmol) of N,N-diethylaminosulfur trifluoride was added dropwise thereto at room temperature, and the resultant mixture was stirred at 70° C. for 1 hour. The reaction mixture was poured into water, the resultant mixture was extracted with toluene, and the resultant extract was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 6.6 g of 8-(4-(trifluoromethyl)cyclohexy-3-en-1-yl)-1,4-dioxaspiro[4,5]decane was obtained.

Third Step

Into a reaction vessel under a nitrogen atmosphere, 6.6 g (23 mmol) of 8-(4-(trifluoromethyl)cyclohexy-3-en-1-yl)-1, 4-dioxaspiro[4,5]decane obtained in the second step, 100 mL of toluene and 8.5 mL of formic acid were put, and the resultant mixture was refluxed at 92° C. The resultant mixture was returned to room temperature, washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 5.1 g of 4'-(trifluoromethyl)-[1,1'-bi(cyclohexane)]-3'-en-4-one was obtained.

Fourth Step

Into a reaction vessel under a nitrogen atmosphere, 8.4 g (25 mmol) of chloro(methoxymethyl)triphenylphosphorane and 50 mL of THF were put, a THF (15 mL) solution of 2.8 g (25 mmol) of potassium tert-butoxide was added dropwise thereto at −15° C., and the resultant mixture was stirred at −15° C. for 1 hour. Then, a THF (20 mL) solution of 5.1 g (21 mmol) of 4'-(trifluoromethyl)-[1,1'-bi(cyclohexane)]-3'-en-4-one obtained in the third step was added dropwise thereto at −15° C., and the resultant mixture was stirred at −15° C. for 1 hour. The mixture was returned to room temperature, 100 mL of water was added thereto, and the resultant mixture was extracted with toluene, and the resultant extract was washed with water and dried over anhydrous magnesium sulfate. Then, an insoluble matter was separated by filtration and then a filtrate was concentrated under reduced pressure. A residue was dissolved in a small amount of toluene, and while stirring, the resultant solution was poured into 200 mL of heptane. Then, an insoluble matter was separated by filtration, and a solvent is distilled off under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 4.9 g of 4'-(methoxymethylene)-4-(trifluoromethyl)-[1,1'-bi(cyclohexane)]-3-en was obtained.

Fifth Step

Into a reaction vessel under a nitrogen atmosphere, 4.9 g (18 mmol) of 4'-(methoxymethylene)-4-(trifluoromethyl)-[1,1'-bi(cyclohexane)]-3-en obtained in the fourth step, 30 mL of acetone and 2.8 mL of hydrochloric acid (4 N) were put, and the resultant mixture was stirred at room temperature for 1 hour. Then, 20 mL of water was added thereto, the resultant mixture was extracted with toluene, and the resultant extract was washed with water, and a solvent was distilled off by means of a rotary evaporator. Then, 50 mL of toluene, 50 mL of ethanol, 2.2 g of sodium hydroxide and 9 mL of water were added thereto, and the resultant mixture was stirred at room temperature for 6 hours. The reaction mixture was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 4.3 g of 4-(trifluoromethyl)-[1,1'-bi(cyclohexane)]-3-en-4-carbaldehyde was obtained.

Sixth Step

Into a reaction vessel, 4.3 g (16 mmol) of 4-(trifluoromethyl)-[1,1'-bi(cyclohexane)]-3-en-4-carboaldehyde obtained in the fifth step and 100 mL of acetone were put, and a Jones reagent was added dropwise thereto at 0° C. until an orange color did not fade away. Then, 2 mL of isopropanol and 4 g of sodium hydrogencarbonate were added thereto, the resultant mixture was filtered, the resultant solid was rinsed with acetone, and a filtrate was concentrated under reduced pressure. Then, 20 mL of water was added thereto, the resultant mixture was extracted with ethyl acetate, the resultant extract was washed with water, and a solvent was distilled off by means of a rotary evaporator. A residue was purified according to fractionation by column chromatography using ethyl acetate as an eluent and silica gel as a filler. The resultant mixture was further purified by recrystallization (heptane), and thus 2.5 g of 4-(trifluoromethyl)-[1,1'-bi(cyclohexane)]-3-ene-4-carboxylic acid was obtained.

Seventh Step

Into a reaction vessel under a nitrogen atmosphere, 2.5 g (8.9 mmol) of 4-(trifluoromethyl)-[1,1'-bi(cyclohexane)]-3-en-4-carboxylic acid obtained in the sixth step, 2.0 g (11 mmol) of 1-ethyl-3-(3-dimethylaminopropyl)carbodiimide hydrochloride, 0.1 g (0.9 mmol) of 4-dimethylaminopyridine, and 30 mL of dichloromethane were put, and a dichloromethane (10 mL) solution of 1.5 g (9.8 mmol) of 3-pentyl-3-hydroxymethyloxetane was added dropwise thereto at room temperature. The resultant mixture was stirred at room temperature for 15 hours, and then concentrated by means of a rotary evaporator, ethyl acetate was added thereto, the resultant mixture was washed with water, and dried over anhydrous magnesium sulfate. Then, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 2.3 g of (3-pentyloxetane-3-yl)methyl 4-(trifluoromethyl)-[1,1'-bi(cyclohexane)]-3-en-4-carboxylate was obtained as a colorless liquid.

Eighth Step

Into a reaction vessel under a nitrogen atmosphere, 2.3 g (5.5 mmol) of (3-pentyloxetane-3-yl)methyl 4-(trifluoromethyl)[1,1'-bi(cyclohexane)]-3-en-4-carboxylate obtained in the seventh step and 50 mL of dichloromethane were put, and the resultant mixture was cooled to −70° C., and 0.20 g (1.4 mmol) of boron trifluoride-diethyl ether complex was added dropwise thereto. The mixture was warmed to room temperature and stirred for 15 hours. Then, 1.5 mL (11 mmol) of triethylamine was added thereto, and the resultant mixture was concentrated by means of a rotary evaporator. Then, 30 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 1.0 g of 4-pentyl-1-(4'-(trifluoromethyl)-[1,1'-bi(cyclohexane)]-3'-en-4-yl)-2,6,7-trioxabicyclo[2.2.2]octane was obtained as a white solid.

Chemical shifts (δ (ppm)) according to $^1$H-NMR analysis are as describe below, and the compound obtained was identified to be 4-pentyl-1-(4'-(trifluoromethyl)-[1,1'-bi(cyclohexane)]-3'-en-4-yl)-2,6,7-trioxabicyclo[2.2.2]octane. A solvent for measurement was $CDCl_3$.

Chemical shifts (δ (ppm)); 3.89 (s, 6H), 2.20 (m, 2H), 2.09 (m, 1H), 2.0-1.7 (m, 6H), 1.53 (m, 1H), 1.4-1.1 (m, 14H), 1.0-0.8 (m, 5H).

A transition temperature of compound (No. 40) obtained is as described below.

Transition temperature: C 160.7 C' 184.4 SB 248.3 I.

Physical Properties of Compound (No. 40)

Liquid crystal composition Q including 97% by weight of base liquid crystal A and 3% by weight of 4-pentyl-1-(4'-(trifluoromethyl)-[1,1'-bi(cyclohexane)]-3'-en-4-yl)-2,6,7-trioxabicyclo[2.2.2]octane (No. 40) obtained in Example 16 was prepared. Physical properties of liquid crystal composition Q obtained were measured, and extrapolated values of physical properties of compound (No. 40) were calculated by extrapolating measured values. Values thereof are as described below.

Maximum temperature ($T_{NI}$)=118.4° C.; dielectric anisotropy ($\Delta\varepsilon$)=28.5; optical anisotropy ($\Delta n$)=0.084; viscosity ($\eta$)=145.2.

Example 17

Synthesis of 3,4,5-trifluorophenyl 4-(4-propyl-2,6,7-trioxabicyclo[2.2.2]octane-1-yl)cyclohexane carboxylate (No. 44)

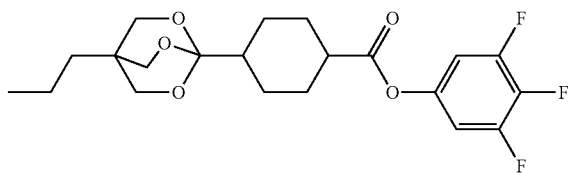 [SMILES: CCCC12COC(C3CCC(C(=O)Oc4cc(F)c(F)c(F)c4)CC3)(OC1)OC2]

First Step

Into a reaction vessel under a nitrogen atmosphere, 10.2 g (59.2 mmol) of cyclohexane-1,4-dicarboxylic acid, 13.6 g (71.0 mmol) of 1-ethyl-3-(3-dimethylaminopropyl)carbodiimide hydrochloride, 0.7 g (6 mmol) of 4-dimethylaminopyridine and 60 mL of dichloromethane were put, and a dichloromethane (20 mL) solution of 8.6 g (58 mmol) of 3,4,5-trifluorophenol was added dropwise thereto at room temperature. The resultant mixture was stirred at room temperature for 20 hours, concentrated by means of a rotary evaporator, ethyl acetate was added thereto, and the resultant mixture was washed with water. The mixture was dried over anhydrous magnesium sulfate. Then, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 5.9 g of 4-(3,4,5-trifluorophenoxy)carbonyl)cyclohexanecarboxylic acid was obtained as a colorless liquid.

Second Step

Into a reaction vessel under a nitrogen atmosphere, 5.9 g (20 mmol) of 4-(3,4,5-trifluorophenoxy)carbonyl)cyclohexanecarboxylic acid, 4.5 g (23 mmol) of 1-ethyl-3-(3-dimethylaminopropyl)carbodiimide hydrochloride, 0.24 g (2.0 mmol) of 4-dimethylaminopyridine and 60 mL of dichloromethane were put, and a dichloromethane (20 mL) solution of 3.1 g (23 mmol) of 3-propyl-3-hydroxymethyloxetane was added dropwise thereto at room temperature. The mixture was stirred at room temperature for 20 hours and then concentrated by means of a rotary evaporator, ethyl acetate was added thereto, and the resultant mixture was washed with water. The mixture was dried over anhydrous magnesium sulfate. Then, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 6.1 g of 1-((3-propyloxetane-3-yl) methyl) 4-((3,4,5-trifluorophenyl)cyclohexane-1,4-dicarboxylate was obtained.

Third Step

Into a reaction vessel under a nitrogen atmosphere, 6.1 g (15 mmol) of (1-((3-propyloxetane-3-yl)methyl)-4-((3,4,5-trifluorophenyl)cyclohexane-1,4-dicarboxylate obtained in the second step and 150 mL of dichloromethane was put, and the resultant mixture was cooled to −70° C., and 0.52 mL (3.7 mmol) of boron trifluoride-diethyl ether complex was added dropwise thereto. The mixture was warmed to room temperature and stirred for 22 hours. Then, 3.9 mL (29 mmol) of triethylamine was added thereto, and the resultant mixture was concentrated by means of a rotary evaporator. Then, 80 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate: heptane=1:4 in a volume ratio) as an eluent and silica gel as a filler. The resultant mixture was further purified by recrystallization (heptane/ethyl acetate=80/20 in a volume ratio), and thus 3.1 g of 4-(3,4,5-trifluorophenyl)cyclohexyl 3,4,5-trifluorophenyl 4-(4-propyl-2,6,7-trioxabicyclo[2.2.2]octane-1-yl)cyclohexane carboxylate was obtained as a white solid.

Chemical shifts ($\delta$ (ppm)) according to $^1$H-NMR analysis are as describe below, and the obtained compound was identified to be 3,4,5-trifluorophenyl 4-(4-propyl-2,6,7-trioxabicyclo[2.2.2]octane-1-yl)cyclohexane carboxylate. A solvent for measurement was $CDCl_3$.

Chemical shifts ($\delta$ (ppm)); 6.78 (t, 2H), 3.91 (s, 6H), 2.43 (m, 1H), 2.13 (m, 2H), 2.00 (m, 2H), 1.61 (m, 1H), 1.46 (m, 2H), 1.3-1.1 (m, 6H), 0.91 (t, 3H).

A transition temperature of compound (No. 44) obtained is as described below.

Transition temperature: C 109.8 $S_B$ 117.3 N 125.1 I.
Physical Properties of Compound (No. 44)

Liquid crystal composition R including 90% by weight of base liquid crystal A and 10% by weight of 3,4,5-trifluorophenyl 4-(4-propyl-2,6,7-trioxabicyclo[2.2.2]octane-1-yl) cyclohexane carboxylate (No. 44) obtained in Example 17 was prepared. Physical properties of liquid crystal composition R obtained were measured, and extrapolated values of physical properties of compound (No. 44) were calculated by extrapolating measured values. Values thereof are as described below.

Maximum temperature ($T_{NI}$)=73.7° C.; dielectric anisotropy ($\Delta\varepsilon$)=39.9; optical anisotropy ($\Delta n$)=0.077; viscosity ($\eta$)=101.7.

Example 18

Synthesis of 3,4,5-trifluorophenyl 4-(4-butyl-2,6,7-trioxabicyclo[2.2.2]octane-1-yl)cyclohexane carboxylate (No. 45)

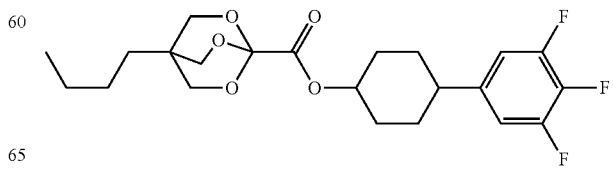

Then, 3,4,5-trifluorophenyl 4-(4-butyl-2,6,7-trioxabicyclo[2.2.2]octane-1-yl)cyclohexane carboxylate was prepared by performing synthesis in a manner similar to the operations in the second step and the third step in Example 17 using 3-butyl-3-hydroxymethyloxetane in place of 3-propyl-3-hydroxymethyloxetane.

Chemical shifts (δ (ppm)) according to $^1$H-NMR analysis are as describe below, and the compound obtained was identified to be 3,4,5-trifluorophenyl 4-(4-butyl-2,6,7-trioxabicyclo[2.2.2]octane-1-yl)cyclohexane carboxylate. A solvent for measurement was $CDCl_3$.

Chemical shifts (δ (ppm)); 6.77 (t, 2H), 3.91 (s, 6H), 2.43 (m, 1H), 2.13 (m, 2H), 2.00 (m, 2H), 1.61 (m, 1H), 1.46 (m, 2H), 1.3-1.1 (m, 8H), 0.89 (t, 3H).

A transition temperature of compound (No. 45) obtained is as described below.

Transition temperature: C 117.3 $S_B$ 126.7 I.

Physical Properties of Compound (No. 45)

Liquid crystal composition S including 95% by weight of base liquid crystal A and 5% by weight of 3,4,5-trifluorophenyl 4-(4-butyl-2,6,7-trioxabicyclo[2.2.2]octane-1-yl)cyclohexane carboxylate (No. 45) obtained in Example 18 was prepared. Physical properties of liquid crystal composition S obtained were measured, and extrapolated values of physical properties of compound (No. 45) were calculated by extrapolating measured values. Values thereof are as described below.

Maximum temperature ($T_{NI}$)=75.7° C.; dielectric anisotropy (Δ∈)=34.2; optical anisotropy (Δn)=0.077; viscosity (η)=96.8.

Example 19

Synthesis of 3,4,5-trifluorophenyl 4-(4-pentyl-2,6,7-trioxabicyclo[2.2.2]octane-1-yl)cyclohexane carboxylate (No. 46)

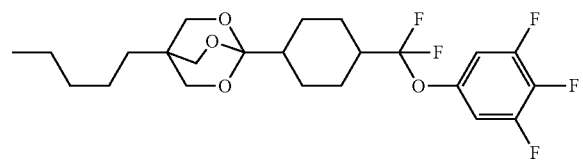 [SMILES: CCCCCC12COC(C3CCC(C(F)(F)Oc4cc(F)c(F)c(F)c4)CC3)(OC1)OC2]

Then, 3,4,5-trifluorophenyl 4-(4-pentyl-2,6,7-trioxabicyclo[2.2.2]octane-1,1-yl)cyclohexane carboxylate was prepared by performing synthesis in a manner similar to the operations in the second step and the third step in Example 17 using 3-pentyl-3-hydroxymethyloxetane in place of 3-propyl-3-hydroxymethyloxetane.

Chemical shifts (δ (ppm)) according to $^1$H-NMR analysis are as describe below, and the compound obtained was identified to be 3,4,5-trifluorophenyl 4-(4-pentyl-2,6,7-trioxabicyclo[2.2.2]octane-1-yl)cyclohexane carboxylate. A solvent for measurement was $CDCl_3$.

Chemical shifts (δ (ppm)); 6.77 (t, 2H), 3.90 (s, 6H), 2.43 (m, 1H), 2.13 (m, 2H), 2.00 (m, 2H), 1.62 (m, 1H), 1.48 (m, 2H), 1.3-1.1 (m, 10H), 0.89 (t, 3H).

A transition temperature of compound (No. 46) obtained is as described below.

Transition temperature: C 118.8 $S_B$ 138.6 N 139.3 I.

Physical Properties of Compound (No. 46)

Liquid crystal composition T including 95% by weight of base liquid crystal A and 5% by weight of 3,4,5-trifluorophenyl 4-(4-pentyl-2,6,7-trioxabicyclo[2.2.2]octane-1-yl) cyclohexane carboxylate (No. 46) obtained in Example 19 was prepared. Physical properties of liquid crystal composition T obtained were measured, and extrapolated values of physical properties of compound (No. 46) were calculated by extrapolating measured values. Values thereof are as described below.

Maximum temperature ($T_{NI}$)=89.7° C.; dielectric anisotropy (Δ∈)=32.2; optical anisotropy (Δn)=0.097; viscosity (η)=98.8.

Example 20

Synthesis of 1-(4-(difluoro(3,4,5-trifluorophenoxy)methyl)cyclohexyl)-4-hexyl)-4-pentyl-2,6,7-trioxabicyclo[2.2.2]octane (No. 49)

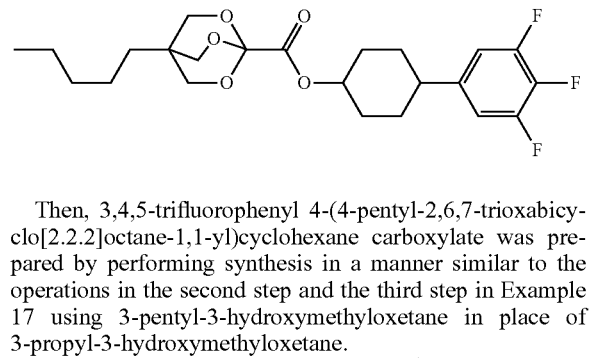

First Step

Into a reaction vessel under a nitrogen atmosphere, 60.9 g (317 mmol) of (1,3-dithiane-2-yl)trimethyl silane and 500 mL of THF were put, 351 mL (379 mmol) of sec-butyl lithium (1.08 M, cyclohexane n-hexane solution) was added dropwise thereto at −70° C., the resultant mixture was slowly warmed to 0° C. and then cooled again to −70° C. Then, a THF (150 mL) solution of 64.6 g of ethyl 4-oxocyclohexane carboxylate was added dropwise thereto at −70° C., and the resultant mixture was stirred at room temperature for 6 hours. Then, 500 mL of hydrochloric acid (1 N) was added to the reaction mixture, the resultant mixture was extracted with ethyl acetate. The resultant extract was washed with water, and dried over anhydrous magnesium sulfate. Then, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization by heptane, and thus 32.7 g of ethyl 4-(1,3-dithiane-2-ylidene)cyclohexane carboxylate was obtained.

Second Step

Into a reaction vessel under a nitrogen atmosphere, 32.7 g (120 mmol) of ethyl 4-(1,3-dithiane-2-ylidene)cyclohexane carboxylate and 800 mL of dichloromethane were put, and the resultant mixture was cooled to −20° C., 172 g of trifluoromethane sulfonic acid was added dropwise thereto, and the resultant mixture was returned to room temperature. Then, the mixture was cooled to −70° C., a dichloromethane (50 mL) solution of 24.7 g (166 mmol) of 3,4,5-trifluorophenol, 18.7 g (185 mmol) of triethylamine, 91.4 g (567 mmol) of triethylamine trihydrofluoride, and a dichloromethane (200 mL) solution of 165 g (577 mmol) of 1,3-dibromo-5,5-dimethylhydantoin were sequentially added dropwise thereto, and the resultant mixture was stirred at room temperature for 15 hours. The reaction mixture was poured into 1,500 mL of ice-cooled saturated aqueous solution of sodium hydrogencarbonate, and the resultant mixture was extracted with ethyl acetate. The resultant extract was washed with water, dried over anhydrous magnesium sulfate. Then, an insoluble matter was separated by filtration, and a solvent was distilled off. A residue was purified according to fractionation by column chromatography using a mixed solvent of heptane and ethyl acetate (ethyl acetate:heptane=1:4 in a volume ratio) as an eluent and silica gel as a filler, and thus 21.1 g of ethyl 4-(difluoro(3,4,5-trifluorophenoxy)methyl)cyclohexane carboxylate was obtained.

Third Step

Into a reaction vessel under a nitrogen atmosphere, 21.1 g (15 mmol) of ethyl 4-difluoro(3,4,5-trifluorophenoxy) methyl)cyclohexane carboxylate obtained in the second step and 700 mL of methanol were put, and the resultant mixture was cooled to 0° C., and 90 mL (3.7 mmol) of aqueous solution of lithium hydroxide (1 N) was added dropwise thereto. The resultant mixture was warmed to room temperature, and stirred for 24 hours. Then, 50 mL of water was added and the resultant mixture was washed with diethyl ether. Then, hydrochloric acid (1 N) was added to adjust pH to 3 to 4, and the resultant mixture was extracted with ethyl acetate, and the resultant extract was dried over anhydrous magnesium sulfate. Then, an insoluble matter was separated by filtration and then a filtrate was concentrated under reduced pressure, and thus 12.0 g of 4-(difluoro(3,4,5-trifluorophenoxy)methyl)cyclohexane carboxylic acid was obtained.

Fourth Step

Into a reaction vessel under a nitrogen atmosphere, 12.0 g (37.0 mmol) of 4-(difluoro(3,4,5-trifluorophenoxy) methyl)cyclohexane carboxylic acid obtained in the third step, 6.4 g (41 mmol) of 3-pentyl-3-hydroxymethyloxetane, 1.4 g (11 mmol) of 4-dimethylaminopyridine and 250 mL of dichloromethane were put, and the resultant mixture was cooled to 0° C., a dichloromethane (30 mL) solution of 8.4 g (41 mmol) of dicyclohexylcarbodiimide was added dropwise thereto at 0° C., and the resultant mixture was stirred at room temperature for 15 hours. Then, an insoluble matter was separated by Celite filtration, and then a filtrate was washed sequentially with hydrochloric acid (1 N), a saturated aqueous solution of sodium hydrogencarbonate and water, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 16.9 g of (3-pentyloxetane-3-yl)methyl 4-(difluoro(3,4,5-trifluorophenoxy)methyl)cyclohexane carboxylate was obtained.

Fifth Step

Into a reaction vessel under a nitrogen atmosphere, 16.9 g (36.4 mmol) of (3-pentyloxetane-3-yl)methyl) 4-(difluoro ((3,4,5-trifluorophenoxy)methyl)cyclohexane carboxylate obtained in the fourth step and 170 mL of dichloromethane were put, and the resultant mixture was cooled to −70° C., and 1.3 g (9.1 mmol) of boron trifluoride-diethyl ether complex was added dropwise thereto. The mixture was warmed to room temperature, and stirred for 15 hours. Then, 5.1 mL (36 mmol) of triethylamine was added thereto, and the resultant mixture was concentrated by means of a rotary evaporator. Then, 100 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate: heptane=1:4 in a volume ratio) as an eluent and silica gel as a filler. The resultant mixture was further purified by recrystallization (heptane/ethyl acetate=80/20 in a volume ratio), and thus 3.2 g of 1-(4-(difluoro(3,4,5-trifluorophenoxy) methyl)cyclohexyl)-4-pentyl-2,6,7-trioxabicyclo[2.2.2]octane was obtained as a white solid.

Chemical shifts (δ (ppm)) according to $^1$H-nuclear magnetic resonance analysis are as describe below, and the obtained compound was identified to be 1-(4-(difluoro(3,4, 5-trifluorophenoxy)methy)cyclohexyl)-4-pentyl-2,6,7-trioxabicyclo[2.2.2]octane. A solvent for measurement was CDCl$_3$.

Chemical shifts (δ(ppm)); 6.83 (t, 2H), 3.90 (s, 6H), 2.00 (m, 5H), 1.58 (m, 1H), 1.4-1.1 (m, 12H), 0.88 (t, 3H).

A transition temperature of compound (No. 49) obtained is as described below.

Transition temperature: C 68.8 C' 83.1 S$_B$ 142.5 I.

Physical Properties of Compound (No. 49)

Liquid crystal composition U including 85% by weight of base liquid crystal A and 15% by weight of 1-(4-(difluoro (3,4,5-trifluorophenoxy)methyl)cyclohexyl)-4-pentyl-2,6,7-trioxabicyclo[2.2.2]octane (No. 49) obtained in Example 20 was prepared. Physical properties of liquid crystal composition U obtained were measured, and extrapolated values of physical properties of compound (No. 49) were calculated by extrapolating measured values. Values thereof are as described below.

Maximum temperature (T$_{NI}$)=81.7° C.; dielectric anisotropy (Δ∈)=36.9; optical anisotropy (Δn)=0.070; viscosity (η)=98.0.

Example 21

Synthesis of 1-(4-(difluoro(3,4,5-trifluorophenoxy) methyl)phenyl)-4-pentyl-2,6,7-trioxabicyclo[2.2.2] octane (No. 60)

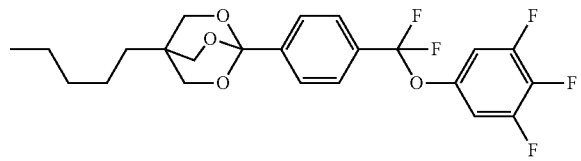 [SMILES: CCCCCC12COC(c3ccc(C(F)(F)Oc4cc(F)c(F)c(F)c4)cc3)(OC1)OC2]

First Step

Into a reaction vessel under a nitrogen atmosphere, 15.0 g (42.5 mmol) of 5-(4-bromophenyl)difluoromethoxy)-1,2, 3-trifluorobenzene, 7.6 g (85 mmol) of copper cyanide and 150 mL of N-methylpyrrolidone were put, and the resultant mixture was stirred at 160° C. for 50 hours. The mixture was returned to room temperature, 50 mL of aqueous ammonia was added thereto, and then the resultant mixture was filtered with Celite, the resultant filtrate was extracted with toluene, and the resultant extract was washed with water. The resultant mixture was dried over anhydrous magnesium sulfate, an insoluble matter was separated by filtration, and a solvent was distilled off. A residue was purified according to fractionation by column chromatography using a mixed solvent of heptane and ethyl acetate (ethyl acetate:heptane=1:1 in a volume ratio) as an eluent and silica gel as a filler, and thus 8.8 g of 4-difluoro(3,4,5-trifluorophenoxy) methyl)benzonitrile was obtained.

Second Step

Into a reaction vessel under a nitrogen atmosphere, 8.8 g (30 mmol) of 4-difluoro(3,4,5-trifluorophenoxy)methyl)benzonitrile and 170 mL of toluene were put, and the resultant mixture was cooled to −70° C., diisobutylaluminum hydride (1.01 M, toluene solution) was added dropwise thereto, and the resultant mixture was stirred for 2 hours. The mixture was returned to room temperature, poured into 200 mL of hydrochloric acid (1 N), the resultant mixture was extracted with toluene. The resultant extract was washed with water, dried over anhydrous magnesium sulfate. Then, an insoluble matter was separated by filtration, and a solvent was distilled off. A residue was purified according to fractionation by column chromatography using toluene as an eluent and silica gel as a filler, and thus 7.7 g of 4-difluoro(3,4,5-trifluorophenoxy)methyl)benzaldehyde was obtained.

Third Step

Into a reaction vessel under a nitrogen atmosphere, 1.9 g (12 mmol) of sodium dihydrogenphosphate dihydrate and 40 mL of water were put, and 3.6 mL of aqueous solution of 2.9 g (32 mmol) of sodium chlorite was added dropwise thereto at room temperature. Then, a THF (38 mL) solution of 7.7 g (25 mmol) of 4-difluoro(3,4,5-trifluorophenoxy)methyl)benzaldehyde obtained in the second step was added dropwise thereto, and the resultant mixture was stirred at room temperature for 2.5 hours. Then, the mixture was poured into 50 mL of hydrochloric acid (1 N), the resultant mixture was extracted with toluene. The resultant extract was washed with water and dried over anhydrous magnesium sulfate. Then, an insoluble matter was separated by filtration and then a filtrate was concentrated under reduced pressure, and thus 7.8 g of 4-difluoro(3,4,5-trifluorophenoxy)methyl)benzoic acid was obtained.

Fourth Step

Into a reaction vessel under a nitrogen atmosphere, 5.0 g (16 mmol) of 4-difluoro(3,4,5-trifluorophenoxy)methyl)benzoic acid obtained in the third step, 2.5 g (16 mmol) of 3-pentyl-3-hydroxymethyloxetane, 0.19 g (1.6 mmol) of 4-dimethylaminopyridine and 50 mL of dichloromethane were put, and the resultant mixture was cooled to 0° C. Then, a dichloromethane (20 mL) solution of 3.4 g (17 mmol) of dicyclohexylcarbodiimide was added dropwise thereto at 0° C., and the resultant mixture was stirred at room temperature for 3 hours. Then, an insoluble matter was separated by Celite filtration, and then a filtrate was washed sequentially with hydrochloric acid (1 N), a saturated aqueous solution of sodium hydrogencarbonate and water, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 6.3 g of (3-pentyloxetane-3-yl)methyl) 4-difluoro(3,4,5-trifluorophenoxy)methyl)benzoate was obtained.

Fifth Step

Into a reaction vessel under a nitrogen atmosphere, 6.3 g (14 mmol) of (3-pentyloxetane-3-yl)methyl) 4-difluoro(3,4,5-trifluorophenoxy)methyl)benzoate obtained in the fourth step and 40 mL of dichloromethane were put, and the resultant mixture was cooled to −70° C., and 0.50 g (3.5 mmol) of boron trifluoride-diethyl ether complex was added dropwise thereto. The resultant mixture was warmed to room temperature and stirred for 15 hours. Then, 0.7 mL (5 mmol) of triethylamine was added thereto, and the resultant mixture was concentrated by means of a rotary evaporator.

Then, 50 mL of diethyl ether was added thereto, and the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane), and thus 3.0 g of 1-(4-(difluoro(3,4,5-trifluorophenoxy)methyl)phenyl)-4-pentyl-2,6,7-trioxabicyclo[2.2.2]octane was obtained as a white solid.

Chemical shifts (δ (ppm)) according to $^1$H-nuclear magnetic resonance analysis are as describe below, and the compound obtained was identified to be 1-(4-(difluoro(3,4,5-trifluorophenoxy)methyl)phenyl)-4-pentyl-2,6,7-trioxabicylo[2.2.2]octane. A solvent for measurement was $CDCl_3$.

Chemical shifts (δ (ppm)); 7.73 (d, 2H), 7.65 (d, 2H), 6.69 (t, 2H), 4.12 (s, 6H), 1.4-1.2 (m, 8H), 0.90 (t, 3H).

A transition temperature of compound obtained (No. 60) is as described below.

Transition temperature: C 106.9 ($S_B$ 84.1 I).

Physical Properties of Compound (No. 60)

Liquid crystal composition V including 90% by weight of mother liquid crystal A and 10% by weight of 1-(4-(difluoro(3,4,5-trifluorphenoxy)methyl)phenyl)-4-pentyl-2,6,7-trioxabicyclo[2.2.2]octane (No. 60) obtained in Example 21 was prepared. Physical properties of liquid crystal composition V obtained were measured, and extrapolated values of physical properties of compound (No. 60) were calculated by extrapolating measured values. Values thereof are as described below.

Maximum temperature ($T_{NI}$)=71.1° C.; dielectric anisotropy (Δ∈)=35.1; optical anisotropy (Δn)=0.087; viscosity (η)=92.3.

Example 22

Synthesis of 1-(4-(difluoro(3,4,5-trifluorophenoxy)methyl)-3-fluorophenyl)-4-pentyl-2,6,7-trioxabicyclo[2.2.2]octane (No. 62)

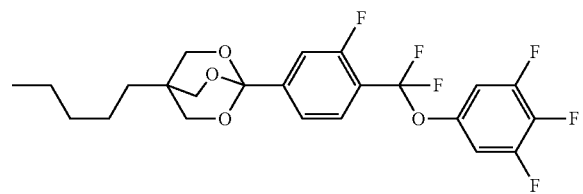 [SMILES: CCCCCC12COC(c3ccc(C(F)(F)Oc4cc(F)c(F)c(F)c4)c(F)c3)(OC1)OC2]

First Step

Into a reaction vessel under a nitrogen atmosphere, 20.2 mL (26.3 mmol) of an isopropylmagnesium chloride-lithium chloride complex solution (1.3 M) was put, a THF (20 mL) solution of 7.5 g (20 mmol) of 5-((4-bromo-2-fluorophenyl)difluoromethoxy)-1,2,3-trifluorobenzene was added dropwise thereto at room temperature, and the resultant mixture was stirred at room temperature for 2 hours. The mixture was cooled to 0° C. and dry carbon dioxide gas was blown thereinto until heat generation stopped. Then, the reaction mixture was poured into 50 mL of hydrochloric acid (2 N), and extracted with diethyl ether. The resultant extract was washed with saturated brine, dried over anhydrous magnesium sulfate. Then, an insoluble matter was separated by filtration, a solvent was distilled off. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethanol=80/20 in a volume ratio), and thus 4.2 g of 4-(difluoro(3,4,5-trifluorophenoxy)methyl)-3-fluorobenzoic acid was obtained.

Second Step

Into a reaction vessel under a nitrogen atmosphere, 2.1 g (6.3 mmol) of 4-(difluoro(3,4,5-trifluorophenoxy)methyl)-3-fluorobenzoic acid obtained in the first step, 1.4 g (7.5 mmol) of 1-ethyl-3-(3-dimethylaminopropyl)carbodiimide hydrochloride, 0.08 g (0.6 mmol) of 4-dimethylaminopyridine and 30 mL of dichloromethane were put. Then, a dichloromethane (10 mL) solution of 1.7 g (6.9 mmol) of 3-pentyl-3-hydroxymethyloxetane was added dropwise thereto at room temperature, and the resultant mixture was stirred for 3 days at room temperature. Then, 30 mL of water was added thereto, the resultant mixture was extracted with diethyl ether, and the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 2.2 g of (3-pentyloxetane-3-yl)methyl) 4-(difluoro(3,4,5-trifluorophenoxy)methyl)-3-fluorobenzoate was obtained.

Third Step

Into a reaction vessel under a nitrogen atmosphere, 2.2 g (4.6 mmol) of 3-pentyloxetane-3-yl)methyl) 4-(difluoro(3,4,5-trifluorophenoxy)methyl)-3-fluorobenzoate obtained in the second step and 50 mL of dichloromethane were put and cooled to −70° C., and 0.17 g (1.2 mmol) of boron trifluoride-diethyl ether complex was added dropwise thereto. The mixture was warmed to room temperature, and stirred for 15 hours. Then, 1.3 mL (9.2 mmol) of triethylamine was added thereto, and the resultant mixture was concentrated by means of a rotary evaporator. Then, 50 mL of diethyl ether was added thereto, and the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 1.0 g of 1-(4-(difluoro(3,4,5-trifluorophenoxy)methyl-3-fluorophenyl)-4-pentyl-2,6,7-trioxabicyclo[2.2.2]octane was obtained as a white solid.

Chemical shifts (δ (ppm)) according to $^1$H-nuclear magnetic resonance analysis are as describe below, and the obtained compound was identified to be 1-(4-(difluoro(3,4,5-trifluorophenoxy)methyl)-3-fluorophenyl)-4-pentyl-2,6,7-trixabicyclo[2.2.2]octane. A solvent for measurement was CDCl$_3$.

Chemical shifts (δ (ppm)); 7.62 (t, 1H), 7.47 (m, 2H), 6.95 (t, 2H), 4.09 (s, 6H), 1.4-1.2 (m, 8H), 0.90 (t, 3H).

A transition temperature of compound (No. 62) obtained is as described below.

Transition temperature: C 94.2 I.

Physical Properties of Compound (No. 62)

Liquid crystal composition W including 85% by weight of base liquid crystal A and 15% by weight of 1-(4-(difluoro (3,4,5-trifluorophenoxy)methyl)-3-fluorophenyl)-4-pentyl-2,6,7-trioxabicyclo[2.2.2]octane (No. 62) obtained in Example 22 was prepared. Physical properties of liquid crystal composition W obtained were measured, and extrapolated values of physical properties of compound (No. 62) were calculated by extrapolating measured values. Values thereof are as described below.

Maximum temperature $(T_{NI})$=45.7° C.; dielectric anisotropy $(\Delta\varepsilon)$=39.2; optical anisotropy $(\Delta n)$=0.084; viscosity $(\eta)$=102.2.

Example 23

Synthesis of 4-butyl-1-(4-(difluoro(3,4,5-trifluorophenoxy)methyl)-3,5-difluorophenyl)-2,6,7-trioxabicyclo[2.2.2]octane (No. 65)

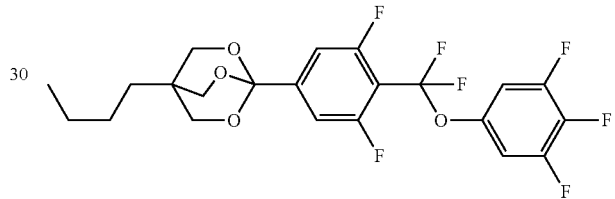

Then, 4-butyl-1-(4-(difluoro(3,4,5-trifluorophenoxy) methyl)-3,5-difluorophenyl)-2,6,7-trioxabicyclo[2.2.2]octane was prepared by performing synthesis in a manner similar to the operations in Example 10 using 3-butyl-3-hydroxymethyloxetane in place of 3-propyl-3-hydroxymethyloxetane in the second step in Example 10.

Chemical shifts (δ (ppm)) according to $^1$H NMR analysis are as described below, and the compound obtained was identified to be 4-butyl-1-(4-(difluor-3,4,5-trifluorophenoxy)methyl)-3,5-difluorophenyl)-2,6,7-trioxabicyclo [2.2.2]octane. A solvent for measurement was CDCl$_3$.

Chemical shifts (δ (ppm)); 7.25 (d, 2H), 6.94 (t, 2H), 4.10 (s, 6H), 1.4-1.2 (m, 6H), 0.92 (t, 3H).

A transition temperature of compound No. 65 obtained is as described below.

Transition temperature: C 75.0 I.

Physical Properties of Compound (No. 65)

Liquid crystal composition X including 85% by weight of base liquid crystal A and 15% by weight of 4-butyl-1-(4-(difluoro(3,4,5-trifluorophenoxy)methyl)-3,5-difluorophenyl)-2,6,7-trioxabicyclo[2.2.2]octane (No. 65) obtained in Example 23 was prepared. Physical properties of liquid crystal composition X obtained were measured, and extrapolated values of physical properties of compound (No. 65) were calculated by extrapolating measured values. Values thereof are as described below.

Maximum temperature $(T_{NI})$=8.4° C.; dielectric anisotropy $(\Delta\varepsilon)$=44.1; optical anisotropy $(\Delta n)$=0.057; viscosity $(\eta)$=82.6.

Example 24

Synthesis of 4-pentyl-1-(4-(difluoro(3,4,5-trifluorophenoxy)methyl)-3,5-difluorophenyl)-2,6,7-trioxabicyclo[2.2.2]octane (No. 66)

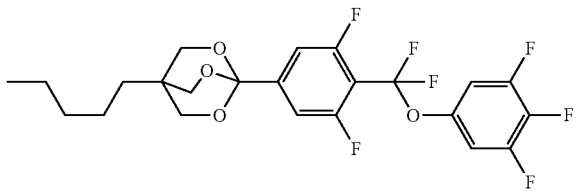 [SMILES: CCCCCC12COC(c3cc(F)c(C(F)(F)Oc4cc(F)c(F)c(F)c4)c(F)c3)(OC1)OC2]

Then, 4-pentyl-1-(4-(difluoro(3,4,5-trifluorophenoxy)methyl)-3,5-difluorophenyl)-2,6,7-trioxabicyclo[2.2.2]octane was prepared by performing synthesis in a manner similar to the operations in Example 10 using 3-pentyl-3-hydroxymethyloxetane in place of 3-propyl-3-hydroxymethyloxetane in the second step in Example 10.

Chemical shifts (δ (ppm)) according to $^1$H-NMR analysis are as described below, and the compound obtained was identified to be 4-pentyl-1-(4-(difluoro(3,4,5-trifluorophenoxy)methyl)-3,5-difluorophenyl)-2,6,7-trioxabicyclo[2.2.2]octane. A solvent for measurement was CDCl$_3$.

Chemical shifts (δ (ppm)); 7.24 (d, 2H), 6.94 (t, 2H), 4.10 (s, 6H), 1.4-1.2 (m, 8H), 0.90 (t, 3H)

A transition temperature of compound (No. 66) obtained is as described below.

Transition temperature: C 88.5 I.

Physical Properties of Compound (No. 66)

Liquid crystal composition Y including 85% by weight of base liquid crystal A and 15% by weight of 4-pentyl-1-(4-(difluoro(3,4,5-trifluorophenoxy)methyl)-3,5-difluorophenyl)-2,6,7-trioxabicyclo[2.2.2]octane (No. 66) obtained in Example 24 was prepared. Physical properties of liquid crystal composition Y obtained were measured, and extrapolated values of physical properties of compound (No. 66) were calculated by extrapolating measured values. Values thereof are as described below.

Maximum temperature (T$_{NI}$)=23.7° C.; dielectric anisotropy (Δ∈)=43.5; optical anisotropy (Δn)=0.077; viscosity (η)=73.9.

Example 25

Synthesis of 4-pentyl-1-(4'-(3,4,5-trifluorophenyl)-[1,1'-bi(cyclohexane)]-4-yl)-2,6,7-trioxabicyclo[2.2.2]octane (No. 69)

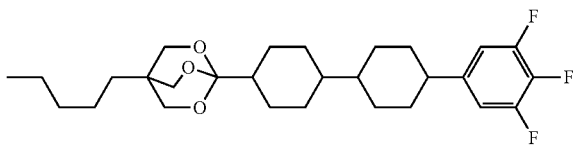 [SMILES: CCCCCC12COC(C3CCC(C4CCC(c5cc(F)c(F)c(F)c5)CC4)CC3)(OC1)OC2]

First Step

Into a reaction vessel under a nitrogen atmosphere, 24.3 g (70.8 mmol) of chloro(methoxymethyl)triphenylphosphorane and 100 mL of THF were put, a THF (50 mL) solution of 8.0 g (71 mmol) of potassium tert-butoxide was added dropwise thereto at −15° C., and the resultant mixture was stirred at −15° C. for 1 hour. Then, a THF (60 mL) solution of 20.0 g (64.4 mmol) of 4'-(3,4,5-trifluorophenyl)-[1,1'-bi(cyclohexane)]-4-one was added dropwise thereto at −15° C., and the resultant mixture was stirred at −15° C. for 1 hour. The mixture was returned to room temperature, 200 mL of water was added thereto, and the resultant mixture was extracted with toluene. The resultant extract was washed with water and dried over anhydrous magnesium sulfate. Then, an insoluble matter was separated by filtration and then a filtrate was concentrated under reduced pressure. A residue was dissolved in a small amount of toluene, and while stirring, the resultant solution was poured into 500 mL of heptane, and an insoluble matter was separated by filtration. A solvent is distilled off under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 20.0 g of 4-(methoxymethylene)-4'-(3,4,5-trifluorophenyl)-1,1'-bi(cyclohexane) was obtained.

Second Step

Into a reaction vessel under a nitrogen atmosphere, 20.0 g (59.1 mmol) of 4-(methoxymethylene)-4'-(3,4,5-trifluorophenyl)-1,1'-bi(cyclohexane) obtained in the first step, 200 mL of methanol, 20 mL of toluene and 3.4 g (18 mmol) of p-toluenesulfonic acid monohydrate were put, and the resultant mixture was refluxed for 23 hours. The reaction mixture was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. Next, 3.8 g (12 mmol) of tetrabutylammonium bromide, 100 mL of formic acid and 100 mL of toluene were added thereto, and the resultant mixture was stirred at room temperature for 15 hours. The reaction mixture was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 11.3 g of 4'-(3,4,5-trifluorophenyl)-[1,1'-bi(cyclohexane)]-4-carboaldehyde was obtained.

Third Step

Into a reaction vessel, 11.3 g (34.7 mmol) of 4'-(3,4,5-trifluorophenyl)-[1,1'-bi(cyclohexane)]-4-carboaldehyde obtained in the second step and 200 mL of acetone were put, and a Jones reagent was added dropwise thereto at 0° C. until an orange color did not fade away. Then, 4 mL of isopropanol and 8 g of sodium hydrogencarbonate were added thereto, the resultant mixture was filtered, a solid was rinsed with acetone, and a filtrate was concentrated under reduced pressure. Then, 50 mL of water was added thereto, the resultant mixture was extracted with ethyl acetate, the resultant extract was washed with water, and a solvent was distilled off by means of a rotary evaporator. A residue was purified according to fractionation by column chromatography using a mixed solvent of toluene and isopropanol (toluene:isopropanol=1:1 in a volume ratio) as an eluent and silica gel as a filler, and thus 10.9 g of 4'-(3,4,5-trifluorophenyl)-[1,1'-bi(cyclohexane)]-4-carboxylic acid was obtained.

Fourth Step

Into a reaction vessel under a nitrogen atmosphere, 3.5 g (10 mmol) of 4'-(3,4,5-trifluorophenyl)-[1,1'-bi(cyclohexane)]-4-carboxylic acid obtained in the third step, 2.3 g (12 mmol) of 1-ethyl-3-(3-dimethylaminopropyl)carbodiimide hydrochloride, 0.13 g (1.1 mmol) of 4-dimethylaminopyridine and 50 mL of dichloromethane were put. Then, a dichloromethane (10 mL) solution of 1.8 g (11 mmol) of 3-pentyl-3-hydroxymethyloxetane was added dropwise thereto at room temperature, and the resultant mixture was stirred at room temperature for 15 hours. Then, 20 mL of water was added thereto, the resultant mixture was extracted with diethyl ether, and the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 3.7 g of (3-pentyloxetane-3-yl)methyl) 4'-(3,4,5-trifluorophenyl)-[1,1'-bi (cyclohexane)]-4-carboxylate was obtained.

Fifth Step

Into a reaction vessel under a nitrogen atmosphere, 3.7 g (7.8 mmol) of (3-pentyloxetane-3-yl)methyl) 4'-(3,4,5-trifluorophenyl)-[1,1'-bi(cyclohexane)]-4-carboxylate obtained in the fourth step and 80 mL of dichloromethane were put, and the resultant mixture was cooled to −70° C., and 0.28 g (1.9 mmol) of boron trifluoride-diethyl ether complex was added dropwise thereto. The resultant mixture was warmed to room temperature and stirred for 15 hours. Then, 2.1 mL (16 mmol) of triethylamine was added thereto, and the resultant mixture was concentrated by means of a rotary evaporator. Then, 100 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 2.0 g of 4-pentyl-1-(4'-(3,4,5-trifluorophenyl)-[1,1'-bi(cyclohexane)]-4-yl)-2,6,7-trioxabicyclo[2.2.2]octane was obtained as a white solid.

Chemical shifts (δ (ppm)) according to $^1$H NMR analysis are as described below, and the compound obtained was identified to be 4-pentyl-1-(4'-(3,4,5-trifluorophenyl)-[1,1'-bi(cyclohexane)]-4-yl)-2,6,7-trioxabicyclo[2.2.2]octane. A solvent for measurement was $CDCl_3$.

Chemical shifts (δ (ppm)); 6.79 (t, 2H), 3.90 (s, 6H), 2.36 (m, 1H), 1.9-1.7 (m, 8H), 1.51 (m, 1H), 1.4-0.9 (m, 18H), 0.87 (t, 3H).

Example 26

Synthesis of 1-(2,3',3'',4'',5''-pentafluoro[1,1':4',1''-terphenyl]-4-yl)-4-pentyl-2,6,7-trioxabicyclo[2.2.2]octane (No. 79)

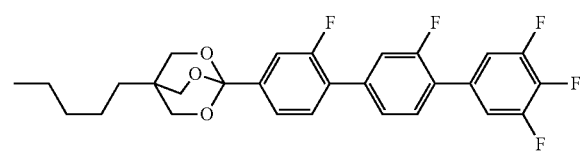 [SMILES: CCCCCC12COC(c3ccc(-c4ccc(-c5cc(F)c(F)c(F)c5)c(F)c4)c(F)c3)(OC1)OC2]

First Step

Into a reaction vessel, 10.2 g (28.7 mmol) of 2,3',3'',4'',5''-pentafluoro[1,1':4',1''-terphenyl]-4-carboaldehyde and 100 mL of acetone were put, and a Jones reagent was added dropwise thereto at 0° C. until an orange color did not fade away. Then, 4 mL of isopropanol and 8 g of sodium hydrogencarbonate were added thereto, the resultant mixture was filtered, a solid was rinsed with acetone, and a filtrate was concentrated under reduced pressure. Then, 40 mL of water was added thereto, the resultant mixture was extracted with ethyl acetate, the resultant extract was washed with water, and a solvent was distilled off by means of a rotary evaporator. A residue was purified according to fractionation by column chromatography using a mixed solvent of methanol and acetone (methanol:acetone=1:4 in a volume ratio) as an eluent and silica gel as a filler. A solid obtained was washed with water and heptane and dried, and thus 4.1 g of 2,3',3'',4'',5''-pentafluoro[1,1':4',1''-terphenyl]-4-carboxylic acid was obtained.

Second Step

Into a reaction vessel under a nitrogen atmosphere, 4.1 g (14 mmol) of 2,3',3'',4'',5''-pentafluoro[1,1':4',1''-terphenyl]-4-carboxylic acid obtained in the first step, 3.2 g (17 mmol) of 1-ethyl-3-(3-dimethylaminopropyl)carbodiimide hydrochloride, 0.14 g (1.4 mmol) of 4-dimethylaminopyridine and 100 mL of DMF were put. Then, a dichloromethane (20 mL) solution of 2.0 g (15 mmol) of 3-pentyl-3-hydroxymethyloxetane was added dropwise thereto at room temperature, and the resultant mixture was stirred at room temperature for 24 hours. Then, 30 mL of water was added thereto, the resultant mixture was extracted with diethyl ether, and the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 1.8 g of (3-pentyloxetane-3-yl)methyl) 2,3',3''4'',5''-pentafluoro[1,1':4',1''-terphenyl]-4-carboxylate was obtained.

Third Step

Into a reaction vessel under a nitrogen atmosphere, 1.8 g (3.7 mmol) of (3-pentyloxetane-3-yl)methyl) 2,3',3'',4'',5''-pentafluoro[1,1':4',1''-terphenyl]-4-carboxylate obtained in the second step and 40 mL of dichloromethane were put, and the resultant mixture was cooled to −70° C., and 0.13 g (0.91 mmol) of boron trifluoride-diethyl ether complex was added dropwise thereto. The resultant mixture was warmed to room temperature, and stirred for 15 hours. Then, 0.95 mL (7.3 mmol) of triethylamine was added thereto, and the resultant mixture was concentrated by means of a rotary evaporator. Then, 50 mL of diethyl ether was added thereto, the resultant mixture was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate: heptane=1:4 in a volume ratio) as an eluent and silica gel as a filler. The resultant mixture was further purified by recrystallization (heptane/ethyl acetate=80/20 in a volume ratio), and thus 1.1 g of 1-(2,3',3'',4'',5''-pentafluoro[1,1':4',1''-terphenyl]-4-yl)-4-pentyl-2,6,7-trioxabicyclo[2.2.2]octane was obtained as a white solid.

Chemical shifts (δ (ppm)) according to $^1$H-nuclear magnetic resonance analysis are as described below, and the compound obtained was identified to be 1-(2,3',3",4",5"-pentafluoro[1,1':4',1"-terphenyl]-4-yl)-4-pentyl-2,6,7-trioxabicyclo[2.2.2]octane. A solvent for measurement was CDCl$_3$.

Chemical shifts (δ (ppm)); 7.6-7.3 (m, 6H), 7.23 (t, 2H), 4.13 (s, 6H), 1.4-1.2 (m, 8H), 0.90 (t, 3H).

A transition temperature of compound (No. 79) obtained is as described below.

Transition temperature: C 99.9 C' 107.7 N 226.2 I.

Physical Properties of Compound (No. 79)

Liquid crystal composition Z including 85% by weight of base liquid crystal A and 15% by weight of 1-(2,3',3",4",5"-pentafluoro[1,1':4',1"-terphenyl]-4-yl)-4-pentyl-2,6,7-trioxabicyclo[2.2.2]octane (No. 79) obtained in Example 26 was prepared. Physical properties of liquid crystal composition Z obtained were measured, and extrapolated values of physical properties of compound (No. 79) were calculated by extrapolating measured values. Values thereof are as described below.

Maximum temperature ($T_{NI}$)=153.7° C.; dielectric anisotropy (Δ∈)=41.5; optical anisotropy (Δn)=0.184; viscosity (η)=170.8.

Example 27

Synthesis of 1-(4'-(4-difluoro(3,4,5-trifluorophenyl)methyl) 3,5-difluorophenyl)cyclohexyl-4-pentyl-2,6,7-trioxabicyclo[2.2.2]octane (No. 95)

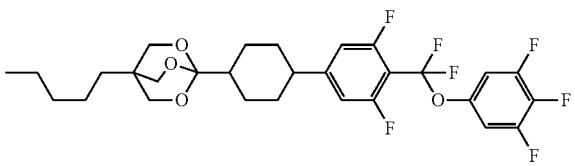 [SMILES: CCCCCC12COC(C3CCC(c4cc(F)c(C(F)(F)Oc5cc(F)c(F)c(F)c5)c(F)c4)CC3)(OC1)OC2]

First Step

Into a reaction vessel under a nitrogen atmosphere, 6.8 g (280 mmol) of magnesium powder and 10 mL of THF were put, a THF (200 mL) solution of 50.0 g (259 mmol) of 1-bromo-3,5-difluorobenzene was added dropwise, and the resultant mixture was refluxed for 1 hour. The resultant mixture was returned to room temperature, a THF (300 mL) solution of 33.7 g (216 mmol) of 1,4-dioxaspiro[4,5]decane-8-one was added dropwise thereto, and the resultant mixture was stirred at room temperature for 2 hours. The reaction liquid was poured into 500 mL of a saturated aqueous solution of ammonium chloride, the resultant mixture was extracted with ethyl acetate, and the resultant extract was washed with saturated brine, and dried over anhydrous magnesium sulfate. Then, an insoluble matter was separated by filtration and then a filtrate was concentrated under reduced pressure. A residue was recrystallized in toluene, and thus 48.7 g of 8-(3,5-difluorophenyl)-1,4-dioxaspiro[4,5]decane-8-ol was obtained.

Second Step

Into a reaction vessel under a nitrogen atmosphere, 48.7 g (180 mmol) of 8-(3,5-difluorophenyl)-1,4-dioxaspiro[4,5]decane-8-ol obtained in the first step, 1.7 g (9.0 mmol) of p-toluenesulfonic acid monohydrate, 10 mL of ethane-1,2-diol, 3.5 mL of water and 250 mL of toluene were put, and the resultant mixture was refluxed for 5 hours. The resultant mixture was returned to room temperature, washed sequentially with a saturated aqueous solution of sodium hydrogencarbonate, water and saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:9 in a volume ratio) as an eluent and silica gel as a filler, and thus 38.1 g of 8-(3,5-difluorophenyl)-1,4-dioxaspiro[4,5]dec-7-ene was obtained.

Third Step

Into a reaction vessel, 38.1 g (151 mmol) of 8-(3,5-difluorophenyl)-1,4-dioxaspiro[4,5]dec-7-ene obtained in the second step, 120 mL of toluene, 80 mL of isopropanol and 2.3 g of Pd/C (E type) were put, and an atmosphere inside the system was replaced by hydrogen. Under the hydrogen atmosphere, the resultant mixture was stirred at room temperature until the mixture did not absorb hydrogen. After reaction completion, Pd/C was removed by filtration and a solvent was distilled off. A residue was purified according to fractionation by column chromatography using a mixed solvent of heptane and ethyl acetate (ethyl acetate:heptane=1:3 in a volume ratio) as an eluent and silica gel as a filler, and thus 38.2 g of 8-(3,5-difluorophenyl)-1,4-dioxaspiro[4,5]decane was obtained.

Fourth Step

Into a reaction vessel, 38.2 g (150 mmol) of 8-(3,5-difluorophenyl)-1,4-dioxaspiro[4,5]decane obtained in the third step, 200 mL of toluene and 113 mL of formic acid were put, and the resultant mixture was refluxed for 2 hours. The resultant mixture was returned to room temperature, 150 mL of water was added thereto, the resultant mixture was extracted with toluene, and the resultant extract was washed with water and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:3 in a volume ratio) as an eluent and silica gel as a filler, and thus 28.3 g of 4-(3,5-difluorophenyl)cyclohexanone was obtained.

Fifth Step

Into a reaction vessel in which an atmosphere was replaced by nitrogen, 66.8 g (195 mmol) of chloro(methoxymethyl)triphenylphosphorane and 150 mL of THF were put. Then, a THF (50 mL) solution of 21.9 g (195 mmol) of potassium tert-butoxide was added dropwise thereto at −40° C., and the resultant mixture was stirred at −40° C. for 1 hour. Then, a THF (150 mL) solution of 28.3 g (134 mmol) of 4-(3,5-difluorophenyl)cyclohexanone obtained in the fourth step was added dropwise thereto at −40° C., and the resultant mixture was stirred at −40° C. for 1 hour. The mixture was returned to room temperature and stirred for 15 hours, and then 400 mL of water was added thereto, the resultant mixture was extracted with ethyl acetate, and the resultant extract was washed with water and dried over anhydrous magnesium sulfate. Then, an insoluble matter was separated by filtration and then a filtrate was concentrated under reduced pressure. A residue was dissolved in a small amount of toluene, and poured into 500 mL of heptane while stirring, and an insoluble matter was separated by filtration. A solvent was distilled off under reduced pressure. A residue was purified according to fractionation by column chromatography using a mixed solvent of heptane and ethyl acetate (ethyl acetate:heptane=1:20 in a volume ratio) as an eluent and silica gel as a filler, and thus 31.9 g of 1,3-difluoro-5-(4-(methoxymethylene)cyclohexyl)benzene was obtained.

Sixth Step

Into a reaction vessel under a nitrogen atmosphere, 31.9 g (134 mmol) of 1,3-difluoro-5-(4-(methoxymethylene)cyclohexyl)benzene obtained in the fifth step, 300 mL of methanol and 7.7 g (40 mmol) of p-toluenesulfonic acid monohydrate were put, and the resultant mixture was stirred for 12 hours. Then, 200 mL of a saturated aqueous solution of sodium hydrogencarbonate was added thereto, the resultant mixture was extracted with toluene, and the resultant extract was washed with water and dried over anhydrous magnesium sulfate. Then, an insoluble matter was separated by filtration and then a filtrate was concentrated under reduced pressure. Then, 70 mL of toluene, 13 g (40 mmol) of tetrabutylammonium bromide, 35 mL of formic acid and 70 mL of toluene were added thereto, and the resultant mixture was refluxed for 3 hours. The reaction mixture was washed with water and dried over anhydrous magnesium sulfate. Then, an insoluble matter was separated by filtration and then a filtrate was concentrated under reduced pressure, and thus 30.3 g of 4-(3,5-difluorophenyl)cyclohexanecarbaldehyde was obtained.

Seventh Step

Into a reaction vessel, 30.3 g (135 mmol) of 4-(3,5-difluorophenyl)cyclohexanecarbaldehyde obtained in the sixth step, and 300 mL of acetone was put, and a Jones reagent was added dropwise thereto at 0° C. until an orange color did not fade away. Then, 10 mL of isopropanol and 20 g of sodium hydrogencarbonate were added thereto, the resultant mixture was filtered, a solid was rinsed with acetone and a filtrate was concentrated under reduced pressure. Then, 200 mL of water was added thereto, the resultant mixture was extracted with ethyl acetate, the resultant extract was washed with water, and a solvent was distilled off by means of a rotary evaporator. A residue was purified according to fractionation by column chromatography using ethyl acetate as an eluent and silica gel as a filler. The resultant mixture was further purified by recrystallization (toluene), and thus 25.0 g of 4-(3,5-difluorophenyl)cyclohexane carboxylic acid was obtained.

Eighth Step

Into a reaction vessel under a nitrogen atmosphere, 10.0 g (41.6 mmol) of 4-(3,5-difluorophenyl)cyclohexane carboxylic acid obtained in the seventh step, 9.6 g (50 mmol) of 1-ethyl-3-(3-dimethylaminopropyl)carbodiimide hydrochloride, 0.51 g (4.2 mmol) of 4-dimethylaminopyridine and 100 mL of dichloromethane were put. Then, a dichloromethane (20 mL) solution of 7.2 g (46 mmol) of 3-pentyl-3-hydroxymethyloxetane was added dropwise thereto at room temperature, and the resultant mixture was stirred at room temperature for 15 hours. Then, 30 mL of water was added thereto, the resultant mixture was extracted with diethyl ether, the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 13.3 g of (3-pentyloxetane-3-yl)methyl) 4-(3,5-difluorophenyl)cyclohexane carboxylate was obtained.

Ninth Step

Into a reaction vessel under a nitrogen atmosphere, 13.3 g (34.9 mmol) of (3-pentyloxetane-3-yl)methyl) 4-(3,5-difluorophenyl)cyclohexane carboxylate obtained in the eighth step and 40 mL of dichloromethane were put, and the resultant mixture was cooled to −70° C. Then, 1.2 g (8.7 mmol) of boron trifluoride-diethyl ether complex was added dropwise thereto. The mixture was warmed to room temperature and stirred for 15 hours. Then, 9.1 mL (70 mmol) of triethylamine was added thereto, and the resultant mixture was concentrated by means of a rotary evaporator. Then, 150 mL of diethyl ether was added thereto, and the resultant mixture was washed with saturated brine and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 10.6 g of 1-(4-(3,5-difluorophenyl)cyclohexyl)-4-pentyl-2,6,7-trioxabicyclo[2.2.2]octane was obtained.

Tenth Step

Into a reaction vessel under a nitrogen atmosphere, 10.6 g (27.8 mmol) of 1-(4-(3,5-difluorophenyl)cyclohexyl)-4-pentyl-2,6,7-trioxabicyclo[2.2.2]octane obtained in the ninth step and 200 mL of THF were put, and the resultant mixture was cooled to −70° C. Then, 22.6 mL (36.1 mmol) of n-butyl lithium (1.60 M, hexane solution) was added dropwise thereto, and the resultant mixture was stirred at −70° C. for 1 hour. Next, a THF (20 mL) solution of 8.8 g (42 mmol) of dibromodifluoromethane was added dropwise thereto at −70° C., and the resultant mixture was stirred at −70° C. for 1 hour. Then, the mixture was returned to room temperature, stirred for 1 hour, and a reaction mixture was poured into 300 mL of ice water, the resultant mixture was extracted with toluene, and the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 3.7 g of 1-(4-(4-(bromodifluoromethyl-3,5-trifluorophenyl)cyclohexyl-2,6,7-trioxabicyclo[2.2.2]octane was obtained.

Eleventh Step

Into a reaction vessel under a nitrogen atmosphere, 3.7 g (7.2 mmol) of 1-(4-(4-(bromodifluoromethyl)-3,5-trifluorophenyl)cyclohexyl)-4-pentyl-2,6,7-trioxabicyclo[2.2.2]octane obtained in the tenth step, 1.1 g (7.2 mmol) of 3,4,5-trifluorophenol, 3.0 g (22 mmol) of potassium carbonate and 100 mL of DMF were put, and the resultant mixture was stirred at 85° C. for 4 hours. The mixture was cooled to room temperature, 100 mL of toluene and 100 mL of aqueous solution of sodium hydroxide (2 N) were added thereto, an organic layer was separated, and an aqueous layer was extracted with toluene, the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 0.2 g of 1-(4'-(4-difluoro(3,4,5-trifluorophenyl)methyl)3,5-difluorophenyl)cyclohexyl-4-pentyl-2,6,7-trioxabicyclo[2.2.2]octane was obtained as a white solid.

Chemical shifts (δ (ppm)) according to $^1$H-nuclear magnetic resonance analysis are as described below, and the compound obtained was identified to be 1-(4'-(4-difluoro(3,4,5-trifluorophenyl)methyl)3,5-difluorophenyl)cyclohexyl-4-pentyl-2,6,7-trioxabicyclo[2.2.2]octane. A solvent for measurement was CDCl$_3$.

Chemical shifts (δ (ppm)); 6.95 (m, 2H), 6.80 (m, 2H), 3.91 (s, 6H), 2.47 (m, 1H), 2.00 (m, 2H), 1.91 (m, 2H), 1.63 (m, 1H), 1.4-1.1 (m, 12H), 0.88 (t, 3H).

Example 28

Synthesis of 1-(4'-(difluoro(3,4,5-trifluorophenoxy)methyl)-3'-fluoro[1,1'-biphenyl]-4-yl)-4-pentyl-2,6,7-trioxabicyclo[2.2.2]octane (No. 101)

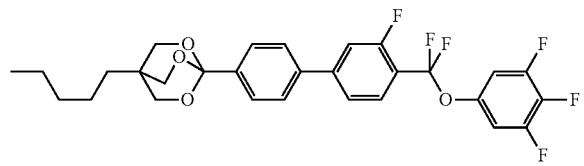 [SMILES: CCCCCC12COC(c3ccc(-c4ccc(C(F)(F)Oc5cc(F)c(F)c(F)c5)c(F)c4)cc3)(OC1)OC2]

First Step

Into a reaction vessel under a nitrogen atmosphere, 3.8 g (10 mmol) of 5-((4-bromo-2-fluorophenyl)difluoromethoxy)-1,2,3-trifluorobenzene, 1.8 g (12 mmol) of 4-formylphenylboronic acid, 0.34 g (0.48 mmol) of dichlorobis(triphenylphosphine) palladium (II), 1.7 g (12 mmol) potassium carbonate, 0.34 g (1.3 mmol) of triphenylphosphine, 20 mL of toluene and 20 mL of ethanol were put, and the resultant mixture was stirred at 80° C. for 5 hours. The mixture was cooled to room temperature, 200 mL of hydrochloric acid (2 N) was added thereto, and the resultant mixture was extracted with toluene, the resultant extract was washed with saturated brine, and dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 3.2 g of 4'-(difluoro(3,4,5-trifluorophenoxy)methyl)-3'-fluoro[1,1'-biphenyl]-4-carboaldehyde was obtained.

Second Step

Into a reaction vessel, 3.2 g (8.1 mmol) of 4'-(difluoro(3,4,5-trifluorophenoxy)methyl)-3'-fluoro[1,1'-biphenyl]-4-carboaldehyde obtained in the first step and 100 mL of acetone were put, and a Jones reagent was added dropwise thereto at 0° C. until an orange color did not fade away. Then, 4 mL of isopropanol and 4 g of sodium hydrogencarbonate were added thereto, the resultant mixture was filtered, a solid was rinsed with acetone and a filtrate was concentrated under reduced pressure. Then, 50 mL of water was added thereto, the resultant mixture was extracted with ethyl acetate, the resultant extract was washed with water, and a solvent was distilled off by means of a rotary evaporator. A residue was purified according to fractionation by column chromatography using a mixed solvent of toluene and ethanol (toluene:ethanol=1:1 in a volume ratio) as an eluent and silica gel as a filler, and thus 32 g of 4'-(difluoro(3,4,5-trifluorophenoxy)methyl)-3'-fluoro[1,1'-biphenyl]-4-carboxylic acid was obtained.

Third Step

Into a reaction vessel under a nitrogen atmosphere, 3.2 (7.8 mmol) of 4'-(difluoro(3,4,5-trifluorophenoxy)methyl)-3'-fluoro[1,1'-biphenyl]-4-carboxylic acid obtained in the second step, 1.8 g (9.3 mmol) of 1-ethyl-3-(3-dimethylaminopropyl)carbodiimide hydrochloride, 0.09 g (0.8 mmol) of 4-dimethylaminopyridine and 20 mL of dichloromethane were put. Then, a dichloromethane (10 mL) solution of 1.4 g (8.5 mmol) of 3-pentyl-3-hydroxymethyloxetane was added dropwise thereto at room temperature, and the resultant mixture was stirred at room temperature for 15 hours. Then, 20 mL of water was added thereto, the resultant mixture was extracted with diethyl ether, and the resultant extract was washed with saturated brine, dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler, and thus 3.0 g of (3-pentyloxetane-3-yl)methyl) 4'-(difluoro(3,4,5-trifluorophenoxy)methyl)-3'-fluoro[1,1'-biphenyl]-4-carboxylate was obtained.

Fourth Step

Into a reaction vessel under a nitrogen atmosphere, 3.0 g (5.6 mmol) of (3-pentyloxetane-3-yl)methyl) 4'-(difluoro(3,4,5-trifluorophenoxy)methyl)-3'-fluoro[1,1'-biphenyl]-4-carboxylate obtained in the third step and 50 mL of dichloromethane was put, and the resultant mixture was cooled to −70° C., and 0.20 g (1.4 mmol) of boron trifluoride-diethyl ether complex was added dropwise thereto. The resultant mixture was warmed to room temperature and stirred for 15 hours. Then, 1.5 mL (11 mmol) of triethylamine was added thereto, and the resultant mixture was concentrated by means of a rotary evaporator. Then, 50 mL of diethyl ether was added thereto, the resultant mixture was washed with saturated brine, dried over anhydrous magnesium sulfate. Then, an insoluble matter was separated by filtration and then a filtrate was concentrated under reduced pressure. A residue was purified according to fractionation by column chromatography using a mixed solvent of heptane and ethyl acetate (ethyl acetate:heptane=1:4 in a volume ratio) as an eluent and silica gel as a filler. The resultant mixture was further purified by recrystallization (heptane/ethyl acetate=80/20 in a volume ratio), and thus 2.3 g of 1-(4'-(difluoro(3,4,5-trifluorophenoxy)methyl)-3'-fluoro[1,1'-biphenyl]-4-yl)-4-pentyl-2,6,7-trioxabicyclo[2.2.2]octane was obtained as a white solid.

Chemical shifts (δ (ppm)) according to $^1$H-nuclear magnetic resonance analysis are as described below, and the compound obtained was identified to be 1-(4'-(difluoro(3,4,5-trifluorophenoxy)methyl)-3'-fluoro[1,1'-biphenyl]-4-yl)-4-pentyl-2,6,7-trioxabicyclo[2.2.2]octane. A solvent for measurement was CDCl$_3$.

Chemical shifts (δ (ppm)); 7.8-7.6 (m, 3H), 7.57 (d, 2H), 7.41 (m, 2H), 6.98 (t, 2H), 4.13 (s, 6H), 1.4-1.2 (m, 8H), 0.92 (t, 3H).

A transition temperature of compound (No. 101) obtained is as described below.

Transition temperature: C 119.5 C' 127.4 S$_A$ 187.0 N 193.5 I.

Physical Properties of Compound (No. 101)

Liquid crystal composition a including 90% by weight of base liquid crystal A and 10% by weight of 1-(4'-(difluoro(3,4,5-trifluorophenoxy)methyl)-3'-fluoro[1,1'-biphenyl]-4-yl)-4-pentyl-2,6,7-trioxabicyclo[2.2.2]octane (No. 101) obtained in Example 28 was prepared. Physical properties of liquid crystal composition a obtained were measured, and extrapolated values of physical properties of compound (No.

101) were calculated by extrapolating measured values. Values thereof are as described below.

Maximum temperature ($T_{NI}$)=151.7° C.; dielectric anisotropy ($\Delta\varepsilon$)=352; optical anisotropy ($\Delta n$)=0.157; viscosity ($\eta$)=134.2.

Example 29

Synthesis of 4-butyl-1-(4'-(difluo-3,4,5-trifluorophenoxy)methyl)2,3',5'-trifluoro-[1,1'-biphenyl]-4-yl)-2,6,7-trioxabicyclo[2.2.2]octane (No. 104)

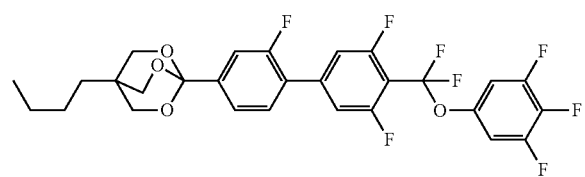 [SMILES: CCCCC12COC(c3ccc(-c4cc(F)c(C(F)(F)Oc5cc(F)c(F)c(F)c5)c(F)c4)c(F)c3)(OC1)OC2]

Then, 4-butyl-1-(4'-(difluoro(3,4,5-trifluorophenoxy)methyl)2,3',5'-trifluoro-[1,1'-biphenyl]-4-yl)-2,6,7-trioxabicyclo[2.2.2]octane was prepared by performing synthesis in a manner similar to the operations in the second step, the third step and the fourth step in Example 8 using 3-butyl-3-hydroxymethyloxetane in place of 3-pentyl-3-hydroxymethyloxetane.

Chemical shifts ($\delta$ (ppm)) according to $^1$H-nuclear magnetic resonance analysis are as described below, and the compound obtained was identified to be 4-butyl-1-(4'-(difluoro(3,4,5-trifluorophenoxy)methyl)2,3',5'-trifluoro-[1,1'-biphenyl]-4-yl)-2,6,7-trioxabicyclo[2.2.2]octane. A solvent for measurement was CDCl$_3$.

Chemical shifts ($\delta$ (ppm)); 7.6-7.4 (m, 3H), 7.19 (d, 2H), 6.99 (t, 2H), 4.13 (s, 6H), 1.4-1.2 (m, 6H), 0.93 (t, 3H).

A transition temperature of compound (No. 104) obtained is as described below.

Transition temperature: C 78.9 C' 106.3 C" 113.1 N 148.3 I.

Physical Properties of Compound (No. 104)

Liquid crystal composition β including 85% by weight of base liquid crystal A and 15% by weight of 4-butyl-1-(4'-(difluoro(3,4,5-trifluorophenoxy)methyl)2,3',5'-trifluoro-[1,1'-biphenyl]-4-yl)-2,6,7-trioxabicyclo[2.2.2]octane (No. 104) obtained in Example 29 was prepared. Physical properties of liquid crystal composition β obtained were measured, and extrapolated values of physical properties of compound (No. 104) were calculated by extrapolating measured values. Values thereof are as described below.

Maximum temperature ($T_{NI}$)=103.7° C.; dielectric anisotropy ($\Delta\varepsilon$)=56.1; optical anisotropy ($\Delta n$)=0.135; viscosity ($\eta$)=126.1.

Example 30

Synthesis of 1-(4'((3,5-difluoro-4-(trifluoromethyl)phenoxy)difluoromethyl)-2,3',5'-trifluoro-[1,1'-biphenyl]-4-yl)-4-pentyl-2,6,7-trioxabicyclo[2.2.2]octane (No. 107)

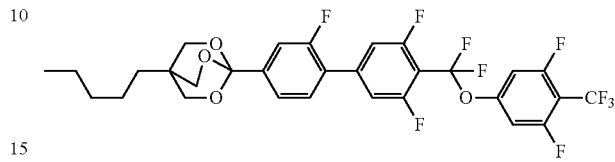

Then, 1-(4'((3,5-difluoro-4-(trifluoromethyl)phenoxy)difluoromethyl)-2,3',5'-trifluoro-[1,1'-biphenyl]-4-yl)-4-pentyl-2,6,7-trioxabicyclo[2.2.2]octane was prepared by performing synthesis in a manner similar to the operations in Example 8 using 3,5-difluoro-4-(trifluoromethyl)phenol in place of 3,4,5-trifluorophenol in the fifth step in Example 8.

Chemical shifts ($\delta$ (ppm)) according to $^1$H-nuclear magnetic resonance analysis are as described below, and the obtained compound was identified to be 1-(4'((3,5-difluoro-4-(trifluoromethyl)phenoxy)difluoromethyl)-2,3',5'-trifluoro-[1,1'-biphenyl]-4-yl)-4-pentyl-2,6,7-trioxabicyclo[2.2.2]octane. A solvent for measurement was CDCl$_3$.

Chemical shifts ($\delta$ (ppm)); 7.6-7.4 (m, 3H), 7.20 (d, 2H), 6.99 (d, 2H), 4.13 (s, 6H), 1.4-1.2 (m, 8H), 0.89 (t, 3H).

A transition temperature of compound (No. 107) obtained is as described below.

Transition temperature: C 152.3 (N 134.8 I).

Physical Properties of Compound (No. 107)

Liquid crystal composition γ including 90% by weight of mother liquid crystal A and 10% by weight of 1-(4'(3,5-difluoro-4-(trifluoromethyl)phenoxy)difluoromethyl)-2,3',5'-trifluoro-[1,1'-biphenyl]-4-yl)-4-pentyl-2,6,7-trioxabicyclo[2.2.2]octane (No. 107) obtained in Example 30 was prepared. Physical properties of liquid crystal composition γ obtained were measured, and extrapolated values of physical properties of compound (No. 107) were calculated by extrapolating measured values. Values thereof are as described below.

Maximum temperature ($T_{NI}$)=97.7° C.; dielectric anisotropy ($\Delta\varepsilon$)=63.2; optical anisotropy ($\Delta n$)=0.137; viscosity ($\eta$)=140.0.

Example 31

Synthesis of 1-(4-(difluoro(2,3',4',5'-tetrafluoro-[1,1'-biphenyl]-4-yl)oxy)methyl)-3,5-difluorophenyl-4-pentyl-2,6,7-trioxabicyclo[2.2.2]octane (No. 115)

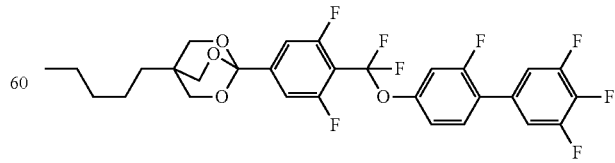

Then, 1-(4-(difluoro(2,3',4',5'-tetrafluoro[1,1'-biphenyl]-4-yl)oxy)methyl)-3,5-difluorophenyl-4-pentyl-2,6,7-trioxabicyclo[2.2.2]octane was prepared by performing synthesis in a manner similar to the operations in Example 10 using 2,3',4',5'-tetrafluoro[1,1'-biphenyl]-4-ol in place of 3,4,5-trifluorophenol in the fifth step in Example 10.

Chemical shifts (δ (ppm)) according to $^1$H-NMR analysis are as described below, and the compound obtained was identified to be 1-(4-(difluoro(2,3',4',5'-tetrafluoro[1,1'-biphenyl]-4-yl)oxy)methyl)-3,5-difluorophenyl-4-pentyl-2,6,7-trioxabicyclo[2.2.2]octane. A solvent for measurement was CDCl$_3$.

Chemical shifts (δ (ppm)); 7.33 (t, 1H), 7.24 (d, 2H), 7.13 (m, 4H), 4.10 (s, 6H), 1.4-1.3 (m, 8H), 0.90 (t, 3H).

A transition temperature of compound (No. 115) obtained is as described below.

Transition temperature: C 115.0 (N 57.9 I).

Physical Properties of Compound (No. 115)

Liquid crystal composition δ including 95% by weight of base liquid crystal A and 5% by weight of 1-(4-(difluoro(2,3',4',5'-tetrafluoro[1,1'-biphenyl]-4-yl)oxy)methyl)-3,5-difluorophenyl-4-pentyl-2,6,7-trioxabicyclo[2.2.2]octane (No. 115) obtained in Example 31 was prepared. Physical properties of liquid crystal composition δ obtained were measured, and extrapolated values of physical properties of compound (No. 115) were calculated by extrapolating measured values. Values thereof are as described below.

Maximum temperature (T$_{NI}$)=89.7° C.; dielectric anisotropy (Δ∈)=44.1; optical anisotropy (Δn)=0.137; viscosity (η)=84.6.

Example 32

Synthesis of 1-(4'-(difluoro((2,3',4',5'-tetrafluoro[1,1'-biphenyl]-4-yl)oxy)methyl)-2,3',5'-trifluoro-[1,1'-biphenyl]-4-yl)-4-pentyl-2,6,7-trioxabicyclo[2.2.2]octane (No. 151)

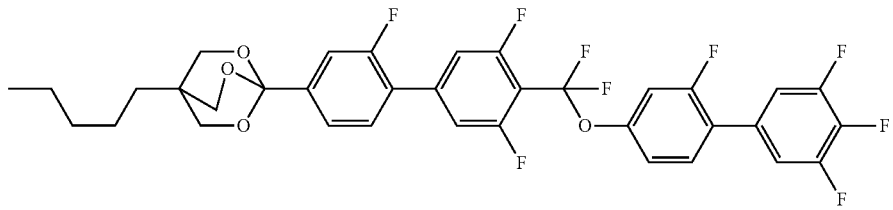 [SMILES: CCCCCC12COC(c3ccc(-c4cc(F)c(C(F)(F)Oc5ccc(-c6cc(F)c(F)c(F)c6)c(F)c5)c(F)c4)c(F)c3)(OC1)OC2]

Then, 1-(4'-(difluoro((2,3',4',5'-tetrafluoro-[1,1'-biphenyl]-4-yl)oxy)methyl)-2,3',5'-trifluoro-[1,1'-biphenyl]-4-yl-4-pentyl-2,6,7-trioxabicyclo[2.2.2]octane was prepared by performing synthesis in a manner similar to the operations in Example 8 using 2,3',4',5'-tetrafluoro[1,1'-biphenyl]-4-ol in place of 3,4,5-trifluorophenol in the fifth step in Example 8.

Chemical shifts (δ (ppm)) according to $^1$H-NMR analysis are as described below, and the compound obtained was identified to be 1-(4'-(difluoro((2,3',4',5'-tetrafluoro[1,1'-biphenyl]-4-yl)oxy)methyl)-2,3',5'-trifluoro-[1,1'-biphenyl]-4-yl)-4-pentyl-2,6,7-trioxabicyclo[2.2.2]octane. A solvent for measurement was CDCl$_3$.

Chemical shifts (δ (ppm)); 7.6-7.3 (m, 4H), 7.18 (m, 6H), 4.12 (s, 6H), 1.4-1.2 (m, 8H), 0.90 (t, 3H).

A transition temperature of compound (No. 151) obtained is as described below.

Transition temperature: C 110.9 S$_A$ 128.8 N 245.7 I.

Physical Properties of Compound (No. 151)

Liquid crystal composition ∈ including 900/by weight of base liquid crystal A and 10% by weight of 1-(4'-(difluoro((2,3',4',5'-tetrafluoro[1,1'-biphenyl]-4-yl)oxy)methyl)-2,3',5'-trifluoro-[1,1'-biphenyl]-4-yl)-4-pentyl-2,6,7-trioxabicyclo[2.2.2]octane (No. 151) obtained in Example 32 was prepared. Physical properties of liquid crystal composition c obtained were measured, and extrapolated values of physical properties of compound (No. 151) were calculated by extrapolating measured values. Values thereof are as described below.

Maximum temperature (T$_{NI}$)=152.7° C.; dielectric anisotropy (Δ∈)=55.2; optical anisotropy (Δn)=0.187; viscosity (η)=127.8.

Compounds (No. 1) to (No. 157) shown below can be synthesized by synthetic methods in a manner similar to the methods described in Examples 1 to 32.

| No. | |
|---|---|
| 1 | 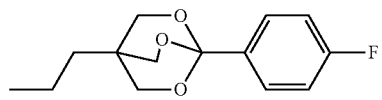 [SMILES: CCCC12COC(c3ccc(F)cc3)(OC1)OC2] |
| 2 | 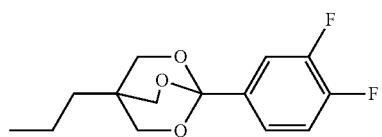 [SMILES: CCCC12COC(c3ccc(F)c(F)c3)(OC1)OC2] |
| 3 | 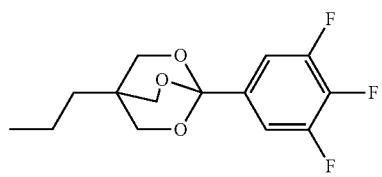 [SMILES: CCCC12COC(c3cc(F)c(F)c(F)c3)(OC1)OC2] |
| 4 | 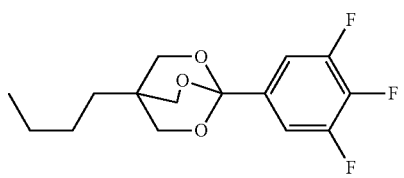 [SMILES: CCCCC12COC(c3cc(F)c(F)c(F)c3)(OC1)OC2] |
| 5 | 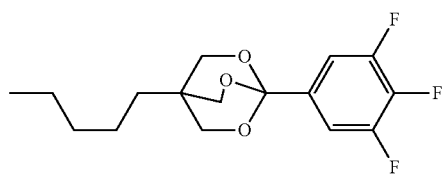 [SMILES: CCCCCC12COC(c3cc(F)c(F)c(F)c3)(OC1)OC2] |
| 6 | 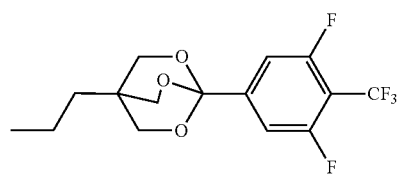 [SMILES: CCCC12COC(c3cc(F)c(C(F)(F)F)c(F)c3)(OC1)OC2] |
| 7 | 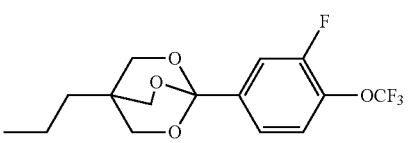 [SMILES: CCCC12COC(c3ccc(OC(F)(F)F)c(F)c3)(OC1)OC2] |
| 8 | 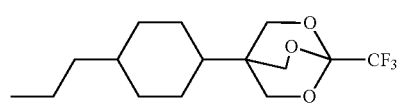 [SMILES: CCCC1CCC(C23COC(C(F)(F)F)(OC2)OC3)CC1] |
| 9 | 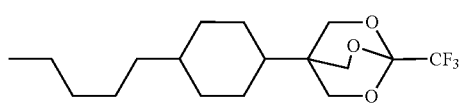 |
| 10 | 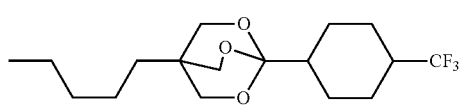 [SMILES: CCCCCC12COC(C3CCC(C(F)(F)F)CC3)(OC1)OC2] |
| 11 | 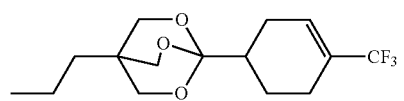 |

| No. | |
|---|---|
| 12 | 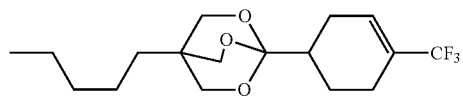 |
| 13 | 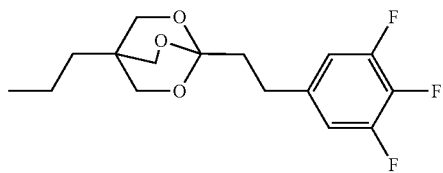 [SMILES: CCCC12COC(CCc3cc(F)c(F)c(F)c3)(OC1)OC2] |
| 14 | 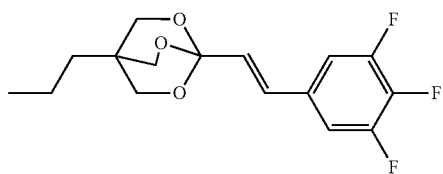 [SMILES: CCCC12COC(/C=C/c3cc(F)c(F)c(F)c3)(OC1)OC2] |
| 15 | 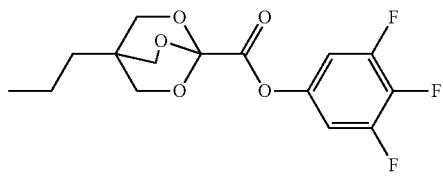 [SMILES: CCCC12COC(C(=O)Oc3cc(F)c(F)c(F)c3)(OC1)OC2] |
| 16 | 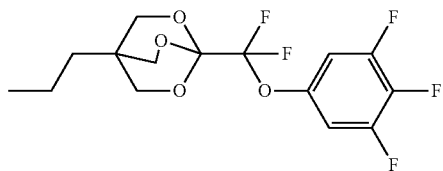 |
| 17 | 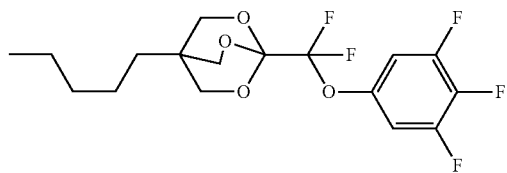 [SMILES: CCCCCC12COC(C(F)(F)Oc3cc(F)c(F)c(F)c3)(OC1)OC2] |
| 18 | 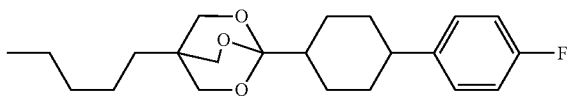 [SMILES: CCCCCC12COC(C3CCC(c4ccc(F)cc4)CC3)(OC1)OC2] |
| 19 | 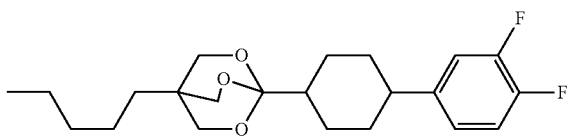 [SMILES: CCCCCC12COC(C3CCC(c4ccc(F)c(F)c4)CC3)(OC1)OC2] |
| 20 | 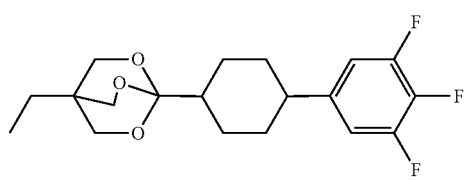 [SMILES: CCC12COC(C3CCC(c4cc(F)c(F)c(F)c4)CC3)(OC1)OC2] |

| No. | |
|---|---|
| 21 | 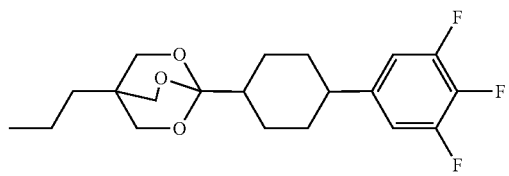 |
| 22 | 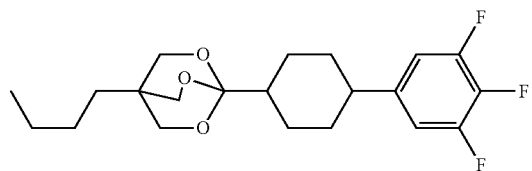 [SMILES: CCCCC12COC(C3CCC(c4cc(F)c(F)c(F)c4)CC3)(OC1)OC2] |
| 23 | 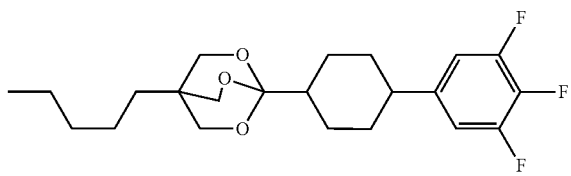 [SMILES: CCCCCC12COC(C3CCC(c4cc(F)c(F)c(F)c4)CC3)(OC1)OC2] |
| 24 | 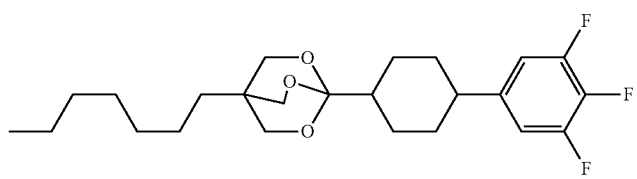 [SMILES: CCCCCCCC12COC(C3CCC(c4cc(F)c(F)c(F)c4)CC3)(OC1)OC2] |
| 25 | 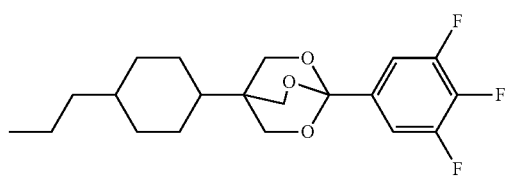 [SMILES: CCCC1CCC(C23COC(c4cc(F)c(F)c(F)c4)(OC2)OC3)CC1] |
| 26 | 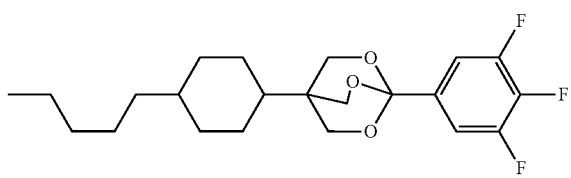 [SMILES: CCCCCC1CCC(C23COC(c4cc(F)c(F)c(F)c4)(OC2)OC3)CC1] |
| 27 | 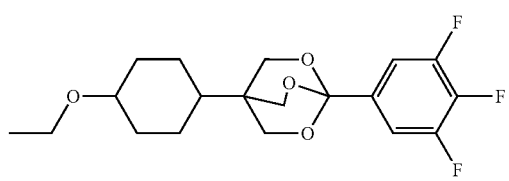 [SMILES: CCOC1CCC(C23COC(c4cc(F)c(F)c(F)c4)(OC2)OC3)CC1] |
| 28 | 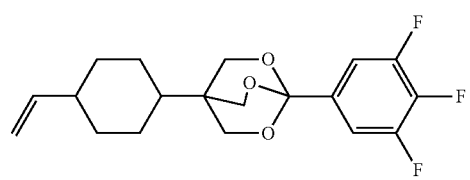 [SMILES: C=CC1CCC(C23COC(c4cc(F)c(F)c(F)c4)(OC2)OC3)CC1] |

| No. | |
|---|---|
| 29 | 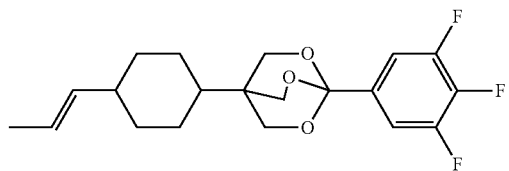 |
| 30 | 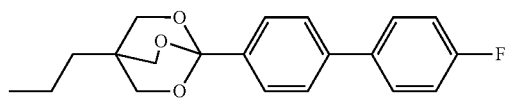 [SMILES: CCCC12COC(c3ccc(-c4ccc(F)cc4)cc3)(OC1)OC2] |
| 31 | 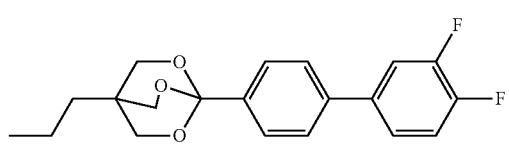 [SMILES: CCCC12COC(c3ccc(-c4ccc(F)c(F)c4)cc3)(OC1)OC2] |
| 32 | 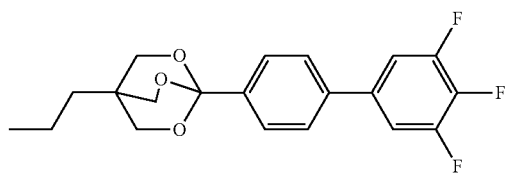 [SMILES: CCCC12COC(c3ccc(-c4cc(F)c(F)c(F)c4)cc3)(OC1)OC2] |
| 33 | 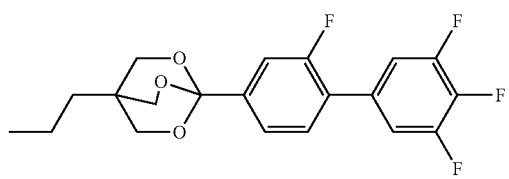 [SMILES: CCCC12COC(c3ccc(-c4cc(F)c(F)c(F)c4)c(F)c3)(OC1)OC2] |
| 34 | 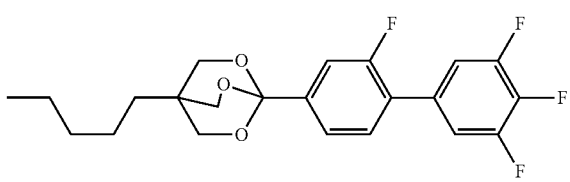 [SMILES: CCCCCC12COC(c3ccc(-c4cc(F)c(F)c(F)c4)c(F)c3)(OC1)OC2] |
| 35 | 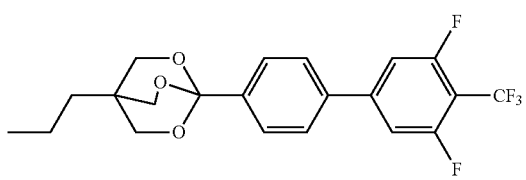 |
| 36 | 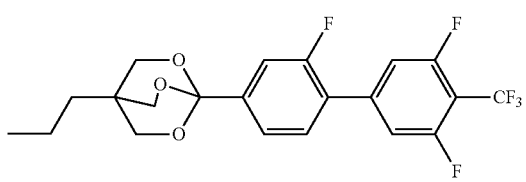 |
| 37 | 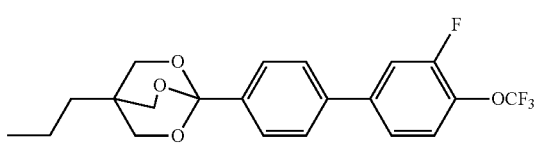 [SMILES: CCCC12COC(c3ccc(-c4ccc(OC(F)(F)F)c(F)c4)cc3)(OC1)OC2] |

| No. | |
|---|---|
| 38 | 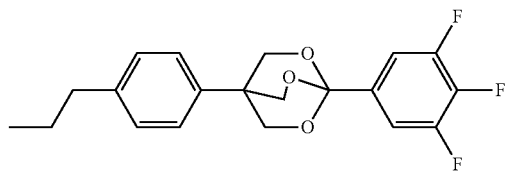 [SMILES: CCCc1ccc(C23COC(c4cc(F)c(F)c(F)c4)(OC2)OC3)cc1] |
| 39 | 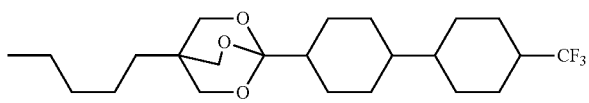 |
| 40 | 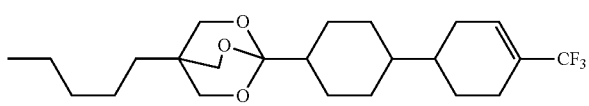 |
| 41 | 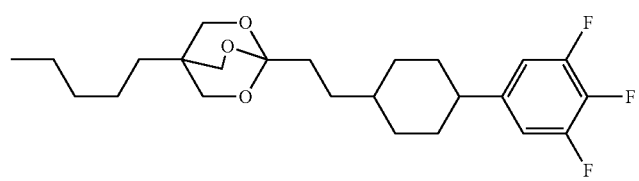 |
| 42 | 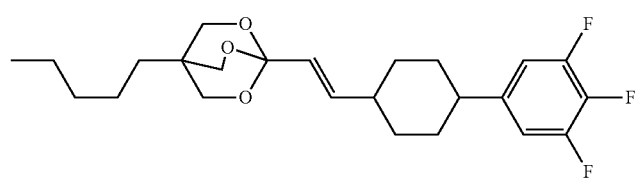 [SMILES: CCCCCC12COC(/C=C/C3CCC(c4cc(F)c(F)c(F)c4)CC3)(OC1)OC2] |
| 43 | 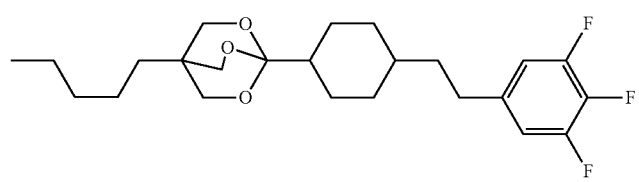 |
| 44 | 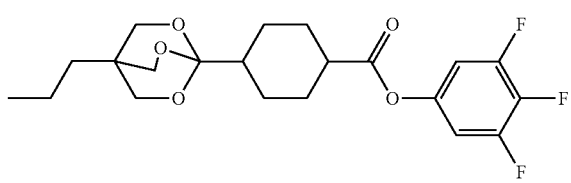 [SMILES: CCCC12COC(C3CCC(C(=O)Oc4cc(F)c(F)c(F)c4)CC3)(OC1)OC2] |
| 45 | |
| 46 | 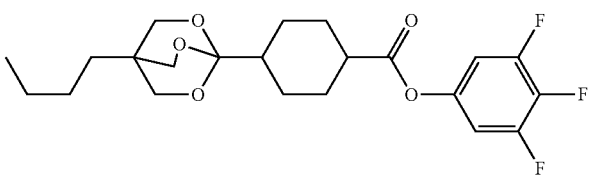 [SMILES: CCCCC12COC(C3CCC(C(=O)Oc4cc(F)c(F)c(F)c4)CC3)(OC1)OC2] |
| 47 | 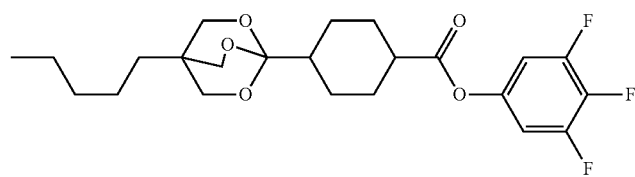 |

| No. | |
|---|---|
| 48 | 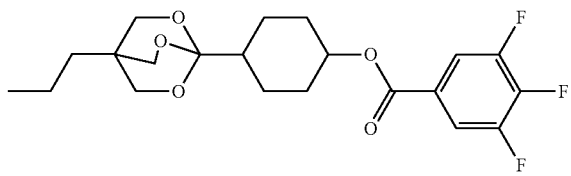 [SMILES: CCCC12COC(C3CCC(OC(=O)c4cc(F)c(F)c(F)c4)CC3)(OC1)OC2] |
| 49 | 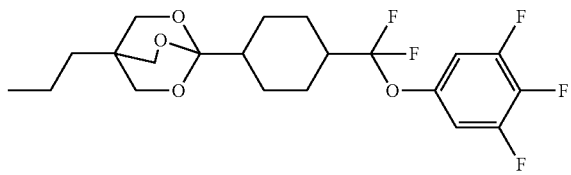 [SMILES: CCCC12COC(C3CCC(C(F)(F)Oc4cc(F)c(F)c(F)c4)CC3)(OC1)OC2] |
| 50 | 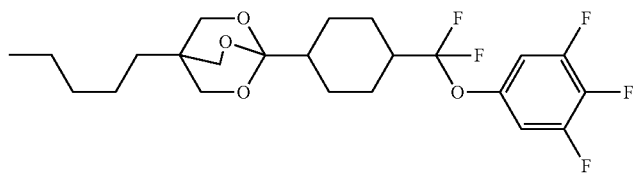 [SMILES: CCCCCC12COC(C3CCC(C(F)(F)Oc4cc(F)c(F)c(F)c4)CC3)(OC1)OC2] |
| 51 | 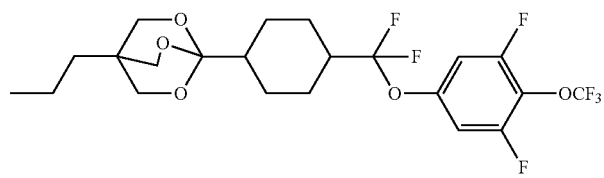 [SMILES: CCCC12COC(C3CCC(C(F)(F)Oc4cc(F)c(OC(F)(F)F)c(F)c4)CC3)(OC1)OC2] |
| 52 | 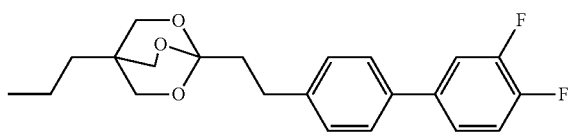 [SMILES: CCCC12COC(CCc3ccc(-c4ccc(F)c(F)c4)cc3)(OC1)OC2] |
| 53 | 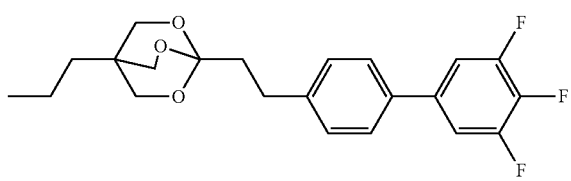 [SMILES: CCCC12COC(CCc3ccc(-c4cc(F)c(F)c(F)c4)cc3)(OC1)OC2] |
| 54 | 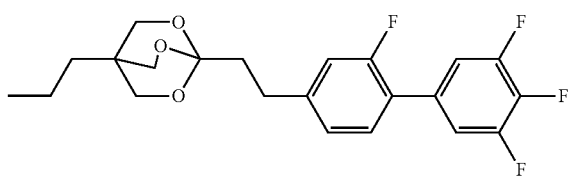 [SMILES: CCCC12COC(CCc3ccc(-c4cc(F)c(F)c(F)c4)c(F)c3)(OC1)OC2] |
| 55 | |
| 56 | 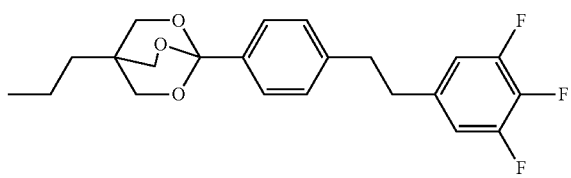 [SMILES: CCCC12COC(c3ccc(CCc4cc(F)c(F)c(F)c4)cc3)(OC1)OC2] |

-continued
| No. | |
|---|---|
| 57 | 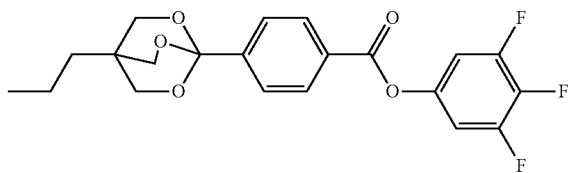 [SMILES: CCCC12COC(c3ccc(C(=O)Oc4cc(F)c(F)c(F)c4)cc3)(OC1)OC2] |
| 58 | 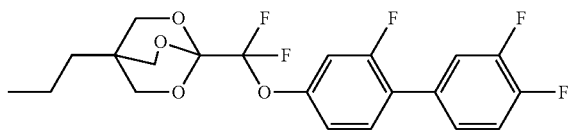 [SMILES: CCCC12COC(C(F)(F)Oc3ccc(-c4ccc(F)c(F)c4)c(F)c3)(OC1)OC2] |
| 59 | 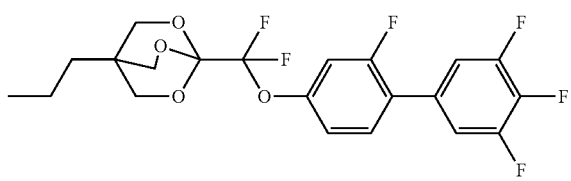 [SMILES: CCCC12COC(C(F)(F)Oc3ccc(-c4cc(F)c(F)c(F)c4)c(F)c3)(OC1)OC2] |
| 60 | 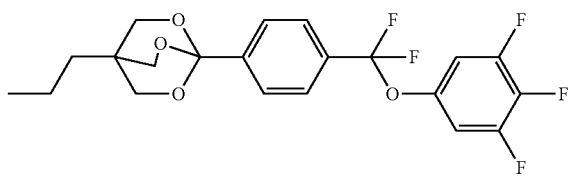 |
| 61 | 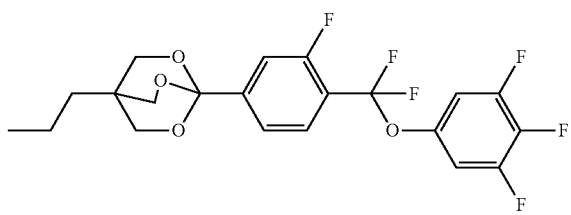 [SMILES: CCCC12COC(c3ccc(C(F)(F)Oc4cc(F)c(F)c(F)c4)c(F)c3)(OC1)OC2] |
| 62 | 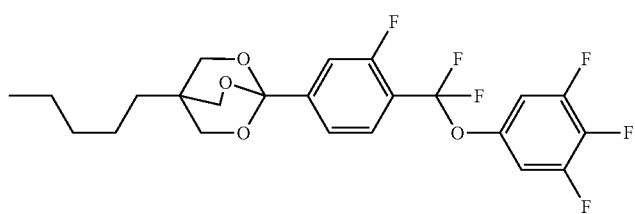 [SMILES: CCCCCC12COC(c3ccc(C(F)(F)Oc4cc(F)c(F)c(F)c4)c(F)c3)(OC1)OC2] |
| 63 | 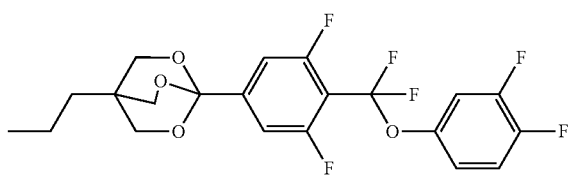 [SMILES: CCCC12COC(c3cc(F)c(C(F)(F)Oc4ccc(F)c(F)c4)c(F)c3)(OC1)OC2] |
| 64 | 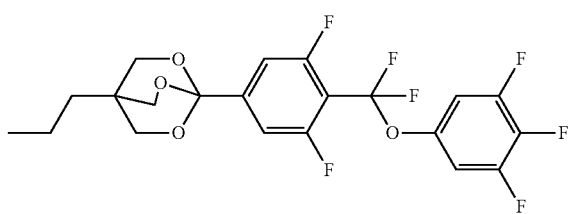 |

-continued
| No. |  |
|---|---|
| 65 | 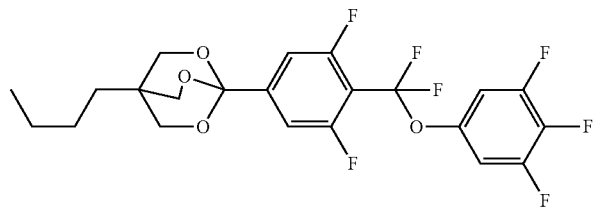 [SMILES: CCCCC12COC(c3cc(F)c(C(F)(F)Oc4cc(F)c(F)c(F)c4)c(F)c3)(OC1)OC2] |
| 66 | 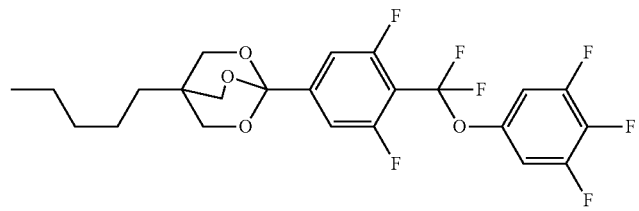 |
| 67 | 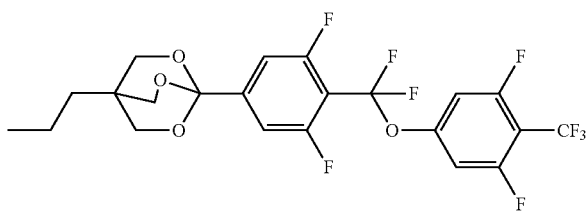 [SMILES: CCCC12COC(c3cc(F)c(C(F)(F)Oc4cc(F)c(C(F)(F)F)c(F)c4)c(F)c3)(OC1)OC2] |
| 68 | 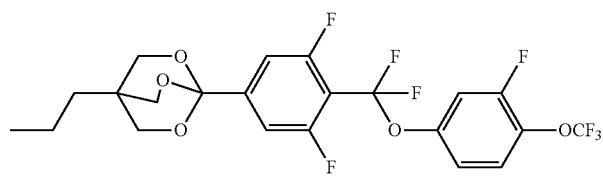 [SMILES: CCCC12COC(c3cc(F)c(C(F)(F)Oc4ccc(OC(F)(F)F)c(F)c4)c(F)c3)(OC1)OC2] |
| 69 | 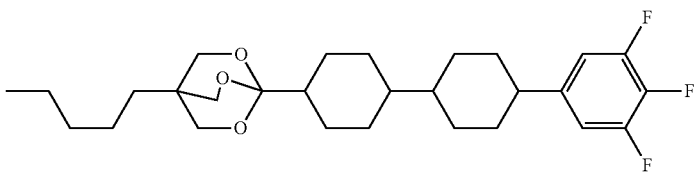 [SMILES: CCCCCC12COC(C3CCC(C4CCC(c5cc(F)c(F)c(F)c5)CC4)CC3)(OC1)OC2] |
| 70 | 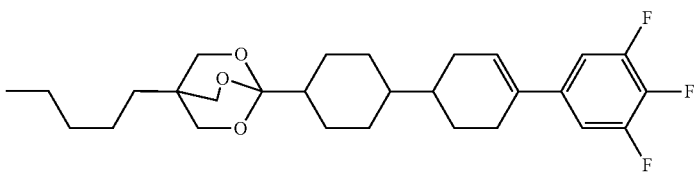 [SMILES: CCCCCC12COC(C3CCC(C4CC=C(c5cc(F)c(F)c(F)c5)CC4)CC3)(OC1)OC2] |
| 71 | 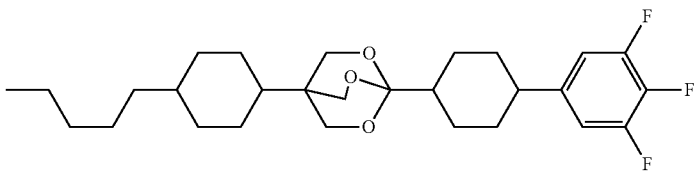 [SMILES: CCCCCC1CCC(C23COC(C4CCC(c5cc(F)c(F)c(F)c5)CC4)(OC2)OC3)CC1] |
| 72 | 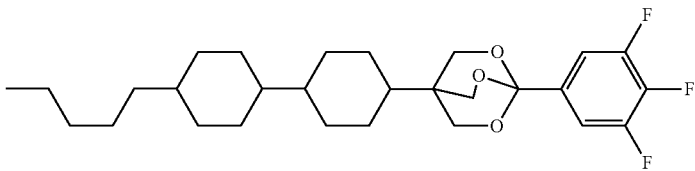 [SMILES: CCCCCC1CCC(C2CCC(C34COC(c5cc(F)c(F)c(F)c5)(OC3)OC4)CC2)CC1] |

| No. | |
|---|---|
| 73 | 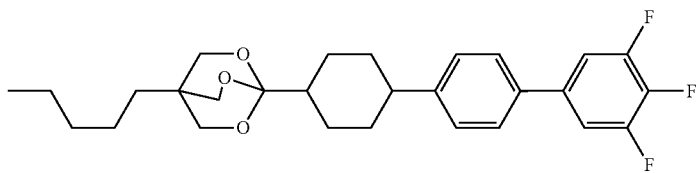 [SMILES: CCCCCC12COC(C3CCC(c4ccc(-c5cc(F)c(F)c(F)c5)cc4)CC3)(OC1)OC2] |
| 74 | 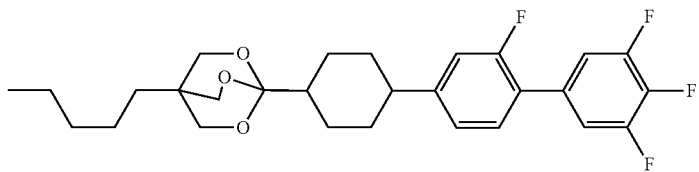 [SMILES: CCCCCC12COC(C3CCC(c4ccc(-c5cc(F)c(F)c(F)c5)c(F)c4)CC3)(OC1)OC2] |
| 75 | 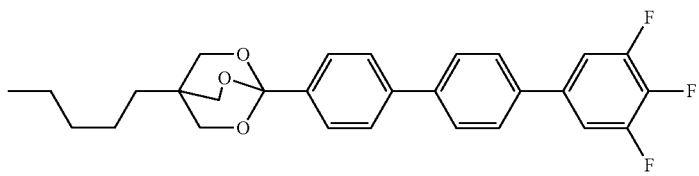 [SMILES: CCCCCC12COC(c3ccc(-c4ccc(-c5cc(F)c(F)c(F)c5)cc4)cc3)(OC1)OC2] |
| 76 | 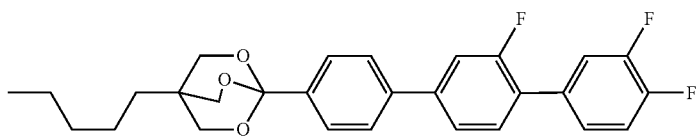 [SMILES: CCCCCC12COC(c3ccc(-c4ccc(-c5ccc(F)c(F)c5)c(F)c4)cc3)(OC1)OC2] |
| 77 | 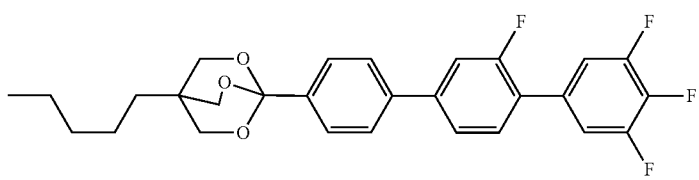 |
| 78 | 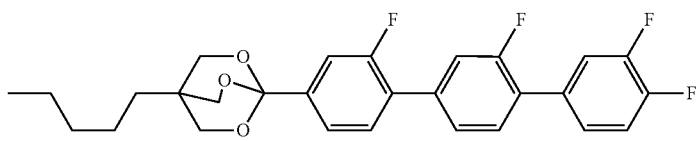 |
| 79 | 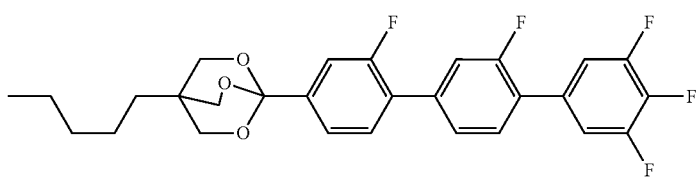 [SMILES: CCCCCC12COC(c3ccc(-c4ccc(-c5cc(F)c(F)c(F)c5)c(F)c4)c(F)c3)(OC1)OC2] |
| 80 | 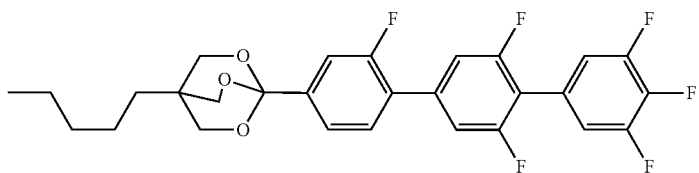 [SMILES: CCCCCC12COC(c3ccc(-c4cc(F)c(-c5cc(F)c(F)c(F)c5)c(F)c4)c(F)c3)(OC1)OC2] |
| 81 | 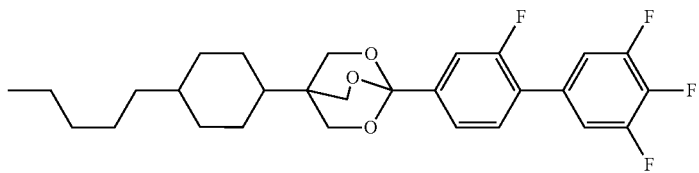 [SMILES: CCCCCC1CCC(C23COC(c4ccc(-c5cc(F)c(F)c(F)c5)c(F)c4)(OC2)OC3)CC1] |

| No. |
|---|
| 82 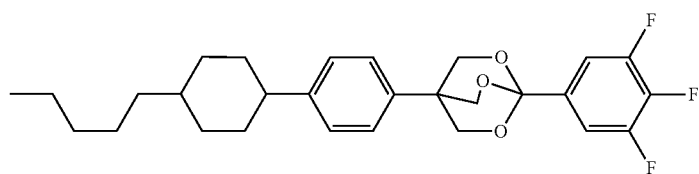 |
| 83 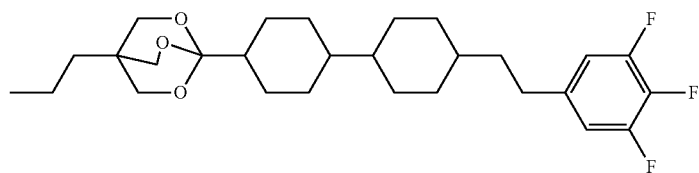 [SMILES: CCCC12COC(C3CCC(C4CCC(CCc5cc(F)c(F)c(F)c5)CC4)CC3)(OC1)OC2] |
| 84 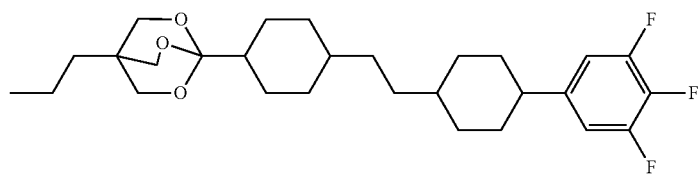 [SMILES: CCCC12COC(C3CCC(CCC4CCC(c5cc(F)c(F)c(F)c5)CC4)CC3)(OC1)OC2] |
| 85 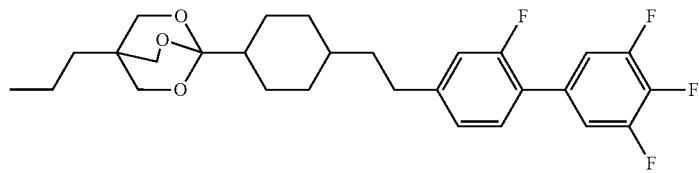 [SMILES: CCCC12COC(C3CCC(CCc4ccc(-c5cc(F)c(F)c(F)c5)c(F)c4)CC3)(OC1)OC2] |
| 86 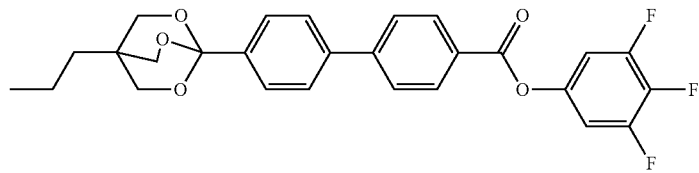 [SMILES: CCCC12COC(c3ccc(-c4ccc(C(=O)Oc5cc(F)c(F)c(F)c5)cc4)cc3)(OC1)OC2] |
| 87 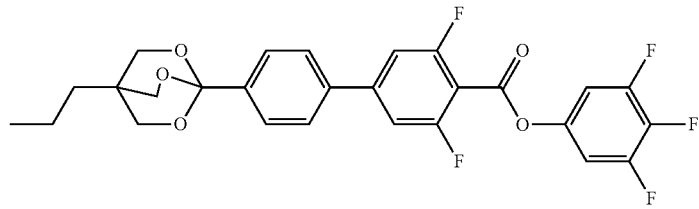 [SMILES: CCCC12COC(c3ccc(-c4cc(F)c(C(=O)Oc5cc(F)c(F)c(F)c5)c(F)c4)cc3)(OC1)OC2] |
| 88 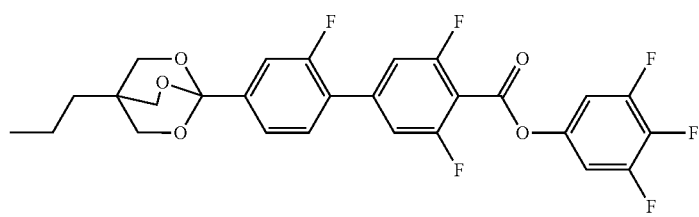 |
| 89 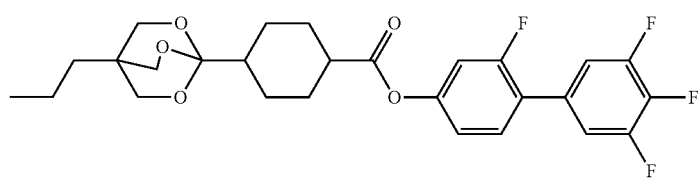 [SMILES: CCCC12COC(C3CCC(C(=O)Oc4ccc(-c5cc(F)c(F)c(F)c5)c(F)c4)CC3)(OC1)OC2] |

| No. |
|---|
| 90 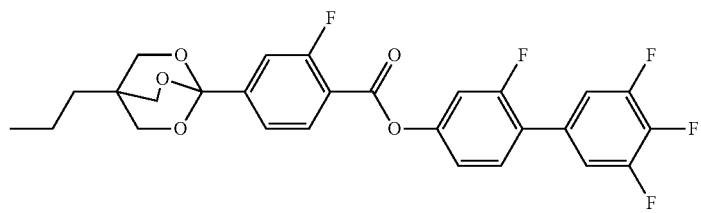 [SMILES: CCCC12COC(c3ccc(C(=O)Oc4ccc(-c5cc(F)c(F)c(F)c5)c(F)c4)c(F)c3)(OC1)OC2] |
| 91 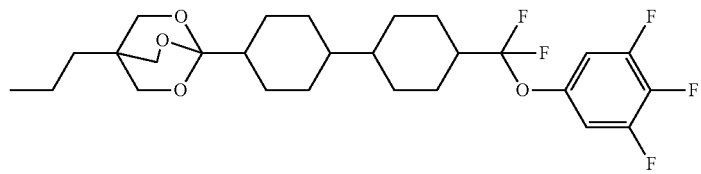 [SMILES: CCCC12COC(C3CCC(C4CCC(C(F)(F)Oc5cc(F)c(F)c(F)c5)CC4)CC3)(OC1)OC2] |
| 92 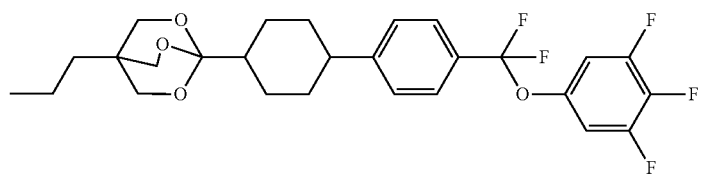 [SMILES: CCCC12COC(C3CCC(c4ccc(C(F)(F)Oc5cc(F)c(F)c(F)c5)cc4)CC3)(OC1)OC2] |
| 93 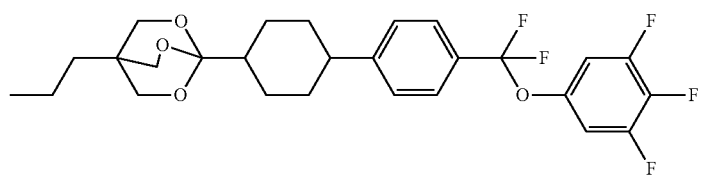 [SMILES: CCCC12COC(C3CCC(c4ccc(C(F)(F)Oc5cc(F)c(F)c(F)c5)cc4)CC3)(OC1)OC2] |
| 94 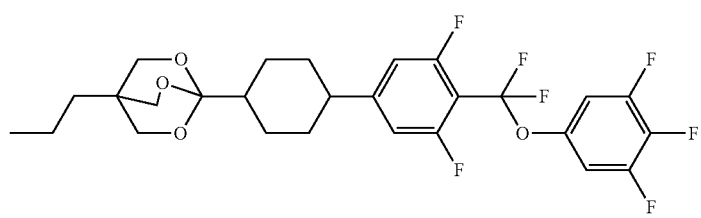 [SMILES: CCCC12COC(C3CCC(c4cc(F)c(C(F)(F)Oc5cc(F)c(F)c(F)c5)c(F)c4)CC3)(OC1)OC2] |
| 95 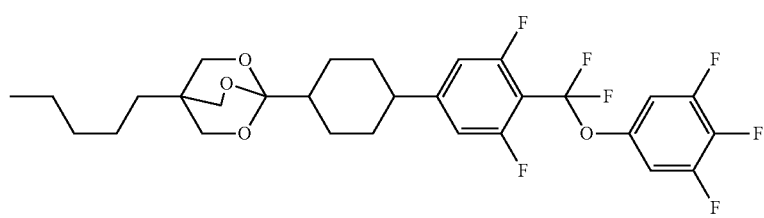 [SMILES: CCCCCC12COC(C3CCC(c4cc(F)c(C(F)(F)Oc5cc(F)c(F)c(F)c5)c(F)c4)CC3)(OC1)OC2] |
| 96 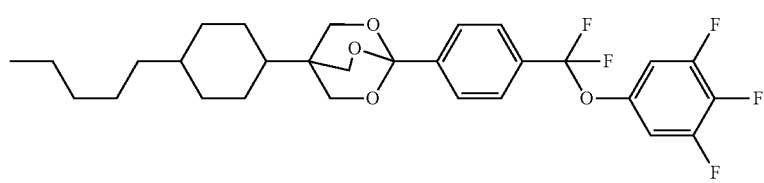 [SMILES: CCCCCC1CCC(C23COC(c4ccc(C(F)(F)Oc5cc(F)c(F)c(F)c5)cc4)(OC2)OC3)CC1] |
| 97 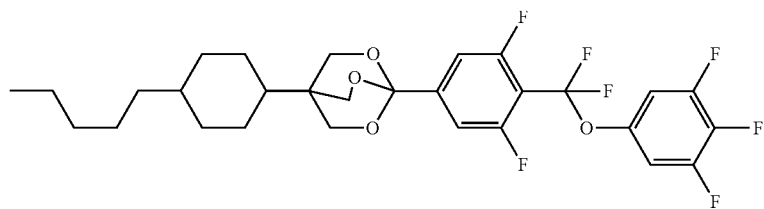 [SMILES: CCCCCC1CCC(C23COC(c4cc(F)c(C(F)(F)Oc5cc(F)c(F)c(F)c5)c(F)c4)(OC2)OC3)CC1] |

| No. | |
|---|---|
| 98 | 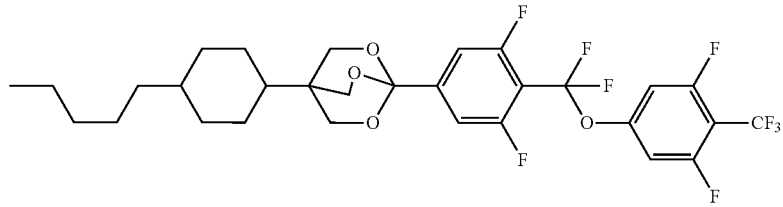 [SMILES: CCCCCC1CCC(C23COC(c4cc(F)c(C(F)(F)Oc5cc(F)c(C(F)(F)F)c(F)c5)c(F)c4)(OC2)OC3)CC1] |
| 99 | 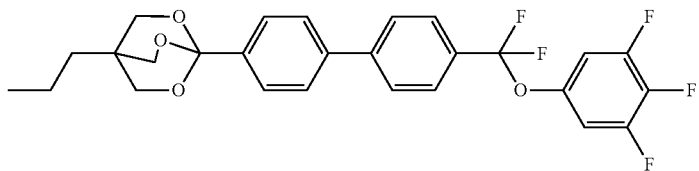 [SMILES: CCCC12COC(c3ccc(-c4ccc(C(F)(F)Oc5cc(F)c(F)c(F)c5)cc4)cc3)(OC1)OC2] |
| 100 | 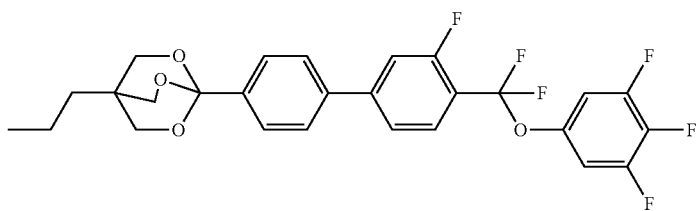 |
| 101 | 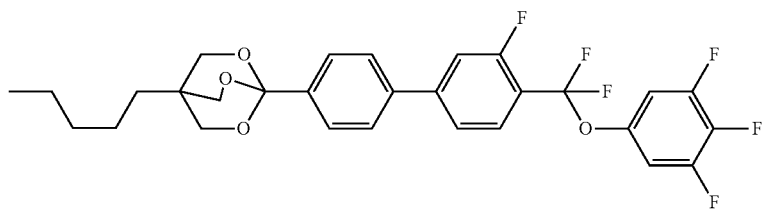 [SMILES: CCCCCC12COC(c3ccc(-c4ccc(C(F)(F)Oc5cc(F)c(F)c(F)c5)c(F)c4)cc3)(OC1)OC2] |
| 102 | 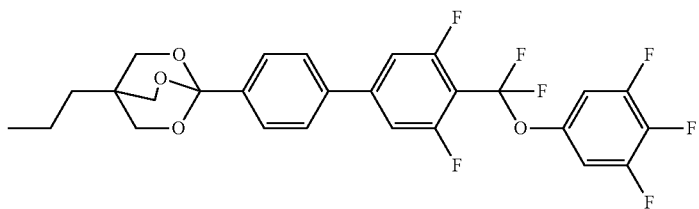 [SMILES: CCCC12COC(c3ccc(-c4cc(F)c(C(F)(F)Oc5cc(F)c(F)c(F)c5)c(F)c4)cc3)(OC1)OC2] |
| 103 | 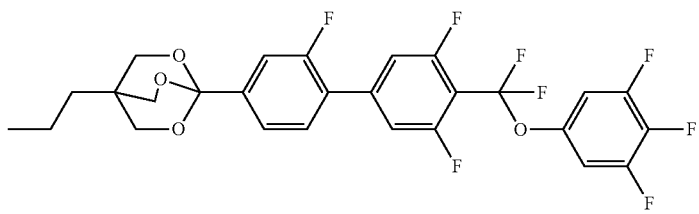 [SMILES: CCCC12COC(c3ccc(-c4cc(F)c(C(F)(F)Oc5cc(F)c(F)c(F)c5)c(F)c4)c(F)c3)(OC1)OC2] |
| 104 | 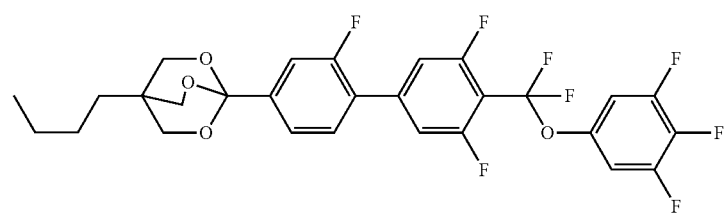 [SMILES: CCCCC12COC(c3ccc(-c4cc(F)c(C(F)(F)Oc5cc(F)c(F)c(F)c5)c(F)c4)c(F)c3)(OC1)OC2] |

| No. | |
|---|---|
| 105 | 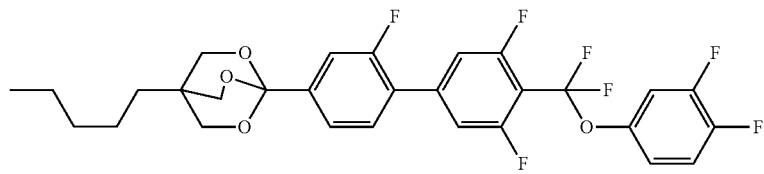 [SMILES: CCCCCC12COC(c3ccc(-c4cc(F)c(C(F)(F)Oc5ccc(F)c(F)c5)c(F)c4)c(F)c3)(OC1)OC2] |
| 106 | 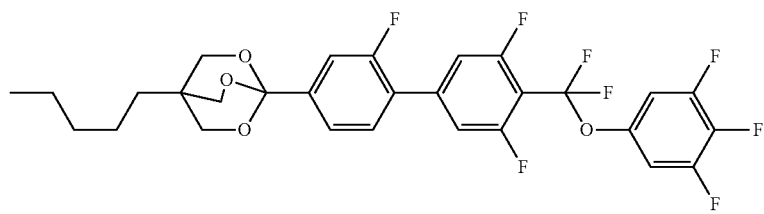 [SMILES: CCCCCC12COC(c3ccc(-c4cc(F)c(C(F)(F)Oc5cc(F)c(F)c(F)c5)c(F)c4)c(F)c3)(OC1)OC2] |
| 107 | 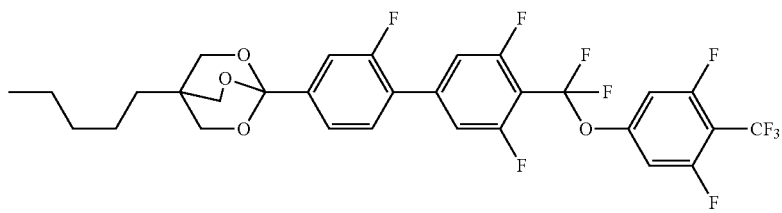 [SMILES: CCCCCC12COC(c3ccc(-c4cc(F)c(C(F)(F)Oc5cc(F)c(C(F)(F)F)c(F)c5)c(F)c4)c(F)c3)(OC1)OC2] |
| 108 | 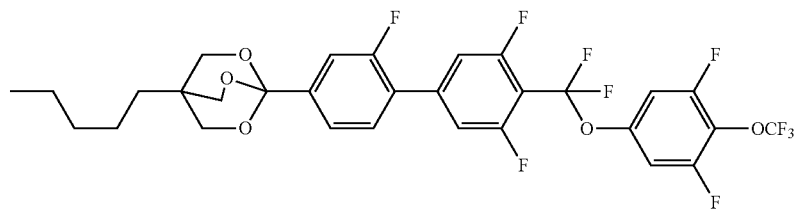 [SMILES: CCCCCC12COC(c3ccc(-c4cc(F)c(C(F)(F)Oc5cc(F)c(OC(F)(F)F)c(F)c5)c(F)c4)c(F)c3)(OC1)OC2] |
| 109 | 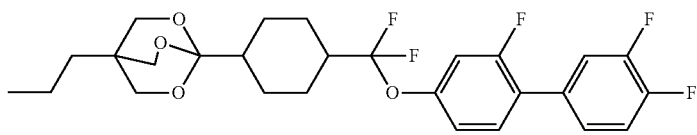 |
| 110 | 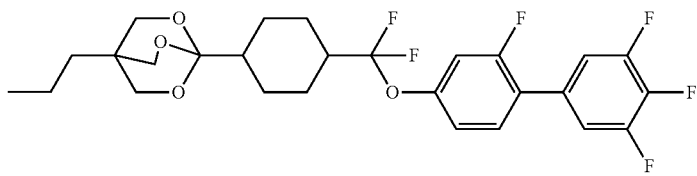 |
| 111 | 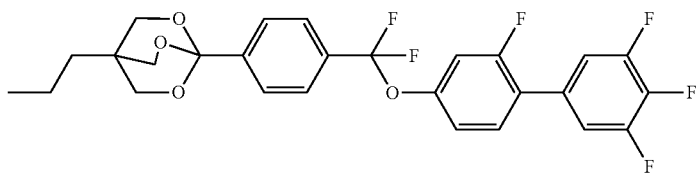 [SMILES: CCCC12COC(c3ccc(C(F)(F)Oc4ccc(-c5cc(F)c(F)c(F)c5)c(F)c4)cc3)(OC1)OC2] |
| 112 | 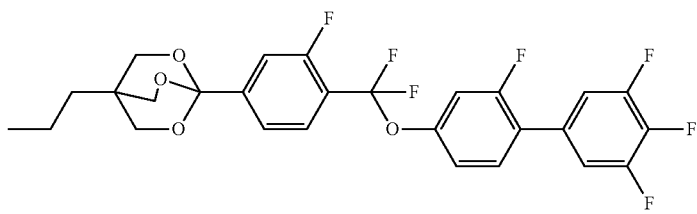 [SMILES: CCCC12COC(c3ccc(C(F)(F)Oc4ccc(-c5cc(F)c(F)c(F)c5)c(F)c4)c(F)c3)(OC1)OC2] |

| No. | |
|---|---|
| 113 | 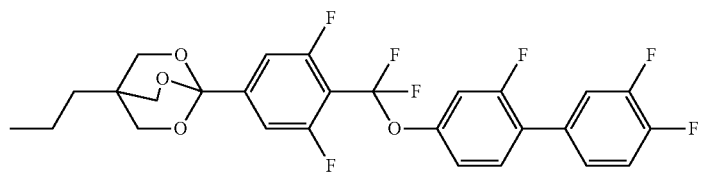 [SMILES: CCCC12COC(c3cc(F)c(C(F)(F)Oc4ccc(-c5ccc(F)c(F)c5)c(F)c4)c(F)c3)(OC1)OC2] |
| 114 | 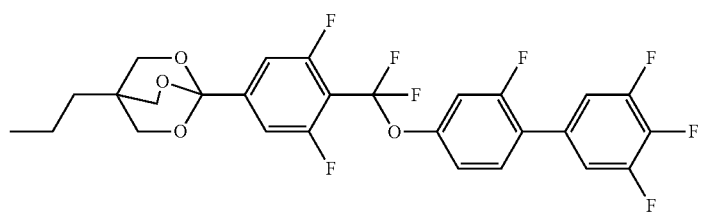 [SMILES: CCCC12COC(c3cc(F)c(C(F)(F)Oc4ccc(-c5cc(F)c(F)c(F)c5)c(F)c4)c(F)c3)(OC1)OC2] |
| 115 | 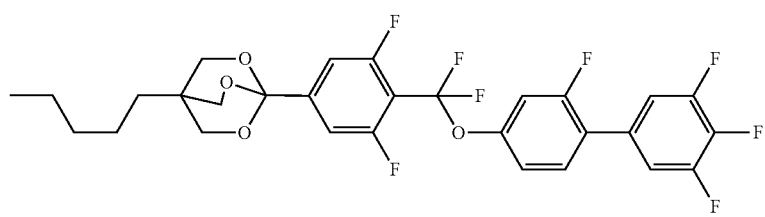 [SMILES: CCCCCC12COC(c3cc(F)c(C(F)(F)Oc4ccc(-c5cc(F)c(F)c(F)c5)c(F)c4)c(F)c3)(OC1)OC2] |
| 116 | 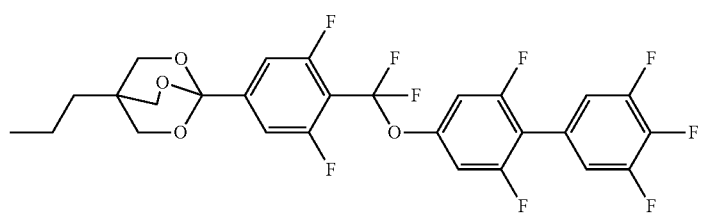 |
| 117 | 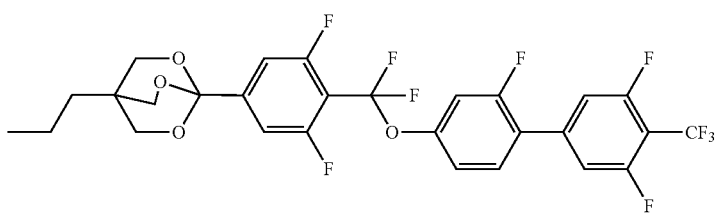 [SMILES: CCCC12COC(c3cc(F)c(C(F)(F)Oc4ccc(-c5cc(F)c(C(F)(F)F)c(F)c5)c(F)c4)c(F)c3)(OC1)OC2] |
| 118 | 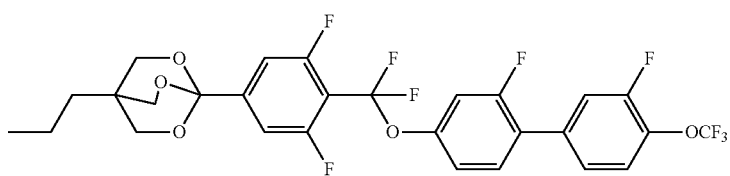 [SMILES: CCCC12COC(c3cc(F)c(C(F)(F)Oc4ccc(-c5ccc(OC(F)(F)F)c(F)c5)c(F)c4)c(F)c3)(OC1)OC2] |
| 119 | 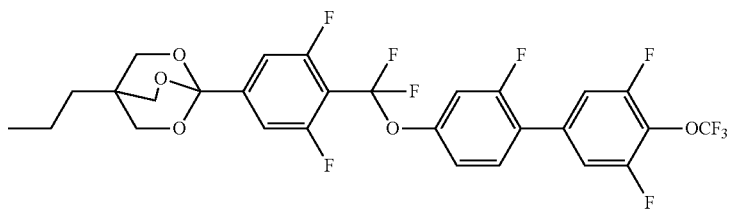 [SMILES: CCCC12COC(c3cc(F)c(C(F)(F)Oc4ccc(-c5cc(F)c(OC(F)(F)F)c(F)c5)c(F)c4)c(F)c3)(OC1)OC2] |

| No. |
|---|
| 120 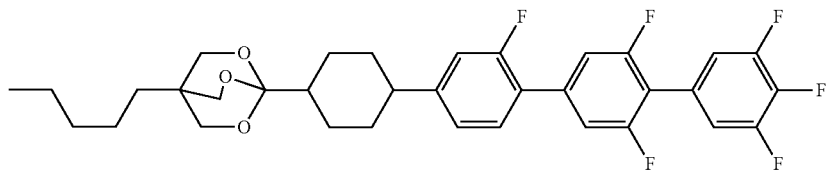 [SMILES: CCCCCC12COC(C3CCC(c4ccc(-c5cc(F)c(-c6cc(F)c(F)c(F)c6)c(F)c5)c(F)c4)CC3)(OC1)OC2] |
| 121 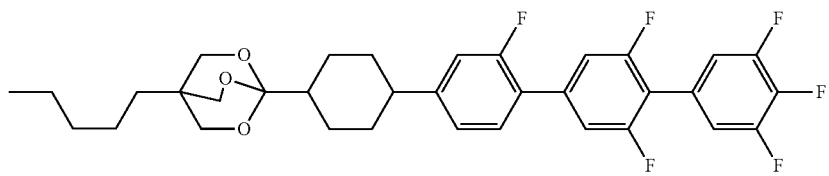 [SMILES: CCCCCC12COC(C3CCC(c4ccc(-c5cc(F)c(-c6cc(F)c(F)c(F)c6)c(F)c5)c(F)c4)CC3)(OC1)OC2] |
| 122 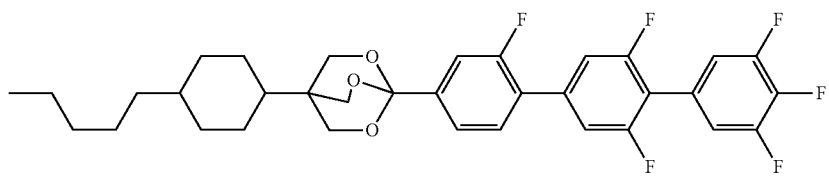 [SMILES: CCCCCC1CCC(C23COC(c4ccc(-c5cc(F)c(-c6cc(F)c(F)c(F)c6)c(F)c5)c(F)c4)(OC2)OC3)CC1] |
| 123 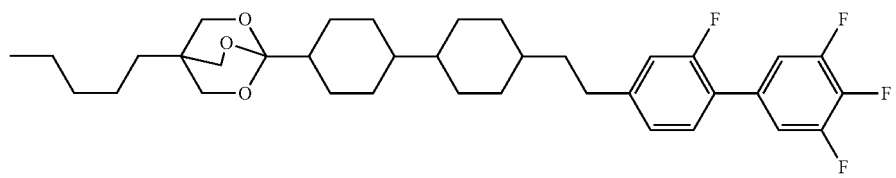 [SMILES: CCCCCC12COC(C3CCC(C4CCC(CCc5ccc(-c6cc(F)c(F)c(F)c6)c(F)c5)CC4)CC3)(OC1)OC2] |
| 124 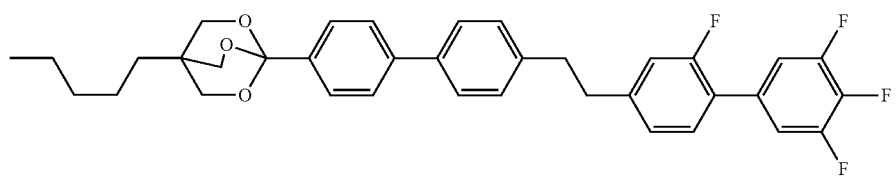 |
| 125 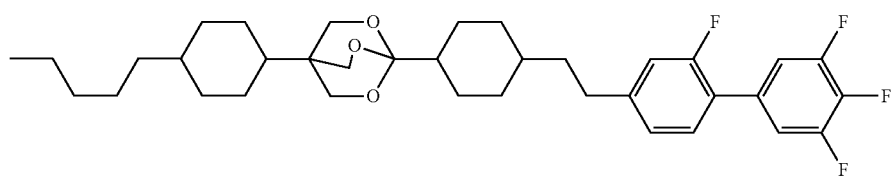 [SMILES: CCCCCC1CCC(C23COC(C4CCC(CCc5ccc(-c6cc(F)c(F)c(F)c6)c(F)c5)CC4)(OC2)OC3)CC1] |
| 126 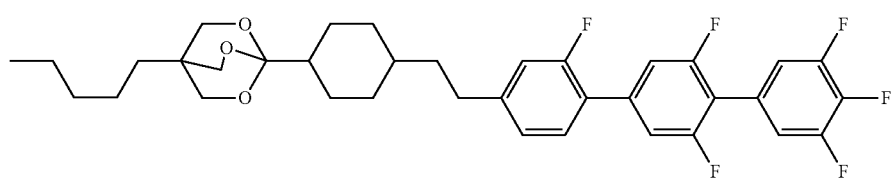 [SMILES: CCCCCC12COC(C3CCC(CCc4ccc(-c5cc(F)c(-c6cc(F)c(F)c(F)c6)c(F)c5)c(F)c4)CC3)(OC1)OC2] |
| 127 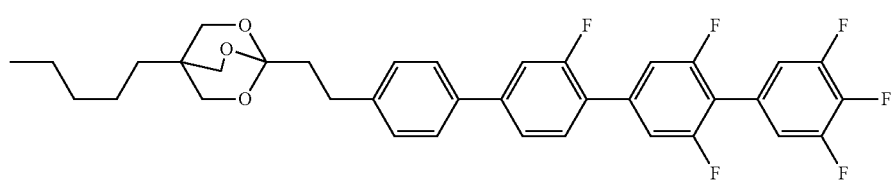 [SMILES: CCCCCC12COC(CCc3ccc(-c4ccc(-c5cc(F)c(-c6cc(F)c(F)c(F)c6)c(F)c5)c(F)c4)cc3)(OC1)OC2] |

| No. |
|---|
| 128 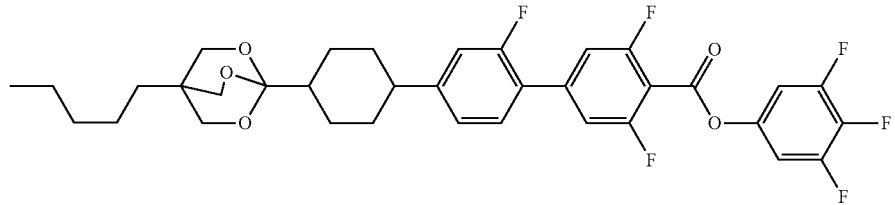 [SMILES: CCCCCC12COC(C3CCC(c4ccc(-c5cc(F)c(C(=O)Oc6cc(F)c(F)c(F)c6)c(F)c5)c(F)c4)CC3)(OC1)OC2] |
| 129 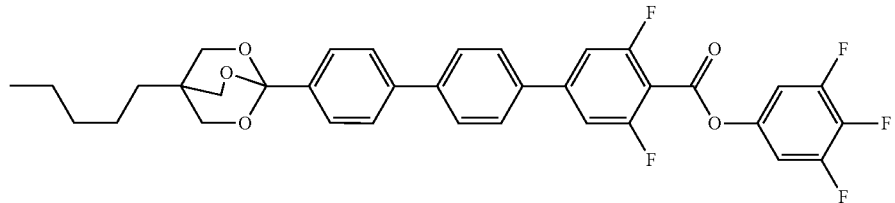 [SMILES: CCCCCC12COC(c3ccc(-c4ccc(-c5cc(F)c(C(=O)Oc6cc(F)c(F)c(F)c6)c(F)c5)cc4)cc3)(OC1)OC2] |
| 130 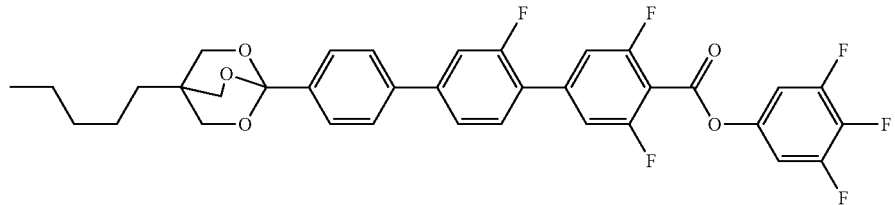 [SMILES: CCCCCC12COC(c3ccc(-c4ccc(-c5cc(F)c(C(=O)Oc6cc(F)c(F)c(F)c6)c(F)c5)c(F)c4)cc3)(OC1)OC2] |
| 131 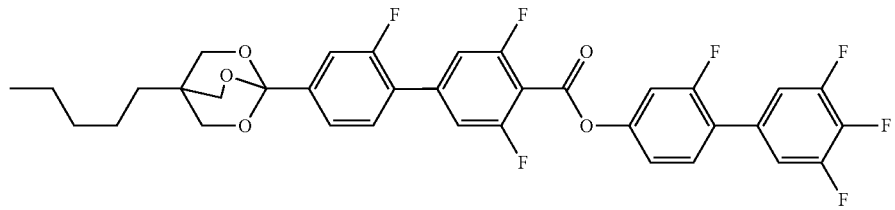 [SMILES: CCCCCC12COC(c3ccc(-c4cc(F)c(C(=O)Oc5ccc(-c6cc(F)c(F)c(F)c6)c(F)c5)c(F)c4)c(F)c3)(OC1)OC2] |
| 132 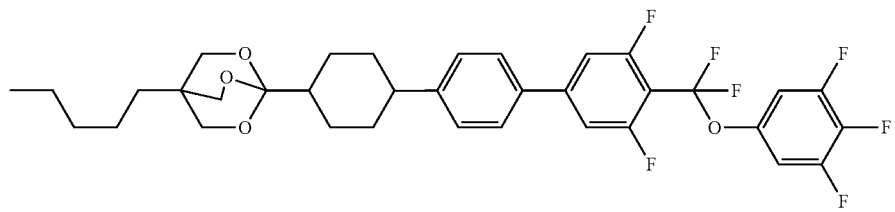 [SMILES: CCCCCC12COC(C3CCC(c4ccc(-c5cc(F)c(C(F)(F)Oc6cc(F)c(F)c(F)c6)c(F)c5)cc4)CC3)(OC1)OC2] |
| 133 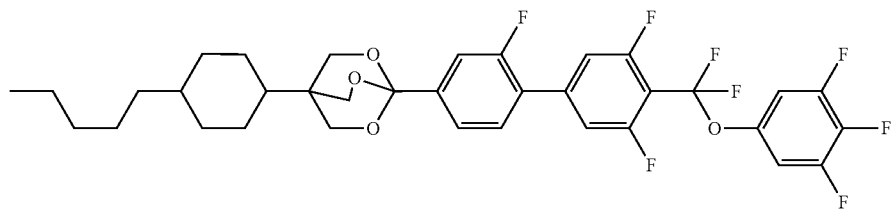 [SMILES: CCCCCC1CCC(C23COC(c4ccc(-c5cc(F)c(C(F)(F)Oc6cc(F)c(F)c(F)c6)c(F)c5)c(F)c4)(OC2)OC3)CC1] |
| 134 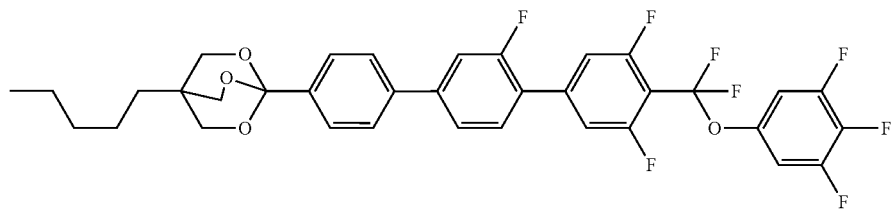 [SMILES: CCCCCC12COC(c3ccc(-c4ccc(-c5cc(F)c(C(F)(F)Oc6cc(F)c(F)c(F)c6)c(F)c5)c(F)c4)cc3)(OC1)OC2] |

| No. |
|---|
| 135 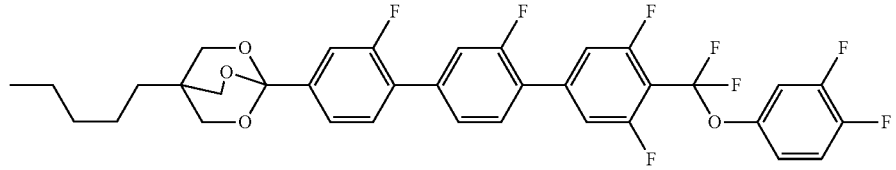 [SMILES: CCCCCC12COC(c3ccc(-c4ccc(-c5cc(F)c(C(F)(F)Oc6ccc(F)c(F)c6)c(F)c5)c(F)c4)c(F)c3)(OC1)OC2] |
| 136 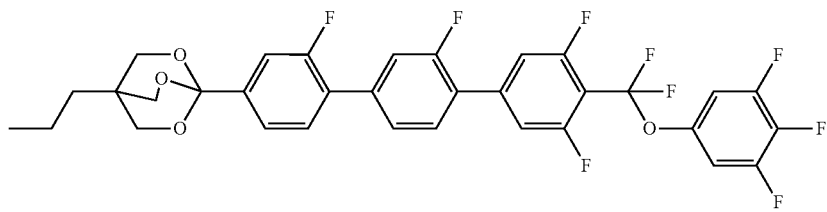 [SMILES: CCCC12COC(c3ccc(-c4ccc(-c5cc(F)c(C(F)(F)Oc6cc(F)c(F)c(F)c6)c(F)c5)c(F)c4)c(F)c3)(OC1)OC2] |
| 137 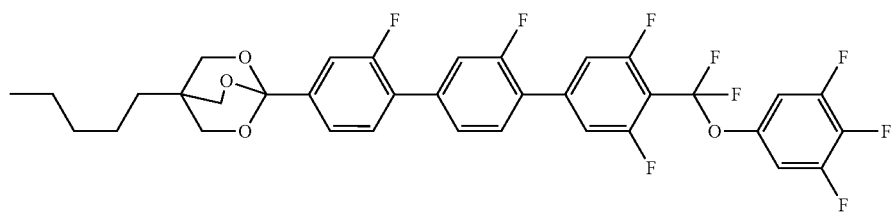 [SMILES: CCCCCC12COC(c3ccc(-c4ccc(-c5cc(F)c(C(F)(F)Oc6cc(F)c(F)c(F)c6)c(F)c5)c(F)c4)c(F)c3)(OC1)OC2] |
| 138 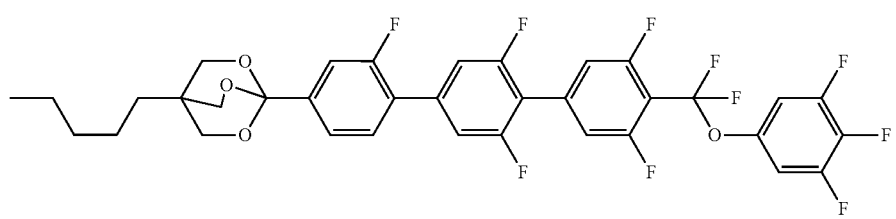 [SMILES: CCCCCC12COC(c3ccc(-c4cc(F)c(-c5cc(F)c(C(F)(F)Oc6cc(F)c(F)c(F)c6)c(F)c5)c(F)c4)c(F)c3)(OC1)OC2] |
| 139 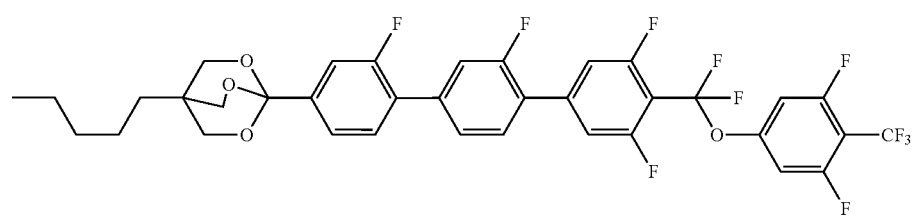 [SMILES: CCCCCC12COC(c3ccc(-c4ccc(-c5cc(F)c(C(F)(F)Oc6cc(F)c(C(F)(F)F)c(F)c6)c(F)c5)c(F)c4)c(F)c3)(OC1)OC2] |
| 140 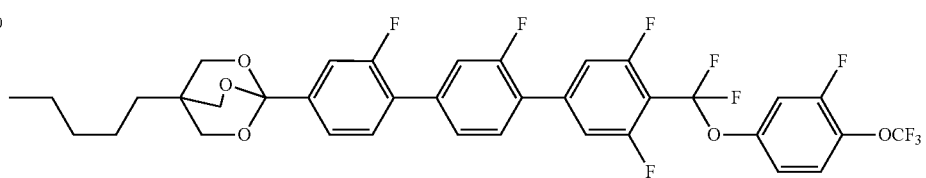 [SMILES: CCCCCC12COC(c3ccc(-c4ccc(-c5cc(F)c(C(F)(F)Oc6ccc(OC(F)(F)F)c(F)c6)c(F)c5)c(F)c4)c(F)c3)(OC1)OC2] |
| 141 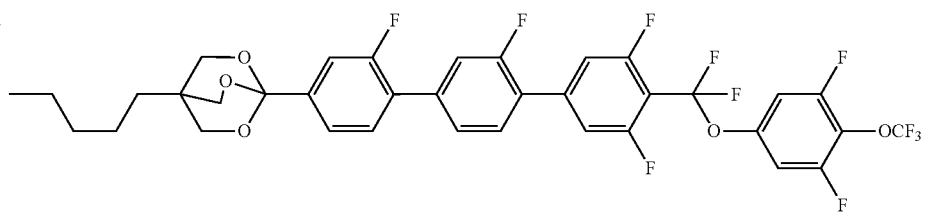 [SMILES: CCCCCC12COC(c3ccc(-c4ccc(-c5cc(F)c(C(F)(F)Oc6cc(F)c(OC(F)(F)F)c(F)c6)c(F)c5)c(F)c4)c(F)c3)(OC1)OC2] |

| No. | |
|---|---|
| 142 | 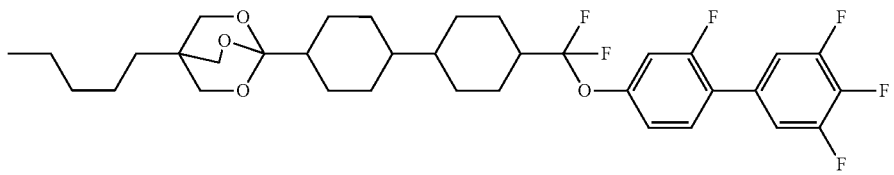 |
| 143 | 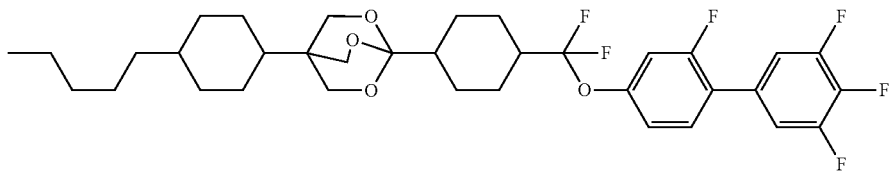 [SMILES: CCCCCC1CCC(C23COC(C4CCC(C(F)(F)Oc5ccc(-c6cc(F)c(F)c(F)c6)c(F)c5)CC4)(OC2)OC3)CC1] |
| 144 | 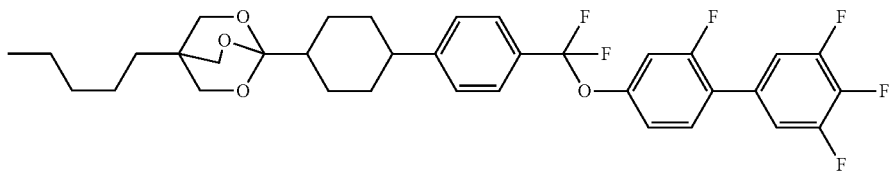 |
| 145 | 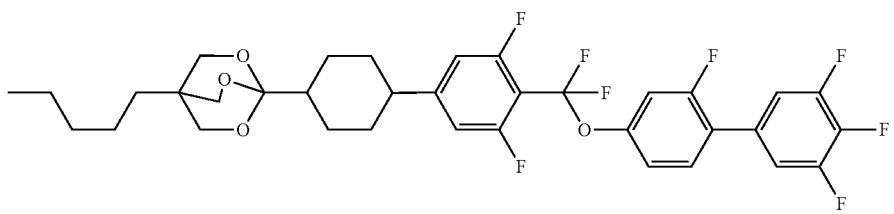 [SMILES: CCCCCC12COC(C3CCC(c4cc(F)c(C(F)(F)Oc5ccc(-c6cc(F)c(F)c(F)c6)c(F)c5)c(F)c4)CC3)(OC1)OC2] |
| 146 | 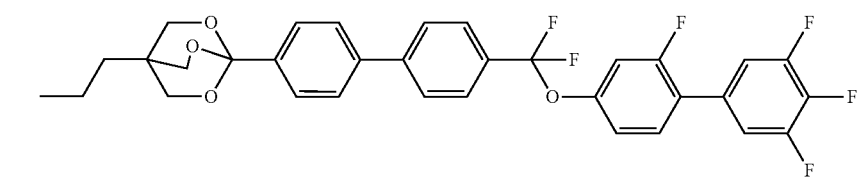 [SMILES: CCCC12COC(c3ccc(-c4ccc(C(F)(F)Oc5ccc(-c6cc(F)c(F)c(F)c6)c(F)c5)cc4)cc3)(OC1)OC2] |
| 147 | 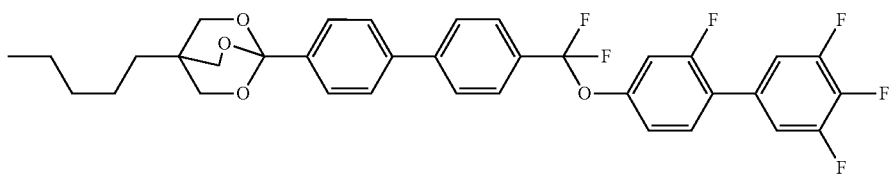 |
| 148 | 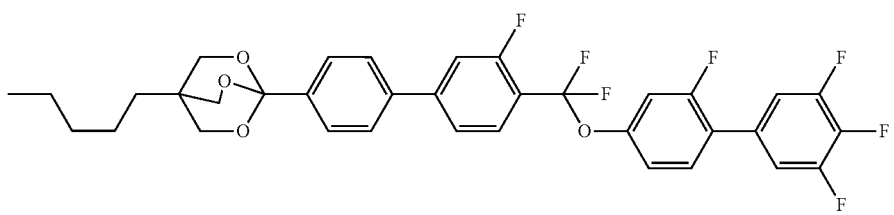 |
| 149 | 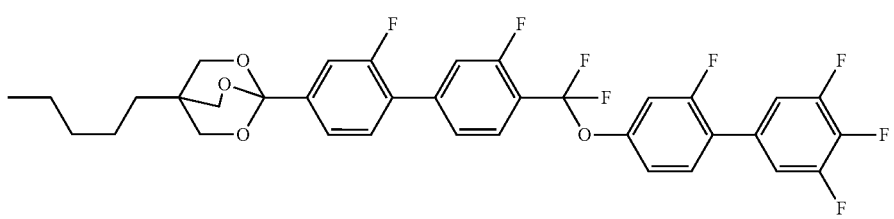 [SMILES: CCCCCC12COC(c3ccc(-c4ccc(C(F)(F)Oc5ccc(-c6cc(F)c(F)c(F)c6)c(F)c5)c(F)c4)c(F)c3)(OC1)OC2] |

| No. | |
|---|---|
| 150 | 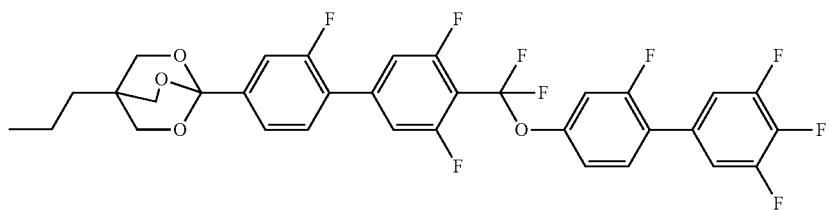 [SMILES: CCCC12COC(c3ccc(-c4cc(F)c(C(F)(F)Oc5ccc(-c6cc(F)c(F)c(F)c6)c(F)c5)c(F)c4)c(F)c3)(OC1)OC2] |
| 151 | 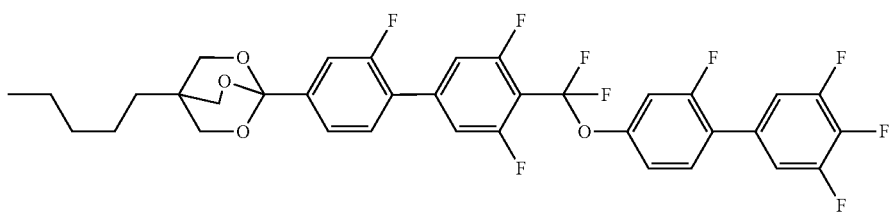 |
| 152 | 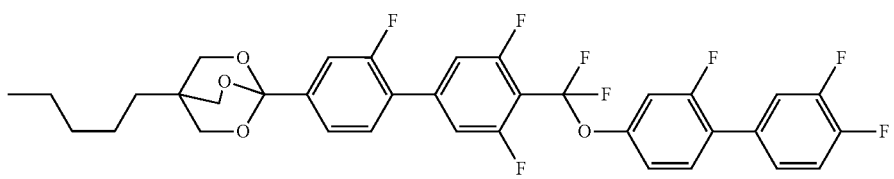 |
| 153 | 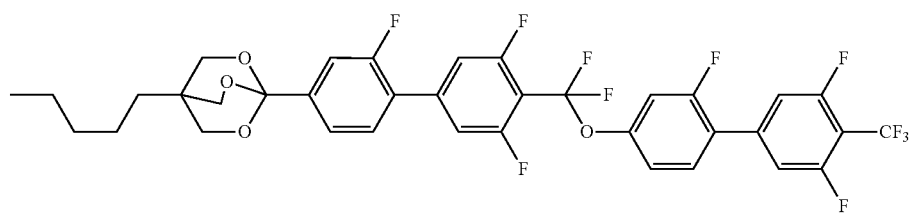 [SMILES: CCCCCC12COC(c3ccc(-c4cc(F)c(C(F)(F)Oc5ccc(-c6cc(F)c(C(F)(F)F)c(F)c6)c(F)c5)c(F)c4)c(F)c3)(OC1)OC2] |
| 154 | 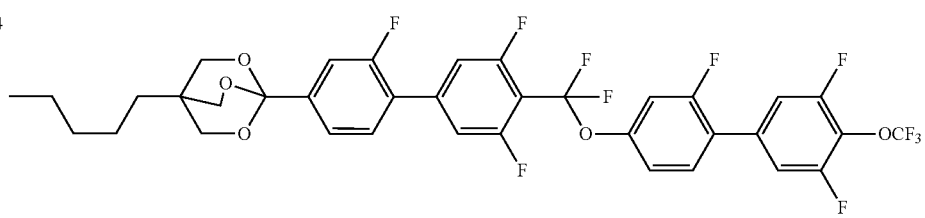 |
| 155 | 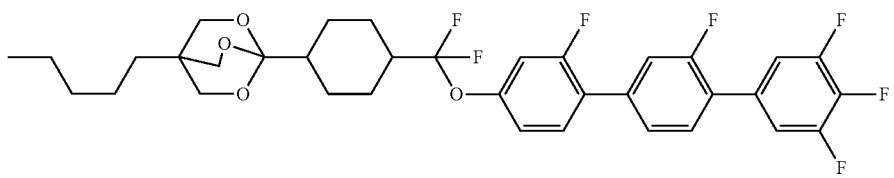 [SMILES: CCCCCC12COC(C3CCC(C(F)(F)Oc4ccc(-c5ccc(-c6cc(F)c(F)c(F)c6)c(F)c5)c(F)c4)CC3)(OC1)OC2] |
| 156 | 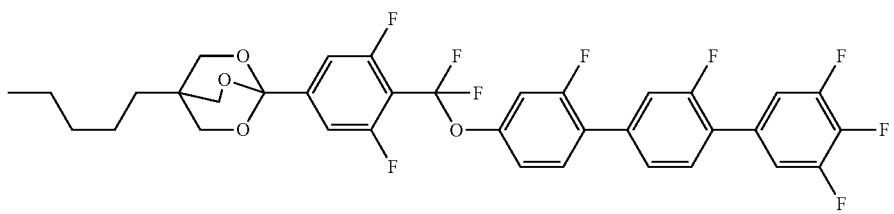 [SMILES: CCCCCC12COC(c3cc(F)c(C(F)(F)Oc4ccc(-c5ccc(-c6cc(F)c(F)c(F)c6)c(F)c5)c(F)c4)c(F)c3)(OC1)OC2] |

| No. |
| --- |
| 157 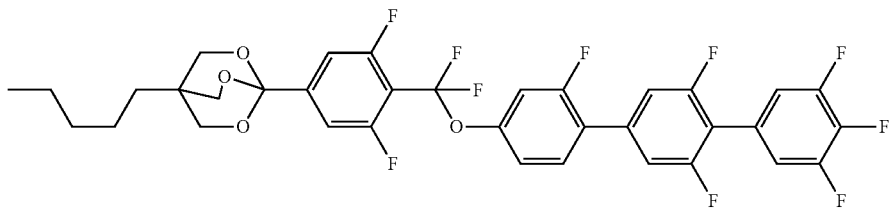 [SMILES: CCCCCC12COC(c3cc(F)c(C(F)(F)Oc4ccc(-c5cc(F)c(-c6cc(F)c(F)c(F)c6)c(F)c5)c(F)c4)c(F)c3)(OC1)OC2] |

Examples of Liquid Crystal Compositions

Hereinafter, liquid crystal compositions to be obtained according to the invention will be explained in detail by way of Examples. In addition, liquid crystal compounds used in Examples are expressed using symbols based on definitions in Table below. In the Table, a configuration of 1,4-cyclohexylene is trans. Unless otherwise noted, a ratio (percentage) of each compound is expressed in terms of weight percent (% by weight) based on the total weight of the composition. Values of characteristics of the composition obtained are presented in the last part of each Example.

In addition, the number described in a part of a liquid crystal compound used in each Example corresponds to the formula number of a liquid crystal compound to be contained in a liquid crystal composition of the invention described above. When only a symbol "-" is simply described without description of the formula number, the compound means any other compound.

A method for description of compounds using symbols is presented below.

TABLE

Method for Description of Compounds using Symbols
$R-(A_1)-Z_1- \ldots -Z_n-(A_n)-R'$

| 1) Left-terminal Group R- | Symbol |
| --- | --- |
| $C_nH_{2n+1}-$ | n- |
| $C_nH_{2n+1}O-$ | nO— |
| $C_mH_{2m+1}OC_nH_{2n}-$ | mOn— |
| $CH_2=CH-$ | V— |
| $C_nH_{2n+1}-CH=CH-$ | nV— |
| $CH_2=CH-C_nH_{2n}-$ | Vn— |
| $C_mH_{2m+1}-CH=CH-C_nH_{2n}-$ | mVn— |
| $CF_2=CH-$ | VFF— |
| $CF_2=CH-C_nH_{2n}-$ | VFFn— |

| 2) Right-terminal Group —R' | Symbol |
| --- | --- |
| $-C_nH_{2n+1}$ | -n |
| $-OC_nH_{2n+1}$ | —On |
| $-CH=CH_2$ | —V |
| $-CH=CH-C_nH_{2n+1}$ | —Vn |
| $-C_nH_{2n}-CH=CH_2$ | —nV |
| $-C_mH_{2m+1}-CH=CH-C_nH_{2n+1}$ | mVn— |
| $-CH=CF_2$ | —VFF |
| —F | —F |
| —Cl | —CL |
| —OCF$_3$ | —OCF3 |
| —CF$_3$ | —CF3 |
| $-COOC_nH_{2n+1}$ | —En |

| 3) Bonding Group —Z$_n$— | Symbol |
| --- | --- |
| $-C_nH_{2n}-$ | n |
| —COO— | E |
| —CH=CH— | V |
| —CH$_2$O— | 1O |
| —OCH$_2$— | O1 |
| —OCF$_2$O— | Si |
| —C≡C— | |

| 4) Ring Structure —A$_n$— | Symbol |
| --- | --- |
| (cyclohexane) | H |

TABLE-continued
Method for Description of Compounds using Symbols
R—(A$_1$)—Z$_1$— . . . —Z$_n$—(A$_n$)—R'
| | |
|---|---|
|  | B |
| 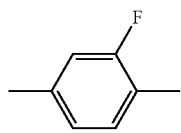 | B(F) |
| 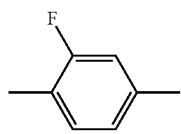 | B(2F) |
| 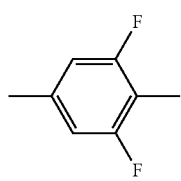 | B(F,F) |
| 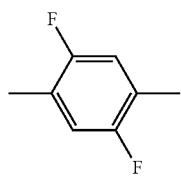 | B(2F,5F) |
| 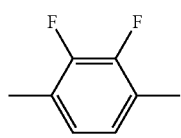 | B(2F,3F) |
| 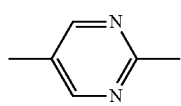 | Py |
| 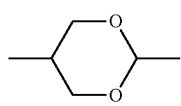 | G |
| 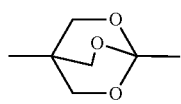 | Oe |
| 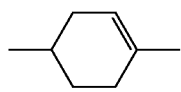 | ch |
| 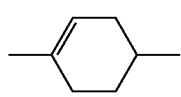 | Ch |

TABLE-continued

Method for Description of Compounds using Symbols
R—(A$_1$)—Z$_1$— . . . —Z$_n$—(A$_n$)—R'

5) Examples of Description

Example 1 3-OeHB(F,F)—F

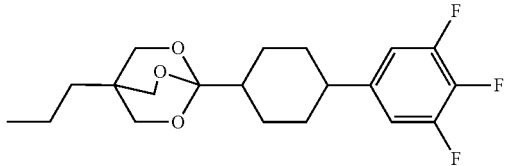 [SMILES: CCCC12COC(C3CCC(c4cc(F)c(F)c(F)c4)CC3)(OC1)OC2]

Example 2 5-OeB(F)B(F,F)XB(F,F)—CF3

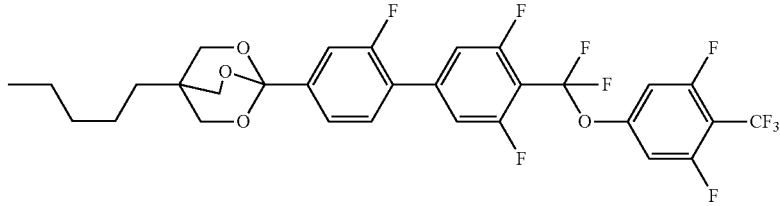 [SMILES: CCCCCC12COC(c3ccc(-c4cc(F)c(C(F)(F)Oc5cc(F)c(C(F)(F)F)c(F)c5)c(F)c4)c(F)c3)(OC1)OC2]

Example 3 3-HB—O2

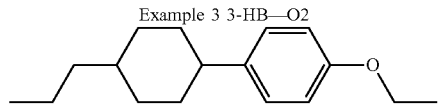

Example 4 1-BB(F)B-2V

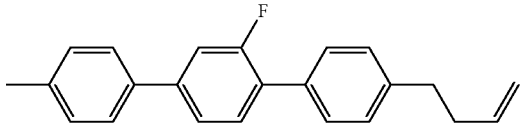 [SMILES: C=CCCc1ccc(-c2ccc(-c3ccc(C)cc3)cc2F)cc1]

Characteristics were measured according to methods as described below. Most of the methods are applied as described in EIAJ ED-2521A of the Standard of Electronic Industries Association of Japan, or modified thereon.

(1) Maximum Temperature of a Nematic Phase (NI; ° C.)

A sample was placed on a hot plate in a melting point apparatus equipped with a polarizing microscope and was heated at a rate of 1° C. per minute. Temperature at which part of the sample began to change from a nematic phase to an isotropic liquid was measured. Hereinafter, a higher limit of a temperature range of the nematic phase may be occasionally abbreviated as "maximum temperature."

(2) Minimum Temperature of a Nematic Phase (TC; ° C.)

Samples each having a nematic phase were kept in freezers at temperatures of 0° C., −10° C., −20° C., −30° C. and −40° C. for 10 days, and then liquid crystal phases were observed. For example, when a sample maintained the nematic phase at −20° C. and changed to crystals or a smectic phase at −30° C., TC was expressed as TC≤−20° C. A lower limit of the temperature range of the nematic phase may be occasionally abbreviated as "minimum temperature."

(3) Optical Anisotropy (Δn; Measured at 25° C.)

Measurement was carried out using an Abbe refractometer with a polarizing plate mounted on an ocular, using light at a wavelength of 589 nanometers. A surface of a main prism was rubbed in one direction, and then a sample was added dropwise on the main prism. A refractive index (n∥) was measured when the direction of polarized light was parallel to the direction of rubbing. A refractive index (n∥) was measured when the direction of polarized light was perpendicular to the direction of rubbing. A value of optical anisotropy (Δn) was calculated from an equation: Δn=n∥−n⊥.

(4) Viscosity (Bulk Viscosity; η; Measured at 20° C.; mPa·s)

A Cone-type (E-type) viscometer was used for measurement.

(5) Dielectric Anisotropy (Δ∈; measured at 25° C.)

A sample was put into a TN device in which a distance (gap) between two glass substrates was about 9 micrometers and a twist angle was 80 degrees. A voltage of 20 V was applied to the cell, and a dielectric constant (∈∥) in the major axis direction of liquid crystal molecules was measured. A voltage of 0.5 V was applied, and a dielectric constant (⊥) in the minor axis direction of the liquid crystal molecules was measured. A value of dielectric anisotropy was calculated from an equation: Δ∈=∈∥−∈⊥.

(6) Voltage Holding Ratio (VHR; Measured at 25° C. and 100° C.; %)

A TN device was prepared by putting a sample into a cell having a polyimide alignment film in which a distance (cell gap) between two glass substrates was 6 micrometers. The TN device was charged at 25° C. by applying pulse voltage (60 microseconds at 5 V). A waveform of voltage applied to the TN device was observed with a cathode ray oscilloscope, and an area between a voltage curve and a horizontal axis in a unit cycle (16.7 milliseconds) was determined. From a waveform of voltage applied after the TN device was removed, an area was determined in a similar manner. A value of voltage holding ratio (%) was calculated from an equation: (voltage holding ratio)=(value of area when a TN device is present)/(value of area when a TN device is absent)×100.

The thus obtained voltage holding ratio was presented as "VHR-1." Next, the TN device was heated at 100° C. for 250 hours. The TN device was returned to 25° C., and then a voltage holding ratio was measured in a manner similar to the method as described above. A voltage holding ratio obtained after the heating test was presented as "VHR-2." In addition, the heating test was conducted as an acceleration test, and used as a test corresponding to a long-term durability test for the TN device.

A ratio (percentage) of components is expressed in terms of weight percent (% by weight) based on the total weight of the components.

Use Example 1

| | | |
|---|---|---|
| 3-OeHB(F,F)-F | (No. 17) | 4% |
| 5-OeHB(F,F)-F | (No. 19) | 3% |
| 5-HB-CL | (2-2) | 16% |
| 3-HB-O2 | (11-5) | 10% |
| 3-HB-O2 | (11-5) | 6% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 5% |
| 1O1-HBBH-5 | (13-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 116.6° C.; Δn = 0.100; Δε = 6.6; Vth = 1.98 V; η = 24.6 mPa · s.

Use Example 2

| | | |
|---|---|---|
| 4-OeHB(F,F)-F | (No. 18) | 3% |
| 3-OeB(F,F)XB(F,F)-F | (No. 54) | 3% |
| 5-OeB(F)B(F,F)XB(F,F)-F | (No. 94) | 3% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 8% |
| 5-HHBB(F,F)-F | (4-6) | 3% |
| 5-HHEBB-F | (4-17) | 2% |
| 1O1-HBBH-5 | (13-1) | 4% |

NI = 87.1° C.; Δn = 0.111; Δε = 12.4; Vth = 1.28 V; η = 39.7 mPa · s.

A helical pitch when 0.5 part by weight of optically active compound (Op-5) was added to 100 parts by weight of the composition described above was 61.0 micrometers.

Use Example 3

| | | |
|---|---|---|
| 3-OeB(F,F)XB(F,F)-F | (No. 102) | 3% |
| 5-OeB(F)B(F,F)XB(F)B(F,F)-F | (No. 139) | 3% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 7% |
| 5-HBB(F)-F | (3-23) | 7% |
| 5-HBBH-3 | (13-1) | 3% |
| 3-HB(F)BH-3 | (13-2) | 3% |

Use Example 4

| | | |
|---|---|---|
| 2-OeHB(F,F)-F | (No. 16) | 3% |
| 7-OeHB(F,F)-F | (No. 20) | 2% |
| 5-OeVHB(F,F)-F | (No. 36) | 3% |
| 5-HB-CL | (2-2) | 8% |
| 3-HB-O2 | (11-5) | 4% |
| 5-HB-O2 | (11-5) | 4% |
| 3-HHB-1 | (12-1) | 2% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 8% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

Use Example 5

| | | |
|---|---|---|
| 3-OeHXB(F,F)-F | (No. 40) | 4% |
| 3-OeBXB(F,F)-F | (No. 51) | 4% |
| 3-HB-CL | (2-2) | 3% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 5% |
| 3-HBEB(F,F)-F | (3-39) | 5% |

Use Example 6

| | | |
|---|---|---|
| 5-OeB(F)B(F,F)XB(F,F)-F | (No. 94) | 5% |
| 5-OeB(F)B(F,F)XB(F,F)-CF3 | (No. 95) | 5% |
| 5-HB-CL | (2-2) | 7% |
| 7-HB(F,F)-F | (2-4) | 3% |
| 7-HB-1 | (11-5) | 5% |
| 3-HB-O2 | (11-5) | 15% |
| V2-BB-1 | (11-8) | 5% |
| 3-HHB-1 | (12-1) | 8% |
| 3-HHB-3 | (12-1) | 5% |
| 3-HHB-O1 | (12-1) | 5% |
| 2-HHB(F)-F | (3-2) | 7% |
| 3-HHB(F)-F | (3-2) | 7% |

-continued

| | | |
|---|---|---|
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Use Example 7

| | | |
|---|---|---|
| 3-OeB(F,F)XB(F)-OCF3 | (No. 58) | 4% |
| 5-OeB(F,F)B(F,F)XB(F)-F | (No. 93) | 3% |
| 5-OeHB(F,F)XB(F,F)-F | (No. 85) | 3% |
| 5-HB-CL | (2-2) | 3% |
| 7-HB(F)-F | (2-3) | 7% |
| 3-HB-O2 | (11-5) | 9% |
| 3-HH-EMe | (11-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 5-HGB(F,F)-F | (3-103) | 6% |
| 2-H2GB(F,F)-F | (3-106) | 4% |
| 5-GHB(F,F)-F | (3-109) | 7% |

Use Example 8

| | | |
|---|---|---|
| 3-OeHB(F,F)-F | (No. 17) | 4% |
| 5-OeHB(F,F)-F | (No. 19) | 4% |
| 3-HB-O1 | (11-5) | 15% |
| 3-HB-O2 | (11-5) | 5% |
| 3-HB(2F,3F)-O2 | (5-1) | 12% |
| 5-HB(2F,3F)-O2 | (5-1) | 12% |
| 2-HHB(2F,3F)-1 | (6-7) | 12% |
| 3-HHB(2F,3F)-1 | (6-7) | 10% |
| 3-HHB(2F,3F)-O2 | (6-7) | 7% |
| 5-HHB(2F,3F)-O2 | (6-7) | 13% |
| 3-HHB-1 | (12-1) | 6% |

NI = 80.5° C.; Δn = 0.091; Δε = 0.3; η = 41.4 mPa · s.

Use Example 9

| | | |
|---|---|---|
| 3-OeB(F,F)-F | (No. 5) | 3% |
| 5-OeXB(F,F)-F | (No. 17) | 4% |
| 5-HB-CL | (2-2) | 16% |
| 3-HB-O2 | (11-5) | 10% |
| 5-HB-O2 | (11-5) | 6% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 5% |
| 1O1-HBBH-5 | (13-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 106.8° C.; Δn = 0.095; Δε = 5.6; Vth = 1.91 V; η = 22.8 mPa · s.

Use Example 10

| | | |
|---|---|---|
| 3-OeB(F,F)-F | (No. 5) | 3% |
| 5-HOeB(F,F)-F | (No. 26) | 3% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 7% |
| 5-HBB(F)-F | (3-23) | 7% |
| 5-HBBH-3 | (13-1) | 3% |
| 3-HB(F)BH-3 | (13-2) | 3% |

NI = 80.5° C.; Δn = 0.087; Δε = 5.6; Vth = 2.02 V; η = 17.7 mPa · s.

Use Example 11

| | | |
|---|---|---|
| 3-OeHEB(F,F)-F | (No. 44) | 3% |
| 4-OeHEB(F,F)-F | (No. 45) | 3% |
| 5-OeHEB(F,F)-F | (No. 46) | 3% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 8% |
| 5-HHBB(F,F)-F | (4-6) | 3% |
| 5-HHEBB-F | (4-17) | 2% |
| 1O1-HBBH-5 | (13-1) | 4% |

NI = 88.8° C.; Δn = 0.109; Δε = 11.5; Vth = 1.30 V; η = 38.7 mPa · s.

Use Example 12

| | | |
|---|---|---|
| 4-OeB(F,F)XB(F,F)-F | (No. 65) | 5% |
| 4-OeB(F)B(F,F)XB(F,F)-F | (No. 104) | 5% |
| 5-HB-CL | (2-2) | 7% |
| 7-HB(F,F)-F | (2-4) | 3% |
| 7-HB-1 | (11-5) | 5% |
| 3-HB-O2 | (11-5) | 15% |
| V2-BB-1 | (11-8) | 5% |
| 3-HHB-1 | (12-1) | 8% |
| 3-HHB-3 | (12-1) | 5% |
| 3-HHB-O1 | (12-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

NI = 84.3° C.; Δn = 0.089; Δε = 7.5; Vth = 1.40 V; η = 24.2 mPa · s.

Use Example 13

| | | |
|---|---|---|
| 3-OeB(F,F)XB(F)-F | (No. 63) | 4% |
| 5-OeB(F,F)XB(F)B(F,F)-F | (No. 115) | 4% |
| 5-HB-CL | (2-2) | 8% |
| 3-HB-O2 | (11-5) | 4% |

-continued

| | | |
|---|---|---|
| 5-HB-O2 | (11-5) | 4% |
| 3-HHB-1 | (12-1) | 2% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 8% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

NI = 75.0° C.; Δn = 0.109; Δε = 11.7; Vth = 1.22 V; η = 27.9 mPa · s.

Use Example 14

| | | |
|---|---|---|
| 5-OeB(F)XB(F,F)-F | (No. 62) | 5% |
| 5-OeBB(F)XB(F,F)-F | (No. 101) | 5% |
| 5-HB-CL | (2-2) | 3% |
| 7-HB(F)-F | (2-3) | 7% |
| 3-HB-O2 | (11-5) | 9% |
| 3-HH-E1 | (11-2) | 23% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 5-HGB(F,F)-F | (3-103) | 6% |
| 2-H2GB(F,F)-F | (3-106) | 4% |
| 5-GHB(F,F)-F | (3-109) | 7% |

NI = 86.0° C.; Δn = 0.076; Δε = 8.2; Vth = 1.36 V; η = 27.0 mPa · s.

Use Example 15

| | | |
|---|---|---|
| 5-OeBXB(F,F)-F | (No. 60) | 4% |
| 5-OeHXB(F,F)-F | (No. 49) | 4% |
| 3-HB-CL | (2-2) | 3% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 5% |
| 3-HBEB(F,F)-F | (3-39) | 5% |

NI = 71.9° C.; Δn = 0.094; Δε = 10.6; Vth = 1.59 V; η = 31.7 mPa · s.

Use Example 16

| | | |
|---|---|---|
| 5-OeB(F)B(F)B(F,F)-F | (No. 79) | 5% |
| 4-OeHch-CF3 | (No. 40) | 5% |
| 3-HB-O2 | (11-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 10% |
| 5-HBB(F)B-3 | (13-5) | 10% |

NI = 89.7° C.; Δn = 0.179; Δε = 11.1; Vth = 1.51 V; η = 49.7 mPa · s.

Use Example 17

| | | |
|---|---|---|
| 5-HOe-CF3 | (No. 9) | 3% |
| 5-OeH-CF3 | (No. 10) | 2% |
| 5-Oech-CF3 | (No. 11) | 3% |
| 3-HB-O1 | (11-5) | 15% |
| 3-HB-O2 | (11-5) | 5% |
| 3-HB(2F,3F)-O2 | (5-1) | 12% |
| 5-HB(2F,3F)-O2 | (5-1) | 12% |
| 2-HHB(2F,3F)-1 | (6-7) | 12% |
| 3-HHB(2F,3F)-1 | (6-7) | 10% |
| 3-HHB(2F,3F)-O2 | (6-7) | 7% |
| 5-HHB(2F,3F)-O2 | (6-7) | 13% |
| 3-HHB-1 | (12-1) | 6% |

INDUSTRIAL APPLICABILITY

A compound of the invention has general physical properties necessary for the compound, namely, stability to heat, light and so forth, a wide temperature range of a liquid crystal phase, a good compatibility with other compounds, a large dielectric anisotropy and a suitable optical anisotropy. A liquid crystal composition of the invention contains at least one of the compounds, and has a high maximum temperature of a nematic phase, a low minimum temperature of the nematic phase, a small viscosity and a low threshold voltage. A liquid crystal display device of the invention includes the composition, and has a wide temperature range in which the device can be used, a short response time, a small electric power consumption, a large contrast ratio and a low driving voltage, and therefore can be widely utilized for display of a liquid crystal television, a monitor of personal computer, a notebook personal computer, a cellular phone, or the like.

What is claimed is:

1. A liquid crystal composition containing a first component and a second component, wherein the first component is at least one compound selected from the compounds represented by formula (1):

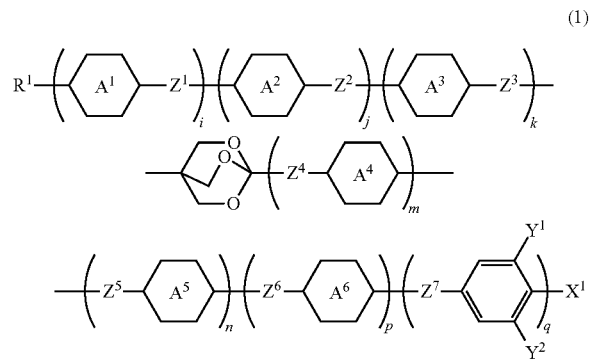

(1)

wherein, in the formula, $R^1$ is alkyl having 1 to 10 carbons, and in the alkyl, at least one of —$CH_2$— may be replaced by —O—, at least one of —$(CH_2)_2$— may be replaced by —CH═CH—, and at least one of hydrogen may be replaced by halogen; ring $A^1$, ring $A^2$, ring $A^3$, ring $A^4$, ring $A^5$ and ring $A^6$ are independently 1,4-cyclohexylene or 1,4-phenylene, at least one of —CH$_2$— in the 1,4-cyclohexylene may be replaced by —O—, at least one of —(CH$_2$)$_2$— in the 1,4-cyclohexylene may be replaced by —CH═CH—, at least one of —CH═ in the 1,4-phenylene may be replaced by —N═, and at least one of hydrogen in the 1,4-phenylene may be replaced by halogen; $Z^1$, $Z^2$, $Z^3$, $Z^4$, $Z^5$, $Z^6$ and $Z^7$ are independently a single bond, —(CH$_2$)$_2$—, —COO—, —OCO—, —CF$_2$O—, —OCF$_2$— or —CH═CH—; $X^1$ is fluorine, —CF$_3$ or —OCF$_3$; $Y^1$ and $Y^2$ are independently hydrogen or fluorine; i, j, k, n, p and q are independently 0 or 1; and a sum of i, j, k, m, n, p and q is 2, 3 or 4.

2. The liquid crystal composition according to claim 1, wherein, in formula (1), q is 1.

3. The liquid crystal composition according to claim 1, wherein, in formula (1), $R^1$ is alkyl having 1 to 10 carbons, alkenyl having 2 to 10 carbons or alkoxy having 1 to 9 carbons; ring $A^1$, ring $A^2$, ring $A^3$, ring $A^4$, ring $A^5$ and ring $A^6$ are independently 1,4-cyclohexylene, 1,4-cyclohexenylene, tetrahydropyran-2,5-diyl, 1,3-dioxane-2,5-diyl, 1,4-phenylene in which at least one of hydrogen may be replaced by fluorine or chlorine, or pyrimidine-2,5-diyl; and $Z^1$, $Z^2$, $Z^3$, $Z^4$, $Z^5$, $Z^6$ and $Z^7$ are independently a single bond, —(CH$_2$)$_2$—, —COO—, —CF$_2$O— or —CH═CH—.

4. The liquid crystal composition according to claim 1, wherein, in formula (1), $R^1$ is alkyl having 1 to 10 carbons; ring $A^1$, ring $A^2$, ring $A^3$, ring $A^4$, ring $A^5$ and ring $A^6$ are independently 1,4-cyclohexylene, 1,4-phenylene, 3-fluoro-1,4-phenylene or 3,5-difluoro-1,4-phenylene; and $Z^1$, $Z^2$, $Z^3$, $Z^4$, $Z^5$, $Z^6$ and $Z^7$ are independently a single bond, —(CH$_2$)$_2$—, —COO—, —CF$_2$O— or —CH═CH—.

5. The liquid crystal composition according to claim 1, represented by formula (1-2-1) or (1-2-2):

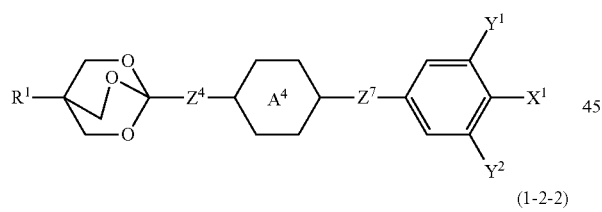

(1-2-1)

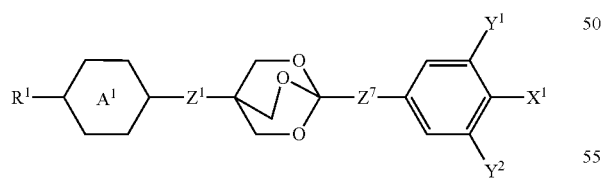

(1-2-2)

wherein, in the formulas, $R^1$ is alkyl having 1 to 10 carbons; ring $A^1$ and ring $A^4$ are independently 1,4-cyclohexylene, 1,4-phenylene, 3-fluoro-1,4-phenylene or 3,5-difluoro-1,4-phenylene; $Z^1$, $Z^4$ and $Z^7$ are independently a single bond, —(CH$_2$)$_2$—, —COO—, —CF$_2$O— or —CH═CH—; $X^1$ is fluorine, —CF$_3$ or —OCF$_3$; $Y^1$ and $Y^2$ are independently hydrogen or fluorine; in formula (1-2-1), at least one of $Z^4$ and $Z^7$ is a single bond; and in formula (1-2-2), at least one of $Z^1$ and $Z^7$ is a single bond.

6. The liquid crystal composition according to claim 5, wherein, in formula (1-2-1), any one of $Z^4$ and $Z^7$ is —CF$_2$O—, or in formula (1-2-2), any one of $Z^1$ and $Z^7$ is —CF$_2$O—.

7. The liquid crystal composition according to claim 1, represented by formula (1-3-1), (1-3-2) or (1-3-3):

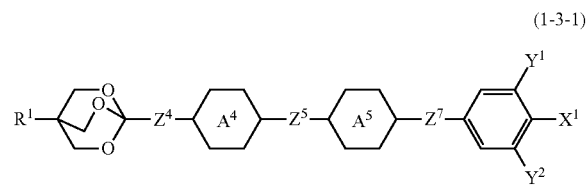

(1-3-1)

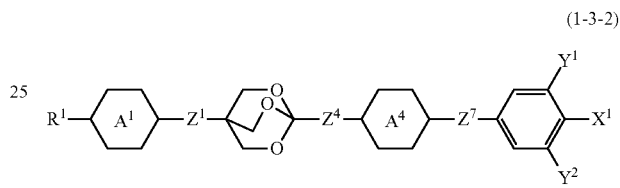

(1-3-2)

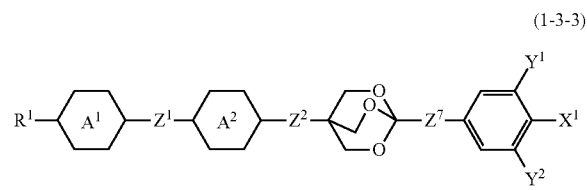

(1-3-3)

wherein, in the formulas, $R^1$ is alkyl having 1 to 10 carbons; ring $A^1$, ring $A^2$, ring $A^4$ and ring $A^5$ are independently 1,4-cyclohexylene, 1,4-phenylene, 3-fluoro-1,4-phenylene or 3,5-difluoro-1,4-phenylene; $Z^1$, $Z^2$, $Z^4$, $Z^5$ and $Z^7$ are independently a single bond, —(CH$_2$)$_2$—, —COO—, —CF$_2$O— or —CH═CH—; $X^1$ is fluorine, —CF$_3$ or —OCF$_3$; and $Y^1$ and $Y^2$ are independently hydrogen or fluorine;

in formula (1-3-1), at least two of $Z^4$, $Z^5$ and $Z^7$ are a single bond;

in formula (1-3-2), at least two of $Z^1$, $Z^4$ and $Z^7$ are a single bond; and in formula (1-3-3), at least two of $Z^1$, $Z^2$ and $Z^7$ are a single bond.

8. The liquid crystal composition according to claim 7, wherein, in formula (1-3-1), any one of $Z^4$, $Z^5$ and $Z^7$ is —CF$_2$O—; in formula (1-3-2), any one of $Z^1$, $Z^4$ and $Z^7$ is —CF$_2$O—; or in formula (1-3-3), any one of $Z^1$, $Z^2$ and $Z^7$ is —CF$_2$O—.

9. The liquid crystal composition according to claim 1, represented by formula (1-4-1), (1-4-2), (1-4-3) or (1-4-4):

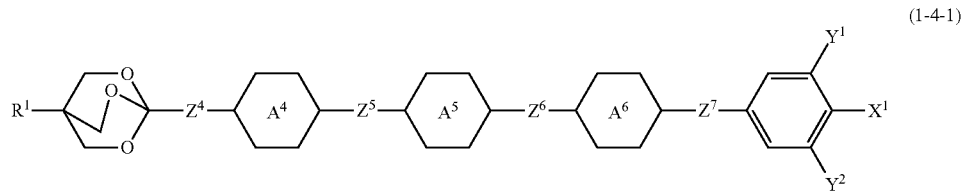
(1-4-1)

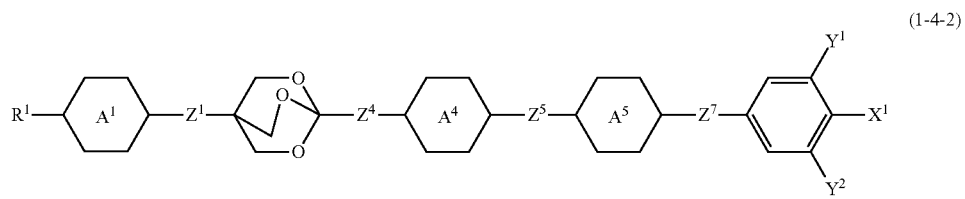
(1-4-2)

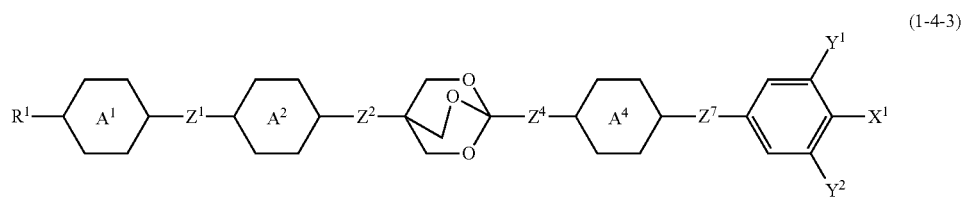
(1-4-3)

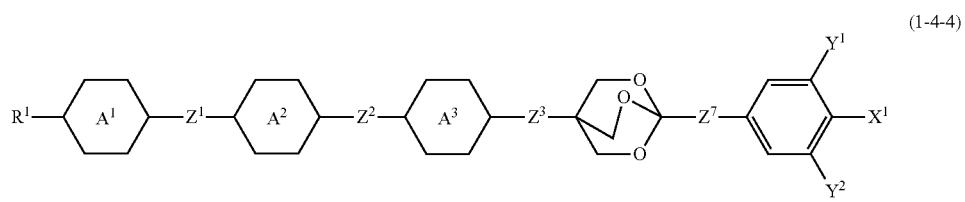
(1-4-4)

wherein, in the formulas, $R^1$ is alkyl having 1 to 10 carbons; ring $A^1$, ring $A^2$, ring $A^3$, ring $A^4$, ring $A^5$ and ring $A^6$ are independently 1,4-cyclohexylene, 1,4-phenylene, 3-fluoro-1,4-phenylene or 3,5-difluoro-1,4-phenylene; $Z^1$, $Z^2$, $Z^3$, $Z^4$, $Z^5$, and $Z^7$ are independently a single bond, —(CH$_2$)$_2$—, —COO—, —CF$_2$O— or —CH=CH—; $X^1$ is fluorine, —CF$_3$ or —OCF$_3$; $Y^1$ and $Y^2$ are independently hydrogen or fluorine;

in formula (1-4-1), at least three of $Z^4$, $Z^5$, $Z^6$ and $Z^7$ are a single bond;

in formula (1-4-2), at least three of $Z^1$, $Z^4$, $Z^5$ and $Z^7$ are a single bond;

in formula (1-4-3), at least three of $Z^1$, $Z^2$, $Z^4$ and $Z^7$ are a single bond; and in formula (1-4-4), at least three of $Z^1$, $Z^2$, $Z^3$ and $Z^7$ are a single bond.

10. The liquid crystal composition according to claim 9, wherein, in formula (1-4-1), any one of $Z^4$, $Z^5$, $Z^6$ and $Z^7$ is —CF$_2$O—; in formula (1-4-2), any one of $Z^1$, $Z^4$, $Z^5$ and $Z^7$ is —CF$_2$O—; in formula (1-4-3), any one of $Z^1$, $Z^2$, $Z^4$ and $Z^7$ is —CF$_2$O—; or in formula (1-4-4), any one of $Z^1$, $Z^2$, $Z^3$ and $Z^7$ is —CF$_2$O—.

11. The liquid crystal composition according to claim 1, wherein the second component is at least one compound selected from the group of compounds represented by formulas (2), (3) and (4):

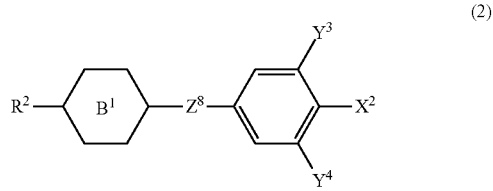
(2)

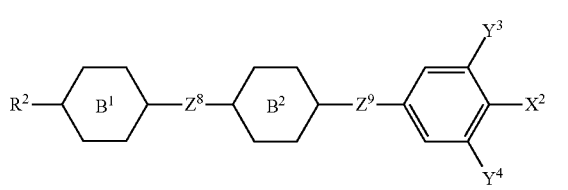
(3)

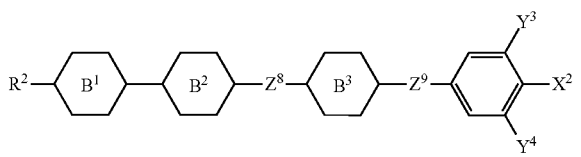
(4)

wherein, in formulas (2) to (4), $R^2$ is independently alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;

X$^2$ is independently fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring B$^1$, ring B$^2$ and ring B$^3$ are independently 1,4-cyclohexylene, 1,3-dioxane-2,5-diyl, pyrimidine-2,5-diyl, tetrahydropyran-2,5-diyl, or 1,4-phenylene in which at least one of hydrogen may be replaced by fluorine;

Z$^8$ and Z$^9$ are independently —(CH$_2$)$_2$—, —(CH$_2$)$_4$—, —COO—, —CF$_2$O—, —OCF$_2$—, —CH=CH—, —C≡C—, —CH$_2$O— or a single bond; and Y$^3$ and Y$^4$ are independently hydrogen or fluorine.

12. The liquid crystal composition according to claim 1, wherein the second component is at least one compound selected from the group of compounds represented by formulas (5), (6), (7), (8), (9) and (10):

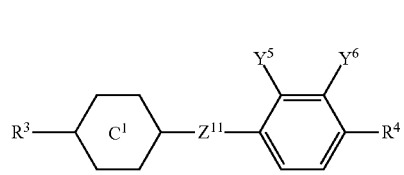

(5)

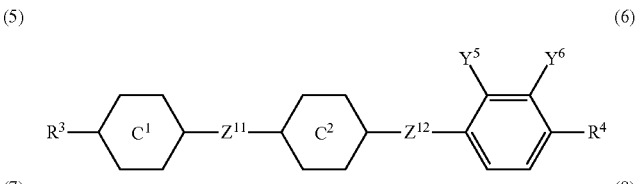

(6)

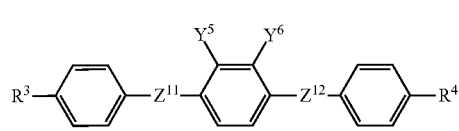

(7)

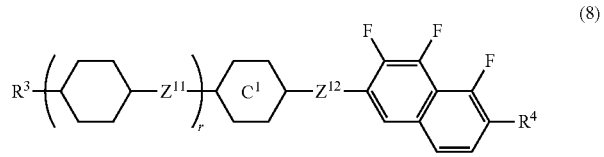

(8)

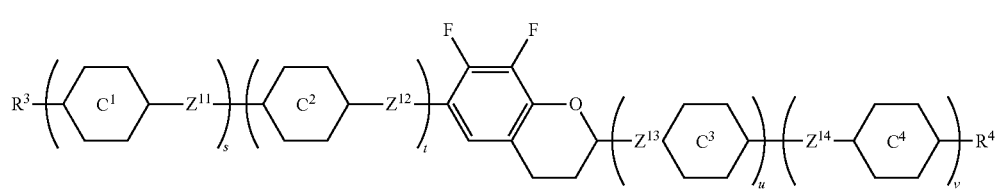

(9)

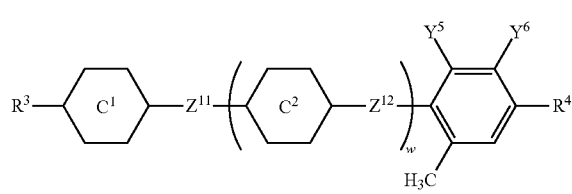

(10)

wherein, in formulas (5) to (10), R$^3$ and R$^4$ are independently alkyl having 1 to 10 carbons or alkenyl having 2 to 10 carbons, at least one of —CH$_2$— in the alkyl or the alkenyl may be replaced by —O—, and at least one of hydrogen in the alkenyl may be replaced by fluorine;

ring C$^1$, ring C$^2$, ring C$^3$ and ring C$^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

Z$^{11}$, Z$^{12}$, Z$^{13}$ and Z$^{14}$ are independently —(CH$_2$)$_2$—, —COO—, —CH$_2$O—, —OCF$_2$—, —OCF$_2$(CH$_2$)$_2$— or a single bond;

Y$^5$ and Y$^6$ are independently fluorine or chlorine; and r, s, t, u, v and w are independently 0 or 1, and a sum of s, t, u and v is 1 or 2.

13. The liquid crystal composition according to claim 1, wherein the second component is at least one compound selected from the group of compounds represented by formulas (11), (12) and (13):

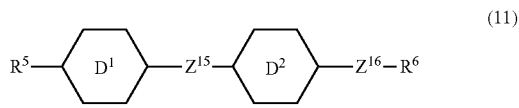

(11)

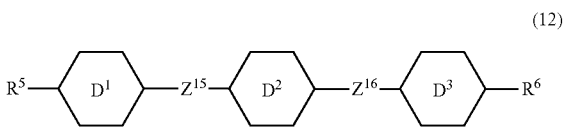

(12)

-continued

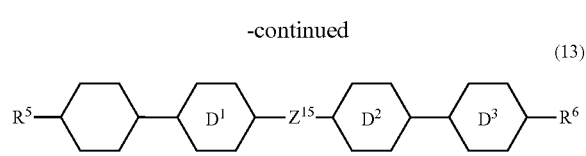

(13)

wherein, in formulas (11) to (13), R$^5$ and R$^6$ are independently alkyl having 1 to 10 carbons or alkenyl having 2 to 10 carbons, at least one of —CH$_2$— in the alkyl or the alkenyl may be replaced by —O—, and at least one of hydrogen in the alkenyl may be replaced by fluorine;

ring D$^1$, ring D$^2$ and ring D$^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{15}$ and $Z^{16}$ are independently —C≡C—, —COO—, —(CH$_2$)$_2$—, —CH═CH— or a single bond.

14. The liquid crystal composition according to claim 11, further containing at least one compound selected from the group of compounds represented by formulas (11), (12) and (13):

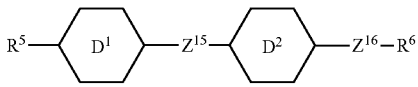
(11)

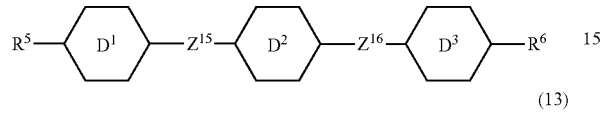
(12)

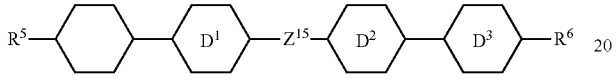
(13)

wherein, in formulas (11) to (13), $R^5$ and $R^6$ are independently alkyl having 1 to 10 carbons or alkenyl having 2 to 10 carbons, at least one of —CH$_2$— in the alkyl or the alkenyl may be replaced by —O—, and at least one of hydrogen in the alkenyl may be replaced by fluorine; ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{15}$ and $Z^{16}$ are independently —C≡C—, —COO—, —(CH$_2$)$_2$—, —CH═CH— or a single bond.

15. The liquid crystal composition according to claim 12, further containing at least one compound selected from the group of compounds represented by formulas (11), (12) and (13):

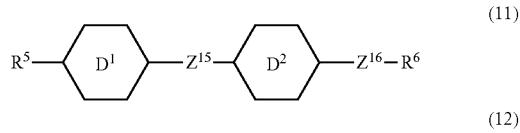
(11)

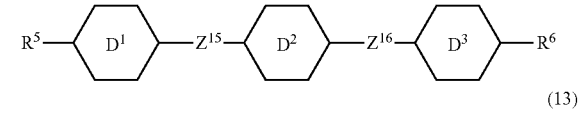
(12)

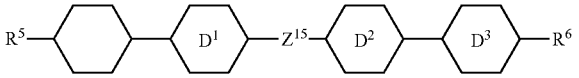
(13)

wherein, in formulas (11) to (13), $R^5$ and $R^6$ are independently alkyl having 1 to 10 carbons or alkenyl having 2 to 10 carbons, at least one of —CH$_2$— in the alkyl or the alkenyl may be replaced by —O—, and at least one of hydrogen in the alkenyl may be replaced by fluorine; ring $D^1$, ring $D^2$ and ring $D^3$ are independently 1,4-cyclohexylene, pyrimidine-2,5-diyl, 1,4-phenylene, 2-fluoro-1,4-phenylene, 3-fluoro-1,4-phenylene or 2,5-difluoro-1,4-phenylene; and $Z^{15}$ and $Z^{16}$ are independently —COO—, —(CH$_2$)$_2$—, —CH═CH— or a single bond.

16. The liquid crystal composition according to claim 1, further containing at least one optically active compound and/or at least one polymerizable compound.

17. The liquid crystal composition according to claim 1, further containing at least one antioxidant and/or at least one ultraviolet light absorber.

18. A liquid crystal display device including the liquid crystal composition according to claim 1.

* * * * *